US007329797B2

(12) United States Patent
Schneeberger et al.

(10) Patent No.: US 7,329,797 B2
(45) Date of Patent: Feb. 12, 2008

(54) MODULATING PLANT CARBON LEVELS

(75) Inventors: Richard Schneeberger, Van Nuys, CA (US); Emilio Margolles-Clark, North Port, FL (US); Joon-Hyun Park, Oak Park, CA (US); Boris Jankowski, Santa Monica, CA (US); Steven Craig Bobzin, Malibu, CA (US)

(73) Assignee: Ceres, Inc., Thousand Oaks, CA (US)

( * ) Notice: Subject to any disclaimer, the term of this patent is extended or adjusted under 35 U.S.C. 154(b) by 76 days.

(21) Appl. No.: 11/296,657

(22) Filed: Dec. 6, 2005

(65) Prior Publication Data

US 2006/0143736 A1 Jun. 29, 2006

Related U.S. Application Data

(60) Provisional application No. 60/704,981, filed on Aug. 2, 2005, provisional application No. 60/634,921, filed on Dec. 8, 2004.

(51) Int. Cl.
*A01H 1/00* (2006.01)
*C07H 21/04* (2006.01)
*C07K 14/415* (2006.01)
*C12N 15/29* (2006.01)

(52) U.S. Cl. .......................... 800/278; 800/295; 435/6; 435/468; 435/419; 435/320.1; 530/370; 536/23.6; 536/24.1

(58) Field of Classification Search .................... 435/6, 435/69.1, 468, 419, 252.3, 320.1; 530/370; 536/23.6; 800/278
See application file for complete search history.

(56) References Cited

U.S. PATENT DOCUMENTS 4,987,071 A 1/1991 Cech et al.
5,204,253 A 4/1993 Sanford et al.
5,254,678 A 10/1993 Haseloff et al.
5,538,880 A 7/1996 Lundquist et al.
5,998,700 A 12/1999 Lightfoot et al.
6,013,863 A 1/2000 Lundquist et al.
6,329,571 B1 12/2001 Hiei
6,423,885 B1 7/2002 Waterhouse et al.
6,906,244 B2 6/2005 Fischer et al.
2003/0233670 A1 12/2003 Edgerton et al.
2005/0108791 A1* 5/2005 Edgerton .................... 800/284
2006/0041952 A1 2/2006 Cook et al.

FOREIGN PATENT DOCUMENTS

JP 2004 121047 4/2004
WO 99/32619 7/1999
WO 00/31281 6/2000
WO 01/18191 3/2001
WO 01/35725 5/2001
WO 01/75164 10/2001
WO 02/10210 2/2002
WO 02/15675 2/2002
WO 02/16655 2/2002
WO 02/46449 6/2002
WO 02/081714 10/2002
WO 03/013227 2/2003
WO 03/095654 11/2003

OTHER PUBLICATIONS

GenBank No. U93215, dated Feb. 27, 2002.
GenBank No. AF129516, dated Apr. 6, 1999.
GenBank No. AF096096, dated Jan. 25, 1999.
GenBank No. L05934, dated Oct. 22, 1993.
GenBank No. AL163815.1 dated Nov. 14, 2006.
GenBank No. Q9LPV5, dated Mar. 1, 2004.
GenBank No. CAB87717, dated Nov. 14, 2006.
GenBank No. NP 196718, dated Jun. 9, 2006.
Abler, "Isolation and characterization of a genomic sequence encoding the maize *Cat3* catalase gene" *Plant Mol. Biol.*, 22:101-31-1038 (1993).
Apuya et al. "RASPBERRY3 Gene Encodes a Novel Protein Important for Embryo Development," *Plant Physiology*, 129(2):691-705 (2002).
Baerson et al., "Developmental regulation of an acyl carrier protein gene promoter in vegetative and reproductive tissues" *Plant Mol Biol.*, 22(2):255-267 (1993).
Bateman et al., "Pfam 3.1: 1313 multiple alignments and profile HMMs match the majority of proteins" *Nucl. Acids Res.* 27:260-262 (1999).
Baud, S.; Boutin, J.-P.; Miquel, M.; Lepiniec, L.; Rochat, C. An integrated overview of seed development in *Arabidopsis thaliana* ecotype WS, *Plant Physiol. Biochem.* 40 (2002) 151-160.
Bechtold et al., "*In planta* Agrobacterium mediated gene transfer by infiltration of adult *Arabidopsis thaliana* plants" *C.R. Acad. Sci. Paris*, 316:1194-1199 (1993).
Bustos, et al., "Regulation of B-Glucuronidase Expression in Transgenic Tobacco Plants by an A/T-Rich, cis-Acting Sequence Found Upstream of a French Bean -Phaseolin Gene" *Plant Cell*, 1:839-854 (1989).
Cerdan et al., "A 146 bp fragment of the tobacco *Lhcb1*2* promoter confers very-low-influence, low-fluence and high-irradiance responses of phytochrome to minimal CaMV 35S promoter" *Plant Mol. Biol.* 33:245-2555 (1997).
Chen et al., "Functional analysis of regulatory elements in a plant embryo-specific gene" *Proc Natl Acad Sci USA*, 83:8560-8564 (1986).
Chenna, et al. "Multiple sequence alignment with the Clustal series of programs" *Nucleic Acids Res.*, 31 (13):3497-500 (2003).
Chichkova et al., "Transgenic tobacco plants that overexpress alfalfa NADH-glutamate synthase have higher carbon and nitrogen content" *Journal of Experimental Botany*, 52(364):2079-2087 (2001).

(Continued)

*Primary Examiner*—Phuong T Bui
(74) *Attorney, Agent, or Firm*—Fish & Richardson P.C.

(57) ABSTRACT

Methods and materials for modulating (e.g., increasing or decreasing) carbon levels in plants are disclosed. For example, nucleic acids encoding carbon-modulating polypeptides are disclosed as well as methods for using such nucleic acids to transform plant cells. Also disclosed are plants having increased carbon levels.

11 Claims, 25 Drawing Sheets

OTHER PUBLICATIONS

Conceicao et al., "a cotyleson region is responsible for the different spatial expression patterns of *Arabidopsis* 2S albumin genes" *The Plant Journal*, 5:493-505 (1994).
Conkling et al., "Isolation of transcriptionally regulated root-specific genes from tobacco" *Plant Physiol.*, 93:1203-1211 (1990).
de Feyter and Gaudron, Methods in Molecular Biology, vol. 74, Chapter 43, "Expressing Ribozymes in Plants", Edited by Turner, P.C, *Humana Press Inc.*, Totowa, NJ.
Dietrich et al., "AtPTR1, a plasma membrane peptide transporter expressed during seed germination and in vascular tissue of *Arabidopsis" Plant Journal*, 40(4):488-499 (2004).
Ezeagu, I.E.; Petzke, J.K.; Metges, C.C.; Akinsoyinu, A.O.; Ologhobo, A.D. Seed protein contents and nitrogen-to-protein conversion factors for some uncultivated tropical plant seeds, *Food Chemistry*, 78 (2002) 105-109.
Fejes et al., "A 268 bp upstream sequence mediates the circadian clock-regulated transcription of the wheat Cab-1 gine in transgenic plants" *Plant Mol. Biol.*, 15:921-932 (1990).
Foyer et al., "Adaptations of photosynthetic electron transport, carbon assimilation , and carbon partitioning in transgenic *Nicotiana plumbaginifolia* plants to changes in nitrate reductase activity" *Plant Physiology*, 104(1):171-178 (1994).
Fraisier et al., *Plant Journal*, 23(4):489-496 (2000).
Fromm et al., "An octopine synthase enhancer directs tissue-specific expression and binds ASF-1, a factor from tobacco nuclear extracts" *The Plant Cell*, 1:977-984 (1989).
Green, et al., "Binding site requirements for pea nuclear protein factor GT-1 correlate with sequences required for light-dependent transcriptional activation of the *rbcS-3A* gene" *EMBO J.* 7, 4035-4044 (1988).
Heath, J.D.; Weldon, R.; Monnot, C.; Meinke, D.W. Analysis of storage proteins in normal and aborted seeds from embryo-lethal mutants of *Arabidopsis thaliana, Planta* 169 91986) 304-312.
Hong et al., "Promoter sequences from two different *Brassica napus* tapetal oleosin-like genes direct tapetal expression of B-glucuronidase in transgenic *Brassica* plants" *Plant Mol Biol.*, 34(3):549-555 (1997).
Huang et al., "Cloning and functional characterization of an *Arabidopsis* nitrate transporter gene that encodes a constitutive component of low-affinity uptake" *Plant Cell*, 11(8):1381-1392 (1999).
Hwang et al., "Aleurone- and embryo-specific expression of the β-glucuronidase gene controlled by the barley *Chi26* and *Ltp1* promoters in transgenic rice" *Plant Cell Rep.*, (2001) 20:647-654.
Hyrup et al., "Peptide nucleic acids (PNA): Synthesis, properties and potential applications" *Bioorganic Med. Chem.*, 4: 5-23 (1996).
Jordano, et al., "A sunflower helianthinin gene upstream sequence ensemble contains an enhancer and sites of nuclear protein interaction" *Plant Cell*, 1:855-866 (1989).
Koch et al., "Reduced amino acid content in transgenic potato tubers due to antisense inhibition of the leaf H+/amino acid symporter StAAP1" *Plant Journal*, 33(2):211-220 (2003).
Lam et al., "Site-specific mutations alter in vitro factor binding and change promoter expression pattern in transgenic plants" *Proc. Natl. Acad. Sci. USA*, 86:7890-7894 (1989).
Li et al., "Oil content of arabidopsis seeds: The influence of seed anatomy, light and plant-to-plant variation" *Phytochemistry*, 2006, 67:904-915.
Luan et al., "A rice *cab* gene promoter contains separate *cis*-Acting elements that upregulate expression in dicot and monocot plants" *Plant Cell*, 4:971-981 (1992).
Lubberstedt et al., "Promoters from genes for plastid proteins possess regions with different sensitivities toward red and blue light" *Plant Physiol.*, 10:997-1006 (1994).
Matsuoka et al., "Tissue-specific light-regulated expression directed by the promoter of a $C_4$ gene, maize pyruvate, orthophosphate dikinase, in a $C_3$ plant, rice" *Proc Natl Acad. Sci. USA*, 90:9586-9590 (1993).
McClure et al., "Transcription, Organization, and Sequence of an Auxin-Regulated Gene Cluster in Soybean" *Plant Cell*, 1:229-239 (1989).
Meier, et al., "Elicitor-inducible and constitutive in Vivo DNA footprints indicate novel *cis*-acting elements in the promoter of a parsley gene encoding pathogenesis-related protein 1" *Plant Cell*, 3, 309-316 (1991).
Perriman, et al., "Effective ribozyme delivery in plant cells" *Proc. Natl. Acad. Sci. USA*, 92(13):6175-6179 (1995).
Rhee, K.C. "Determination of Total Nitrogen In Handbook of Food Analytical Chemistry—Water, Proteins, Enzymes, Lipids, and Carbohydrates. (R. Wrolstad, et. al, ed.)" *John Wiley and Sons, Inc.*, 2005, pp. 105.
Riggs et al., "Cotyledon nuclear proteins bind to DNA fragments harboring regulatory elements of phytohemagglutinin genes" *The Plant Cell*, 1(6):609-621 (1989).
Rivera et al., "Genomic evidence for two functionally distinct gene classes" *Proc. Natl. Acad. Sci. USA*, 95:6239-6244 (1998).
Sheridan et al., "the *macl* gene: Controlling the commitment to the meiotic pathway in maize" *Genetics*, 142:1009-1020 (1996).
Slocombe et al., "Temporal and tissue-specific regulation of a *Brassica napus* stearoyl-acyl carrier protein desaturase gene" *Plant Physiol*, 104(4):167-176 (1994).
Sonnhammer et al., "Pfam: multiple sequence alignments and HMM-profiles of protein domains" *Nucl. Acids Res.*, 26: 320-322 (1998).
Sonnhammer et al., "Pfam: A comprehensive database of protein domain families based on seed alignments", *Proteins*, 28:405-420 (1997).
Summerton and Weller, "Morpholino antisense oligomers: Design, preparation, and properties", *Antisense Nucleic Acid Drug Dev.*, 7:187-195 (1997).
Truernit et al., "The promoter of the *Arabidopsis thaliana SUC2* sucrose-H+ symporter gene directs expression of B-glucuronidase to the phloen: evidence for phloem loading and unloading the SUC2" *Planta*, 196:564-570 (1995).
Tuskan et al., "The genome of black cottonwood, *Populus trichocarpa" Science*, 2006, 313(5793):1596-604.
Urao et al., "Molecular cloning and characterization of a gene that encodes a MYC-related protein in *Arabidopsis" Plant Mol. Biol*, 32:571-57 (1996).
Weber et al., "Interaction of cytosolic and plastidic nitrogen metabolism in plants" *Journal of Experimental Botany*, 53(370):865-874 (2002).
Yamamoto et al., "The promoter of a pine photosynthetic gene allows expression of a B-glucuronidase reporter gene in transgenic rice plants in a light-independent but tissue-specific manner" *Plant Cell Physiol.* 35:773-778 (1994).
Yanagisawa et al., "Metabolic engineering with Dof1 transcription factor in plants: Improved nitrogen assimilation and growth under low-nitrogen conditions" *PNAS*, 101(20):7833-7838 (2004).
Zhang, et al., "DNA sequences that activate isocitrate lyase gene expression during late embryogenesis and during postgerminative growth" *Plant Physiology* 110: 1069-1079 (1996).
Zheng et al., "SPK1 is an essential S-phase-specific gene of *Saccharomyces cerevisiae* that encodes a nuclear serine/threonine/tyrosine kinase" *Mol. Cell Biol.* 13:5829-5842 (1993).
GenBank Accession No.: BAC43284, dated Feb. 14, 2004.
Hill et al. "Carbon supply for storage-product synthesis in developing seeds of oilseed rape" *Biochemical Society Transactions*, 28(6):667-669 (2000).
Katavic et al "Utility of the *Arabidopsis* FAE1 and yeast SLC1-1 genes for improvements in erucic acid and oil content in rapeseed" *Biochemical Society Transactions*, 28(6):935-937 (2000).
Singh et al. "Transgenic expression of a delta 12-epoxygenase gene in *Arabidopsis* seeds inhibits accumulation of linoleic acid" *Planta*, 212(5-6):872-879 (2001).
Tomlinson et al. "Evidence that the hexose-to sucrose ration does not control the switch to storage product accumulation in oilseeds: analysis of tobacco seed development and effects of overexpressing apoplastic invertase" *Journal of Experimental Botany*, 55(406):2291-2303 (2004).
GenBank Accession No. NM_121195, dated Jan. 10, 2002.
Gou et al. "Protein tolerance to random amino acid change" *PNAS*, 101(25):9205-9210 (2004).
Keskin et al. "A new, structurally nonredundant, diverse data set of protein-protein interfaces and its implications" *Protein Science*, 13:1043-1055 (2004).
Thornton et al. "From structure to function: approaches and limitations" *Nature Structural Biology*, 991-994 (2000).

* cited by examiner

Figure 1A

```
SEQ·ID·NO-4·CeresClone:1545993  ---------- MAEGEFKPAA MQVEAPA--- ---------E AAAAPSKPRF  28
SEQ·ID·NO-5·gi|34911556         ----MEAKPV AMEVEGVEAA GG-------- ---------- ------KPRF  22
Lead·SEQ·ID·NO-2·cDNA·3080447   ---------- -MEVEGKCGE ACTTTTT--- ---------- -----APRRF  21
SEQ·ID·NO-3·gi|57283317         ---------- -MEIEG---Q ATVKESQ--- ---------- ------PPKF  17
SEQ·ID·NO-7·gi|37999150         MADLSSSAVG DRNAKGDPGS SMHGVTGKEA LYAFSLHDGD KMNYDPDAKF  50
SEQ·ID·NO-14·gi|15990600        ---------- -MEVE----S SAHGDAA--- ---------- ------ASKF  16
SEQ·ID·NO-17·gi|9858859         ---------- -MEVE----A SAHGDTA--- ---------- ------ASKF  16
SEQ·ID·NO-15·gi|4731146         ---------- -MEVE----A GAHGDTA--- ---------- ------ASKF  16
SEQ·ID·NO-10·gi|9931082         ---------- MGDSTGEPGS SMHGVTGREQ TFAFSV-ASP IVPTDKTAKF  39
SEQ·ID·NO-11·gi|39573544        ---------- MAEVEGEPGS SMHGVTGREQ TFAFSV-ASP IVPTDPTAKF  39
SEQ·ID·NO-6·gi|3005576          ---------- MAEIEGSPGS SMHGVTGREQ TFVASV-ASP IVPTDTTAKF  39
SEQ·ID·NO-13·gi|13539545        ---------- MVEIEGSPGT SMHGVTGREQ TFISSV-SSP MVPTDTTAKF  39

Consensus                       ---------- -MEVEG-PGS S-HG-T---- ---------- -------AKF  50

SEQ·ID·NO-4·CeresClone:1545993  RMPVDSDNKA TEFWLFSFAR PHMSAFHMSW FSFFCCFLST FAAPPLLPLI  78
SEQ·ID·NO-5·gi|34911556         RMPVDSDLKA TEFWLFSFAR PHMASFHMAW FSFFCCFVST FAAPPLLPLI  72
Lead·SEQ·ID·NO-2·cDNA·3080447   ALPVDAENKA TTFRLFSVAK PHMRAFHLSW FQFFCCFVST FAAPPLLPVI  71
SEQ·ID·NO-3·gi|57283317         ALPVDSEHKA TEFRLFSVAA PHMRAFHLSW VSFFACFVSS FAAPPLLPII  67
SEQ·ID·NO-7·gi|37999150         ALPVDSEHKA TTMRIHSFSR PHMLTFHLSW FSFFTCFMST FAAPPLIPVI  100
SEQ·ID·NO-14·gi|15990600        TLPVDSEHKA KSFRLFSFAN PHMRTFHLSW ISFFTCFVST FAAAPLVPII  66
SEQ·ID·NO-17·gi|9858859         TLPVDSEHKA KSFRLFSFAN PHMRTFHLSW ISFFTCFVST FAAAPLVPII  66
SEQ·ID·NO-15·gi|4731146         TLPVDSEHKA KSFRLFSFAN PHMRTFHLSW ISFFTCFVST FAAAPLVPII  66
SEQ·ID·NO-10·gi|9931082         DLPVDSEHKA TVFKLFSFAK PHMRTFHLSW ISFSTCFVST FAAAPLVPII  89
SEQ·ID·NO-11·gi|39573544        DLPVDSEHKA KVFKIFSLAN PHMRTFHLSW ISFFTCFVST FAAAPLVPII  89
SEQ·ID·NO-6·gi|3005576          ALPVDSEHKA KVFKLFSLAN PHMRTFHLSW ISFFTCFVST FAAAPLVPII  89
SEQ·ID·NO-13·gi|13539545        DLPVDSQHKA KVFKLFSLAN PHMTTFHLSW ISFFTCFVST FAAAPLVPII  89

Consensus                       -LPVDSEHKA --FRLFSFAN PHMRTFHLSW ISFFTCFVST FAAAPLVPII  100
```

Figure 1B

| Sequence | | | | | | |
|---|---|---|---|---|---|---|
| SEQ-ID-NO-4-CeresClone:1545993 | RDTLGLTATD | IGNAGIASVS | GAVFARVAMG | TACDLVGPRL | ASAAILLLTT | 128 |
| SEQ-ID-NO-5-gi\|34911556 | RDTLGLTATD | IGNAGIASVS | GAVFARLAMG | TACDLVGPRL | ASASLILLTT | 122 |
| Lead-SEQ-ID-NO-2-cDNA-3080447 | RENLNLTATD | IGNAGIASVS | GAVFARIVMG | TACDLFGPRL | ASAALTLSTA | 121 |
| SEQ-ID-NO-3-gi\|57283317 | RDNLNLTASD | IGNAGIASVS | GAVFARVAMG | TACDLFGPRL | ASASLILLTA | 117 |
| SEQ-ID-NO-7-gi\|37999150 | RDNLNLNKED | IGHAAIASVT | GSILSRLLMG | SLCDMIGPRY | GCAFLVMILS | 150 |
| SEQ-ID-NO-14-gi\|15990600 | RDNLNLAKAD | IGNAGVASVS | GSIFSRLAMG | AVCDLLGPRY | GCAFLVMLSA | 116 |
| SEQ-ID-NO-17-gi\|9858859 | RDNLNLAKAD | IGNAGVASVS | GSIFSRLAMG | AICDLLGPRY | GCAFLVMLSA | 116 |
| SEQ-ID-NO-15-gi\|4731146 | RDNLNLAKAD | IGNAGVASVS | GSIFSRLAMG | AICDLLGPRY | GCAFLVMLSA | 116 |
| SEQ-ID-NO-10-gi\|9931082 | RENLNLTKQD | IGNAGVASVS | GSIFSRLVMG | AVCDLLGPRY | GCAFLVMLSA | 139 |
| SEQ-ID-NO-11-gi\|39573544 | RDNLNLTKQD | IGNAGVASVS | GSIFSRLVMG | AVCDLLGPRY | GCAFLIMLSA | 139 |
| SEQ-ID-NO-6-gi\|3005576 | RDNLNLTKSD | IGNAGVASVS | GSIFSRLAMG | AVCDMLGPRY | GCAFLIMLSA | 139 |
| SEQ-ID-NO-13-gi\|13539545 | RDNLNLTKSD | IGNAGVASVS | GSIFSRLTMG | VICDLLGPRY | GCAFLIMLSA | 139 |
| Consensus | RDNLNLTK-D | IGNAGVASVS | GSIFSRLAMG | AVCDLLGPRY | GCAFLIMLSA | 150 |

| Sequence | | | | | | |
|---|---|---|---|---|---|---|
| SEQ-ID-NO-4-CeresClone:1545993 | PAVYYSAVID | SASSYLLVRF | FTGFSLASFV | STQFWMSSMF | SPPKVGLANG | 178 |
| SEQ-ID-NO-5-gi\|34911556 | PAVYCSSIIQ | SPSCYLLVRF | FTGISLASFV | SAQFWMSSMF | SAPKVGLANG | 172 |
| Lead-SEQ-ID-NO-2-cDNA-3080447 | PAVYFTAGIK | SPIGFIMVRF | FAGFSLATFV | STQFWMSSMF | SGPVVGSANG | 171 |
| SEQ-ID-NO-3-gi\|57283317 | PAVYFTSMAS | SSTSFLLVRF | FTGFSLATFV | STQFWMSSMF | SAPVVGTANG | 167 |
| SEQ-ID-NO-7-gi\|37999150 | PAVYAMAVVD | SAAGFTAVRF | FVGFSLATFV | SCQYWMSSMF | NGKIVGTANG | 200 |
| SEQ-ID-NO-14-gi\|15990600 | PTVFCMAVID | DASGYIAVRF | LIGFSLAAFV | SCQYWMSTMF | NSKIIGTVNG | 166 |
| SEQ-ID-NO-17-gi\|9858859 | PTVFCMAAID | DASGYIAVRF | LIGFSLATFV | SCQYWMSTMF | NSKIIGTVNG | 166 |
| SEQ-ID-NO-15-gi\|4731146 | PTVFCMAVID | DASGYIAVRF | LIGFSLATFV | SCQYWMSTMF | NSKIIGTVNG | 166 |
| SEQ-ID-NO-10-gi\|9931082 | PTVFSMSFVS | GAAGFITVRF | MIGFCLATFV | SCQYGMSTMF | NSQIIGLVNG | 189 |
| SEQ-ID-NO-11-gi\|39573544 | PTVFCMSFVS | DAGGYLAVRF | MIGFSLATFV | SCQYWMSTMF | NSKIIGLVNG | 189 |
| SEQ-ID-NO-6-gi\|3005576 | PTVFCMSFVK | DAAGYIAVRF | LIGFSLATFV | SCQYWMSTMF | NSKIIGLANG | 189 |
| SEQ-ID-NO-13-gi\|13539545 | PTVFCMSFVN | DAAGYIVVRF | MIGFSLATFV | SCQYWMSTMF | NSKIIGLVNG | 189 |
| Consensus | PTVFCM-VI- | DASGYIAVRF | LIGFSLATFV | SCQYWMSTMF | NSKIIG--NG | 200 |

Figure 1C

```
SEQ-ID-NO-4-CeresClone:1545993   VAGGWGNLGG GAVQLIMPLV FEAIRKAGAT P-FTAWRVAF FVPGLLQTLS  227
SEQ-ID-NO-5-gi|34911556          VAGGWGNLGG GAVQLLMPLV YEAIHKIGST P-FTAWRIAF FIPGLMQTFS  221
Lead-SEQ-ID-NO-2-cDNA-3080447    IAAGWGNLGG GATQLIMPIV FSLIRNMGAT K-FTAWRIAF FIPGLFQTLS  220
SEQ-ID-NO-3-gi|57283317          VAGGWGNLGG GATQLIMPLV FGLIRDIGAT K-FTAWRIAF FIPALFQTLS  216
SEQ-ID-NO-7-gi|37999150          IAAGWGNLGG GATQMIMPLV YALIKDSFHS PSYTAWRLAF FLPGVMHTVI  250
SEQ-ID-NO-14-gi|15990600         LAAGWGNMGG GATQLIMPLV FHAIQKCGAT P-FVAWRIAY FVPGMMHIVM  215
SEQ-ID-NO-17-gi|9858859          LAAGWGNMGG GATQLIMPLV FHAIQKCGAT P-FVAWRIAY FVPGMMHIVM  215
SEQ-ID-NO-15-gi|4731146          LAAGWGNMGG GATQLIMPLV FHAIQKCGAT P-FVAWRIAY FVPGMMHIVM  215
SEQ-ID-NO-10-gi|9931082          TAAGWGNMGG GITQLLMPVV YEIIRRCGAT A-FTAWRLAF FVPGWLHIIM  238
SEQ-ID-NO-11-gi|39573544         TAAGWGNMGG GATQLLMPLV FDIIGRVGAT P-FTAWRIAF FIPGMLHVIM  238
SEQ-ID-NO-6-gi|3005576           TAAGWGNMGG GATQLIMPLV YELIRRAGAT P-FTAWRIAF FVPGFMHVIM  238
SEQ-ID-NO-13-gi|13539545         TAAGWGNMGG GATQLIMPIV YELIRRAGST G-FTAWRIAF FIPGFMHVFM  238

Consensus                        -AAGWGNMGG GATQLIMPLV FELIRK-GAT P-FTAWRIAF FVPGMMHVIM  250

SEQ-ID-NO-4-CeresClone:1545993   AVAVLAFGQD MPDGNYRKLH RSGDMHKDSF GNVLRHAVTN YRAWILALTY  277
SEQ-ID-NO-5-gi|34911556          AIAVLAFGQD MPGGNYGKLH KTGDMHKDSF GNVLRHALTN YRGWILALTY  271
Lead-SEQ-ID-NO-2-cDNA-3080447    AFAVLLFGQD LPDGDYWAMH KSGEREKDDV GKVISNGIKN YRGWITALAY  270
SEQ-ID-NO-3-gi|57283317          AFAVLIFGKD LPDGNFRRLQ KAGDKTKDKF SNVFYHGIKN YRGWILALSY  266
SEQ-ID-NO-7-gi|37999150          GLLVLFLGQD LPDGNFKELQ EQGTKPKDSF KKVFINAITN YRTWIFLITY  300
SEQ-ID-NO-14-gi|15990600         GLLVLTMGQD LPDGNLASLQ KKGDMAKDKF SKVLWGAVTN YRTWIFVLLY  265
SEQ-ID-NO-17-gi|9858859          GLLVLTMGQD LPDGNLASLQ KKGDMAKDKF SKVLWGAVTN YRTWIFVLLY  265
SEQ-ID-NO-15-gi|4731146          GLLVLTMGQD LPDGNLASLQ KRGDMAKDKF SKVLWGAVTN YRTWIFVLLY  265
SEQ-ID-NO-10-gi|9931082          GVLVLNLGQD LPDGNRSALE KKGEVAKDKF GKIMWYAVTN YRTWIFVLLY  288
SEQ-ID-NO-11-gi|39573544         GIMVLTLGQD LPDGNLAALQ KKGDVAKDQF SKVLWHAITN YRTWIFVLLY  288
SEQ-ID-NO-6-gi|3005576           GILVLTLGQD LPDGNLGALR KKGDVAKDKF SKVLWYAITN YRTWIFALLY  288
SEQ-ID-NO-13-gi|13539545         GILVLTLGQD LPDGNLSALQ KKGDVAKDKF SKVLWYAITN YRTWIFALLY  288

Consensus                        G-LVLTLGQD LPDGNLAALQ KKGDMAKDKF SKVLWHAITN YRTWIF-LLY  300
```

Figure 1D

```
SEQ-ID-NO-4-CeresClone:1545993    GYCFGVELAV DNIVAQYFYD RFGVKLSTAG FIAASFGMAN IVSRPGGGLL  327
SEQ-ID-NO-5-gi|34911556           GYSFGVELTI DNVVHQYFYD RFDVNLQTAG LIAASFGMAN IISRPGGGLL  321
Lead-SEQ-ID-NO-2-cDNA-3080447     GYCFGVELTI DNIIAEYFFD RFHLKLQTAG IIAASFGLAN FFARPGGGIF  320
SEQ-ID-NO-3-gi|57283317           GYCFGVELTI DNIVAEYFYD RFDLKLHTAG MIAASFGLAN IVSRPGGGMI  316
SEQ-ID-NO-7-gi|37999150           GYCFGVELTV DNIIAEYFYD RFGLSLSTAG IIASSFGLMN IFSRPLGGIL  350
SEQ-ID-NO-14-gi|15990600          GYCMGVELTT DNVIAEYYYD HFHLHLRAAG TIAACFGMAN IVARPMGGYL  315
SEQ-ID-NO-17-gi|9858859           GYCMGVELTT DNVIAEYYYD HFHLDLRAAG TIAACFGMAN IVARPMGGYL  315
SEQ-ID-NO-15-gi|4731146           GYCMGVELTT DNVIAEYYFD HFHLDLRAAG TIAACFGMAN IVARPMGGYL  315
SEQ-ID-NO-10-gi|9931082           GYSMGVELST DNVIAEYFFD RFHLKLHTAG IIAACFGMAN FFARPAGGYA  338
SEQ-ID-NO-11-gi|39573544          GYSMGVELSI DNVIAEYFYD RFNLKLHTAG IIAAAFGMAN IVARPFGGFA  338
SEQ-ID-NO-6-gi|3005576            GYSMGVELTT DNVIAEYFYD RFNLKLHTAG IIAASFGMAN LVARPFGGYA  338
SEQ-ID-NO-13-gi|13539545          GYSMGVELTT DNVIAEYFYD RFNLKLHTVG IIAASFGMAN LVARPFGGYV  338

Consensus                         GYCMGVELT- DNVIAEYFYD RF-LKL-TAG IIAASFGMAN IVARP-GGYL  350

SEQ-ID-NO-4-CeresClone:1545993    SDWLSSRFGM RGRLWGLWVV QTIGGVLCVV LGAVDYSFAA SVAVMILFSM  377
SEQ-ID-NO-5-gi|34911556           SDWLSSRYGM RGRLWGLWTV QTIGGVLCVV LGIVDFSFAA SVAVMVLFSF  371
Lead-SEQ-ID-NO-2-cDNA-3080447     SDFMSRRFGM RGRLWAWWIV QTSGGVLCAC LGQIS-SLTV SIIVMLVFSV  369
SEQ-ID-NO-3-gi|57283317           SDAVGKRFGM RGKLWALWVV QTLGGVFCII LGRVG-SLGA SIVVMIVFFL  365
SEQ-ID-NO-7-gi|37999150           SDVVARRYGM QGRLWNLWII QTLGGVFCIV LGKTA-ALGP AIGVMIVFSF  399
SEQ-ID-NO-14-gi|15990600          SDLGARYFGM RARLWNIWIL QTAGGAFCIW LGRAS-ALPA SVTAMVLFSI  364
SEQ-ID-NO-17-gi|9858859           SDLGARYFGM RARLWNIWIL QTAGGAFCIW LGRAS-ALPA SVTAMVLFSI  364
SEQ-ID-NO-15-gi|4731146           SDLGARYFGM RA-LWNIWIL QTAGGAFCIW LGRAS-ALPA SVTAMVLFSI  363
SEQ-ID-NO-10-gi|9931082           SDLAAKYFGM RGRLWALWII QTAGGVFCVW LGRAN-TLVT AVVAMVLFSL  387
SEQ-ID-NO-11-gi|39573544          SDRAARYFGM RGRLWTLWIL QTLGGVFCIW LGRAN-SLPI AVFAMILFSV  387
SEQ-ID-NO-6-gi|3005576            SDVAARLFGM RGRLWTLWIL QTLGGVFCIW LGRAN-SLPI AVLAMILFSI  387
SEQ-ID-NO-13-gi|13539545          SDVAARLFGM RGRLWTLWIL QTLGGVFCIW LGRAN-SLPI AVLAMILFSV  387

Consensus                         SDL-AR-FGM RGRLW-LWII QTLGGVFCIW LGRA--SLPA SV-AMILFSI  400
```

Figure 1E

```
SEQ·ID·NO–4·CeresClone:1545993   FVQAACGLTF GIVPFVSRRS LGLISGMTGG GGNVGAVLTQ LIFFHGSKYK  427
SEQ·ID·NO–5·gi|34911556          FVQAACGLTF GIVPFVSRRS LGLISGMTGG GGNVGAVLTQ YIFFHGTKYK  421
Lead·SEQ·ID·NO–2·cDNA·3080447    FVQAACGLTF GVVPFISRRS LGVVSGMTGA GGNVGAVLTQ LIFFKGSTYT  419
SEQ·ID·NO–3·gi|57283317          FCQAACGLTF GVVPFVSRRS LGLISGMTGC GGNVGAVLTQ LIFFRGSKYS  415
SEQ·ID·NO–7·gi|37999150          FVQAACGATF GVIPFVSRRS LGVISGFTGA GGNVGAVLTQ TIFFTQATYH  449
SEQ·ID·NO–14·gi|15990600         CAQAACGAVF GVAPFVSRRS LGIISGLTGA GGNVGAGLTQ LLFFTSSQYS  414
SEQ·ID·NO–17·gi|9858859          CAQAACGAVF GVAPFVSRRS LGIISGLTGA GGNVGAGLTQ LLFFTSSQYS  414
SEQ·ID·NO–15·gi|4731146          CAQAACGALF GVAPFVSRRS LGIISGLTGA GGNVGAGLTQ LLFFTSSQYS  413
SEQ·ID·NO–10·gi|9931082          GAQAACGATF AIVPFVSRRA LGIISGLTGA GGNFGSGLTQ LIFFSTSRFT  437
SEQ·ID·NO–11·gi|39573544         GAQAACGATF GVIPFISRRS LGIISGLTGA GGNFGSGLTQ LVFFSSAAFS  437
SEQ·ID·NO–6·gi|3005576           GAQAACGATF GIIPFISRRS LGIISGLTGA GGNFGSGLTQ LVFFSTSKFS  437
SEQ·ID·NO–13·gi|13539545         GAQAACGATF GIIPFISKRS LGIISGLTGA GGNFGSGLTQ LVFFSTSRFS  437

Consensus                        -AQAACGATF GVVPFVSRRS LGIISGLTGA GGNVGAGLTQ LIFF-SSKYS  450

SEQ·ID·NO–4·CeresClone:1545993   TETGIKYMGF MIIACTLPIT LIYFPQWGGM FLGPRPG--- ATAEDYYNRE  474
SEQ·ID·NO–5·gi|34911556          TETGIKYMGL MIIACTLPVM LIYFPQWGGM LVGPRKG--- ATAEEYYSRE  468
Lead·SEQ·ID·NO–2·cDNA·3080447    RETGITLMGV MSIACSLPIC LIYFPQWGGM FCGPSSK--K VTEEDYYLAE  467
SEQ·ID·NO–3·gi|57283317          KERGIMLMGV MIICCTLPIC LIHFPQWGGM FCGPSSTKI- ATEEDYYLSE  464
SEQ·ID·NO–7·gi|37999150          TEVGIENMGI MIICCTALVL FVWFPQWGSM FFKSSR---- MTEEDYYASE  495
SEQ·ID·NO–14·gi|15990600         TGRGLEYMGI MIMACTLPIT LVHFPQWGSM FFPASAD--- ATEEEYYASE  461
SEQ·ID·NO–17·gi|9858859          TGRGLEYMGI MIMACTLPVA LVHFPQWGSM FFPASAD--- ATEEEYYASE  461
SEQ·ID·NO–15·gi|4731146          TGRGLEYMGI MIMACTLPVA LVHFPQWGSM FFPASAD--- ATEEEYYASE  460
SEQ·ID·NO–10·gi|9931082          TEQGLTWMGV MIVACTLPVT LIHFPQWGSM FLPPSTDPVK GPKEHYYASE  487
SEQ·ID·NO–11·gi|39573544         TATGLSLMGV MIVCCTLPVT LVHFPQWGSM FLPPSKDVVK STEEFYYGAE  487
SEQ·ID·NO–6·gi|3005576           TATGLSLMGV MIVACTLPVS VVHFPQWGSM FLPPSKDVSK STEEFYYTSE  487
SEQ·ID·NO–13·gi|13539545         TGAGLSWMGV MIVGCTLPVT LVHFPQWGSM FLPPSKDINK SSEEHYYTAE  487

Consensus                        TE-GLEYMGV MIIACTLPV- LVHFPQWGSM FLPPS-D--- ATEE-YY-SE  500
```

Figure 1F

```
SEQ-ID-NO-4-CeresClone:1545993   WTAHECDKGF NTASVRFAEN SVREGGRS-- ----GSQSKH TTVPVESSPA   518
SEQ-ID-NO-5-gi|34911556          WSDHEREKGF NAASVRFAEN SVREGGRS-- -SANGGQPRH T-VPVDASPA   514
Lead-SEQ-ID-NO-2-cDNA-3080447    WNDEEKEKNL HI GSQKFAET SLSERGRA-- -TTTHPQT-- ----------   502
SEQ-ID-NO-3-gi|57283317          WNSEEKEKGL HLSSLKFADN SRSERGRK-- -EDSETRP-- ---VDETLST   506
SEQ-ID-NO-7-gi|37999150          YSEGEQDQGL HQASLKFAEN AKSERGRS-- -KGSKSPP-- ---ENGK-PD   536
SEQ-ID-NO-14-gi|15990600         WSEEEKGKGL HI AGQKFAEN SRSERGRRNV ILATSATP-- ---PNNT-PQ   505
SEQ-ID-NO-17-gi|9858859          WSEEEKGKGL HI TGQKFAEN SRSERGRRNV ILATSATP-- ---PNNT-PQ   505
SEQ-ID-NO-15-gi|4731146          WSEEEKGKGL HI AGQKFAEN SRSERGRRNV IFATSATP-- ---PNNT-PQ   504
SEQ-ID-NO-10-gi|9931082          WNEQEKEKNM HQGSLRFAKN AKSEGGRR-- -VRSAATP-- ---PENT-PN   528
SEQ-ID-NO-11-gi|39573544         WNEEEKQKGL HQQSLRFAEN SRSERGRR-- -VASAPTP-- ---PNTT-PS   528
SEQ-ID-NO-6-gi|3005576           WNEEEKQKGL HQQSLKFAEN SRSERGKR-- -VASAPTP-- ---PNAT-PT   528
SEQ-ID-NO-13-gi|13539545         WDEEERKKGL HSQSLKFAEN SRSERGKR-- -VSSAPTP-- ---PNTT-PT   528

Consensus                        W-EEEKEKGL H--SLKFAEN SRSERGRR-- -VASS-TP-- ---PN-T-P-   550

SEQ-ID-NO-4-CeresClone:1545993   DV-------- -   520
SEQ-ID-NO-5-gi|34911556          GV-------- -   516
Lead-SEQ-ID-NO-2-cDNA-3080447    ---------- -   502
SEQ-ID-NO-3-gi|57283317          KV-------- -   508
SEQ-ID-NO-7-gi|37999150          GLKGI KEGAE V   547
SEQ-ID-NO-14-gi|15990600         HV-------- -   507
SEQ-ID-NO-17-gi|9858859          HV-------- -   507
SEQ-ID-NO-15-gi|4731146          QV-------- -   506
SEQ-ID-NO-10-gi|9931082          NV-------- -   530
SEQ-ID-NO-11-gi|39573544         HV-------- -   530
SEQ-ID-NO-6-gi|3005576           HV-------- -   530
SEQ-ID-NO-13-gi|13539545         HV-------- -   530

Consensus                        -V-------- -   561
```

Figure 2B

```
SEQ-ID-NO-33-gi|11066960          IAAAGITSGS IAERTQFVAY LIYSSFLTGF VYPVVSHWFW SPDGWASPFR  189
SEQ-ID-NO-26-gi|50910611          IAAAGITSGS IAERTQFVAY LIYSAFLTGF VYPVVSHWIW SADGWASASR  178
SEQ-ID-NO-32-gi|38684027          VAAAGITSGS IAERTQFVAY LIYSAFLTGF VYPVVSHWIW SVDGWASAAR  179
SEQ-ID-NO-25-gi|31322044          IAAAGITSGS IAERTQFVAY LIYSSFLTGF VYPVVSHWLW SSDGWASPTR  192
Lead-SEQ-ID-NO-22-cDNA-1828694    IAAAGITSGS IAERTQFVAY LIYSTFLTGF VYPTVSHWFW SSDGWASASR  198
SEQ-ID-NO-24-gi|57283313          IAAAGITSGS IAERTQFVAY LIYSTFLTGF VYPVVSHWLW SGDGWANPAK  187
SEQ-ID-NO-23-gi|2065194           IAAAGITSGS IAERTQFVAY LIYSSFLTGF VYPIVSHWFW SGDGWASASK  191
SEQ-ID-NO-27-gi|50428339          IAAAGITSGS IAERTQFVAY LIYSSFLTAF VYPIVSHWVW SGDGWLSASR  193

Consensus                         IAAAGITSGS IAERTQFVAY LIYSSFLTGF VYPVVSHW-W S-DGWASASR  200

SEQ-ID-NO-33-gi|11066960          SADDRLFSTG AIDFAGSGVV HMVGGIAGLW GALIEGPRRG RFEKGGRAIA  239
SEQ-ID-NO-26-gi|50910611          TSGSLLFGSG VIDFAGSGVV HMVGGVAGLW GALIEGPRIG RFDHAGRSVA  228
SEQ-ID-NO-32-gi|38684027          TSGPLLFKSG VIDFAGSGVV HMVGGIAGFW GALIEGPRIG RFDHAGRSVA  229
SEQ-ID-NO-25-gi|31322044          TTGSLLFGSG AIDFAGSGVV HMVGGIAGLW GAFIEGPRIG RFDRTGRSVA  242
Lead-SEQ-ID-NO-22-cDNA-1828694    SDNNLLFGSG AIDFAGSGVV HMVGGIAGLC GALVEGPRIG RFDRSGRSVA  248
SEQ-ID-NO-24-gi|57283313          SDNNLLFGSG AIDFAGSGVV HMVGGIAGLW GALIEGPRIG RFDHNGRSVA  237
SEQ-ID-NO-23-gi|2065194           TDGNLLLRFG VIDFAGSGVV HMVGGIAGLW GAFIEGPRIG RFDRSGRSVA  241
SEQ-ID-NO-27-gi|50428339          TSGALLFSSG AIDFAGSGVV HMVGGIAGLW GALIEGPRIG RFDRSGRSVA  243

Consensus                         TSGNLLFGSG AIDFAGSGVV HMVGGIAGLW GALIEGPRIG RFDRSGRSVA  250

SEQ-ID-NO-33-gi|11066960          LRGHSASLVV LGTFLLWFGW YGFNPGSFTK ILVPYN---- SGSNYGQWSC  285
SEQ-ID-NO-26-gi|50910611          LRGHSASLVV LGSFLLWFGW YGFNPGSFLT ILKSYG-PP- -GSIHGQWSA  275
SEQ-ID-NO-32-gi|38684027          LKGHSASLVV LGTFLLWFGW YGFNPGSFVT ILKSYG-PP- -GSLNGQWSG  276
SEQ-ID-NO-25-gi|31322044          LRGHSASLVV LGSFLLWFGW YGFNPGSFLT IAKAYGNNGE NGNYYGQWSA  292
Lead-SEQ-ID-NO-22-cDNA-1828694    LRGHSASLVV LGTFLLWFGW YGFNPGSFLT ILKGYD-KS- -RPYYGQWSA  295
SEQ-ID-NO-24-gi|57283313          LRGHSASLVV LGSFLLWFGW YGFNPGSFLL ILKSYG-GGA -GGYYGQWSA  285
SEQ-ID-NO-23-gi|2065194           LRGHSASLVV LGTFLLWFGW YGFNPGSFLT ILKSYD-HTI RGTYYGQWSA  290
SEQ-ID-NO-27-gi|50428339          LRGHSASLVV LGSFLLWFGW YGFNPGSFLT ILKSYG-TA- -GTYYGQWSA  290

Consensus                         LRGHSASLVV LG-FLLWFGW YGFNPGSFLT ILKSYG---- -GSYYGQWSA  300
```

Figure 2C

```
SEQ-ID-NO-33-gi|11066960           IGRTAVNTTL SGCTAALTTL FGKRLLSGHW NVIDVCNGLL GGFAAITAGC  335
SEQ-ID-NO-26-gi|50910611           VGRTAVTTTL AGSTAALTTL FGKRLQTGHW NVIDVCNGLL GGFAAITAGC  325
SEQ-ID-NO-32-gi|38684027           VGRTAVTTTL AGSVAALTTL FGKRLQTGHW NVVDVCNGLL GGFAAITAGC  326
SEQ-ID-NO-25-gi|31322044           IGRTAVTTTL AGCTAALTTL FSKRLLEGHW KVLDVCNGLL GGFAAITSGC  342
Lead-SEQ-ID-NO-22-cDNA-1828694     VGRTAVTTTL SGCTAALTTL FSKRLLAGHW NVIDVCNGLL GGFAAITSGC  345
SEQ-ID-NO-24-gi|57283313           VGRTAVTTTL AGSTAALTTL FGKRLLSGHW NVIDVCNGLL RGFAAITAGC  335
SEQ-ID-NO-23-gi|2065194            IGRTAVTTTL AGCTAALTTL FCKRLLVAHW NVVDVCNGLL GGFAAITSGC  340
SEQ-ID-NO-27-gi|50428339           VGRTAVTTTL AGCTAALTTL FGKRLLDGHW NVVDVCNGLL GGFAAITSGC  340

Consensus                          VGRTAVTTTL AGCTAALTTL FGKRLL-GHW NV-DVCNGLL GGFAAIT-GC  350

SEQ-ID-NO-33-gi|11066960           SVVEPWAAIV CGFMTSLVLI GCNKLAELVQ YGDPLEAAQL HGGCGAWGLI  385
SEQ-ID-NO-26-gi|50910611           SVVDPWAAII CGFVSAWVLI GLNALAARLK FDDPLEAAQL HGGCGAWGVI  375
SEQ-ID-NO-32-gi|38684027           SVVDPWAAVI CGFVSAWVLI GLNALAGRLK YDDPLEAAQL HGGCGAWGII  376
SEQ-ID-NO-25-gi|31322044           SVVEPWPAIV CGFVAAWVLI GLNLVAAKMK YDDPLEAAQL HGGCGAWGVL  392
Lead-SEQ-ID-NO-22-cDNA-1828694     AVVEPWAAIV CGFVASWVLI GFNLLAKKLK YDDPLEAAQL HGGCGAWGLI  395
SEQ-ID-NO-24-gi|57283313           SVVEPWAAII CGFVAAWVLI GCNKLAEKLQ YDDPLEAAQL HGGCGMWGLL  385
SEQ-ID-NO-23-gi|2065194            AVVEPWAAIV CGFIAAWVLI GFNALAAKLK YDDPLEAAQL HGGCGSWGII  390
SEQ-ID-NO-27-gi|50428339           SVVEPWAAIV CGFVSAWVLI GCNKVAEKLK YDDPLEAAQL HGGCGSWGIL  390

Consensus                          SVVEPWAAIV CGFVAAWVLI G-N-LAEKLK YDDPLEAAQL HGGCGAWG-I  400

SEQ-ID-NO-33-gi|11066960           FVGLFAKEKY LNEVYGAIPG RPYGLFMGGG GKLLGAQLVQ ILVIVGWVSA  435
SEQ-ID-NO-26-gi|50910611           FTALFARKEY VDQIFGQ-PG RPYGLFMGGG GRLLGAHIVV ILVIAAWVSF  424
SEQ-ID-NO-32-gi|38684027           FTALFAKKQY VEEIYGA--G RPYGLFLGGG GRLLAAHIVQ ILAIAGFVSC  424
SEQ-ID-NO-25-gi|31322044           FTGLFAKGEY VAEVYGS-AG RPYGLLMGGG GKLLAAQVIE ILVVCGWVTA  441
Lead-SEQ-ID-NO-22-cDNA-1828694     FTGLFARKEY VNEIYSG--D RPYGLFMGGG EKLLAAQIVQ IIVIIGWVTV  443
SEQ-ID-NO-24-gi|57283313           FTGLFAKKAY VNEVYSNKPG RPYGLFMGGG GKLLAAQIIE ILVIVGWVSA  435
SEQ-ID-NO-23-gi|2065194            FTGLFAKKEY VNEVYPCFPN RPYGLFMGGG GKLLGAQVIQ VVVIIGWVSV  440
SEQ-ID-NO-27-gi|50428339           FTGLFAKKKY VDEVYSA--G RPYGLFMGGG GKLLAAQLIE ILVIFGWVSV  438

Consensus                          FTGLFAKKEY VNEVYG--PG RPYGLFMGGG GKLLAAQI-Q ILVI-GWVS-  450
```

Figure 2D

```
SEQ·ID·NO-33·gi|11066960          TMGTLFFILK RLNLLRISEQ HEMQGMDMTR HGGFAYLYHD NDDESHRVDP   485
SEQ·ID·NO-26·gi|50910611          TMAPLFLVLN KLGLLRISAE DEMAGMDQTR HGGFAYAYHD -DDASGK--P   471
SEQ·ID·NO-32·gi|38684027          TMGPLFLALK KLGLLRISAE DEMAGMDLTR HGGFAYVYHD DDEHDKS--V   472
SEQ·ID·NO-25·gi|31322044          TMGPLFYGLH KTKLLRISED DETAGMDLTR HGGFAYAYHD DDDVSTK--R   489
Lead·SEQ·ID·NO-22·cDNA·1828694    TMGPLFYGLH KMNLLRISAE DEMAGMDMTR HGGFAYAYND EDDVSTK--P   491
SEQ·ID·NO-24·gi|57283313          TMGPLFYGLH KLKLLRISSE DEMAGMDLTR HGGFAYAYDA EDDVSGK--P   483
SEQ·ID·NO-23·gi|2065194           TMGPLFYLLH KFKLLRISRD DETAGMDLTR HGGFAYTYHD EDEGSSM--P   488
SEQ·ID·NO-27·gi|50428339          TMGPLFYGLK KLKLLRISRE DEMAGMDLTR HGGFAYIYRD EDDLANR--P   486

Consensus                         TMGPLFYGLH KLKLLRISAE DEMAGMDLTR HGGFAY-YHD EDDVS-K--P   500

SEQ·ID·NO-33·gi|11066960          ----GSPFPR SALPLAFNFQ LFGNLLPFKY CLGFGFEI-- -   519
SEQ·ID·NO-26·gi|50910611          DRSVGGFMLK SAHGTQ---- ---------V AAEMGGHV-- -   496
SEQ·ID·NO-32·gi|38684027          ----GGFMLR SAQTRV---- --EP------ AAAANSQV-- -   494
SEQ·ID·NO-25·gi|31322044          -----GVMMS RIGPGS---- --SS-PSTMN TPAASAAAND C   518
Lead·SEQ·ID·NO-22·cDNA·1828694    ----WGHFAG RVEPTS---- --RS-----S TPTPTLTV-- -   514
SEQ·ID·NO-24·gi|57283313          -----SFMMR KVLPAN---- --NT-TPNEN SPSINV---- -   507
SEQ·ID·NO-23·gi|2065194           -----GFKMT RVEPTN---- --TS-TPDHQ NRSVNVVV-- -   514
SEQ·ID·NO-27·gi|50428339          -----GFMMR KVEPQN---- --SSPTPDHN SSSPAEAV-- -   513

Consensus                         -----GFMMR RVEP------ --SS--P--N --S----V-- -   541
```

Figure 3A

```
SEQ·ID·NO–38·gi|47900739                MESSVRGVDE AAI-MKSSTR RKNGCWITFP FIIVSATMAG LSLASGGWTS   49
Lead·SEQ·ID·NO–36·cDNA·3086062          MSGSVSRDAE ALKSADSSTR R-SGGRITFP FMIV--TLFG LTLATLGWLQ   47
SEQ·ID·NO–37·CeresClone:100299          MASSVTGDAE TAISADSSTK RRGGGWITFP FMIA--TLLG LTIAAWGWLL   48

Consensus                               M-SSV-GDAE AAISADSSTR R--GGWITFP FMIV--TL-G LTLA--GWL-   50

SEQ·ID·NO–38·gi|47900739                NLIVYLIDEF NMKSIKTAKV YNVINGCTTL FPLVGGILAD SYLGSFSVIW   99
Lead·SEQ·ID·NO–36·cDNA·3086062          NLIVYLIEEY NMKSIAAAKI LNIFSGFTFM FPAIGAIAAD SFFGTIPVIL   97
SEQ·ID·NO–37·CeresClone:100299          NLIVYLIEEF NVKSIAAAQI ANIVSGCICM VPAVAAIASD SFFGTIPVIS   98

Consensus                               NLIVYLIEEF NMKSIAAAKI -NI-SGCT-M FPAVGAIAAD SFFGTIPVI-  100

SEQ·ID·NO–38·gi|47900739                FSSLISALGI LLLLFTSAID VLRPPPCDDG SSLCTSPSTH QYAVLYVALA  149
Lead·SEQ·ID·NO–36·cDNA·3086062          VSSFISLVGV VLLALTTLFD SLRPQACETA SSLCQAPTNI QLGVLYTAIT  147
SEQ·ID·NO–37·CeresClone:100299          VSAFISLMGV ALLTLTASLD TLRPRPCETA SILCQSPSKT QLGVLYTAIT  148

Consensus                               VSSFISL-GV -LL-LT---D -LRP-PCETA SSLCQSPS-- QLGVLYTAIT  150

SEQ·ID·NO–38·gi|47900739                LASLGVAGTR FLIAPMGANQ FDKPKHQAIF FNWYLFAFYM SFAISLTVIV  199
Lead·SEQ·ID·NO–36·cDNA·3086062          LGCVGAGGLR FTLATAGANQ YEKAKDQGSF FNWFFFTWYL AASISATAIV  197
SEQ·ID·NO–37·CeresClone:100299          LASIGTGGTR FTLATAGANQ YEKTKDQGSF FNWFFFTFYL AGAISATAIV  198

Consensus                               LAS-G-GGTR FTLATAGANQ YEK-KDQGSF FNWFFFT-YL A-AISATAIV  200

SEQ·ID·NO–38·gi|47900739                YVEDNVSWSW GYGISMAFNI LGLAMFLIGK RFYCDVKEQG GSPFVNLARV  249
Lead·SEQ·ID·NO–36·cDNA·3086062          YAEENISWSF GFGLCVAANL FGLIVFILGK RFYKHDKPL- GSPFTSLLRV  246
SEQ·ID·NO–37·CeresClone:100299          YTEDNISWTL GFGLSVAANF FSFLVFVSGK RFYKHDKPL- GSPFTSLLCV  247

Consensus                               Y-EDNISWS- GFGLSVAAN- FGL-VF--GK RFYKHDKPL- GSPFTSLLRV  250

SEQ·ID·NO–38·gi|47900739                IVVAIQKWRV PLSEQTQHYY HDPSDTTTTL TITQIPTKSF KFLNCAAFIT  299
Lead·SEQ·ID·NO–36·cDNA·3086062          IFVAIRKRKA VVSTNEKDYH SES------- --KKAPTKSF RFFNRAALKQ  287
SEQ·ID·NO–37·CeresClone:100299          IFAALRKRKA VVSTNEKDYH NES------- --ITMPTKSF RFFNRAALKQ  288

Consensus                               IFVAIRKRKA VVSTNEKDYH -ES------- -----PTKSF RFFNRAALKQ  300
```

Figure 3B

```
SEQ-ID-NO-38-gi|47900739                 EGDIKPDGSI SNPWRLCTVQ QVEDLKSLIK LEPLWASGFL ISTQLVIQAS  349
Lead-SEQ-ID-NO-36-cDNA-3086062           NDEVNADGTI HNQWRLCSVQ QVEDFKAVIR IIPLVLAILF LSTPIAMQLC  337
SEQ-ID-NO-37-CeresClone:100299           EDEVKPDGTI RNPWRLCSVQ QVEDFKAVIR IIPLALATIF LSTPIAMQLS  338

Consensus                                EDEVKPDGTI -NPWRLCSVQ QVEDFKAVIR IIPL-LA--F LSTPIAMQLS  350

SEQ-ID-NO-38-gi|47900739                 LLILQALKMD RHMGPHFEIP AGSMLVFILL FITCIAIFLD RFLYPFLAKY  399
Lead-SEQ-ID-NO-36-cDNA-3086062           LTVLQGLVMD RRLGPHFKIP AGSLQVITLL STCLFIIVND RFLYPFYQKL  387
SEQ-ID-NO-37-CeresClone:100299           LTVLQGLVMD RRLGPSFKIP AGSLQVITLL STCLFIIVND RVLYPFYQKL  388

Consensus                                LTVLQGLVMD RRLGPHFKIP AGSLQVITLL STCLFIIVND RFLYPFYQKL  400

SEQ-ID-NO-38-gi|47900739                 TTFSLTPLQR IGIGHVITII SMAVSALVES RRLRIVRTHK LQGQNNDIVP  449
Lead-SEQ-ID-NO-36-cDNA-3086062           TGKFPTPIQR VGIGHVFNIL SMAVTAIVEA KRLKIVQKGH FLG-SSSVAD  436
SEQ-ID-NO-37-CeresClone:100299           TGKHLTPLQR VGIGHAFNIL SMAVTAIVEA KRLKIVQKGH FLG-SSSVAD  437

Consensus                                TGK-LTPLQR VGIGHVFNIL SMAVTAIVEA KRLKIVQKGH FLG-SSSVAD  450

SEQ-ID-NO-38-gi|47900739                 MSVFWLVPQL ALNGIGEGFH FPGHIAFYYQ EFPTSLKSTS TAMVALFIGI  499
Lead-SEQ-ID-NO-36-cDNA-3086062           MSVLWLFPPL VIVGIGEAFH FPGNVALCYQ EFPESMRSTA TSITSVLIGI  486
SEQ-ID-NO-37-CeresClone:100299           MSVLWLFPPL VIVGIGEAFH FPGNVALCYQ EFPESMRSTA TSITSVVIGI  487

Consensus                                MSVLWLFPPL VIVGIGEAFH FPGNVALCYQ EFPESMRSTA TSITSV-IGI  500

SEQ-ID-NO-38-gi|47900739                 AHYLGNTLID LVQRLSGWLP DNINKGRTDN VFWLCCILGS ANFMYYVVCA  549
Lead-SEQ-ID-NO-36-cDNA-3086062           CFYTSTALID LIQKTTAWLP DDINHGRVDN VYWILVIGGV LNLGYFLVCS  536
SEQ-ID-NO-37-CeresClone:100299           CFYTSTALID LIQRTTAWLP DDINHGRVDN VYWILVIGGV LNLGYFLVCS  537

Consensus                                CFYTSTALID LIQRTTAWLP DDINHGRVDN VYWILVIGGV LNLGYFLVCS  550

SEQ-ID-NO-38-gi|47900739                 SLYKYKNV-- -DNKSNLAPS K      567
Lead-SEQ-ID-NO-36-cDNA-3086062           WFYKYRNLEN ADHEQDANVS H      557
SEQ-ID-NO-37-CeresClone:100299           WLYRYRNLKD DDHKQAANVS H      558

Consensus                                WLYKYRNL-- -DHKQ-ANVS H      571
```

Figure 4A

```
SEQ·ID·NO−48·gi|48675345          ----------  --MSNCTLPE  TQ-EKLTLPD  AWDFKGRPAE  RSKTGGWTAA   37
SEQ·ID·NO−52·gi|9581817           ----------  -----MALPE  TQQDTKTLPD  AWDYKGRPAV  RSSSGGWSSA   35
SEQ·ID·NO−53·gi|28273094          ----------  -----MALPE  TQQDTKTLPD  AWDYKGRPAV  RSSSGGWSSA   35
SEQ·ID·NO−51·gi|47717628          MDSTDRFDKS  PLLDGGSSSQ  ENSTEYTGDG  SVCTSGHPAS  RKHTGNWKVS   50
Lead·SEQ·ID·NO−40·cDNA·3091277    ----------  -----MDQKV  RQFEVCTQDG  SVDRHGNPAI  RANTGKWLTA   35
SEQ·ID·NO−41·gi|50912139          ----------  --MAPTAVDS  KRISDITEDG  SMDRRGNPAV  KAKTGNWRSS   38

Consensus                         ----------  --M--MALPE  -Q----TL--  --DYKG-PAV  RS-TGGWSSA   50

SEQ·ID·NO−48·gi|48675345          AMILGGEACE  RLTTLGIAVN  LVTYLTGTMH  LGNATSANTV  TNFLGTSFML   87
SEQ·ID·NO−52·gi|9581817           AMILGIEAVE  RLTTLGIAVN  LVTYLTGTMH  LGNASSANNV  TNFLGTSFML   85
SEQ·ID·NO−53·gi|28273094          AMILGIEAVE  RLTTLGIAVN  LVTYLTGTMH  LGNASSANNV  TNFLGTSFML   85
SEQ·ID·NO−51·gi|47717628          SLTIVCSFCC  YLAYSSIGKN  LVSYLTKVLD  ETNLDAARHV  ATWQGTSYLA  100
Lead·SEQ·ID·NO−40·cDNA·3091277    ILILVNQGLA  TLAFFGVGVN  LVLFLTRVMG  QDNAEAANNV  SKWTGTVYIF   85
SEQ·ID·NO−41·gi|50912139          ILLLVNYGLV  TCAFFGVGVN  LVVFLRRVLH  QDNAEAANSI  SKWTGTVYIF   88

Consensus                         A-IL--EA-E  RL--LGI-VN  LVTYLT--MH  -GNA--ANNV  TN-LGTS-ML  100

SEQ·ID·NO−48·gi|48675345          CLLGGFVADT  FLGRYLTIAI  FATFQAMGVT  ILTISTIIPS  LRPPKCTSDT  137
SEQ·ID·NO−52·gi|9581817           TLLGGFVADT  FLGRYLTIGI  FTTIQAMGVT  ILTISTIIPS  LRPPKCSPGS  135
SEQ·ID·NO−53·gi|28273094          TLLGGFVADT  FLGRYLTIGI  FTTIQAMGVT  ILTISTIIPS  LRPPKCSPGS  135
SEQ·ID·NO−51·gi|47717628          PLVGAFVADS  YLGKYRTALI  SCTIFIMGMM  MLLLSAALPL  I-SAGPHAWT  149
Lead·SEQ·ID·NO−40·cDNA·3091277    SLLGAFLSDS  YWGRYKTCAI  FQASFVAGLM  MLSLSTGALL  LEPSGCGVED  135
SEQ·ID·NO−41·gi|50912139          SLIGAFMSDS  YWGRYITCAI  FQMLYVTGLV  ILSLASWFLL  VKPTGCGAAG  138

Consensus                         -LLG-FVAD-  -LGRYLTIAI  F-TI--MGV-  ILT-ST-IP-  LRP--CSA--  150

SEQ·ID·NO−48·gi|48675345          STPCIPASGK  QLMVLYIALY  LTALGTGGLK  SSVSGFGSDQ  FDESDKQERR  187
SEQ·ID·NO−52·gi|9581817           S-TCIPASSK  QLMVLYIALY  MTALGTGGLK  SSVSGFGSDQ  FDETDKKERG  184
SEQ·ID·NO−53·gi|28273094          S-TCIPASSK  QLMVLYIALY  MTALGTGGLK  SSVSGFGSDQ  FDETDKKERG  184
SEQ·ID·NO−51·gi|47717628          L-WADPISS-  RYIIFLVGLY  MVGLGYGAQC  PCVTSFGADQ  FDDTNEMEKT  197
Lead·SEQ·ID·NO−40·cDNA·3091277    S-PCKPHSTF  KTVLFYLSVY  LIALGYGGYQ  PNIATFGADQ  FDAEDSVEGH  184
SEQ·ID·NO−41·gi|50912139          E-HCDAPSSA  GVALFYLSTY  MIAFGNGGYQ  PSIATFGSDQ  FDETDPREAR  187

Consensus                         S--CIPASSK  QLMV-YIALY  M-ALGTGGLK  -SVS-FGSDQ  FDETDKKER-  200
```

Figure 4B

```
SEQ-ID-NO-48-gi|48675345           QMTNFFNWFF FFISIGSLAA VTVLVYIQDN LGRQWGYGIC VCAIVLGLIV  237
SEQ-ID-NO-52-gi|9581817            QMIKFFNWFF FFINVGSLGA VTVLVYIQDN LGREYGYGIC ACAIVIGLVI  234
SEQ-ID-NO-53-gi|28273094           QMIKFFNWFF FFINVGSLGA VTVLVYIQDN LGREYGYGIC ACAIVIGLVI  234
SEQ-ID-NO-51-gi|47717628           RKSSFFNWHY FSINAGSLIA GTVIVWVQEH EGWLWGFTIS TLFVTLGISV  247
Lead-SEQ-ID-NO-40-cDNA-3091277     SKIAFFSYFY LALNLGSLFS NTVLGYFEDQ GEWPLGFWAS AGSAFAGLVL  234
SEQ-ID-NO-41-gi|50912139           SKVAFFSYFY LALNVGSLFS NTVLVYYEDE GRWVMGFWVS AAAAAMALVL  237

Consensus                          Q-I-FFNWF- F-INVGSL-A VTVLVYIQDN LG-E-G-GI- ACAIV-GLV-  250

SEQ-ID-NO-48-gi|48675345           FLSGTRRYRF KKLVGSPLTQ ISGVCVAAWR KRNMELPSDM SFLYNVDDID  287
SEQ-ID-NO-52-gi|9581817            FLSGTRKYRF KKLVGSPLTQ IASVFVAAWN KRHMDLPSDS TLLYNIDDIP  284
SEQ-ID-NO-53-gi|28273094           FLSGTRKYRF KKLVGSPLTQ IASVFVAAWN KRHMDLPSDS YLLYNIDDIP  284
SEQ-ID-NO-51-gi|47717628           FFLGSIVYRF QKPGGSPLAR LWQVVVAASR NFDKVLPCDS SALYEFSG--  295
Lead-SEQ-ID-NO-40-cDNA-3091277     FLICTPKYRH FTPRESPWSR FCQVLVAATR KAKLDVFHEE LNLYD-----  279
SEQ-ID-NO-41-gi|50912139           FLLGTPNYRH FKPTGNPLTR IAQVFVAAFR KWRAEVPRSE -LLHEVDG--  284

Consensus                          FL-GTRKYRF KK-VGSPLT- IAQVFVAAWR KR-MDLPSDS SLLYN-DDI-  300

SEQ-ID-NO-48-gi|48675345           DGLKKKKKQK LPHSKQFRFL DKAAIKEPKT TS---GTAM  INKWSLSTLT  334
SEQ-ID-NO-52-gi|9581817            GDGNKKAKQR LPHSKEFRFL DKAAIKVQDT ES---AGITV VNKWNLSTLT  331
SEQ-ID-NO-53-gi|28273094           GDGNKKAKQR LPHSKEFRFL DKAAIKVQDP ES---AGITV VNKWNLSTLT  331
SEQ-ID-NO-51-gi|47717628           QGSAIEGSRK SEHTSGLEFF DKAAILTLPD -C---ESPGQ LNKWKICTVT  341
Lead-SEQ-ID-NO-40-cDNA-3091277     SETQYTGDKK ILHTKGFRFL DRAAIVTPDD EAEKVESGSK YDPWRLCSVT  329
SEQ-ID-NO-41-gi|50912139           DESQIAGIRK ILHSDQIRFL DKAATVTEED YC---TPENM QDPWRLCTVT  331

Consensus                          --SQKKGKQK LPHSK-FRFL DKAAI-TQDD ES----S--V VNKW-L-T-T  350

SEQ-ID-NO-48-gi|48675345           DVEEVKLIIR MLPIWATTIM FWTVYAQMTT FSVSQATSMD RHIGKSFQIP  384
SEQ-ID-NO-52-gi|9581817            DVEEVKLVVR MLPTWATTIM FWTVYAQMTT FSVSQATTMD RHIG-NFEIP  380
SEQ-ID-NO-53-gi|28273094           DVEEVKLVVR MLPTWATTIM FWTVYAQMTT FSVSQATTMD RHIG-NFEIP  380
SEQ-ID-NO-51-gi|47717628           QVEELKILIR MFPIWSAMVL FAAVQEQMFS TFVEQGMTME KHVG-SFEIP  390
Lead-SEQ-ID-NO-40-cDNA-3091277     QVEEVKCVLR LLPIWLCTIL YSVVFTQMAS LFVVQGAAMK TNIK-NFRIP  378
SEQ-ID-NO-41-gi|50912139           QVEEVKCILK MLPIWLCTIV YSVVFTQMAS LFVEQGTTMN TNIG-SFHVP  380

Consensus                          -VEEVKLI-R MLPIWATTIM F-TVYAQMT- F-VSQ-TTMD RHIG--FEIP  400
```

Figure 4C

| Sequence | | | | | | Position |
|---|---|---|---|---|---|---|
| SEQ·ID·NO−48·gi\|48675345 | PASLTAFFVG | SILLTVPVYD | RLIVPMARKA | --LENPQGLT | PLQRMGVGLV | 432 |
| SEQ·ID·NO−52·gi\|9581817 | PASLTLFFVG | SILLTCIFYD | RAVVPVCRRV | --LNNPHGTT | PLQRIAVGLI | 428 |
| SEQ·ID·NO−53·gi\|28273094 | PASLTLFFVG | SILLTCIFYD | RAVVPVCRRV | --LNNPHGTT | PLQRIAVGLI | 428 |
| SEQ·ID·NO−51·gi\|47717628 | TASFQSIDIL | TVIMLVPLYE | RVLVPVIRKF | --TGRANGIS | SPQRIGIGLC | 438 |
| Lead·SEQ·ID·NO−40·cDNA·3091277 | ASSMSSFDIL | SVAFFIFAYR | RFLDPLFARL | NKTERNKGLT | ELQRMGIGLV | 428 |
| SEQ·ID·NO−41·gi\|50912139 | AASMSVFDIL | SVLAFIAIYR | RVLVPVMSRL | --SGNPQGLT | ELQRMGVGLV | 428 |
| Consensus | PASLT-F-V- | S-LLT--IYD | RVIVPV-RR- | ----NP-GLT | PLQR-GVGLV | 450 |
| SEQ·ID·NO−48·gi\|48675345 | FSIFAMVAAA | LTEVKRLNIA | RSHGLTDNPT | AEIPLSVFWL | VPQFFFVGSG | 482 |
| SEQ·ID·NO−52·gi\|9581817 | LSIIAMVAAA | LTEVKRLNVA | HLHGLTNDAN | AKVPLSVFWL | VPQFLLVGAG | 478 |
| SEQ·ID·NO−53·gi\|28273094 | LSIIAMVAAA | LTEVKRLNVA | HLHGLTNDAN | AKVPLSVFWL | VPQFLLVGAG | 478 |
| SEQ·ID·NO−51·gi\|47717628 | FSMLSMVLAA | LVESNRLQLA | QSEGLV-HSK | VTVPMSILWQ | GPQYFLLGVA | 487 |
| Lead·SEQ·ID·NO−40·cDNA·3091277 | IAIMAMISAG | IVEIHRLKNK | EPESAT-SIS | SSSTLSIFWQ | VPQYMLIGAS | 477 |
| SEQ·ID·NO−41·gi\|50912139 | VGMAAMVVAG | VVEVERLKRV | GA------PD | QPSSLSVLWQ | VPQYALIGAS | 472 |
| Consensus | LSIIAMVAAA | L-EVKRL--A | -SHGLTN-AN | AKVPLSVFW- | VPQ-LLVGA- | 500 |
| SEQ·ID·NO−48·gi\|48675345 | EAFTYIGQLD | FFLRECPKGM | KTMSTGLFLS | TLSLGFFFSS | LLVTIVHKLT | 532 |
| SEQ·ID·NO−52·gi\|9581817 | EAFTYIGQLD | FFLRECPKGM | KTMSTGLFLS | TLSLGFFVSS | ILVTIVHKVT | 528 |
| SEQ·ID·NO−53·gi\|28273094 | EAFTYIGQLD | FFLRECPKGM | KTMSTGLFLS | TLSLGFFFSS | ILVTIVHKVT | 528 |
| SEQ·ID·NO−51·gi\|47717628 | EVFSNIGLTE | FFCDESPDAM | RSLGMAFSLL | NISAGNYLSS | FILSLVPVFT | 537 |
| Lead·SEQ·ID·NO−40·cDNA·3091277 | EVFMYVGQLE | FFNSQAPTGL | KSFASALCMA | SISLGNYVSS | LLVSIVMKIS | 527 |
| SEQ·ID·NO−41·gi\|50912139 | EVFMYVGQLE | FFNGQAPDGV | KSFGSSLCMA | SISLGNYVSS | MLVSVVTSLT | 522 |
| Consensus | E-FTYIGQL- | FFLRE-PKGM | K-MST-LFLS | T-SLG--VSS | -LV-IVHKVT | 550 |
| SEQ·ID·NO−48·gi\|48675345 | GHNK--PWLA | DNLNQGKLYD | FYWLLALLSA | LNLVIYLFCA | NWYVYKDKRL | 580 |
| SEQ·ID·NO−52·gi\|9581817 | VKN---PWLA | DNLNQGRLYD | FYWLLATLSV | LNLMVFLFIS | RRYVYKEKRL | 575 |
| SEQ·ID·NO−53·gi\|28273094 | VKN---PWLA | DNLNQGRLYD | FYWLLATLSV | LNLMIFLFIS | RRYVYKEKRL | 575 |
| SEQ·ID·NO−51·gi\|47717628 | ARGGSPGWIP | DNLNEGHLDR | FYLMMAGLSL | LNIFVFVFYA | RRYKCKKAS- | 586 |
| Lead·SEQ·ID·NO−40·cDNA·3091277 | TTDDVHGWIP | ENLNKGHLER | FYFLLAGLTA | ADFVVYLFCA | KWYKYIKSEA | 577 |
| SEQ·ID·NO−41·gi\|50912139 | AGDRRPGWIP | GNLNSGHLDR | FYFLLAALSL | VDLAVYVACA | VWYKGIKLDS | 572 |
| Consensus | -KN----W-- | DNLNQG-L-- | FYWLLA-LS- | LNL-V-LFCA | R-Y-YKKKRL | 600 |

Figure 4D

```
SEQ-ID-NO-48-gi|48675345          AEEGIELEEP EHICA   594
SEQ-ID-NO-52-gi|9581817           AECGIEMEDS EPACH   590
SEQ-ID-NO-53-gi|28273094          AECGIEMEDS EPACH   590
SEQ-ID-NO-51-gi|47717628          ---------- -----   586
Lead-SEQ-ID-NO-40-cDNA-3091277    SFSESVTEEE EV---   589
SEQ-ID-NO-41-gi|50912139          NEEKANKITV HV---   584

Consensus                         AE-GIEME-- E--C-   615
```

Figure 5A

```
SEQ-ID-NO-61-gi|15391731-T           MEIESLRVSV DEKVLKDEEK NEKEEMKMKM KMKRKLGGVK TMPFIL--GN   48
SEQ-ID-NO-63-gi|54291818-T           MEEERSRAGG AAVAVD---- GESLRRPEEE GGRRKKGGWI TFPFMA--VS   44
SEQ-ID-NO-64-gi|34905798-T           ---------- ---------- ---------- ---------- ----------   0
SEQ-ID-NO-65-gi|47900739-T           ---------- MESSVR---- GVDEAAI MKS STRRKNGGWI TFPFITVSAT  36
Lead-SEQ-ID-NO-55-cDNA-2997404       ---------- MARSV----- -DTEAMTTRD PSSKR-GGWK TFPFMI--AT  31
SEQ-ID-NO-62-CeresClone:114413       ---------- MASLVS---- GDKEAQISGD PGSKR-GGWI TFPFML--AT  33

Consensus                            ---------- MA-AV----- G--EA---KD --RRK-GGWI TFPFM---AT  50

SEQ-ID-NO-61-gi|15391731-T           EVCDRFASSG FHSNIITYLT QDLNMPLVPA SNILTNFAAT SSFTSLIGAL  98
SEQ-ID-NO-63-gi|54291818-T           LLAFGLSSAG AMGNLVVYLV KEYHVPSVDA AQISTIVSGC ISVAPVAGAI  94
SEQ-ID-NO-64-gi|34905798-T           -----MAMSA TSSNLIVYLV HKYNVKAIHA AQISNVVRGC MQLAPVLAAA  45
SEQ-ID-NO-65-gi|47900739-T           MAGLSLASGG MTSNLIVYLI DEFNMKSIKT AKVYNVINGC TTLFPIVGGI  86
Lead-SEQ-ID-NO-55-cDNA-2997404       LLGLSIASFG WVMNLVVFLI KEFNIKSIAA TQISNIVNGC VSMFPVIAAI  81
SEQ-ID-NO-62-CeresClone:114413       LLGLSVTSFG WVMNLIVFLI EEFNIKSIAA AQISNVANGC LSMLPVVAAI  83

Consensus                            LLGLSLASSG WVSNLIVYLV -EFN-KSI-A AQISNVVNGC -S--PV--AI  100

SEQ-ID-NO-61-gi|15391731-T           IADSFAGRFW TITIASIIYE LGMVTITISA ILPSLHPPPC PT--------  140
SEQ-ID-NO-63-gi|54291818-T           VADAFFGCFP VVAVAMVFSV LALVVFTLTA SVRGLRPAAC VPG-------  137
SEQ-ID-NO-64-gi|34905798-T           LSDAFFGPYP IAVAGLVFSL LSFVLFTLTA ALPSLLPPPC QRCAGGGGAT  95
SEQ-ID-NO-65-gi|47900739-T           LADSYLGSFS VIWFSSLISA LGILLLLFTS AIDVLRPPPC DDC-------  129
Lead-SEQ-ID-NO-55-cDNA-2997404       LADSFFGNIP VISVSAFISL LGIVLLTMIT SLDYLRPPPC ETG-------  124
SEQ-ID-NO-62-CeresClone:114413       LADSFFGNIP VIAASSFISL LGIVLLTLIA SLDYLRPRPC EAG-------  126

Consensus                            LADSFFGNFP VI-VSSIISL LGIVLLTLTA SLD-LRPPPC E-G-------  150

SEQ-ID-NO-61-gi|15391731-T           QINCTQASGT QLMLYLALL LTSLGAGGIR PCVVAFAADQ F---DMTKVG  187
SEQ-ID-NO-63-gi|54291818-T           ATACEAATAG QMAVLYAGVF LLCVSSAGAR FNQATMGADQ F---DAAADR  184
SEQ-ID-NO-64-gi|34905798-T           ATSCEPPNAA QSAVLYAALC LLAAGNGGTR YNMAALGADQ FAGEGQPRRR  145
SEQ-ID-NO-65-gi|47900739-T           SSLCTSPSTH QYAVLYVALA LASLGVAGTR FIIAPMGANQ F---DKPKHQ  176
Lead-SEQ-ID-NO-55-cDNA-2997404       SILCQSSSKL QLGILYIALA LVIIGSAGTR FTLASAGANQ Y---EKPKEQ  171
SEQ-ID-NO-62-CeresClone:114413       SVLCTPPSKL HLGILYTALA LVTTGAGGTR FTMASAGANQ Y---EKPKEQ  173

Consensus                            S--C-S-S-- QLA-LY-ALA L-SLG--GTR F-MA-MGA-Q F---DKPKEQ  200
```

Figure 5B

```
SEQ-ID-NO-61-gi|15391731-T          IAGRTWNFFN WYYFCMGMAT LTALTVVVYI QDNVGWGWGF GLPTIAMALS  237
SEQ-ID-NO-63-gi|54291818-T          -----DVFFN WYFIFFYGSA VLGSTVLVYV QDAVSWELGF GLAATIAAAC  229
SEQ-ID-NO-64-gi|34905798-T          RQG--GGFFS CYFAFLYASY AIGDTVLVYV QDGVSWALGF GVCVATTGLA  193
SEQ-ID-NO-65-gi|47900739-T          -----AIFFN WYIFAFYMSF AISTTVIVYV EDNVSWSWGY GISMAFNTLG  221
Lead-SEQ-ID-NO-55-cDNA-2997404      -----GSFFN WYFLTLYTGA ITGATAIVYT QENASWKLGF GLCAVANLIS  216
SEQ-ID-NO-62-CeresClone:114413      -----GSFFN WYFLTLYAGA ITGATAIVYI QDNASWKLGF GLCAAANLIS  218

Consensus                           -----GSFFN WYFL-LY-SA VTG-TVIVYV QDNVSWKLGF GLCAAANLLS  250

SEQ-ID-NO-61-gi|15391731-T          VVAFVVGSPL YNKLKPS-GS PLVRLAQVVV AAFKNRKAVL PD------DS  280
SEQ-ID-NO-63-gi|54291818-T          LAALLLGARY YRRPAAR-GS PFTGIARVVV AAARKRKIDV AAAAAASGDL  278
SEQ-ID-NO-64-gi|34905798-T          LAALLLGSRH YRRPVPK-GS PFTAMARVAV AAARKATVDL GS------RV  236
SEQ-ID-NO-65-gi|47900739-T          LAMFLIGKRF YCDVKEQGGS PFVNLARVIV VAIQKWRVPL SE------QT  265
Lead-SEQ-ID-NO-55-cDNA-2997404      FIVFVSGKRY YKHDKPM-GS PFTNLIRVVV AATRKRKAVI SS------RE  259
SEQ-ID-NO-62-CeresClone:114413      FIVFVSGKRY YKHDKPM-GS PFTSLIRVVV SATVKRKAVI SC------NE  261

Consensus                           L--F-LG-RY Y-R-KP--GS PFT-LARVVV AA-RKRK-VL SS--------  300

SEQ-ID-NO-61-gi|15391731-T          KLLY----R- NHELDAAIAI QGRLVHTDQF KWLDKAAVIT SPD---STAN  322
SEQ-ID-NO-63-gi|54291818-T          KFYYGPRSGD GDDDGGKPSD DNNFAPSDSF SFLNRAAVIT DGDVDAADAA  328
SEQ-ID-NO-64-gi|34905798-T          QYYH----GC NRDDAVPRAD Q---APSDRF RFLNRAAMVV AGETREEDGS  279
SEQ-ID-NO-65-gi|47900739-T          QHYY----HD PSDTTTTLTI TQ--TPTKSF KFLNCAAFIT EGDTK-PDGS  308
Lead-SEQ-ID-NO-55-cDNA-2997404      EDYH----H- GLGREGKTSS A---MPSKSF RFFNRAALKT EDD------S  295
SEQ-ID-NO-62-CeresClone:114413      EDYH----HY GLEKEVKTSA A---MPSKSF RFLNRAALMT KDDLNQKEGS  304

Consensus                           --Y-----H- G-D-E-K-S- ----MPS-SF RFLNRAA-IT EGD----DGS  350

SEQ-ID-NO-61-gi|15391731-T          PP-NLWRLAT VHRVEELKSI IRMLPIWAAG ILLVTASSHQ HSFTIQQART  371
SEQ-ID-NO-63-gi|54291818-T          APLRPWRVCT VRQVEDLKAV LRILPLWSSS IFLSISIGVQ LNFTVLQALA  378
SEQ-ID-NO-64-gi|34905798-T          VA-KPWRLCT VQQVEDVKSV VRVLPLWSSG ILVSVTVNAQ VSLTVLQALT  328
SEQ-ID-NO-65-gi|47900739-T          IS-NPWRLCT VQQVEDLKSL LKLFPLWASG FLISTQLVIQ ASLLILQALK  357
Lead-SEQ-ID-NO-55-cDNA-2997404      VN-NNWRLCS VQEVEDFKAV FRVLPLLLAI IFVSTPMVTQ TSLIILKALV  344
SEQ-ID-NO-62-CeresClone:114413      VN-NIWRLCS VQEVEDFKAI LRVFPLWLSI IFVSTPMVMQ TSLIVLQALV  353

Consensus                           V--NPWRLCT VQQVEDLK-I -RVLPLW-SG I-VST-MV-Q -SL--LQAL-  400
```

Figure 5C

```
SEQ·ID·NO−61·gi|15391731·T              MNRHLTPTFQ IPPATLSIFG ILSMLTGLVL YDRLLVPFAK KLTHNPSGIT  421
SEQ·ID·NO−63·gi|54291818·T              MDRAIG-RFH VPAASMVVSS FVAVVVSLGL IDRALLPLWR ALTGGRRAPT  427
SEQ·ID·NO−64·gi|34905798·T              MDRAVGPRFA VPAASITVTV LAAFVLAAAL FDRVAAPLCA AAG--KLAIT  376
SEQ·ID·NO−65·gi|47900739·T              MDRHMGPHFE IPAGSMLVFI LLFTCIAIFI IDRFLYPFLA KYI--TFSLT  405
Lead·SEQ·ID·NO−55·cDNA·2997404          TDRGLGPHFK IPAGSLQVIV IITACIVILM NNCLVYPMYQ KLA--HKPLT  392
SEQ·ID·NO−62·CeresClone:114413          TDRGLGPNFK VPAGSLQVII IITACIVIIM NNWLVFPMYK KLT--HKLLT  401

Consensus                               MDR-LGPHFK -PA-SL-V-- I----IAI-L -DRLLYP-YK KLT---KALT  450

SEQ·ID·NO−61·gi|15391731·T              CLQRMGVGFA INLATLLVSS IVEIKRKKVA ANHG--LLDN PTATIPFSVF  469
SEQ·ID·NO−63·gi|54291818·T              PLQRIGVGHV LTVLSMAASA AVERRRLATV RAHGEAARDD PAWVSPLPAA  477
SEQ·ID·NO−64·gi|34905798·T              PLRRVGLGHA LNVASMAVAA LVERRRIGAA RGRA----AA AAAVVPMSVL  422
SEQ·ID·NO−65·gi|47900739·T              PLQRIGIGHV LTIISMAVSA LVESRRLRLV RTHK--LQGQ NNDIVPMSVF  453
Lead·SEQ·ID·NO−55·cDNA·2997404          PLQKVGIGHV FTILSMAISA IVEAKRLKTV TNGH------ -----SMSVL  431
SEQ·ID·NO−62·CeresClone:114413          PLQKVGIGQV LTILSMALSA VVEAKRLKTV ENGH------ -----PMSVL  440

Consensus                               PLQRVGIGHV LTILSMAVSA -VEA-RLKTV RNH------- ---VVPMSVL  500

SEQ·ID·NO−61·gi|15391731·T              WLVPQFWL-- ---------- ---------- -----  477
SEQ·ID·NO−63·gi|54291818·T              WLVLPFAL-- ---------- ---------- -----  485
SEQ·ID·NO−64·gi|34905798·T              WLVPQLAL-- ---------- ---------- -----  430
SEQ·ID·NO−65·gi|47900739·T              WLVPQLAL-- ---------- ---------- -----  461
Lead·SEQ·ID·NO−55·cDNA·2997404          WLHRDFIDLS GDWNIFLPEH SSDHSDPEDH QVVTK  466
SEQ·ID·NO−62·CeresClone:114413          WLFPPLVI-- ---------- ---------- -----  448

Consensus                               WLVPQ-AL-- ---------- ---------- -----  535
```

Figure 6A

```
SEQ-ID-NO-77-gi|4584852              MATTSFHHPL LPNVH----- -NDDELA--- -HI PS-SAH QVSNDSWFQV  39
SEQ-ID-NO-73-gi|21069018             -MESQGREDV VGCSGAGGRV HSDGHI D--- - EI PE-TAH QI SNDSWFQA  44
SEQ-ID-NO-81-gi|21069016             -MDVRGGEDV TGGSGAGRKV HSEDMA---- -VEVPE-TAH QI SNDSWLQA  43
SEQ-ID-NO-74-gi|8571474              MSSYDPENAA TNGVPPVKND NSNHQQQHQQ TVVVPE-TAH QI STDSWLQV  49
SEQ-ID-NO-75-gi|50933631             --------MN IDMAN----- -SDDK----- -ALISEDTAH QI SADPWYQV  30
SEQ-ID-NO-78-gi|16215723             MAMPPAEKVI VVDANPSKNG HGDEI DD--- -LPVADAISH QI GVDPWYQV  46
SEQ-ID-NO-72-CeresClone:526395       --------MTL ISNSD----- -VESHAD--- -VQI PD-TAH QI STDSWFQV  32
Lead-SEQ-ID-NO-67-cDNA-4904707       MTATEAKNRK INVGD----- -GDDVVD--- - EI PD-TAH QI SSDSWFQV  39
SEQ-ID-NO-71-gi|31376371             MDTSEARNRK VVAVE----- ----QFD--- -LEVPE-TAH QI SSDSWFQV  36

Consensus                            M--------- ---A------ -SDD--D--- --EI PE-TAH QI S-DSWFQV  50

SEQ-ID-NO-77-gi|4584852              GVVLSTGI NS AFALGYAGLI MVPLGWVGGV VGLI LSSAI S LYASTLI AKL  89
SEQ-ID-NO-73-gi|21069018             GFVLTTGI NS AYVLGYPGAV MVPLGWI GGV I GLI LATVVS LHANALVAKL  94
SEQ-ID-NO-81-gi|21069016             GFVLTTGVNS AYVLGYSGAV MVPLGWI GGV VGLI LATLVS LHANALVAQL  93
SEQ-ID-NO-74-gi|8571474              GFVLTTGI NS AYVLGYSGAI MVPLGWI PAV LGLI AATLI S LYANSLVAKL  99
SEQ-ID-NO-75-gi|50933631             GFVLTTGVNS AYVLGYSGSV MVPLGWI GGT CGLI LAAAI S LYANALLARL  80
SEQ-ID-NO-78-gi|16215723             AFVLTTGVNS AYVLGYSGSL MVPLGWVGGT VGLLLAAAVS MYANALLGRL  96
SEQ-ID-NO-72-CeresClone:526395       GFVLTTGI NS AYVLGYSGTI MVPLGWAGGV VGLI LATAI S LYANALI ARL  82
Lead-SEQ-ID-NO-67-cDNA-4904707       AFVLTTGI NS AYVLGYSGTI MVPLGWI GGV VGLLI ATAI S LYANTLI AKL  89
SEQ-ID-NO-71-gi|31376371             AFVLTTGI NS AYVLGYSGTV MVPLGWI GGV VGLI LATAI S LYANTLI AKL  86

Consensus                            GFVLTTGI NS AYVLGYSG-- MVPLGWI GGV VGLI LATAI S LYANALI AKL  100

SEQ-ID-NO-77-gi|4584852              HEYGGRRHI R YRDLAGFMYG QTAYSLVWAS QYANLFLI NT GYVI LGGQAL  139
SEQ-ID-NO-73-gi|21069018             HDFGGKRRI R YRDLAGSI YG GKAYSI TWGM QYVNLVMI NV GYI I LAGNSL  144
SEQ-ID-NO-81-gi|21069016             HEYGGKRHI R YRDLAGRI YG RRAYSVTWGM QYVNLFMI NV GFVI LAGNSL  143
SEQ-ID-NO-74-gi|8571474              HEYGGKRHI R YRDLAGFI YG PKAYSLTWAL QYI NLFMI NT GFI I LAGSSI  149
SEQ-ID-NO-75-gi|50933631             HEI GGKRHI R YRDLAGHI YG RKMYSLTWAL QYVNLFMI NT GFI I LAGQAL  130
SEQ-ID-NO-78-gi|16215723             HLLGGKRHI R YRDLAGHI YG PKMYRLTWAM QYVNLFMI NT GFI I I AGQAL  146
SEQ-ID-NO-72-CeresClone:526395       HEYGGTRHI R YRDLAGFI YG RKAYSLTWAL QYVNLFMI NA GYI I LAGSAL  132
Lead-SEQ-ID-NO-67-cDNA-4904707       HEFGGRRHI R YRDLAGFI YG RKAYHLTWGL QYVNLFMI NC GFI I LAGSAL  139
SEQ-ID-NO-71-gi|31376371             HEFGGKRHI R YRDLAGFI YG KKMYRVTWGL QYVNLFMI NC GFI I LAGSAL  136

Consensus                            HEYGGKRHI R YRDLAGFI YG RKAYSLTWAM QYVNLFMI N- GFI I LAGSAL  150
```

Figure 6B

```
SEQ-ID-NO-77-gi|4584852                KAFYVLFRDD HQMKLPHFIA VAGLACVLFA IAIPHLSALR IWLGFSTFFS 189
SEQ-ID-NO-73-gi|21069018               KAVYLLFRDD HVMKLPHFIA IAGLACGLFA ISVPHLSALR NWLAFSTLFS 194
SEQ-ID-NO-81-gi|21069016               KAVYTLFRHD HVMKLPHFIA IAAIACGLFA ISIPHLSAMR IWLAFSMFFS 193
SEQ-ID-NO-74-gi|8571474                KAAYHLFTDD PALKLPYCIL ISGFVCALFA IGIPHLSALR IWLGVSTFFC 199
SEQ-ID-NO-75-gi|50933631               KATYVLFRDD GVLKLPYCIA LSGFVCALFA FGIPYLSALR IWLGFSTFFS 180
SEQ-ID-NO-78-gi|16215723               KALYLLISND GAMKLPYCIA VSGFVCALFA FGIPYLSALR IWLGFSTVFS 196
SEQ-ID-NO-72-CeresClone:526395         KATYVLFRED DGMKLPYFIG IAGFVCAMFA ICIPHLSALG IWLGFSTVFS 182
Leod-SEQ-ID-NO-67-cDNA-4904707         KAVYVLFRDD HTMKLPHFIA IAGLICAIFA IGIPHLSALG VWLGVSTFLS 189
SEQ-ID-NO-71-gi|31376371               KAVYVLFRDD SLMKLPHFIA IAGVVCAIFA IGIPHLSALG IWLGVSTFLS 186

Consensus                              KAVYVLFRDD --MKLPHFIA IAGLVCALFA IGIPHLSALR IWLGFSTFFS 200

SEQ-ID-NO-77-gi|4584852                LVYICIMITL SLKDGLEAPP RDYSIPGTKN SKTWATIGAA ANLVFAYNTG 239
SEQ-ID-NO-73-gi|21069018               MIYIVGGLAL AIKDGFKAPP RDYSIPGTKT SRIFTTIGAS ANLVFSFNTG 244
SEQ-ID-NO-81-gi|21069016               LVYIIVGFAL SLKDGIEAPP RDYTLPEKGA DKVFTI GAA AELVFSFNTG 243
SEQ-ID-NO-74-gi|8571474                LIYIIIAIAL SLKDGINSPP RDYSVP-TER GKVFTTIGAA ANLVFAFNTG 248
SEQ-ID-NO-75-gi|50933631               LIYITIAFVL SLRDGITTPA KDYTIPGSHS ARIFTTIGAV ANLVFAYNTG 230
SEQ-ID-NO-78-gi|16215723               LTYIVAACTL SLKDGMRSPP RDYSIQGDPS SRVFTTIGAA ASLVFAYNTG 246
SEQ-ID-NO-72-CeresClone:526395         LVYIVIAFVL SIKDXKSPP RDYSIPGTST SKISTTIGAS ANLVFAYNTG 232
Leod-SEQ-ID-NO-67-cDNA-4904707         LIYIVVAIVL SVRDGVKTPS RDYEIQGSSL SKLFTI TGAA ANLVFAFNTG 239
SEQ-ID-NO-71-gi|31376371               LIYIIVAIVL SAKDGVNKPE RDYNIQGSSI NKLFTI TGAA ANLVFAFNTG 236

Consensus                              LIYIVVAI-L SLKDGIK-PP RDYSIPGT-- SK-FTTIGAA ANLVFAYNTG 250

SEQ-ID-NO-77-gi|4584852                MLPEIQATVR EPVVDNMIKA LNFQFTLGVI PMHAVTYIGY WAYGSSASSY 289
SEQ-ID-NO-73-gi|21069018               MLPEIQATVR PPVVENMMKC LYFQFTVGVV PMYAIIFAGY WAYGSTTSSY 294
SEQ-ID-NO-81-gi|21069016               MLPEIQATVR PPVIGNMMKA LYFQFTVGVV PMYSIIFVGY WAYGSKTTSY 293
SEQ-ID-NO-74-gi|8571474                MLPEIQATVR KPVVGNMMKG LYFQFTAGVV PMYAIVFIGY WAYGNKTDSY 298
SEQ-ID-NO-75-gi|50933631               MLPEIQATIR PPVVKNMEKA LWFQFTVGSL PLYAVTFMGY WAYGSSTSSY 280
SEQ-ID-NO-78-gi|16215723               MLPEIQATVR APVVKNMEKA LWFQFTAGCV PLYAIIVIGY WAYGNQTTTY 296
SEQ-ID-NO-72-CeresClone:526395         MLPXIQATIR XPVVKNMMKA LYFQFTXGVL PLYLVTFXGY WAYGSSTATY 282
Leod-SEQ-ID-NO-67-cDNA-4904707         MLPEIQATVR QPVVKNMMKA LYFQFTAGVL PMYAVTFIGY WAYGSSTSTY 289
SEQ-ID-NO-71-gi|31376371               MLPEIQATVK QPVVKNMMKA LYFQFTVGVL PMYAVTFIGY WAYGSSTSTY 286

Consensus                              MLPEIQATVR -PVVKNMMKA LYFQFTVGV- PMYAVTFIGY WAYGSSTSTY 300
```

Figure 6C

```
SEQ-ID-NO-77-gi|4584852             LLNNVSGPIW LKGMANIAAF LQSIIALHIF ASPTYEFLDT KYGVT-GSAL  338
SEQ-ID-NO-73-gi|21069018            LLNNVHGPIW LKTTTNISAF LQSVIALHIF ASPMYEFLDT KYGIK-GSAL  343
SEQ-ID-NO-81-gi|21069016            LLNNVHGPIW LMTVANIAAF LQSVISLHIF ASPMYEIWIP DLESK-EVLW  342
SEQ-ID-NO-74-gi|8571474             LLNNVHGPVW LKALANISTF LQTVIALHIF ASPMYEYLDT RFGIT-GSAL  347
SEQ-ID-NO-75-gi|50933631            LLNSVKGPVW VKAMANLSAF LQTVIALHIF ASPMYEFLDT KYGSGHGGPF  330
SEQ-ID-NO-78-gi|16215723            LLNNVHGPVW IKAVANLSAF LQTVIALHIF ASPMYEYLDT RFGSKVGGPF  346
SEQ-ID-NO-72-CeresClone:526395      LMSDVXGPVX AKAMANXXAF LQSVIALHIF ASPMYEYXDT KYGIK-GSAL  331
Lead-SEQ-ID-NO-67-cDNA-4904707      LLNSVNGPLW VKALANVSAI LQSVISLHIF ASPTYEYMDT KYGIK-GNPF  338
SEQ-ID-NO-71-gi|31376371            LLNSVSGPVW VKALANISAF LQSVISLHIF ASPTYEYMDT KYGVK-GSPL  335

Consensus                           LLNNV-GPVW LKA-ANISAF LQSVIALHIF ASPMYEYLDT KYGIK-GS-L  350

SEQ-ID-NO-77-gi|4584852             ACKNLAFRII VRGGYIAITA FLSALLPFLG DFMNLAGAIS TFPLTFILPN  388
SEQ-ID-NO-73-gi|21069018            AVRNLSFRIL VRGGYVAMTS LVSALLPFLG DFMSLTGALS TFPLTFILAN  393
SEQ-ID-NO-81-gi|21069016            PLRNLSFRVV VRGGYVATTA FVSALLPFLG DFMSLTGAIS TFPLTFILAN  392
SEQ-ID-NO-74-gi|8571474             NPKNLGSRVL IRGGYLAVNT FVAALLPFLG DFMSLTGAIS TFPLTFILAN  397
SEQ-ID-NO-75-gi|50933631            AIHNVMFRVG VRGGYLTVNT LVAAMLPFLG DFMSLTGALS TFPLTFVLAN  380
SEQ-ID-NO-78-gi|16215723            AMHNVIFRVG VRGGYLAVNT LMAAMLPFLG DFMSLTGALS TFPLTFVLAN  396
SEQ-ID-NO-72-CeresClone:526395      AFKNXSFRVX VRXGYLTLNT FVSALLPFLG DFMSLTGAIS TFPLTFILAN  381
Lead-SEQ-ID-NO-67-cDNA-4904707      AIKNLLFRIM ARGGYIAVST LISALLPFLG DFMSLTGAVS TFPLTFILAN  388
SEQ-ID-NO-71-gi|31376371            AMKNLLFRTV ARGSYIAVST LLSALLPFLG DFMSLTGAIS TFPLTFILAN  385

Consensus                           AIKNL-FRV- VRGGYIAV-T LVSALLPFLG DFMSLTGAIS TFPLTFILAN  400

SEQ-ID-NO-77-gi|4584852             HMYIVAKRKK LSFLKKSWHW LNIIFFSCIA VAAFVAALRF ITVDSLTYHV  438
SEQ-ID-NO-73-gi|21069018            HMYLVANRNK MSLLQKNWHW LNVVLFSCMA VAAAVAALRL IAVDSRTYHV  443
SEQ-ID-NO-81-gi|21069016            HMYLVAKGNK LSPLHKTGLW LNIGFFGCLA VAAAVAALRE IVVDSKTYHL  442
SEQ-ID-NO-74-gi|8571474             HMYFKAKRNK LSMAMKIWLW INIVFFSCMA VASFIAALRL IATDSKQYHV  447
SEQ-ID-NO-75-gi|50933631            HMYLMVKRHK LSTLQISWHW LNVAGFSLLS IAAAVAALRL IMVDSRTYHL  430
SEQ-ID-NO-78-gi|16215723            HMYLVSNRQR LSSLQKSWHW LNIVFFTILS ITAAIAALRL IARDSKEYHI  446
SEQ-ID-NO-72-CeresClone:526395      HMYLVANANK LTSIQKLWHW INICFFAFMS VAATIAALRL IDLDSKTYHV  431
Lead-SEQ-ID-NO-67-cDNA-4904707      HMYYKAKNNK LNAMQKLWHW LNVVFFSLMS VAAAIAAVRL IAVDSKNFHV  438
SEQ-ID-NO-71-gi|31376371            HMYLVAMNDE LSLVQKLWHW LNVCFFGLMS LAAAIAAVRL ISVDSKNFHV  435

Consensus                           HMYLVAKRNK LS-LQKSWHW LNIVFFS-MS VAAAIAALRL I-VDSKTYHV  450
```

Figure 6D

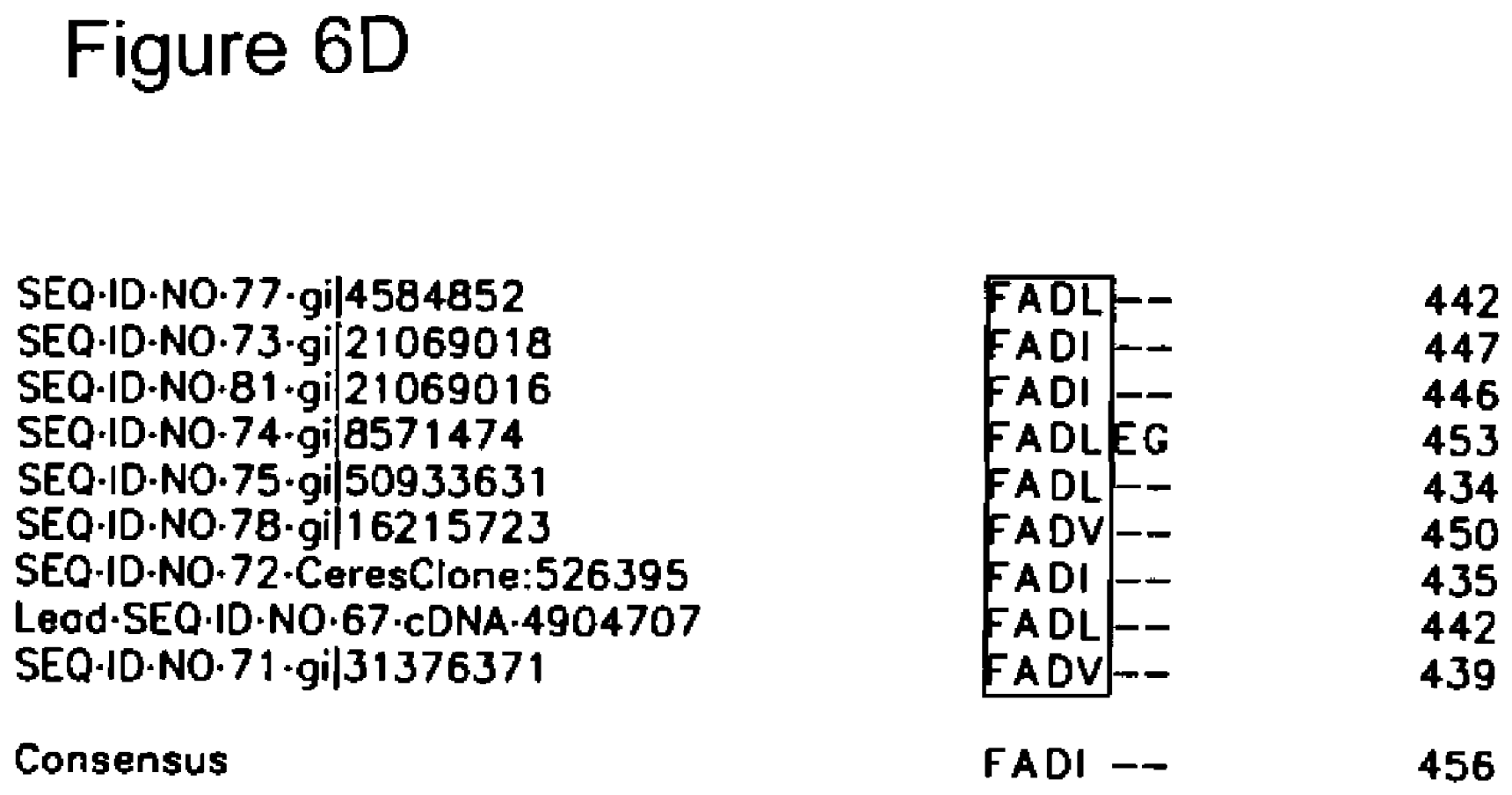

| | | |
|---|---|---|
| SEQ·ID·NO·77·gi\|4584852 | FADL-- | 442 |
| SEQ·ID·NO·73·gi\|21069018 | FADI -- | 447 |
| SEQ·ID·NO·81·gi\|21069016 | FADI -- | 446 |
| SEQ·ID·NO·74·gi\|8571474 | FADLEG | 453 |
| SEQ·ID·NO·75·gi\|50933631 | FADL-- | 434 |
| SEQ·ID·NO·78·gi\|16215723 | FADV-- | 450 |
| SEQ·ID·NO·72·CeresClone:526395 | FADI -- | 435 |
| Lead·SEQ·ID·NO·67·cDNA·4904707 | FADL-- | 442 |
| SEQ·ID·NO·71·gi\|31376371 | FADV-- | 439 |
| Consensus | FADI -- | 456 |

Figure 7A

```
SEQ-ID-NO-88-CeresClone:214246     --MACSHIVA AAGVSSPAAA AARSPAHSPA SAFARLRSTP RFASAGLSVK  48
SEQ-ID-NO-91-CeresClone:686561     --MACTHLAA ASSPAT-TAA ALRARATAPA AGFARLPATL HPENGGLALR  47
SEQ-ID-NO-92-gi|50918343           MATAARLLPK IQSPASPAVA EARRRRPSS- ---LRLGVTS GPART-----  41
Lead-SEQ-ID-NO-83-cDNA-5669462     --MAASTLYK SC-LLQPKSG STTRRLNPS- ----LVNPLT NPTRVSVLGK  42
SEQ-ID-NO-87-CeresClone:967151     --MAATTLNN SSSLLQPKSG STTRLNPSS- ----LLKPCP NPTRVSFSGK  43

Consensus                          --MAA--L-- -SSLASP--A --RRR--SS- ----RL--T- NP-R--LS-K  50

SEQ-ID-NO-88-CeresClone:214246     GNGAAFP-LV AAAGPAAAAP VADLDGRPAT EKQPIIVIDN YDSFTYNLCQ  97
SEQ-ID-NO-91-CeresClone:686561     GRRAVTP-VV LAAGPAAAAP VADRDGTPAA VKQPIIVIDN YDSFTYNLCQ  96
SEQ-ID-NO-92-gi|50918343           LKQKLVAKSA VSVVEGENAF DGVK-----Q DTRPIIVIDN YDSFTYNLCQ  86
Lead-SEQ-ID-NO-83-cDNA-5669462     SRRDVFAKAS IEMAESNSIP SVVV--NSSK QHGPIIVIDN YDSFTYNLCQ  90
SEQ-ID-NO-87-CeresClone:967151     SRGHVVTKAS IEMAHSNSTP AAVVVNSSSK QKGPIIVIDN YDSFTYNLCQ  93

Consensus                          -RR-V--KAA IAM-----AP -AVV-----K -KQPIIVIDN YDSFTYNLCQ  100

SEQ-ID-NO-88-CeresClone:214246     YMGELGLNFE VYRNDELTIE DVRRKNPRGI LISPGPGEPQ DSGISLQTVL  147
SEQ-ID-NO-91-CeresClone:686561     YMGELGLNFE VYRNDELTIE EVKRMKPRGI LISPGPGEPQ DSGISLQTVL  146
SEQ-ID-NO-92-gi|50918343           YMGEVGANFE VYRNDDITVE EIKKLSPRGI LISPGPGTPQ DSGISLQTVQ  136
Lead-SEQ-ID-NO-83-cDNA-5669462     YMGELGCHFE VYRNDELTVE ELKKKNPRGV LISPGPGTPQ DSGISLQTVL  140
SEQ-ID-NO-87-CeresClone:967151     YMGELGCHFE VYRNDELTVE ELKSKNPRGV LISPGPGTPQ DSGISLQTVX  143

Consensus                          YMGELG-NFE VYRNDELTVE E-K-KNPRGI LISPGPGTPQ DSGISLQTVL  150

SEQ-ID-NO-88-CeresClone:214246     ELGPTIPIFG VCMGLQCIGE AFGGKIIRAP SGVMHGKSSP VYYDEELGKA  197
SEQ-ID-NO-91-CeresClone:686561     ELGPTIPIFG VCMGLQCIGE AFGGKIIRVP SGVMHGKSSP VYYDEVLGKS  196
SEQ-ID-NO-92-gi|50918343           DLGPSTPLFG VCMGLQCIGE AFGGKVVRSP YGVVHGKGSL VHYEEKLDGT  186
Lead-SEQ-ID-NO-83-cDNA-5669462     ELGPLVPLFG VCMGLQCIGE AFGGKIVRSP FGVMHGKSSM VHYDEKGEEG  190
SEQ-ID-NO-87-CeresClone:967151     ELGPRVPLFG VCMGLQCIGE AFGGXIVRSP YGVMHGKSSM VPYYXKGEEG  193

Consensus                          ELGPT-PLFG VCMGLQCIGE AFGGKIVRSP YGVMHGKSSM V-YDEKLD--  200
```

Figure 7B

```
SEQ-ID-NO-88-CeresClone:214246       LFNGLPNPFT AARYHSLVIE RETFPHDALE ATAWTEDGLI MAARHKKYKH  247
SEQ-ID-NO-91-CeresClone:686561       IFEGLSNPFT AARYHSLVIE EETFPHDELE VTAWTEDGLV MAARHKKYTH  246
SEQ-ID-NO-92-gi|50918343             LFSGLPNPFQ AGRYHSLVIE KDSFPHDALE ITAWTDDGLI MAARHRKYKH  236
Lead-SEQ-ID-NO-83-cDNA-5669462       LFSGLSNPFI VGRYHSLVIE KDTFPSDELE VTAWTEDGLV MAARHRKYKH  240
SEQ-ID-NO-87-CeresClone:967151       LFSGLXNPFL VGRYXSLVIE KDTFPSDELE VTXWTEXGLV MAAXHRKXKH  243

Consensus                            LFSGL-NPF- AGRYHSLVIE KDTFPHDELE VTAWTEDGLV MAARHRKYKH  250

SEQ-ID-NO-88-CeresClone:214246       IQGVQFHPES IITPEGKKII LNFVRFIEEL EKQRS---  282
SEQ-ID-NO-91-CeresClone:686561       IQGVQFHPES IITPEGKKII LNFARYVEEF EKQTSEGK  284
SEQ-ID-NO-92-gi|50918343             IQGVQFHPES IITTEGRLMV KNFIKIIEGY EALNCLP-  273
Lead-SEQ-ID-NO-83-cDNA-5669462       IQGVQFHPES IITTEGKTIV RNFIKIVEKK ESEKLT--  276
SEQ-ID-NO-87-CeresClone:967151       IQGVQFHPEX IITXEGXTIV XNFIKLVXKK EAEXLT--  279

Consensus                            IQGVQFHPES IIT-EGK-IV -NFIKIVE-- EA------  288
```

MODULATING PLANT CARBON LEVELS

CROSS-REFERENCE TO RELATED APPLICATIONS

This application claims priority under 35 U.S.C. § 119 to U.S. Provisional Application No. 60/634,921, filed Dec. 8, 2004, and to U.S. Provisional Application No. 60/704,981, filed Aug. 2, 2005, both of which are incorporated herein by reference in their entireties.

INCORPORATION-BY-REFERENCE & TEXT

The material on the accompanying compact discs is hereby incorporated by reference into this application. The accompanying compact discs contain one file, 60326849.txt, which was created on Dec. 5, 2005. The file named 60326849.txt is 386 kb. The file can be accessed using Microsoft Word on a computer that uses Windows OS.

TECHNICAL FIELD

This document provides methods and materials related to modulating (e.g., increasing or decreasing) carbon levels in plants. For example, this document provides plants having increased carbon levels as well as materials and methods for making plants and plant products having increased carbon levels.

BACKGROUND

The ability of a plant to grow and develop under diverse and changing environmental conditions depends on the ability of the plant to utilize carbon and/or nitrogen. Specifically, the accumulation of one or both of these elements suggests that the plant is storing, synthesizing, or utilizing components such as nitrate, amino acids, proteins, sugars and/or carbohydrates to compensate for the changing environment. The balance of carbon and nitrogen in plants is an important aspect of how plants utilize nitrogen efficiently. Carbon skeletons and energy are required in ample supply for nitrogen assimilation and re-assimilation (photorespiratory $NH_4$). Conversely, primary carbon assimilation is highly dependent on nitrogen assimilation because much of the nitrogen in a plant is invested in the proteins and chlorophyll of the photosynthetic machinery. Therefore, fixed carbon must be partitioned between amino acids and carbohydrate synthesis in a flexible manner that is responsive to the external and internal availability of nitrogen. There is a need for compositions and methods that can increase fixed carbon content under varying nitrogen conditions.

SUMMARY

This document provides methods and materials related to plants having modulated (e.g., increased or decreased) levels of carbon. For example, this document provides transgenic plants and plant cells having increased levels of carbon, nucleic acids used to generate transgenic plants and plant cells having increased levels of carbon, and methods for making plants and plant cells having increased levels of carbon. Such plants and plant cells can be grown to produce, for example, seeds having increased carbon content. Seeds having modulated carbon levels may be useful to produce foodstuffs and animal feed having increased or decreased oil, carbohydrate, and/or caloric content, which may benefit both food producers and consumers.

In one embodiment, a method of modulating the level of carbon in a plant is provided. The method comprises introducing into a plant cell an isolated nucleic acid comprising a nucleotide sequence encoding a polypeptide having 80 percent or greater sequence identity to an amino acid sequence selected from the group consisting of SEQ ID NOs:2-20, SEQ ID NOs:22-34, SEQ ID NOs:36-38, SEQ ID NOs:40-43, SEQ ID NO:48, SEQ ID NOs:51-53, SEQ ID NOs:55-65, SEQ ID NOs:67-81, SEQ ID NOs:83-92, and the consensus sequences set forth in FIGS. 1-7, where a tissue of a plant produced from the plant cell has a difference in the level of carbon as compared to the corresponding level in tissue of a control plant that does not comprise the nucleic acid.

In another embodiment, a method of modulating the level of carbon in a plant is provided. The method comprises introducing into a plant cell an isolated nucleic acid comprising a nucleotide sequence encoding a polypeptide having 80 percent or greater sequence identity to an amino acid sequence selected from the group consisting of SEQ ID NO:2, SEQ ID NO:4, SEQ ID NO:22, SEQ ID NO:36, SEQ ID NO:37, SEQ ID NO:40, SEQ ID NO:55, SEQ ID NO:57, SEQ ID NO:62, SEQ ID NO:67, SEQ ID NO:70, SEQ ID NO:72, SEQ ID NO:83, SEQ ID NO:85, SEQ ID NO:87, SEQ ID NO:88, SEQ ID NO:89, SEQ ID NO:90, SEQ ID NO:91, and the consensus sequences set forth in FIGS. 1-7, where a tissue of a plant produced from the plant cell has a difference in the level of carbon as compared to the corresponding level in tissue of a control plant that does not comprise the nucleic acid.

In a further embodiment, a method of modulating the level of carbon in a plant is provided. The method comprises introducing into a plant cell an isolated nucleic acid comprising a nucleotide sequence encoding a polypeptide having 80 percent or greater sequence identity to an amino acid sequence selected from the group consisting of SEQ ID NO:2, SEQ ID NO:4, SEQ ID NO:22, SEQ ID NO:36, SEQ ID NO:37, SEQ ID NO:40, SEQ ID NO:55, SEQ ID NO:57, SEQ ID NO:62, SEQ ID NO:67, SEQ ID NO:70, SEQ ID NO:72, SEQ ID NO:83, SEQ ID NO:85, SEQ ID NO:87, SEQ ID NO:88, SEQ ID NO:89, SEQ ID NO:90, and SEQ ID NO:91, where a tissue of a plant produced from the plant cell has a difference in the level of carbon as compared to the corresponding level in tissue of a control plant that does not comprise the nucleic acid.

The sequence identity can be 85 percent or greater, 90 percent or greater, or 95 percent or greater. The nucleotide sequence can encode a polypeptide comprising an amino acid sequence corresponding to SEQ ID NO:2. The nucleotide sequence can encode a polypeptide comprising an amino acid sequence corresponding to SEQ ID NO:22. The nucleotide sequence can encode a polypeptide comprising an amino acid sequence corresponding to SEQ ID NO:36. The nucleotide sequence can encode a polypeptide comprising an amino acid sequence corresponding to SEQ ID NO:40. The nucleotide sequence can encode a polypeptide comprising an amino acid sequence corresponding to SEQ ID NO:55. The nucleotide sequence can encode a polypeptide comprising an amino acid sequence corresponding to SEQ ID NO:67. The nucleotide sequence can encode a polypeptide comprising an amino acid sequence corresponding to SEQ ID NO:83. The nucleotide sequence can encode a polypeptide comprising an amino acid sequence corresponding to a consensus sequence set forth in FIG. 1, FIG.

2, FIG. 3, FIG. 4, FIG. 5, FIG. 6, or FIG. 7. The difference can be an increase in the level of carbon or oil.

The isolated nucleic acid can be operably linked to a regulatory region. The regulatory region can be a tissue-specific regulatory region. The tissue-specific regulatory region can be a promoter. The promoter can be selected from the group consisting of YP0092, PT0676, PT0708, the napin promoter, the Arcelin-5 promoter, the phaseolin gene promoter, the soybean trypsin inhibitor promoter, the ACP promoter, the stearoyl-ACP desaturase gene, the soybean α' subunit of β-conglycinin promoter, the oleosin promoter, the 15 kD zein promoter, the 16 kD zein promoter, the 19 kD zein promoter, the 22 kD zein promoter, the 27 kD zein promoter, the Osgt-1 promoter, the beta-amylase gene promoter, and the barley hordein gene promoter. The promoter can be selected from the group consisting of PT0613, PT0672, PT0678, PT0688, PT0837, YP0128, YP0275, PT0625, PT0660, PT0683, and PT0758. The regulatory region can be a broadly expressing promoter. The broadly expressing promoter can be selected from the group consisting of p13879, p32449, 21876, p326, YP0158, YP0214, YP0380, PT0848, PT0633, YP0050, YP0144, and YP0190. The regulatory region can be an inducible promoter.

The plant can be a dicot. The plant can be a member of the genus *Brassica, Glycine, Gossypium, Lactuca, Lycopersicon, Medicago, Solanum, Carthamus, Pisum, Trifolium, Helianthus, Arachis, Olea, Vitis*, or *Linum*. The plant can be a monocot. The plant can be a member of the genus *Zea, Triticum, Hordeum, Secale, Oryza, Triticosecale, Avena, Musa, Elaeis, Phleum*, or *Sorghum*. The tissue can be seed tissue.

A method of producing a plant tissue is also provided. The method comprises growing a plant cell comprising an isolated nucleic acid comprising a nucleotide sequence encoding a polypeptide having 80 percent or greater sequence identity to an amino acid sequence selected from the group consisting of SEQ ID NOs:2-20, SEQ ID NOs:22-34, SEQ ID NOs:36-38, SEQ ID NOs:40-43, SEQ ID NO:48, SEQ ID NOs:51-53, SEQ ID NOs:55-65, SEQ ID NOs:67-81, SEQ ID NOs:83-92, and the consensus sequences set forth in FIGS. 1-7, where the tissue has a difference in the level of carbon as compared to the corresponding level in tissue of a control plant that does not comprise the nucleic acid.

In another embodiment, a method of producing a plant tissue is provided. The method comprises growing a plant cell comprising an isolated nucleic acid comprising a nucleotide sequence encoding a polypeptide having 80 percent or greater sequence identity to an amino acid sequence selected from the group consisting of SEQ ID NO:2, SEQ ID NO:4, SEQ ID NO:22, SEQ ID NO:36, SEQ ID NO:37, SEQ ID NO:40, SEQ ID NO:55, SEQ ID NO:57, SEQ ID NO:62, SEQ ID NO:67, SEQ ID NO:70, SEQ ID NO:72, SEQ ID NO:83, SEQ ID NO:85, SEQ ID NO:87, SEQ ID NO:88, SEQ ID NO:89, SEQ ID NO:90, SEQ ID NO:91, and the consensus sequences set forth in FIGS. 1-7, where the tissue has a difference in the level of carbon as compared to the corresponding level in tissue of a control plant that does not comprise the nucleic acid.

In a further embodiment, a method of producing a plant tissue is provided. The method comprises growing a plant cell comprising an isolated nucleic acid comprising a nucleotide sequence encoding a polypeptide having 80 percent or greater sequence identity to an amino acid sequence selected from the group consisting of SEQ ID NO:2, SEQ ID NO:4, SEQ ID NO:22, SEQ ID NO:36, SEQ ID NO:37, SEQ ID NO:40, SEQ ID NO:55, SEQ ID NO:57, SEQ ID NO:62, SEQ ID NO:67, SEQ ID NO:70, SEQ ID NO:72, SEQ ID NO:83, SEQ ID NO:85, SEQ ID NO:87, SEQ ID NO:88, SEQ ID NO:89, SEQ ID NO:90, and SEQ ID NO:91, where the tissue has a difference in the level of carbon as compared to the corresponding level in tissue of a control plant that does not comprise the nucleic acid.

The sequence identity can be 85 percent or greater, 90 percent or greater, or 95 percent or greater. The nucleotide sequence can encode a polypeptide comprising an amino acid sequence corresponding to SEQ ID NO:2. The nucleotide sequence can encode a polypeptide comprising an amino acid sequence corresponding to SEQ ID NO:22. The nucleotide sequence can encode a polypeptide comprising an amino acid sequence corresponding to SEQ ID NO:36. The nucleotide sequence can encode a polypeptide comprising an amino acid sequence corresponding to SEQ ID NO:40. The nucleotide sequence can encode a polypeptide comprising an amino acid sequence corresponding to SEQ ID NO:55. The nucleotide sequence can encode a polypeptide comprising an amino acid sequence corresponding to SEQ ID NO:67. The nucleotide sequence can encode a polypeptide comprising an amino acid sequence corresponding to SEQ ID NO:83. The nucleotide sequence can encode a polypeptide comprising an amino acid sequence corresponding to a consensus sequence set forth in FIG. 1, FIG. 2, FIG. 3, FIG. 4, FIG. 5, FIG. 6, or FIG. 7. The difference can be an increase in the level of carbon or oil.

The isolated nucleic acid can be operably linked to a regulatory region. The regulatory region can be a tissue-specific regulatory region. The tissue-specific regulatory region can be a promoter. The promoter can be selected from the group consisting of YP0092, PT0676, PT0708, the napin promoter, the Arcelin-5 promoter, the phaseolin gene promoter, the soybean trypsin inhibitor promoter, the ACP promoter, the stearoyl-ACP desaturase gene, the soybean α' subunit of β-conglycinin promoter, the oleosin promoter, the 15 kD zein promoter, the 16 kD zein promoter, the 19 kD zein promoter, the 22 kD zein promoter, the 27 kD zein promoter, the Osgt-1 promoter, the beta-amylase gene promoter, and the barley hordein gene promoter. The promoter can be selected from the group consisting of PT0613, PT0672, PT0678, PT0688, PT0837, YP0128, YP0275, PT0625, PT0660, PT0683, and PT0758. The regulatory region can be a broadly expressing promoter. The broadly expressing promoter can be selected from the group consisting of p13879, p32449, 21876, p326, YP0158, YP0214, YP0380, PT0848, PT0633, YP0050, YP0144, and YP0190. The regulatory region can be an inducible promoter.

The plant tissue can be dicotyledonous. The plant tissue can be a member of the genus *Brassica, Glycine, Gossypium, Lactuca, Lycopersicon, Medicago, Solanum, Carthamus, Pisum, Trifolium, Helianthus, Arachis, Olea, Vitis*, or *Linum*. The plant tissue can be monocotyledonous. The plant tissue can be a member of the genus *Zea, Triticum, Hordeum, Secale, Oryza, Triticosecale, Avena, Musa, Elaeis, Phleum*, or *Sorghum*. The tissue can be seed tissue.

A plant cell is also provided. The plant cell comprises an isolated nucleic acid comprising a nucleotide sequence encoding a polypeptide having 80 percent or greater sequence identity to an amino acid sequence selected from the group consisting of SEQ ID NOs:2-20, SEQ ID NOs: 22-34, SEQ ID NOs:36-38, SEQ ID NOs:40-43, SEQ ID NO:48, SEQ ID NOs:51-53, SEQ ID NOs:55-65, SEQ ID NOs:67-81, SEQ ID NOs:83-92, and the consensus sequences set forth in FIGS. 1-7, where a tissue of a plant produced from the plant cell has a difference in the level of carbon as compared to the corresponding level in tissue of a control plant that does not comprise the nucleic acid.

In another embodiment, a plant cell is provided. The plant cell comprises an isolated nucleic acid comprising a nucleotide sequence encoding a polypeptide having 80 percent or greater sequence identity to an amino acid sequence selected from the group consisting of SEQ ID NO:2, SEQ ID NO:4, SEQ ID NO:22, SEQ ID NO:36, SEQ ID NO:37, SEQ ID NO:40, SEQ ID NO:55, SEQ ID NO:57, SEQ ID NO:62, SEQ ID NO:67, SEQ ID NO:70, SEQ ID NO:72, SEQ ID NO:83, SEQ ID NO:85, SEQ ID NO:87, SEQ ID NO:88, SEQ ID NO:89, SEQ ID NO:90, SEQ ID NO:91, and the consensus sequences set forth in FIGS. 1-7, where a tissue of a plant produced from the plant cell has a difference in the level of carbon as compared to the corresponding level in tissue of a control plant that does not comprise the nucleic acid.

In yet another embodiment, a plant cell is provided. The plant cell comprises an isolated nucleic acid comprising a nucleotide sequence encoding a polypeptide having 80 percent or greater sequence identity to an amino acid sequence selected from the group consisting of SEQ ID NO:2, SEQ ID NO:4, SEQ ID NO:22, SEQ ID NO:36, SEQ ID NO:37, SEQ ID NO:40, SEQ ID NO:55, SEQ ID NO:57, SEQ ID NO:62, SEQ ID NO:67, SEQ ID NO:70, SEQ ID NO:72, SEQ ID NO:83, SEQ ID NO:85, SEQ ID NO:87, SEQ ID NO:88, SEQ ID NO:89, SEQ ID NO:90, and SEQ ID NO:91, where a tissue of a plant produced from the plant cell has a difference in the level of carbon as compared to the corresponding level in tissue of a control plant that does not comprise the nucleic acid.

The sequence identity can be 85 percent or greater, 90 percent or greater, or 95 percent or greater. The nucleotide sequence can encode a polypeptide comprising an amino acid sequence corresponding to SEQ ID NO:2. The nucleotide sequence can encode a polypeptide comprising an amino acid sequence corresponding to SEQ ID NO:22. The nucleotide sequence can encode a polypeptide comprising an amino acid sequence corresponding to SEQ ID NO:36. The nucleotide sequence can encode a polypeptide comprising an amino acid sequence corresponding to SEQ ID NO:40. The nucleotide sequence can encode a polypeptide comprising an amino acid sequence corresponding to SEQ ID NO:55. The nucleotide sequence can encode a polypeptide comprising an amino acid sequence corresponding to SEQ ID NO:67. The nucleotide sequence can encode a polypeptide comprising an amino acid sequence corresponding to SEQ ID NO:83. The nucleotide sequence can encode a polypeptide comprising an amino acid sequence corresponding to a consensus sequence set forth in FIG. 1, FIG. 2, FIG. 3, FIG. 4, FIG. 5, FIG. 6, or FIG. 7. The difference can be an increase in the level of carbon or oil.

The isolated nucleic acid can be operably linked to a regulatory region. The regulatory region can be a tissue-specific regulatory region. The tissue-specific regulatory region can be a promoter. The promoter can be selected from the group consisting of YP0092, PT0676, PT0708, the napin promoter, the Arcelin-5 promoter, the phaseolin gene promoter, the soybean trypsin inhibitor promoter, the ACP promoter, the stearoyl-ACP desaturase gene, the soybean α' subunit of β-conglycinin promoter, the oleosin promoter, the 15 kD zein promoter, the 16 kD zein promoter, the 19 kD zein promoter, the 22 kD zein promoter, the 27 kD zein promoter, the Osgt-1 promoter, the beta-amylase gene promoter, and the barley hordein gene promoter. The promoter can be selected from the group consisting of PT0613, PT0672, PT0678, PT0688, PT0837, YP0128, YP0275, PT0625, PT0660, PT0683, and PT0758. The regulatory region can be a broadly expressing promoter. The broadly expressing promoter can be selected from the group consisting of p13879, p32449, 21876, p326, YP0158, YP0214, YP0380, PT0848, PT0633, YP0050, YP0144, and YPO190. The regulatory region can be an inducible promoter.

The plant can be a dicot. The plant can be a member of the genus *Brassica, Glycine, Gossypium, Lactuca, Lycopersicon, Medicago, Solanum, Carthamus, Pisum, Trifolium, Helianthus, Arachis, Olea, Vitis*, or *Linum*. The plant can be a monocot. The plant can be a member of the genus *Zea, Triticum, Hordeum, Secale, Oryza, Triticosecale, Avena, Musa, Elaeis, Phleum*, or *Sorghum*. The tissue can be seed tissue.

A transgenic plant is also provided. The transgenic plant comprises any of the plant cells described above. Progeny of the transgenic plant are also provided. The progeny have a difference in the level of carbon as compared to the level of carbon in a corresponding control plant that does not comprise the isolated nucleic acid. Seed and vegetative tissue from the transgenic plant are also provided. In addition, food products and feed products comprising vegetative tissue from the transgenic plant are provided.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIG. 1A-F is an alignment of SEQ ID NO:2 with orthologous amino acid sequences SEQ ID NOs:3-7, SEQ ID NOs:10-11, SEQ ID NOs:13-15, and SEQ ID NO:17. The consensus sequence determined by the alignment is set forth.

FIG. 2A-D is an alignment of SEQ ID NO:22 with orthologous amino acid sequences SEQ ID NOs:23-27, SEQ ID NO:32, and SEQ ID NO:33. The consensus sequence determined by the alignment is set forth.

FIG. 3A-B is an alignment of SEQ ID NO:36 with homologous and orthologous amino acid sequences SEQ ID NOs:37-38. The consensus sequence determined by the alignment is set forth.

FIG. 4A-D is an alignment of SEQ ID NO:40 with orthologous amino acid sequences SEQ ID NO:41, SEQ ID NO:48, and SEQ ID NOs:51-53. The consensus sequence determined by the alignment is set forth.

FIG. 5A-C is an alignment of SEQ ID NO:55 with homologous and orthologous amino acid sequences SEQ ID NOs:61-65. The consensus sequence determined by the alignment is set forth.

FIG. 6A-D is an alignment of SEQ ID NO:67 with homologous and orthologous amino acid sequences SEQ ID NOs:71-75, SEQ ID NOs:77-78, and SEQ ID NO:81. The consensus sequence determined by the alignment is set forth.

FIG. 7A-B is an alignment of SEQ ID NO:83 with orthologous amino acid sequences SEQ ID NOs:87-88 and SEQ ID NOs:91-92. The consensus sequence determined by the alignment is set forth.

DETAILED DESCRIPTION

Figure 2A:
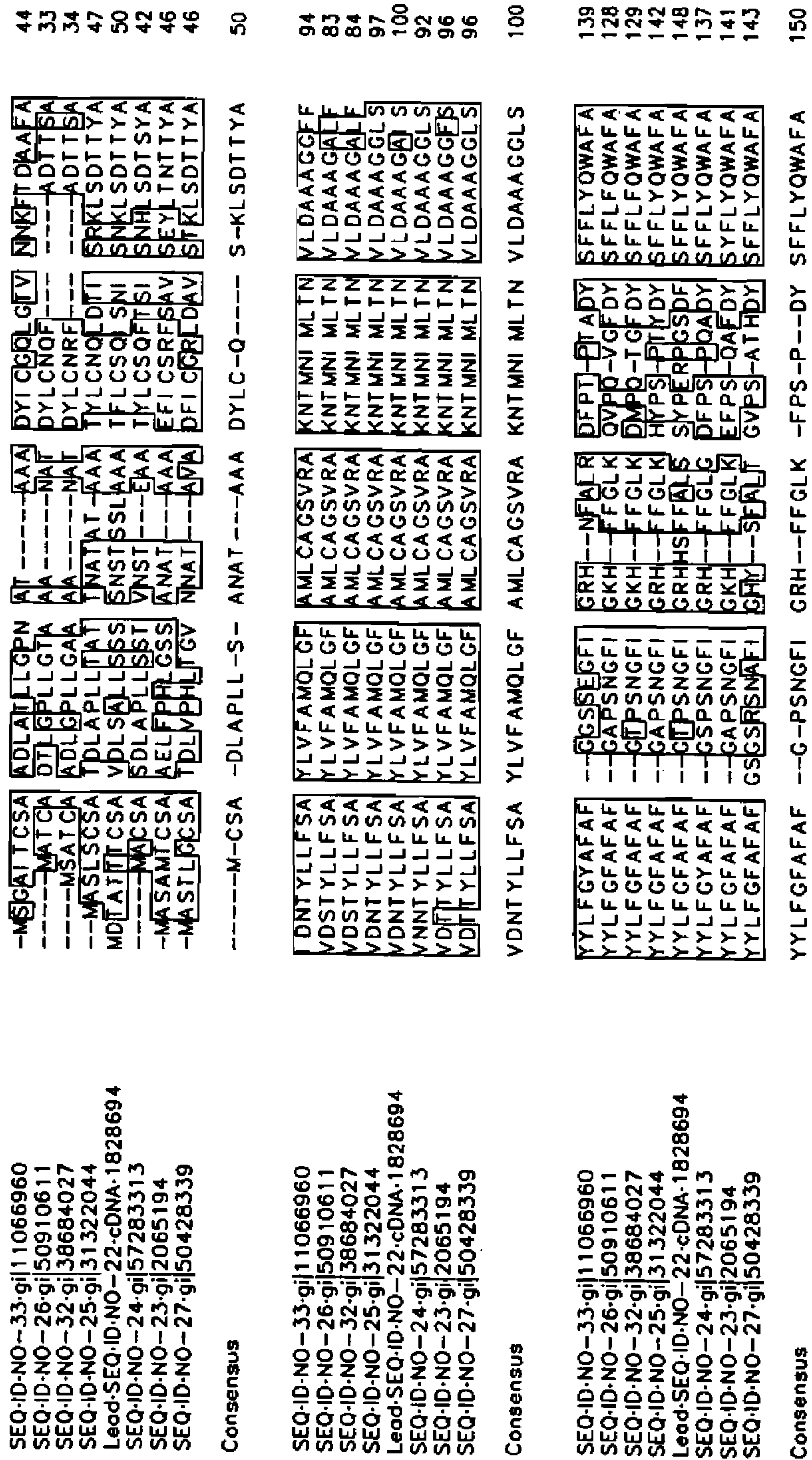

The invention features methods and materials related to modulating (e.g., increasing or decreasing) carbon levels in plants. In some embodiments, the plants may also have modulated levels of nitrogen. The methods can include transforming a plant cell with a nucleic acid encoding a carbon-modulating polypeptide, wherein expression of the polypeptide results in a modulated level of carbon. Plant cells produced using such methods can be grown to produce plants having an increased or decreased carbon content. Seeds from such plants may be used to produce, for example, foodstuffs and animal feed having increased or decreased oil, carbohydrate, and/or caloric content, which may benefit both food producers and consumers.

Polypeptides

The term "polypeptide" as used herein refers to a compound of two or more subunit amino acids, amino acid analogs, or other peptidomimetics, regardless of post-translational modification, e.g., phosphorylation or glycosylation. The subunits may be linked by peptide bonds or other bonds such as, for example, ester or ether bonds. The term "amino acid" refers to natural and/or unnatural or synthetic amino acids, including D/L optical isomers. Full-length proteins, analogs, mutants, and fragments thereof are encompassed by this definition.

Described herein are carbon-modulating polypeptides. Carbon-modulating polypeptides can be effective to modulate carbon levels when expressed in a plant or plant cell. Modulation of the level of carbon can be either an increase or a decrease in the level of carbon relative to the corresponding level in a control plant. A carbon-modulating polypeptide can be a transporter polypeptide, such as a nitrate, proline, ammonium, or oligopeptide transporter polypeptide. A carbon-modulating polypeptide can also be an enzyme, such as anthranilate synthase, that catalyzes a reaction in an amino acid biosynthetic pathway.

A carbon-modulating polypeptide can be a nitrate transporter polypeptide, such as a NRT2.5 nitrate transporter polypeptide. Nitrate transporter polypeptides are involved in the nitrate uptake process in plants. SEQ ID NO:2 sets forth the amino acid sequence of an *Arabidopsis* clone, identified herein as Ceres cDNA ID 3080447 (SEQ ID NO:1), that is predicted to encode a NRT2.5 nitrate transporter polypeptide.

A carbon-modulating polypeptide can comprise the amino acid sequence set forth in SEQ ID NO:2. Alternatively, a carbon-modulating polypeptide can be a homolog, ortholog, or variant of the polypeptide having the amino acid sequence set forth in SEQ ID NO:2. For example, a carbon-modulating polypeptide can have an amino acid sequence with at least 55% sequence identity, e.g., 56%, 57%, 58%, 59%, 60%, 61%, 65%, 66%, 67%, 70%, 75%, 80%, 85%, 90%, 95%, 97%, 98%, or 99% sequence identity, to the amino acid sequence set forth in SEQ ID NO:2.

Amino acid sequences of orthologs of the polypeptide having the amino acid sequence set forth in SEQ ID NO:2 are provided in FIG. 1, along with a consensus sequence. A consensus amino acid sequence for such orthologs was determined by aligning amino acid sequences, e.g., amino acid sequences related to SEQ ID NO:2, from a variety of species and determining the most common amino acid or type of amino acid at each position. For example, the alignment in FIG. 1 provides the amino acid sequences of Ceres cDNA ID 3080447 (SEQ ID NO:2), gi|57283317 (SEQ ID NO:3), CeresClone:1545993 (SEQ ID NO:4), gi|34911556 (SEQ ID NO:5), gi|3005576 (SEQ ID NO:6), gi|37999150 (SEQ ID NO:7), gi|9931082 (SEQ ID NO:10), gi|39573544 (SEQ ID NO:11), gi|13539545 (SEQ ID NO:13), gi|15990600 (SEQ ID NO:14), gi|4731146 (SEQ ID NO:15), and gi|9858859 (SEQ ID NO:17). Other orthologs include gi|37999148 (SEQ ID NO:8), gi|37999154 (SEQ ID NO:9), gi|38636547 (SEQ ID NO:12), gi|1680655 (SEQ ID NO:16), gi|13345827 (SEQ ID NO:18), gi|4731148 (SEQ ID NO:19), and gi|37999156 (SEQ ID NO:20).

In some cases, a carbon-modulating polypeptide includes a polypeptide having at least 80% sequence identity, e.g., 80%, 85%, 90%, 93%, 95%, 97%, 98%, or 99% sequence identity, to an amino acid sequence corresponding to SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, or the consensus sequence set forth in FIG. 1.

A carbon-modulating polypeptide can be an ammonium transporter polypeptide, such as an ATM1;2 ammonium transporter polypeptide. Ammonium transporter polypeptides are involved in regulating ammonium uptake in plants. SEQ ID NO:22 sets forth the amino acid sequence of an *Arabidopsis* clone, identified herein as Ceres cDNA ID 1828694 (SEQ ID NO:21), that is predicted to encode an ATM1;2 ammonium transporter polypeptide.

A carbon-modulating polypeptide can comprise the amino acid sequence set forth in SEQ ID NO:22. Alternatively, a carbon-modulating polypeptide can be a homolog, ortholog, or variant of the polypeptide having the amino acid sequence set forth in SEQ ID NO:22. For example, a carbon-modulating polypeptide can have an amino acid sequence with at least 65% sequence identity, e.g., 66%, 67%, 68%, 69%, 70%, 71%, 72%, 75%, 76%, 77%, 79%, 80%, 81%, 85%, 90%, 95%, 97%, 98%, or 99% sequence identity, to the amino acid sequence set forth in SEQ ID NO:22.

Amino acid sequences of orthologs of the polypeptide having the amino acid sequence set forth in SEQ ID NO:22 are provided in FIG. 2, along with a consensus sequence. A consensus amino acid sequence for such orthologs was determined by aligning amino acid sequences, e.g., amino acid sequences related to SEQ ID NO:22, from a variety of species and determining the most common amino acid or type of amino acid at each position. For example, the alignment in FIG. 2 provides the amino acid sequences of Ceres cDNA ID 1828694 (SEQ ID NO:22), gi|2065194 (SEQ ID NO:23), gi|57283313 (SEQ ID NO:24), gi|31322044 (SEQ ID NO:25), gi|50910611 (SEQ ID NO:26), gi|50428339 (SEQ ID NO:27), gi|38684027 (SEQ ID NO:32), and gi|1066960 (SEQ ID NO:33). Other orthologs include gi|5705368 (SEQ ID NO:28), gi|52550773 (SEQ ID NO:29), gi|22001520 (SEQ ID NO:30), gi|50926368 (SEQ ID NO:31), and gi|50910607 (SEQ ID NO:34).

In some cases, a carbon-modulating polypeptide includes a polypeptide having at least 80% sequence identity, e.g., 80%, 85%, 90%, 93%, 95%, 97%, 98%, or 99% sequence identity, to an amino acid sequence corresponding to SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, or the consensus sequence set forth in FIG. 2.

A carbon-modulating polypeptide can be a proton-dependent oligopeptide transport (POT) family polypeptide. POT family polypeptides seem to be mainly involved in the intake of small peptides with the concomitant uptake of a proton. SEQ ID NO:36 sets forth the amino acid sequence of an *Arabidopsis* clone, identified herein as Ceres cDNA ID 3086062 (SEQ ID NO:35), that has a PTR2 domain characteristic of a peptide transporter polypeptide.

A carbon-modulating polypeptide can comprise the amino acid sequence set forth in SEQ ID NO:36. Alternatively, a carbon-modulating polypeptide can be a homolog, ortholog, or variant of the polypeptide having the amino acid sequence set forth in SEQ ID NO:36. For example, a carbon-modulating polypeptide can have an amino acid sequence with at least 45% sequence identity, e.g., 46%, 47%, 48%, 49%, 50%, 51%, 55%, 60%, 61%, 63%, 63%, 66%, 67%, 68%, 69%, 70%, 71%, 72%, 75%, 76%, 77%, 79%, 80%, 81%, 85%, 90%, 95%, 97%, 98%, or 99% sequence identity, to the amino acid sequence set forth in SEQ ID NO:36.

Amino acid sequences of a homolog and an ortholog of the polypeptide having the amino acid sequence set forth in SEQ ID NO:36 are provided in FIG. 3, along with a consensus sequence. A consensus amino acid sequence for such a homolog and ortholog was determined by aligning amino acid sequences, e.g., amino acid sequences related to SEQ ID NO:36, from a variety of species and determining the most common amino acid or type of amino acid at each position. For example, the alignment in FIG. 3 provides the amino acid sequences of Ceres cDNA ID 3086062 (SEQ ID NO:36), CeresClone:1002997 (SEQ ID NO:37), and gi|47900739 (SEQ ID NO:38).

In some cases, a carbon-modulating polypeptide can include a polypeptide having at least 80% sequence identity, e.g., 80%, 85%, 90%, 93%, 95%, 97%, 98%, or 99% sequence identity, to an amino acid sequence corresponding to SEQ ID NO:36, SEQ ID NO:37, SEQ ID NO:38, or the consensus sequence set forth in FIG. 3.

A carbon-modulating polypeptide can also comprise the amino acid sequence of an *Arabidopsis* clone, identified herein as Ceres cDNA ID 3091277 SEQ ID NO:39), that is predicted to encode a POT family polypeptide (SEQ ID NO:40). Alternatively, a carbon-modulating polypeptide can be a homolog, ortholog, or variant of the polypeptide having the amino acid sequence set forth in SEQ ID NO:40. For example, a carbon-modulating polypeptide can have an amino acid sequence with at least 35% sequence identity, e.g., 36%, 38%, 39%, 40%, 41%, 42%, 43%, 44%, 45%, 46%, 47%, 48%, 49%, 50%, 51%, 55%, 60%, 61%, 63%, 63%, 66%, 67%, 68%, 69%, 70%, 71%, 72%, 75%, 76%, 77%, 79%, 80%, 81%, 85%, 90%, 95%, 97%, 98%, or 99% sequence identity, to the amino acid sequence set forth in SEQ ID NO:40.

Amino acid sequences of orthologs of the polypeptide having the amino acid sequence set forth in SEQ ID NO:40 are provided in FIG. 4, along with a consensus sequence. A consensus amino acid sequence for such orthologs was determined by aligning amino acid sequences, e.g., amino acid sequences related to SEQ ID NO:40, from a variety of species and determining the most common amino acid or type of amino acid at each position. For example, the alignment in FIG. 4 provides the amino acid sequences of Ceres cDNA ID 3091277 (SEQ ID NO:40), gi|50912139 (SEQ ID NO:41), gi|48675345 (SEQ ID NO:48), gi|47717628 (SEQ ID NO:51), gi|9581817 (SEQ ID NO:52), and gi|28273094 (SEQ ID NO:53). Other orthologs include gi|50911647 (SEQ ID NO:42) and gi|54290524 (SEQ ID NO:43).

In some cases, a carbon-modulating polypeptide can include a polypeptide having at least 80% sequence identity, e.g., 80%, 85%, 90%, 93%, 95%, 97%, 98%, or 99% sequence identity, to an amino acid sequence corresponding to SEQ ID NO:40, SEQ ID NO:41, SEQ ID NO:42, SEQ ID NO:43, SEQ ID NO:48, SEQ ID NO:51, SEQ ID NO:52, SEQ ID NO:53, or the consensus sequence set forth in FIG. 4.

A carbon-modulating polypeptide can be a transporter polypeptide. Transporter polypeptides allow uptake of essential nutrients and ions, excretion of end products of metabolism and deleterious substances, and communication between cells and the environment. Transporter polypeptides also provide essential constituents of energy-generating and energy-consuming systems. SEQ ID NO:55 sets forth the amino acid sequence of an *Arabidopsis* clone, identified herein as Ceres cDNA ID 2997404 (SEQ ID NO:54), that has a PTR2 domain characteristic of a transporter polypeptide.

A carbon-modulating polypeptide can comprise the amino acid sequence set forth in SEQ ID NO:55. Alternatively, a carbon-modulating polypeptide can be a homolog, ortholog, or variant of the polypeptide having the amino acid sequence set forth in SEQ ID NO:55. For example, a carbon-modulating polypeptide can have an amino acid sequence with at least 30% sequence identity, e.g., 31%, 32%, 33%, 34%, 35%, 36%, 37%, 39%, 40%, 41%, 42%, 43%, 44%, 45%, 46%, 47%, 48%, 49%, 50%, 51%, 55%, 60%, 61%, 63%, 63%, 66%, 67%, 68%, 69%, 70%, 71%, 72%, 75%, 76%, 77%, 79%, 80%, 81%, 85%, 90%, 95%, 97%, 98%, or 99% sequence identity, to the amino acid sequence set forth in SEQ ID NO:55.

Amino acid sequences of orthologs and a homolog of the polypeptide having the amino acid sequence set forth in SEQ ID NO:55 are provided in FIG. 5, along with a consensus sequence. A consensus amino acid sequence for such orthologs and homolog was determined by aligning amino acid sequences, e.g., amino acid sequences related to SEQ ID NO:55, from a variety of species and determining the most common amino acid or type of amino acid at each position. For example, the alignment in FIG. 5 provides the amino acid sequences of Ceres cDNA ID 2997404 (SEQ ID NO:55), gi|5391731_T (SEQ ID NO:61), CeresClone: 1144139_T (SEQ ID NO:62), gi|54291818_T (SEQ ID NO:63), gi|34905798_T (SEQ ID NO:64), and gi|47900739_T (SEQ ID NO:65). Other orthologs and homologs include gi|5391731 (SEQ ID NO:56), CeresClone:1144139 (SEQ ID NO:57), gi|54291818 (SEQ ID NO:58), gi|34905798 (SEQ ID NO:59), and gi|47900739 (SEQ ID NO:60).

In some cases, a carbon-modulating polypeptide can include a polypeptide having at least 80% sequence identity, e.g., 80%, 85%, 90%, 93%, 95%, 97%, 98%, or 99% sequence identity, to an amino acid sequence corresponding to SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, or the consensus sequence set forth in FIG. 5.

A carbon-modulating polypeptide can be a proline transporter polypeptide, such as a ProT1 proline transporter polypeptide. Proline transporter polypeptides transport proline but not other amino acids in plants. SEQ ID NO:67 sets forth the amino acid sequence of an *Arabidopsis* clone, identified herein as Ceres cDNA ID 4904707 (SEQ ID NO:66), that is predicted to encode a proline transporter polypeptide.

A carbon-modulating polypeptide can comprise the amino acid sequence set forth in SEQ ID NO:67. Alternatively, a carbon-modulating polypeptide can be a homolog, ortholog, or variant of the polypeptide having the amino acid sequence set forth in SEQ ID NO:67. For example, a carbon-modulating polypeptide can have an amino acid sequence with at least 60% sequence identity, e.g., 61%, 65%, 66%, 67%, 69%, 70%, 71%, 74%, 75%, 80%, 85%, 90%, 91%, 95%, 97%, 98%, or 99% sequence identity, to the amino acid sequence set forth in SEQ ID NO:67.

Amino acid sequences of orthologs and a homolog of the polypeptide having the amino acid sequence set forth in SEQ ID NO:67 are provided in FIG. 6, along with a consensus sequence. A consensus amino acid sequence for such orthologs and homolog was determined by aligning amino acid sequences, e.g., amino acid sequences related to SEQ ID NO:67, from a variety of species and determining the most common amino acid or type of amino acid at each position. For example, the alignment in FIG. 6 provides the amino acid sequences of Ceres cDNA ID 4904707 (SEQ ID NO:67), gi|31376371 (SEQ ID NO:71), CeresClone:526395 (SEQ ID NO:72), gi|21069018 (SEQ ID NO:73), gi|8571474 (SEQ ID NO:74), gi|50933631 (SEQ ID NO:75), gi|4584852 (SEQ ID NO:77), gi|6215723 (SEQ ID NO:78), and gi|21069016 (SEQ ID NO:81). Other homologs and orthologs include gi|28393251 (SEQ ID NO:68), gi|21554196 (SEQ ID NO:69), CeresClone:20959 (SEQ ID NO:70), gi|53749423 (SEQ ID NO:76), gi|4584848 (SEQ ID NO:79), and gi|4584850 (SEQ ID NO:80).

In some cases, a carbon-modulating polypeptide can include a polypeptide having at least 80% sequence identity, e.g., 80%, 85%, 90%, 93%, 95%, 97%, 98%, or 99% sequence identity, to an amino acid sequence corresponding to SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, or the consensus sequence set forth in FIG. 6.

A carbon-modulating polypeptide can be a subunit of an enzyme, such as anthranilate synthase, that catalyzes a reaction in an amino acid biosynthetic pathway. Anthranilate synthase catalyzes the first reaction in the tryptophan biosynthetic pathway. SEQ ID NO:83 sets forth the amino acid sequence of an *Arabidopsis* clone, identified herein as Ceres cDNA ID 5669462 (SEQ ID NO:82), that is predicted to encode an anthranilate synthase beta chain polypeptide.

A carbon-modulating polypeptide can comprise the amino acid sequence set forth in SEQ ID NO:83. Alternatively, a carbon-modulating polypeptide can be a homolog, ortholog, or variant of the polypeptide having the amino acid sequence set forth in SEQ ID NO:83. For example, a carbon-modulating polypeptide can have an amino acid sequence with at least 65% sequence identity, e.g., 66%, 67%, 69%, 70%, 71%, 74%, 75%, 80%, 85%, 90%, 91%, 95%, 97%, 98%, or 99% sequence identity, to the amino acid sequence set forth in SEQ ID NO:83.

Amino acid sequences of orthologs of the polypeptide having the amino acid sequence set forth in SEQ ID NO:83 are provided in FIG. 7, along with a consensus sequence. A consensus amino acid sequence for such orthologs was determined by aligning amino acid sequences, e.g., amino acid sequences related to SEQ ID NO:83, from a variety of species and determining the most common amino acid or type of amino acid at each position. For example, the alignment in FIG. 7 provides the amino acid sequences of Ceres cDNA ID 5669462 (SEQ ID NO:83), CeresClone:967151 (SEQ ID NO:87), CeresClone:214246 (SEQ ID NO:88), CeresClone:686561 (SEQ ID NO:91), and gi|50918343 (SEQ ID NO:92). Other orthologs and homologs include gi|21594026 (SEQ ID NO:84), CeresClone:6495 (SEQ ID NO:85), gi|9758358 (SEQ ID NO:86), CeresClone:257290 (SEQ ID NO:89), and CeresClone:341958 (SEQ ID NO:90).

In some cases, a carbon-modulating polypeptide can include a polypeptide having at least 80% sequence identity (e.g., 80%, 85%, 90%, 93%, 95%, 97%, 98%, or 99% sequence identity) to an amino acid sequence corresponding to SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, or the consensus sequence set forth in FIG. 7.

It will be appreciated that a number of nucleic acids can encode a polypeptide having a particular amino acid sequence. The degeneracy of the genetic code is well known to the art; ie., for many amino acids, there is more than one nucleotide triplet that serves as the codon for the amino acid. For example, codons in the coding sequence for a given carbon-modulating polypeptide can be modified such that optimal expression in a particular plant species is obtained, using appropriate codon bias tables for that species.

A carbon-modulating polypeptide encoded by a recombinant nucleic acid can be a native carbon-modulating polypeptide, i.e., one or more additional copies of the coding sequence for a carbon-modulating polypeptide that is naturally present in the cell. Alternatively, a carbon-modulating polypeptide can be heterologous to the cell, e.g., a transgenic Lycopersicon plant can contain the coding sequence for a transporter polypeptide from a Glycine plant.

A carbon-modulating polypeptide can include additional amino acids that are not involved in carbon modulation, and thus can be longer than would otherwise be the case. For example, a carbon-modulating polypeptide can include an amino acid sequence that functions as a reporter. Such a carbon-modulating polypeptide can be a fusion protein in which a green fluorescent protein (GFP) polypeptide is fused to SEQ ID NO:2, or in which a yellow fluorescent protein (YFP) polypeptide is fused to SEQ ID NO:22. In some embodiments, a carbon-modulating polypeptide includes a purification tag or a leader sequence added to the amino or carboxy terminus.

Carbon-modulating polypeptide candidates suitable for use in the invention can be identified by analysis of nucleotide and polypeptide sequence alignments. For example, performing a query on a database of nucleotide or polypeptide sequences can identify orthologs of carbon-modulating polypeptides. Sequence analysis can involve BLAST, Reciprocal BLAST, or PSI-BLAST analysis of nonredundant databases using known carbon-modulating polypeptide amino acid sequences. Those proteins in the database that have greater than 40% sequence identity can be identified as candidates for further evaluation for suitability as a carbon-modulating polypeptide. If desired, manual inspection of such candidates can be carried out in order to narrow the number of candidates to be further evaluated. Manual inspection can be performed by selecting those candidates that appear to have domains suspected of being present in carbon-modulating polypeptides, e.g., conserved functional domains.

The identification of conserved regions in a template or subject polypeptide can facilitate production of variants of wild type carbon-modulating polypeptides. Conserved regions can be identified by locating a region within the primary amino acid sequence of a template polypeptide that is a repeated sequence, forms some secondary structure (e.g., helices and beta sheets), establishes positively or negatively charged domains, or represents a protein motif or domain. See, e.g., the Pfam web site describing consensus sequences for a variety of protein motifs and domains at sanger.ac.uk/Pfam and genome.wustl.edu/Pfam. A description of the information included at the Pfam database is described in Sonnhammer et al., 1998, *Nucl. Acids Res*. 26: 320-322; Sonnhammer et al., 1997, *Proteins* 28:405-420; and Bateman et al., 1999, *Nucl. Acids Res*. 27:260-262.

Conserved regions also can be determined by aligning sequences of the same or related polypeptides from closely related species. Closely related species preferably are from the same family. In some embodiments, alignment of sequences from two different species is adequate. For example, sequences from *Arabidopsis* and *Zea mays* can be used to identify one or more conserved regions.

Typically, polypeptides that exhibit at least about 40% amino acid sequence identity are useful to identify conserved regions. Conserved regions of related polypeptides can exhibit at least 45% amino acid sequence identity (e.g., at least 50%, at least 60%, at least 70%, at least 80%, or at least 90% amino acid sequence identity). In some embodiments, a conserved region of target and template polypeptides exhibit at least 92, 94, 96, 98, or 99% amino acid sequence identity. Amino acid sequence identity can be deduced from amino acid or nucleotide sequences. In certain cases, highly conserved domains have been identified within carbon-modulating polypeptides. These conserved regions can be useful in identifying functionally similar (orthologous) carbon-modulating polypeptides.

In some instances, suitable carbon-modulating polypeptides can be synthesized on the basis of consensus functional domains and/or conserved regions in polypeptides that are homologous carbon-modulating polypeptides. Domains are groups of substantially contiguous amino acids in a polypeptide that can be used to characterize protein families and/or parts of proteins. Such domains have a "fingerprint" or "signature" that can comprise conserved (1) primary sequence, (2) secondary structure, and/or (3) three-dimensional conformation. Generally, domains are correlated with specific in vitro and/or in vivo activities. A domain can have a length of from 10 amino acids to 400 amino acids, e.g., 10 to 50 amino acids, or 25 to 100 amino acids, or 35 to 65 amino acids, or 35 to 55 amino acids, or 45 to 60 amino acids, or 200 to 300 amino acids, or 300 to 400 amino acids.

Consensus domains and conserved regions can be identified by homologous polypeptide sequence analysis as described above. The suitability of polypeptides for use as carbon-modulating polypeptides can be evaluated by functional complementation studies.

Nucleic Acids

Isolated nucleic acids are provided herein. The terms "nucleic acid" and "polynucleotide" are used interchangeably herein, and refer to both RNA and DNA, including cDNA, genomic DNA, synthetic DNA, and DNA (or RNA) containing nucleic acid analogs. Polynucleotides can have any three-dimensional structure. A nucleic acid can be double-stranded or single-stranded (i.e., a sense strand or an antisense strand). Non-limiting examples of polynucleotides include genes, gene fragments, exons, introns, messenger RNA (mRNA), transfer RNA, ribosomal RNA, siRNA, micro-RNA, ribozymes, cDNA, recombinant polynucleotides, branched polynucleotides, plasmids, vectors, isolated DNA of any sequence, isolated RNA of any sequence, nucleic acid probes, and primers, as well as nucleic acid analogs.

An isolated nucleic acid can be, for example, a naturally-occurring DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule, independent of other sequences (e.g., a chemically synthesized nucleic acid, or a cDNA or genomic DNA fragment produced by the polymerase chain reaction (PCR) or restriction endonuclease treatment). An isolated nucleic acid also refers to a DNA molecule that is incorporated into a vector, an autonomously replicating plasmid, a virus, or into the genomic DNA of a prokaryote or eukaryote. In addition, an isolated nucleic acid can include an engineered nucleic acid such as a DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not to be considered an isolated nucleic acid.

Isolated nucleic acid molecules can be produced by standard techniques. For example, polymerase chain reaction (PCR) techniques can be used to obtain an isolated nucleic acid containing a nucleotide sequence described herein. PCR can be used to amplify specific sequences from DNA as well as RNA, including sequences from total genomic DNA or total cellular RNA. Various PCR methods are described, for example, in PCR Primer: A Laboratory Manual, Dieffenbach and Dveksler, eds., Cold Spring Harbor Laboratory Press, 1995. Generally, sequence information from the ends of the region of interest or beyond is employed to design oligonucleotide primers that are identical or similar in sequence to opposite strands of the template to be amplified. Various PCR strategies also are available by which site-specific nucleotide sequence modifications can be introduced into a template nucleic acid. Isolated nucleic acids also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector. Isolated nucleic acids of the invention also can be obtained by mutagenesis of, e.g., a naturally occurring DNA.

As used herein, the term "percent sequence identity" refers to the degree of identity between any given query sequence and a subject sequence. A subject sequence typically has a length that is more than 80 percent, e.g., more than 82, 85, 87, 89, 90, 93, 95, 97, 99, 100, 105, 110, 115, or 120 percent, of the length of the query sequence. A query nucleic acid or amino acid sequence is aligned to one or more subject nucleic acid or amino acid sequences using the computer program ClustalW (version 1.83, default parameters), which allows alignments of nucleic acid or protein sequences to be carried out across their entire length (global alignment). Chenna, et al. (2003) *Nucleic Acids Res* 31 (13):3497-500.

ClustalW calculates the best match between a query and one or more subject sequences, and aligns them so that identities, similarities and differences can be determined. Gaps of one or more residues can be inserted into a query sequence, a subject sequence, or both, to maximize sequence alignments. For fast pairwise alignment of nucleic acid sequences, the following default parameters are used: word size: 2; window size: 4; scoring method: percentage; number of top diagonals: 4; and gap penalty: 5. For multiple alignment of nucleic acid sequences, the following parameters are used: gap opening penalty: 10.0; gap extension penalty: 5.0; and weight transitions: yes. For fast pairwise alignment of protein sequences, the following parameters are used: word size: 1; window size: 5; scoring method: percentage; number of top diagonals: 5; gap penalty: 3. For multiple alignment of protein sequences, the following parameters are used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; residue-specific gap penalties: on. The output is a sequence alignment that reflects the relationship between sequences. ClustalW can be run, for example, at the Baylor College of Medicine Search Launcher site (searchlauncher.bcm.tmc.edu/multi-align/multi-align.html) and at the European Bioinformatics Institute site on the World Wide Web (ebi.ac.uk/clustalw).

To determine a percent identity between a query sequence and a subject sequence, ClustalW divides the number of identities in the best alignment by the number of residues compared (gap positions are excluded), and multiplies the result by 100. The output is the percent identity of the subject sequence with respect to the query sequence. It is noted that the percent identity value can be rounded to the nearest tenth. For example, 78.11, 78.12, 78.13, and 78.14 are rounded down to 78.1, while 78.15, 78.16, 78.17, 78.18, and 78.19 are rounded up to 78.2.

The term "exogenous" with respect to a nucleic acid indicates that the nucleic acid is part of a recombinant nucleic acid construct, or is not in its natural environment. For example, an exogenous nucleic acid can be a sequence from one species introduced into another species, i.e., a heterologous nucleic acid. Typically, such an exogenous nucleic acid is introduced into the other species via a recombinant nucleic acid construct. An exogenous nucleic acid can also be a sequence that is native to an organism and that has been reintroduced into cells of that organism. An exogenous nucleic acid that includes a native sequence can often be distinguished from the naturally occurring sequence by the presence of non-natural sequences linked to the exogenous nucleic acid, e.g., non-native regulatory sequences flanking a native sequence in a recombinant nucleic acid construct. In addition, stably transformed exogenous nucleic acids typically are integrated at positions other than the position where the native sequence is found. It will be appreciated that an exogenous nucleic acid may have been introduced into a progenitor and not into the cell under consideration. For example, a transgenic plant containing an exogenous nucleic acid can be the progeny of a cross between a stably transformed plant and a non-transgenic plant. Such progeny are considered to contain the exogenous nucleic acid.

Recombinant constructs are also provided herein and can be used to transform plants or plant cells in order to modulate carbon levels. A recombinant nucleic acid construct comprises a nucleic acid encoding a carbon-modulating polypeptide as described herein, operably linked to a regulatory region suitable for expressing the carbon-modulating polypeptide in the plant or cell. Thus, a nucleic acid can comprise a coding sequence that encodes any of the carbon-modulating polypeptides as set forth in SEQ ID NOs:2-20, SEQ ID NOs:22-34, SEQ ID NOs:36-38, SEQ ID NOs:40-43, SEQ ID NO:48, SEQ ID NOs:51-53, SEQ ID NOs:55-65, SEQ ID NOs:67-81, SEQ ID NOs:83-92, and the consensus sequences set forth in FIGS. 1-7.

Vectors containing nucleic acids such as those described herein also are provided. A "vector" is a replicon, such as a plasmid, phage, or cosmid, into which another DNA segment may be inserted so as to bring about the replication of the inserted segment. Generally, a vector is capable of replication when associated with the proper control elements. Suitable vector backbones include, for example, those routinely used in the art such as plasmids, viruses, artificial chromosomes, BACs, YACs, or PACs. The term "vector" includes cloning and expression vectors, as well as viral vectors and integrating vectors. An "expression vector" is a vector that includes a regulatory region. Suitable expression vectors include, without limitation, plasmids and viral vectors derived from, for example, bacteriophage, baculoviruses, and retroviruses. Numerous vectors and expression systems are commercially available from such corporations as Novagen (Madison, Wis.), Clontech (Palo Alto, Calif.), Stratagene (La Jolla, Calif.), and Invitrogen/Life Technologies (Carlsbad, Calif.).

The vectors provided herein also can include, for example, origins of replication, scaffold attachment regions (SARs), and/or markers. A marker gene can confer a selectable phenotype on a plant cell. For example, a marker can confer biocide resistance, such as resistance to an antibiotic (e.g., kanamycin, G418, bleomycin, or hygromycin), or an herbicide (e.g., chlorosulfuron or phosphinothricin). In addition, an expression vector can include a tag sequence designed to facilitate manipulation or detection (e.g., purification or localization) of the expressed polypeptide. Tag sequences, such as green fluorescent protein (GFP), glutathione S-transferase (GST), polyhistidine, c-myc, hemagglutinin, or Flag™ tag (Kodak, New Haven, Conn.) sequences typically are expressed as a fusion with the encoded polypeptide. Such tags can be inserted anywhere within the polypeptide, including at either the carboxyl or amino terminus.

Regulatory Regions

The term "regulatory region" refers to nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, and introns.

As used herein, the term "operably linked" refers to positioning of a regulatory region and a sequence to be transcribed in a nucleic acid so as to influence transcription or translation of such a sequence. For example, to bring a coding sequence under the control of a promoter, the translation initiation site of the translational reading frame of the polypeptide is typically positioned between one and about fifty nucleotides downstream of the promoter. A promoter can, however, be positioned as much as about 5,000 nucleotides upstream of the translation initiation site, or about 2,000 nucleotides upstream of the transcription start site. A promoter typically comprises at least a core (basal) promoter. A promoter also may include at least one control element, such as an enhancer sequence, an upstream element or an upstream activation region (UAR). For example, a suitable enhancer is a cis-regulatory element (−212 to −154) from the upstream region of the octopine synthase (ocs) gene. Fromm et al., *The Plant Cell* 1:977-984 (1989). The choice of promoters to be included depends upon several factors, including, but not limited to, efficiency, selectability, inducibility, desired expression level, and cell- or tissue-preferential expression. It is a routine matter for one of skill in the art to modulate the expression of a coding sequence by appropriately selecting and positioning promoters and other regulatory regions relative to the coding sequence.

Some suitable promoters initiate transcription only, or predominantly, in certain cell types. For example, a promoter that is active predominantly in a reproductive tissue (e.g., fruit, ovule, pollen, pistils, female gametophyte, egg cell, central cell, nucellus, suspensor, synergid cell, flowers, embryonic tissue, embryo sac, embryo, zygote, endosperm, integument, or seed coat) can be used. Thus, as used herein a cell type- or tissue-preferential promoter is one that drives expression preferentially in the target tissue, but may also lead to some expression in other cell types or tissues as well. Methods for identifying and characterizing promoter regions in plant genomic DNA include, for example, those described in the following references: Jordano, et al., *Plant Cell*, 1:855-866 (1989); Bustos, et al., *Plant Cell*, 1:839-854 (1989); Green, et al., *EMBO J*. 7, 4035-4044 (1988); Meier, et al., *Plant Cell*, 3, 309-316 (1991); and Zhang, et al., *Plant Physiology* 110: 1069-1079 (1996).

Examples of various classes of promoters are described below. Some of the promoters indicated below are described in more detail in U.S. patent application Ser. Nos. 60/505,689; 60/518,075; 60/544,771; 60/558,869; 60/583,691; 60/619,181; 60/637,140; 10/950,321; 10/957,569; 11/058,689; 11/172,703; 11/208,308; and PCT/US05/23639. It will be appreciated that a promoter may meet criteria for one classification based on its activity in one plant species, and yet meet criteria for a different classification based on its activity in another plant species. Nucleotide sequences of promoters are set forth in SEQ ID NOs:93-100.

Broadly Expressing Promoters

A promoter can be said to be “broadly expressing” when it promotes transcription in many, but not necessarily all, plant tissues. For example, a broadly expressing promoter can promote transcription of an operably linked sequence in one or more of the shoot, shoot tip (apex), and leaves, but weakly or not at all in tissues such as roots or stems. As another example, a broadly expressing promoter can promote transcription of an operably linked sequence in one or more of the stem, shoot, shoot tip (apex), and leaves, but can promote transcription weakly or not at all in tissues such as reproductive tissues of flowers and developing seeds. Non-limiting examples of broadly expressing promoters that can be included in the nucleic acid constructs provided herein include the p326 (SEQ ID NO:94), YP0144 (SEQ ID NO:95), YP0190 (SEQ ID NO:96), p13879 (SEQ ID NO:97), YP0050 (SEQ ID NO:98), p32449 (SEQ ID NO:99), 21876 (SEQ ID NO:100), YP0158, YP0214, YP0380, PT0848, and PT0633 promoters. Additional examples include the cauliflower mosaic virus (CaMV) 35S promoter, the mannopine synthase (MAS) promoter, the 1' or 2' promoters derived from T-DNA of Agrobacterium tumefaciens, the figwort mosaic virus 34S promoter, actin promoters such as the rice actin promoter, and ubiquitin promoters such as the maize ubiquitin-1 promoter. In some cases, the CaMV 35S promoter is excluded from the category of broadly expressing promoters.

Root Promoters

Root-active promoters confer transcription in root tissue, e.g., root endodermis, root epidermis, or root vascular tissues. In some embodiments, root-active promoters are root-preferential promoters, i.e., confer transcription only or predominantly in root tissue. Root-preferential promoters include the YP0128, YP0275, PT0625, PT0660, PT0683, and PT0758 promoters. Other root-preferential promoters include the PT0613, PT0672, PT0688, and PT0837 promoters, which drive transcription primarily in root tissue and to a lesser extent in ovules and/or seeds. Other examples of root-preferential promoters include the root-specific subdomains of the CaMV 35S promoter (Lam et al., *Proc. Natl. Acad. Sci. USA* 86:7890-7894 (1989)), root cell specific promoters reported by Conkling et al., *Plant Physiol*. 93:1203-1211 (1990), and the tobacco RD2 gene promoter.

Maturing Endosperm Promoters

In some embodiments, promoters that drive transcription in maturing endosperm can be useful. Transcription from a maturing endosperm promoter typically begins after fertilization and occurs primarily in endosperm tissue during seed development and is typically highest during the cellularization phase. Most suitable are promoters that are active predominantly in maturing endosperm, although promoters that are also active in other tissues can sometimes be used. Non-limiting examples of maturing endosperm promoters that can be included in the nucleic acid constructs provided herein include the napin promoter, the Arcelin-5 promoter, the phaseolin gene promoter (Bustos et al., *Plant Cell* 1(9):839-853 (1989)), the soybean trypsin inhibitor promoter (Riggs et al., *Plant Cell* 1(6):609-621 (1989)), the ACP promoter (Baerson et al., *Plant Mol Biol*, 22(2):255-267 (1993)), the stearoyl-ACP desaturase gene (Slocombe et al., *Plant Physiol* 104(4):167-176 (1994)), the soybean α' subunit of β-conglycinin promoter (Chen et al., *Proc Natl Acad Sci USA* 83:8560-8564 (1986)), the oleosin promoter (Hong et al., *Plant Mol Biol* 34(3):549-555 (1997)), and zein promoters, such as the 15 kD zein promoter, the 16 kD zein promoter, 19 kD zein promoter, 22 kD zein promoter and 27 kD zein promoter. Also suitable are the Osgt-1 promoter from the rice glutelin-1 gene (Zheng et al., *Mol. Cell Biol*. 13:5829-5842 (1993)), the beta-amylase gene promoter, and the barley hordein gene promoter. Other maturing endosperm promoters include the YP0092, PT0676, and PT0708 promoters.

Ovary Tissue Promoters

Promoters that are active in ovary tissues such as the ovule wall and mesocarp can also be useful, e.g., a polygalacturonidase promoter, the banana TRX promoter, and the melon actin promoter. Examples of promoters that are active primarily in ovules include YP0007, YP0111, YP0092, YP0103, YP0028, YP0121, YP0008, YP0039, YP0115, YP0119, YP0120, and YP0374.

Embryo Sac/Early Endosperm Promoters

To achieve expression in embryo sac/early endosperm, regulatory regions can be used that are active in polar nuclei and/or the central cell, or in precursors to polar nuclei, but not in egg cells or precursors to egg cells. Most suitable are promoters that drive expression only or predominantly in polar nuclei or precursors thereto and/or the central cell. A pattern of transcription that extends from polar nuclei into early endosperm development can also be found with embryo sac/early endosperm-preferential promoters, although transcription typically decreases significantly in later endosperm development during and after the cellularization phase. Expression in the zygote or developing embryo typically is not present with embryo sac/early endosperm promoters.

Promoters that may be suitable include those derived from the following genes: *Arabidopsis* viviparous-1 (see, GenBank No. U93215); *Arabidopsis* atmycl (see, Urao (1996) *Plant Mol. Biol.*, 32:571-57; Conceicao (1994) *Plant*, 5:493-505); *Arabidopsis* FIE (GenBank No. AF129516); *Arabidopsis* MEA; *Arabidopsis* FIS2 (GenBank No. AF096096); and FIE 1.1 (U.S. Pat. No. 6,906,244). Other promoters that may be suitable include those derived from the following genes: maize MAC1 (see, Sheridan (1996) *Genetics*, 142: 1009-1020); maize Cat3 (see, GenBank No. L05934; Abler (1993) *Plant Mol. Biol.*, 22:10131-1038). Other promoters include the following *Arabidopsis* promoters: YP0039, YP0101, YP0102, YP0110, YP0117, YP0119, YP0137, DME, YP0285, and YP0212. Other promoters that may be useful include the following rice promoters: p530c10, pOsFIE2-2, pOsMEA, pOsYp102, and pOsYp285.

Embryo Promoters

Regulatory regions that preferentially drive transcription in zygotic cells following fertilization can provide embryo-preferential expression. Most suitable are promoters that preferentially drive transcription in early stage embryos prior to the heart stage, but expression in late stage and maturing embryos is also suitable. Embryo-preferential promoters include the barley lipid transfer protein (Ltp1) promoter (*Plant Cell Rep* (2001) 20:647-654), YP0097, YP0107, YP0088, YP0143, YP0156, PT0650, PT0695, PT0723, PT0838, PT0879, and PT0740.

Photosynthetic Tissue Promoters

Promoters active in photosynthetic tissue confer transcription in green tissues such as leaves and stems. Most suitable are promoters that drive expression only or predominantly in such tissues. Examples of such promoters include the ribulose-1,5-bisphosphate carboxylase (RbcS) promoters such as the RbcS promoter from eastern larch (Larix laricina), the pine cab6 promoter (Yamamoto et al., *Plant Cell Physiol.* 35:773-778 (1994)), the Cab-1 gene promoter from wheat (Fejes et al., *Plant Mol. Biol.* 15:921-932 (1990)), the CAB-1 promoter from spinach (Lubberstedt et al., *Plant Physiol.* 104:997-1006 (1994)), the cab1R promoter from rice (Luan et al., *Plant Cell* 4:971-981 (1992)), the pyruvate orthophosphate dikinase (PPDK) promoter from corn (Matsuoka et al., *Proc Natl Acad. Sci USA* 90:9586-9590 (1993)), the tobacco Lhcb1*2 promoter (Cerdan et al., *Plant Mol. Biol.* 33:245-255 (1997)), the *Arabidopsis thaliana* SUC2 sucrose-H+symporter promoter (Truernit et al., *Planta* 196:564-570 (1995)), and thylakoid membrane protein promoters from spinach (psaD, psaF, psaE, PC, FNR, atpC, atpD, cab, rbcS). Other photosynthetic tissue promoters include PT0535, PT0668, PT0886, PR0924, YP0144, YP0380, and PT0585.

Inducible Promoters

Inducible promoters confer transcription in response to external stimuli such as chemical agents or environmental stimuli. For example, inducible promoters can confer transcription in response to hormones such as giberellic acid or ethylene, or in response to light or drought. Examples of drought-inducible promoters include YP0380, PT0848, YP0381, YP0337, PT0633, YP0374, PT0710, YP0356, YP0385, YP0396, YP0388, YP0384, PT0688, YP0286, YP0377, PD1367, PD0901, and PD0898. Nitrogen-inducible promoters include PT0863, PT0829, PT0665, and PT0886. An example of a shade-inducible promoter is PR0924.

Basal Promoters

A basal promoter is the minimal sequence necessary for assembly of a transcription complex required for transcription initiation. Basal promoters frequently include a "TATA box" element that may be located between about 15 and about 35 nucleotides upstream from the site of transcription initiation. Basal promoters also may include a "CCAAT box" element (typically the sequence CCAAT) and/or a GGGCG sequence, which can be located between about 40 and about 200 nucleotides, typically about 60 to about 120 nucleotides, upstream from the transcription start site.

Other Promoters

Other classes of promoters include, but are not limited to, leaf-preferential, stem/shoot-preferential, callus-preferential, guard cell-preferential, such as PT0678, and senescence-preferential promoters. Promoters designated YP0086, YP01 88, YP0263, PT0758, PT0743, PT0829, YP0119, and YP0096, as described in the above-referenced patent applications, may also be useful.

Other Regulatory Regions

A 5' untranslated region (UTR) can be included in nucleic acid constructs described herein. A 5' UTR is transcribed, but is not translated, and lies between the start site of the transcript and the translation initiation codon and may include the +1 nucleotide. A 3' UTR can be positioned between the translation termination codon and the end of the transcript. UTRs can have particular functions such as increasing mRNA stability or attenuating translation. Examples of 3' UTRs include, but are not limited to, polyadenylation signals and transcription termination sequences, e.g., a nopaline synthase termination sequence.

It will be understood that more than one regulatory region may be present in a recombinant polynucleotide, e.g., introns, enhancers, upstream activation regions, transcription terminators, and inducible elements. Thus, more than one regulatory region can be operably linked to the sequence of a polynucleotide encoding a carbon-modulating polypeptide.

Transgenic Plants and Plant Cells

The invention also features transgenic plant cells and plants comprising at least one recombinant nucleic acid construct described herein. A plant or plant cell can be transformed by having a construct integrated into its genome, i.e., can be stably transformed. Stably transformed cells typically retain the introduced nucleic acid with each cell division. A plant or plant cell can also be transiently transformed such that the construct is not integrated into its genome. Transiently transformed cells typically lose all or some portion of the introduced nucleic acid construct with each cell division such that the introduced nucleic acid cannot be detected in daughter cells after a sufficient number of cell divisions. Both transiently transformed and stably transformed transgenic plants and plant cells can be useful in the methods described herein.

Transgenic plant cells used in methods described herein can constitute part or all of a whole plant. Such plants can be grown in a manner suitable for the species under consideration, either in a growth chamber, a greenhouse, or in a field. Transgenic plants can be bred as desired for a particular purpose, e.g., to introduce a recombinant nucleic acid into other lines, to transfer a recombinant nucleic acid to other species, or for further selection of other desirable traits. Alternatively, transgenic plants can be propagated vegetatively for those species amenable to such techniques. Progeny include descendants of a particular plant or plant line. Progeny of an instant plant include seeds formed on $F_1$, $F_2$, $F_3$, $F_4$, $F_5$, $F_6$ and subsequent generation plants, or seeds formed on $BC_1$, $BC_2$, $BC_3$, and subsequent generation plants, or seeds formed on $F_1BC_1$, $F_1BC_2$, $F_1BC_3$, and subsequent generation plants. The designation $F_1$ refers to the progeny of a cross between two parents that are genetically distinct. The designations $F_2$, $F_3$, $F_4$, $F_5$ and $F_6$ refer to subsequent generations of self- or sib-pollinated progeny of an $F_1$ plant. Seeds produced by a transgenic plant can be grown and then selfed (or outcrossed and selfed) to obtain seeds homozygous for the nucleic acid construct.

Transgenic plants can be grown in suspension culture, or tissue or organ culture. For the purposes of this invention, solid and/or liquid tissue culture techniques can be used. When using solid medium, transgenic plant cells can be placed directly onto the medium or can be placed onto a filter that is then placed in contact with the medium. When using liquid medium, transgenic plant cells can be placed onto a flotation device, e.g., a porous membrane that contacts the liquid medium. Solid medium typically is made from liquid medium by adding agar. For example, a solid medium can be Murashige and Skoog (MS) medium containing agar and a suitable concentration of an auxin, e.g., 2,4-dichlorophenoxyacetic acid (2,4-D), and a suitable concentration of a cytokinin, e.g., kinetin.

When transiently transformed plant cells are used, a reporter sequence encoding a reporter polypeptide having a reporter activity can be included in the transformation procedure and an assay for reporter activity or expression can be performed at a suitable time after transformation. A suitable time for conducting the assay typically is about 1 -21 days after transformation, e.g., about 1-14 days, about 1-7 days, or about 1-3 days. The use of transient assays is particularly convenient for rapid analysis in different species, or to confirm expression of a heterologous carbon-modulating polypeptide whose expression has not previously been confirmed in particular recipient cells.

Techniques for introducing nucleic acids into monocotyledonous and dicotyledonous plants are known in the art, and include, without limitation, Agrobacterium-mediated transformation, viral vector-mediated transformation, electroporation and particle gun transformation, e.g., U.S. Pat. Nos. 5,538,880; 5,204,253; 6,329,571 and 6,013,863. If a cell or cultured tissue is used as the recipient tissue for transformation, plants can be regenerated from transformed cultures if desired, by techniques known to those skilled in the art.

Plant Species

The polynucleotides and vectors described herein can be used to transform a number of monocotyledonous and dicotyledonous plants and plant cell systems, including dicots such as alfalfa, amaranth, apple, beans (including kidney beans, lima beans, dry beans, green beans), broccoli, cabbage, carrot, castor bean, cherry, chick peas, chicory, clover, cocoa, coffee, cotton, crambe, flax, grape, grapefruit, lemon, lentils, lettuce, linseed, mango, melon (e.g., watermelon, cantaloupe), mustard, orange, peach, peanut, pear, peas, pepper, plum, potato, oilseed rape, rapeseed (high erucic acid and canola), safflower, sesame, soybean, spinach, strawberry, sugar beet, sunflower, sweet potatoes, tea, tomato, and yams, as well as monocots such as banana, barley, bluegrass, date palm, fescue, field corn, garlic, millet, oat, oil palm, onion, pineapple, popcorn, rice, rye, ryegrass, sorghum, sudangrass, sugarcane, sweet corn, switchgrass, timothy, and wheat. Brown seaweeds, green seaweeds, red seaweeds, and microalgae can also be used.

Thus, the methods and compositions described herein can be used with dicotyledonous plants belonging, for example, to the orders *Apiales, Arecales, Aristochiales, Asterales, Batales, Campanulales, Capparales, Caryophyllales, Casuarinales, Celastrales, Cornales, Cucurbitales, Diapensales, Dilleniales, Dipsacales, Ebenales, Ericales, Eucomiales, Euphorbiales, Fabales, Fagales, Gentianales, Geraniales, Haloragales, Hamamelidales, Illiciales, Juglandales, Lamiales, Laurales, Lecythidales, Leitneriales, Linales, Magniolales, Malvales, Myricales, Myrtales, Nymphaeales, Papaverales, Piperales, Plantaginales, Plumbaginales, Podostemales, Polemoniales, Polygalales, Polygonales, Primulales, Proteales, Rafflesiales, Ranunculales, Rhamnales, Rosales, Rubiales, Salicales, Santales, Sapindales, Sarraceniaceae, Scrophulariales, Solanales, Trochodendrales, Theales, Umbellales, Urticales*, and *Violales*. The methods and compositions described herein also can be utilized with monocotyledonous plants such as those belonging to the orders *Alismatales, Arales, Arecales, Asparagales, Bromeliales, Commelinales, Cyclanthales, Cyperales, Eriocaulales, Hydrocharitales, Juncales, Liliales, Najadales, Orchidales, Pandanales, Poales, Restionales, Triuridales, Typhales, Zingiberales*, and with plants belonging to *Gymnospermae*, e.g., *Cycadales, Ginkgoales, Gnetales*, and *Pinales*.

The methods and compositions can be used over a broad range of plant species, including species from the dicot genera *Amaranthus, Arachis, Brassica, Calendula, Camellia, Capsicum, Carthamus, Cicer, Cichorium, Cinnamomum, Citrus, Citrullus, Coffea, Crambe, Cucumis, Cucurbita, Daucus, Dioscorea, Fragaria, Glycine, Gossypium, Helianthus, Lactuca, Lens, Linum, Lycopersicon, Malus, Mangifera, Medicago, Mentha, Nicotiana, Ocimum, Olea, Phaseolus, Pistacia, Pisum, Prunus, Pyrus, Rosmarinus, Salvia, Sesamum, Solanum, Spinacia, Theobroma, Thymus, Trifolium, Vaccinium, Vigna*, and *Vitis*; and the monocot genera *Allium, Ananas, Asparagus, Avena, Curcuma, Elaeis, Festuca, Festulolium, Hordeum, Lemna, Lolium, Musa, Oryza, Panicum, Pennisetum, Phleum, Poa, Saccharum, Secale, Sorghum, Triticosecale, Triticum*, and *Zea*; and the gymnosperm genera *Abies, Cunninghamia, Picea, Pinus, Populus*, and *Pseudotsuga*.

The methods and compositions described herein also can be used with brown seaweeds, e.g., *Ascophyllum nodosum, Fucus vesiculosus, Fucus serratus, Himanthalia elongata*, and *Undaria pinnatifida*; red seaweeds, e.g., *Chondrus crispus, Cracilaria verrucosa, Porphyra umbilicalis*, and *Palmariapalmata*; green seaweeds, e.g., *Enteromorpha* spp. and *Ulva* spp.; and microalgae, e.g., *Spirulina* spp. (*S. platensis* and *S. maxima*) and *Odontella aurita*. In addition, the methods and compositions can be used with *Crypthecodinium cohnii, Schizochytrium* spp., and *Haematococcus pluvialis*.

In some embodiments, a plant is a member of the species *Ananus comosus, Brassica campestris, Brassica napus, Brassica oleracea, Glycine max, Gossypium* spp., *Lactuca sativa, Lycopersicon esculentum, Musa paradisiaca, Oryza sativa, Solanum tuberosum, Triticum aestivum, Vitis vinifera*, or *Zea mays*.

Methods of Inhibiting Expression of Carbon-Modulating Polypeptides

The polynucleotides and recombinant vectors described herein can be used to express or inhibit expression of a carbon-modulating polypeptide in a plant species of interest. The term "expression" refers to the process of converting genetic information of a polynucleotide into RNA through transcription, which is catalyzed by an enzyme, RNA polymerase, and into protein, through translation of MRNA on ribosomes. "Up-regulation" or "activation" refers to regulation that increases the production of expression products (MRNA, polypeptide, or both) relative to basal or native states, while "down-regulation" or "repression" refers to regulation that decreases production of expression products (mRNA, polypeptide, or both) relative to basal or native states.

A number of nucleic-acid based methods, including antisense RNA, ribozyme directed RNA cleavage, and interfering RNA (RNAi) can be used to inhibit protein expression in plants. Antisense technology is one well-known method. In this method, a nucleic acid segment from the endogenous gene is cloned and operably linked to a promoter so that the antisense strand of RNA is transcribed. The recombinant vector is then transformed into plants, as described above, and the antisense strand of RNA is produced. The nucleic acid segment need not be the entire sequence of the endogenous gene to be repressed, but typically will be substantially identical to at least a portion of the endogenous gene to be repressed. Generally, higher homology can be used to compensate for the use of a shorter sequence. Typically, a sequence of at least 30 nucleotides is used, e.g., at least 40, 50, 80, 100, 200, 500 nucleotides or more.

Thus, for example, an isolated nucleic acid provided herein can be an antisense nucleic acid to one of the aforementioned nucleic acids encoding a carbon-modulating polypeptide, e.g., SEQ ID NOs:2-20, SEQ ID NOs:22-34, SEQ ID NOs:36-38, SEQ ID NOs:40-43, SEQ ID NO:48, SEQ ID NOs:51-53, SEQ ID NOs:55-65, SEQ ID NOs:67-81, SEQ ID NOs:83-92, or a consensus sequence set forth in FIGS. 1-7. A nucleic acid that decreases the level of a transcription or translation product of a gene encoding a carbon-modulating polypeptide is transcribed into an antisense nucleic acid similar or identical to the sense coding sequence of the carbon-modulating polypeptide. Alternatively, the transcription product of an isolated nucleic acid can be similar or identical to the sense coding sequence of a carbon-modulating polypeptide, but is an RNA that is unpolyadenylated, lacks a 5' cap structure, or contains an unsplicable intron.

In another method, a nucleic acid can be transcribed into a ribozyme, or catalytic RNA, that affects expression of an mRNA. (See, U.S. Pat. No. 6,423,885). Ribozymes can be designed to specifically pair with virtually any target RNA and cleave the phosphodiester backbone at a specific location, thereby functionally inactivating the target RNA. Heterologous nucleic acids can encode ribozymes designed to cleave particular MRNA transcripts, thus preventing expression of a polypeptide. Hammerhead ribozymes are useful for destroying particular mRNAs, although various ribozymes that cleave mRNA at site-specific recognition sequences can be used. Hammerhead ribozymes cleave mRNAs at locations dictated by flanking regions that form complementary base pairs with the target mRNA. The sole requirement is that the target RNA contain a 5'-UG-3' nucleotide sequence. The construction and production of hammerhead ribozymes is known in the art. See, for example, U.S. Pat. No. 5,254,678 and WO 02/46449 and references cited therein. Hammerhead ribozyme sequences can be embedded in a stable RNA such as a transfer RNA (tRNA) to increase cleavage efficiency in vivo. Perriman, et al., *Proc. Natl. Acad. Sci.* USA, 92(13):6175-6179 (1995); de Feyter and Gaudron, Methods in Molecular Biology, Vol. 74, Chapter 43, "Expressing Ribozymes in Plants", Edited by Turner, P. C, Humana Press Inc., Totowa, N.J. RNA endoribonucleases such as the one that occurs naturally in *Tetrahymena thermophila*, and which have been described extensively by Cech and collaborators can be useful. See, for example, U.S. Pat. No. 4,987,071.

Methods based on RNA interference (RNAi) can be used. RNA interference is a cellular mechanism to regulate the expression of genes and the replication of viruses. This mechanism is thought to be mediated by double-stranded small interfering RNA molecules. A cell responds to such a double-stranded RNA by destroying endogenous mRNA having the same sequence as the double-stranded RNA. Methods for designing and preparing interfering RNAs are known to those of skill in the art; see, e.g., WO 99/32619 and WO 01/75164. For example, a construct can be prepared that includes a sequence that is transcribed into an interfering RNA. Such an RNA can be one that can anneal to itself, e.g., a double stranded RNA having a stem-loop structure. One strand of the stem portion of a double stranded RNA comprises a sequence that is similar or identical to the sense coding sequence of the polypeptide of interest, and that is from about 10 nucleotides to about 2,500 nucleotides in length. The length of the sequence that is similar or identical to the sense coding sequence can be from 10 nucleotides to 500 nucleotides, from 15 nucleotides to 300 nucleotides, from 20 nucleotides to 100 nucleotides, or from 25 nucleotides to 100 nucleotides. The other strand of the stem portion of a double stranded RNA comprises an antisense sequence of the carbon-modulating polypeptide of interest, and can have a length that is shorter, the same as, or longer than the corresponding length of the sense sequence. The loop portion of a double stranded RNA can be from 10 nucleotides to 5,000 nucleotides, e.g., from 15 nucleotides to 1,000 nucleotides, from 20 nucleotides to 500 nucleotides, or from 25 nucleotides to 200 nucleotides. The loop portion of the RNA can include an intron. See, e.g., WO 99/53050.

In some nucleic-acid based methods for inhibition of gene expression in plants, a suitable nucleic acid can be a nucleic acid analog. Nucleic acid analogs can be modified at the base moiety, sugar moiety, or phosphate backbone to improve, for example, stability, hybridization, or solubility of the nucleic acid. Modifications at the base moiety include deoxyuridine for deoxythymidine, and 5-methyl-2'-deoxycytidine and 5-bromo-2'-deoxycytidine for deoxycytidine. Modifications of the sugar moiety include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six-membered morpholino ring, or peptide nucleic acids, in which the deoxyphosphate backbone is replaced by a pseudopeptide backbone and the four bases are retained. See, for example, Summerton and Weller, 1997, *Antisense Nucleic Acid Drug Dev*., 7:187-195; Hyrup et al., 1996, *Bioorgan. Med. Chem*., 4: 5-23. In addition, the deoxyphosphate backbone can be replaced with, for example, a phosphorothioate or phosphorodithioate backbone, a phosphoroamidite, or an alkyl phosphotriester backbone.

Transgenic Plant Phenotypes

A transformed cell, callus, tissue, or plant can be identified and isolated by selecting or screening the engineered plant material for particular traits or activities, e.g., those encoded by marker genes or antibiotic resistance genes. Such screening and selection methodologies are well known to those having ordinary skill in the art. In addition, physical and biochemical methods can be used to identify transformants. These include Southern analysis or PCR amplification for detection of a polynucleotide; Northern blots, S1 RNase protection, primer-extension, or RT-PCR amplification for detecting RNA transcripts; enzymatic assays for detecting enzyme or ribozyme activity of polypeptides and polynucleotides; and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the referenced techniques are well known.

Transgenic plants can have an altered phenotype as compared to a corresponding control plant that either lacks the transgene or does not express the transgene. A polypeptide can affect the phenotype of a plant (e.g., a transgenic plant) when expressed in the plant, e.g., at the appropriate time(s), in the appropriate tissue(s), or at the appropriate expression levels. Phenotypic effects can be evaluated relative to a control plant that does not express the exogenous polynucleotide of interest, such as a corresponding wild type plant, a corresponding plant that is not transgenic for the exogenous polynucleotide of interest but otherwise is of the same genetic background as the transgenic plant of interest, or a corresponding plant of the same genetic background in which expression of the polypeptide is suppressed, inhibited, or not induced (e.g., where expression is under the control of an inducible promoter). A plant can be said "not to express" a polypeptide when the plant exhibits less than 10%, e.g., less than 9%, 8%, 7%, 6%, 5%, 4%, 3%, 2%, 1%, 0.5%, 0.1%, 0.01%, or 0.001%, of the amount of polypeptide or MRNA encoding the polypeptide exhibited by the plant of interest. Expression can be evaluated using methods including, for example, RT-PCR, Northern blots, S1 RNase protection, primer extensions, Western blots, protein gel electrophoresis, immunoprecipitation, enzyme-linked immunoassays, chip assays, and mass spectrometry. It should be noted that if a polypeptide is expressed under the control of a tissue-specific or broadly expressing promoter, expression can be evaluated in the entire plant or in a selected tissue. Similarly, if a polypeptide is expressed at a particular time, e.g., at a particular time in development or upon induction, expression can be evaluated selectively at a desired time period.

In some embodiments, a plant in which expression of a carbon-modulating polypeptide is modulated can have increased levels of seed carbon. For example, a carbon-modulating polypeptide described herein can be expressed in a transgenic plant, resulting in increased levels of seed carbon. The seed carbon level can be increased by at least 2 percent, e.g., 2, 3, 4, 5, 6, 7, 8, 9, 10, 11, 12, 13, 14, 15, 16, 17, 18, 19, 20, 25, 30, 35, 40, 45, or more than 45 percent, as compared to the seed carbon level in a corresponding control plant that does not express the transgene. In some embodiments, a plant in which expression of a carbon-modulating polypeptide is modulated can have decreased levels of seed carbon. The seed carbon level can be decreased by at least 2 percent, e.g., 2, 3, 4, 5, 10, 15, 20, 25, 30, 35, or more than 35 percent, as compared to the seed carbon level in a corresponding control plant that does not express the transgene.

Plants for which modulation of levels of seed carbon can be useful include, without limitation, alfalfa, lettuce, carrot, onion, broccoli, tomato, potato, sugarcane, grape, cotton, canola, sweet corn, popcorn, field corn, peas, beans, safflower, soybean, coffee, amaranth, rapeseed, peanut, sunflower, oil palm, corn, clover, wheat, rye, barley, oat, rice, millet, strawberry, pineapple, melon, peach, pear, apple, cherry, orange, lemon, grapefruit, plum, mango, banana, clover, sudangrass, switchgrass, and sorghum. Increases in seed carbon in such plants can provide increased oil, carbohydrate, and/or caloric content in geographic locales where caloric intake is problematic. Decreases in seed carbon in such plants can be useful in situations where caloric intake should be restricted.

In some embodiments, a plant in which expression of a carbon-modulating polypeptide is modulated can have increased or decreased levels of fixed carbon in one or more non-seed tissues, e.g., leaf tissues, stem tissues, root or corm tissues, or fruit tissues other than seed. For example, the carbon level can be increased by at least 2 percent, e.g., 2, 3, 4, 5, 10, 15, 20, 25, 30, 35, 40, 45, or more than 45 percent, as compared to the carbon level in a corresponding control plant that does not express the transgene. In some embodiments, a plant in which expression of a carbon-modulating polypeptide is modulated can have decreased levels of fixed carbon in one or more non-seed tissues. The carbon level can be decreased by at least 2 percent, e.g., 2, 3, 4, 5, 10, 15, 20, 25, 30, 35, or more than 35 percent, as compared to the carbon level in a corresponding control plant that does not express the transgene.

Plants for which modulation of levels of fixed carbon in non-seed tissues can be useful include, without limitation, alfalfa, lettuce, carrot, onion, broccoli, tomato, potato, peanut, sugarcane, sudangrass, grape, timothy, strawberry, pineapple, melon, peach, pear, apple, cherry, orange, lemon, grapefruit, plum, mango, banana, grand fir, balsam fir, yellow pine, jack pine, loblolly pine, white pine, blue spruce, poplar, fescue, ryegrass, bluegrass and switchgrass. Increases in non-seed carbon in such plants can provide improved renewable energy sources; increased oil, carbohydrate, and/or caloric content in edible plants; increased production of building materials; or increased production of animal forage.

In some embodiments, a plant in which expression of a carbon-modulating polypeptide having an amino acid sequence corresponding to SEQ ID NO:22, SEQ ID NO:36, SEQ ID NO:40, SEQ ID NO:55, or SEQ ID NO:67 is modulated can have decreased levels of seed nitrogen accompanying increased levels of seed carbon. The nitrogen level can be decreased by at least 5 percent, e.g., 5, 10, 15, 20, 25, 30, 35, or 40 percent, as compared to the nitrogen level in a corresponding control plant that does not express the transgene.

In another embodiment, a plant in which expression of a carbon-modulating polypeptide having an amino acid sequence corresponding to SEQ ID NO:83 is modulated can have an increased seed nitrogen level accompanying an increased seed carbon level. The nitrogen level can be increased by at least 5 percent, e.g., 5, 10, 15, 20, 25, or 30 percent, as compared to the nitrogen level in a corresponding control plant that does not express the transgene.

Typically, a difference (e.g., an increase) in the amount of carbon or nitrogen in a transgenic plant or cell relative to a control plant or cell is considered statistically significant at $p \leqq 0.05$ with an appropriate parametric or non-parametric statistic, e.g., Chi-square test, Student's t-test, Mann-Whitney test, or F-test. In some embodiments, a difference in the amount of carbon or nitrogen is statistically significant at $p<0.01$, $p<0.005$, or $p<0.001$. A statistically significant difference in, for example, the amount of carbon in a transgenic plant compared to the amount in cells of a control plant indicates that (1) the recombinant nucleic acid present in the transgenic plant results in altered carbon levels and/or (2)

the recombinant nucleic acid warrants further study as a candidate for altering the amount of carbon in a plant.

Articles of Manufacture

Also provided herein are articles of manufacture that comprise seeds from transgenic plants provided herein. The seeds can be conditioned using means known in the art and packaged using packaging material well known in the art to prepare an article of manufacture. A package of seed can have a label e.g., a tag or label secured to the packaging material, a label printed on the packaging material or a label inserted within the package. The label can indicate that plants grown from the seeds contained within the package can produce a crop having an altered level of carbon relative to corresponding control plants.

The invention will be further described in the following examples, which do not limit the scope of the invention described in the claims.

EXAMPLES

Example 1

Transgenic Plants

The following symbols are used in the Examples: $T_1$: first generation transformant; $T_2$: second generation, progeny of self-pollinated $T_1$ plants; $T_3$: third generation, progeny of self-pollinated $T_2$ plants; $T_4$: fourth generation, progeny of self-pollinated $T_3$ plants. Independent transformations are referred to as events.

The following is a list of nucleic acids that were isolated from *Arabidopsis thaliana* ecotype Wassilewskija (Ws) plants. Ceres cDNA ID 3080447 (SEQ ID NO:1) is a cDNA clone that is predicted to encode a 502 amino acid (SEQ ID NO:2) nitrate transporter (NRT2.5) polypeptide. Ceres cDNA ID 1828694 (SEQ ID NO:21) is a genomic DNA clone that is predicted to encode a 514 amino acid (SEQ ID NO:22) ammonium transporter (AMT1;2) polypeptide. Ceres cDNA ID 3086062 (SEQ ID NO:35) is a cDNA clone that is predicted to encode a 557 amino acid (SEQ ID NO:36) putative transporter polypeptide. Ceres cDNA ID 3091277 (SEQ ID NO:39) is a cDNA clone that is predicted to encode a 589 amino acid (SEQ ID NO:40) proton-dependent oligopeptide transport (POT) family polypeptide. Ceres cDNA ID 2997404 (SEQ ID NO:54) is a genomic DNA clone that is predicted to encode a 466 amino acid (SEQ ID NO:55) putative transporter polypeptide. Ceres cDNA ID 4904707 (SEQ ID NO:66) is a cDNA clone that is predicted to encode a 442 amino acid (SEQ ID NO:67) proline transporter 1 (ProT1) polypeptide. Ceres cDNA ID 5669462 (SEQ ID NO:82) is a genomic DNA clone that is predicted to encode a 276 amino acid (SEQ ID NO:83) anthranilate synthase beta chain polypeptide.

Each isolated nucleic acid described above was cloned into a vector containing a phosphinothricin acetyltransferase gene, which confers Finale™ resistance to transformed plants. NB42-35S binary vectors were constructed that contained Ceres cDNA ID 3080447, Ceres cDNA ID 1828694, Ceres cDNA ID 3086062, Ceres cDNA ID 3091277, or Ceres cDNA ID 2997404 operably linked to the cauliflower mosaic virus (CaMV) 35S regulatory region. The NB42-35S binary vector is a derivative of the pMOG800 binary vector. A Ti plasmid vector, CRS 338, was constructed that contained Ceres cDNA ID 4904707 operably linked to the CaMV 35S regulatory region. Another CRS 338 vector was constructed containing Ceres cDNA ID 5669462 operably linked to a regulatory region set forth in SEQ ID NO:93.

Wild-type *Arabidopsis thaliana* ecotype C24 plants were transformed separately with each NB42-35S binary vector containing Ceres cDNA ID 3080447, Ceres cDNA ID 1828694, Ceres cDNA ID 3086062, Ceres cDNA ID 3091277, or Ceres cDNA ID 2997404. Wild-type *Arabidopsis thaliana* ecotype Ws plants were transformed separately with each Ti plasmid vector containing Ceres cDNA ID 4904707 or Ceres cDNA ID 5669462. The transformations were performed essentially as described in Bechtold et al., *C. R. Acad. Sci. Paris*, 316:1194-1199 (1993).

Transgenic *Arabidopsis* lines containing Ceres cDNA ID 3080447, Ceres cDNA ID 1828694, Ceres cDNA ID 3086062, Ceres cDNA ID 3091277, Ceres cDNA ID 2997404, Ceres cDNA ID 4904707, or Ceres cDNA ID 5669462 were designated SR00882, SR05002, SR05003, SR05004, SR05005, ME06182, or ME08125, respectively. The presence of the Ceres cDNA ID 3080447 vector in SR00882, the Ceres cDNA ID 1828694 vector in SR05002, the Ceres cDNA ID 3086062 vector in SE05003, the Ceres cDNA ID 3091277 vector in SR05004, the Ceres cDNA ID 2997404 vector in SR05005, the Ceres cDNA ID 4904707 vector in ME06182, and the Ceres cDNA ID 5669462 vector in ME08125 was confirmed by Finale™ resistance, polymerase chain reaction (PCR) amplification from green leaf tissue extract, and sequencing of PCR products. As controls for transgenic *Arabidopsis ecotype C*24 plants, wild-type *Arabidopsis* ecotype C24 plants were transformed with the empty vector NB42-35S. As controls for transgenic *Arabidopsis* ecotype Ws plants, wild-type *Arabidopsis* ecotype Ws plants were transformed with the empty vector CRS 338.

The in planta nucleotide sequences of Ceres cDNA ID 3080447, Ceres cDNA ID 1828694, Ceres cDNA ID 3086062, Ceres cDNA ID 3091277, Ceres cDNA ID 2997404, Ceres cDNA ID 4904707, and Ceres cDNA ID 5669462 were compared to the homologous *Arabidopsis* ecotype Columbia sequences. The in planta sequence of Ceres cDNA ID 1828694 differed from the homologous Columbia sequence by six single nucleotide polymorphisms (SNPs) that resulted in two amino acid changes. The in planta sequence of Ceres cDNA ID 3086062 differed from the homologous Columbia sequence by 20 SNPs that resulted in nine amino acid changes. The in planta sequences of Ceres cDNA ID 3080447, Ceres cDNA ID 3091277, and Ceres cDNA ID 5669462 matched the homologous Columbia sequences. The in planta sequence of Ceres cDNA ID 2997404 differed from the homologous Columbia sequence in that it contained a nucleotide insertion near the 3' end, which resulted in a frameshift and a premature stop codon. The in planta nucleotide sequence of Ceres cDNA ID 4904707 differed from the Columbia sequence by four SNPs that did not result in any amino acid changes.

Transgenic *Arabidopsis* lines were screened as follows: 1) $T_1$ candidates in the greenhouse were screened for morphological phenotypes, 2) $T_2$ seeds were analyzed for carbon and nitrogen content, 3) increased carbon and/or nitrogen content was confirmed in $T_3$ seeds, and 4) $T_2$ plants were evaluated for negative phenotypes and Finale™ segregation.

Five events of each of SR00882, SR05002, SR05003, SR05004, and SR05005, and ten events of each of ME06182 and ME08125 were screened for visible phenotypic alterations in the $T_1$ generation. The physical appearance of all of the $T_1$ plants was identical to that of the corresponding control plants.

Example 2

Analysis of Carbon and Nitrogen content in Transgenic *Arabidopsis* Seeds

Approximately 2.00±0.15 mg of dried transgenic *Arabidopsis* seeds (about 100 seeds) were weighed into a tin cup and analyzed for total carbon and nitrogen content. Three matched controls were prepared in a manner identical to the experimental samples and spaced evenly throughout the batch. The first three samples in every batch were a blank (empty tin cup), bypass, (approximately 5 mg of aspartic acid), and a standard (5.00±0.15 mg aspartic acid), respectively. Aspartic acid was weighed into a tin cup using an analytical balance. Blanks were entered between every 15 experimental samples.

Analysis was completed using a FlashEA 1112 NC Analyzer (Thermo Finnigan, San Jose, Calif.). The instrument parameters were as follows: left firnace 900° C., right furnace 840° C., oven 50° C., gas flow carrier 130 mL/min., and gas flow reference 100 mL/min. The data parameter LLOD was 0.25 mg for the standard and different for other materials. The data parameter LLOQ was 3 mg for the standard, 1 mg for seed tissue, and different for other materials.

Instrument maintenance and performance management included removal of ashes after every 85 analyses, change of oxidation catalyst in the left (reaction) chamber after every 1000 analyses, change of copper in the right (copper reduction) chamber after every 375 analyses, and change of $Mg(ClO_4)_2$ after every 250 analyses, or more often if the samples had moisture in them.

Quantification was performed using EA 1112 software. The results were normalized and expressed in absolute percentages. Each sample was analyzed in triplicate, and the standard deviation was calculated. Non-transgenic controls were previously determined to have a total carbon content of 53.3±2.4% and a total nitrogen content of 3.9±0.3%. The deviation from theoretical of the aspartic acid standard was ±2.0% for carbon and ±1.0% for nitrogen. To be declared valid, each run was required to have an aspartic acid (standard) weight of 5 mg±0.15 mg, and the blank(s) were required to have no recorded nitrogen or carbon content. The percent standard deviation between replicate samples was required to be below 10%.

Example 3

Results for SR00882 Events $T_2$ and $T_3$ seeds from two events of SR00882 containing Ceres cDNA ID 3080447 were analyzed for total carbon and nitrogen content as described in Example 2.

The carbon content of $T_2$ seeds from two events of SR00882 was significantly increased compared to the carbon content of corresponding control seeds. As presented in Table 1, the carbon content was increased to 112% in seeds from events −02 and −03 compared to the carbon content in control seeds.

TABLE 1

| | Total carbon content (% control) of $T_2$ and $T_3$ seeds from SR00882 events | | |
|---|---|---|---|
| | Event -02 | Event -03 | Control |
| $T_2$ | 112 ± 3 | 112 ± 6 | 100 ± 3 |
| p-value | <0.01 | 0.04 | NA |
| $T_3$ | 117 ± 6 | 112 ± 5 | 100 ± 2 |
| p-value | 0.03 | 0.04 | NA |

The carbon content of $T_3$ seeds from two events of SR00882 was significantly increased compared to the carbon content of corresponding control seeds. As presented in Table 1, the carbon content was increased to 117% and 112% in seeds from events −02 and −03, respectively, compared to the carbon content in control seeds.

The nitrogen content of $T_2$ and $T_3$ seeds from SR00882 events was not observed to differ significantly from the nitrogen content of corresponding control seeds.

$T_3$ seeds from SR00882 events analyzed for carbon and nitrogen content were collected from one $T_2$ plant from each event.

The segregation of Finale™ resistance in $T_2$ plants from events −02 and −03 of SR00882 was a 3:1 ratio of resistant to sensitive.

There were no observable or statistically significant differences between $T_2$ SR00882 and control plants in germination, onset of flowering, rosette area, fertility, plant height, and general morphology/architecture.

Example 4

Results for SR05002 Events $T_2$ and $T_3$ seeds from three events of SR05002 containing Ceres cDNA ID 1828694 were analyzed for total carbon and nitrogen content as described in Example 2.

The carbon content of $T_2$ seeds from three events of SR05002 was significantly increased compared to the carbon content of corresponding control seeds. As presented in Table 2, the carbon content was increased to 108%, 110%, and 108% in seeds from events −01, −03, and −06, respectively, compared to the carbon content in control seeds.

TABLE 2

| | Total carbon content (% control) of $T_2$ and $T_3$ seeds from SR05002 events | | | |
|---|---|---|---|---|
| | Event -01 | Event -03 | Event -06 | Control |
| $T_2$ | 108 ± 2 | 110 ± 1 | 108 ± 2 | 100 ± 2 |
| p-value | 0.01 | <0.01 | 0.01 | NA |
| $T_3$ | 107 ± 2 | 111 ± 3 | 109 ± 4 | 100 ± 2 |
| p-value | 0.02 | 0.01 | 0.02 | NA |

The nitrogen content of $T_2$ seeds from three events of SR05002 was significantly decreased compared to the nitrogen content of corresponding control seeds. As presented in Table 3, the nitrogen content was decreased to 85%, 90%, and 86% in seeds from events −01, −03, and −06, respectively, compared to the nitrogen content in control seeds.

TABLE 3

| | Total nitrogen content (% control) of $T_2$ and $T_3$ seeds from SR05002 events | | | |
|---|---|---|---|---|
| | Event -01 | Event -03 | Event -06 | Control |
| $T_2$ | 85 ± 3 | 90 ± 2 | 86 ± 2 | 100 ± 1 |
| p-value | <0.01 | <0.01 | <0.01 | NA |
| $T_3$ | 87 ± 1 | 101 ± 3 | 91 ± 4 | 100 ± 2 |
| p-value | <0.01 | 0.65 | 0.01 | NA |

The carbon content of $T_3$ seeds from three events of SR05002 was significantly increased compared to the carbon content of corresponding control seeds. As presented in Table 2, the carbon content was increased to 107%, 111%, and 109% in seeds from events −01, −03, and −06, respectively, compared to the carbon content in control seeds.

The nitrogen content of $T_3$ seeds from two events of SR05002 was significantly decreased compared to the nitrogen content of corresponding control seeds. As presented in Table 3, the nitrogen content was decreased to 87% and 91% in seeds from events −01 and −06, respectively, compared to the nitrogen content in control seeds.

$T_3$ seeds from SR05002 events analyzed for carbon and nitrogen content were collected from one $T_2$ plant from each event.

The segregation of Finale resistance in $T_2$ plants from events −01, −03, and −06 of SR05002 was a 3:1 ratio of resistant to sensitive.

There were no observable or statistically significant differences between $T_2$ SR05002 and control plants in germination, onset of flowering, rosette area, fertility, seed size, and general morphology/architecture.

Example 5

Results for SR05003 Events $T_2$ and $T_3$ seeds from two events of SR05003 containing Ceres cDNA ID 3086062 were analyzed for total carbon and nitrogen content as described in Example 2.

The carbon content of $T_2$ seeds from two events of SR05003 was significantly increased compared to the carbon content of corresponding control seeds. As presented in Table 4, the carbon content was increased to 107% and 103% in seeds from events −01 and −04, respectively, compared to the carbon content in control seeds.

TABLE 4

| | Total carbon content (% control) of $T_2$ and $T_3$ seeds from SR05003 events | | |
|---|---|---|---|
| | Event -01 | Event -04 | Control |
| $T_2$ | 107 ± 4 | 103 ± 1 | 100 ± 1 |
| p-value | 0.03 | 0.03 | NA |
| $T_3$ | 108 ± 3 | 107 ± 2 | 100 ± 3 |
| p-value | 0.01 | <0.01 | NA |

The nitrogen content of $T_2$ seeds from two events of SR05003 was significantly decreased compared to the nitrogen content of corresponding control seeds. As presented in Table 5, the nitrogen content was decreased to 89% in seeds from events −01 and −04 compared to the nitrogen content in control seeds.

TABLE 5

| | Total nitrogen content (% control) of $T_2$ and $T_3$ seeds from SR05003 events | | |
|---|---|---|---|
| | Event -01 | Event -04 | Control |
| $T_2$ | 89 ± 1 | 89 ± 0 | 100 ± 4 |
| p-value | 0.02 | 0.01 | NA |
| $T_3$ | 81 ± 2 | 92 ± 4 | 100 ± 4 |
| p-value | <0.01 | <0.01 | NA |

The carbon content of $T_3$ seeds from two events of SR05003 was significantly increased compared to the carbon content of corresponding control seeds. As presented in Table 4, the carbon content was increased to 108% and 107% in seeds from events −01 and −04, respectively, compared to the carbon content in control seeds.

The nitrogen content of $T_3$ seeds from two events of SR05003 was significantly decreased compared to the nitrogen content of corresponding control seeds. As presented in Table 5, the nitrogen content was decreased to 81% and 92% in seeds from events −01 and −04, respectively, compared to the nitrogen content in control seeds.

$T_3$ seeds from SR05003 events analyzed for carbon and nitrogen content were collected from one $T_2$ plant from each event.

The segregation of Finale™ resistance in $T_2$ plants from events −01 and −04 of SR05003 was a 3:1 ratio of resistant to sensitive.

There were no observable or statistically significant differences between $T_2$ SR05003 and control plants in germination, onset of flowering, rosette area, fertility, seed size, and general morphology/architecture.

Example 6

Results for SR05004 Events $T_2$ and $T_3$ seeds from two events of SR05004 containing Ceres cDNA ID 3091277 were analyzed for total carbon and nitrogen content as described in Example 2.

The carbon content of $T_2$ seeds from two events of SR05004 was significantly increased compared to the carbon content of corresponding control seeds. As presented in Table 6, the carbon content was increased to 122% and 115% in seeds from events −01 and −02, respectively, compared to the carbon content in control seeds.

TABLE 6

| | Total carbon content (% control) of $T_2$ and $T_3$ seeds from SR05004 events | | |
|---|---|---|---|
| | Event -01 | Event -02 | Control |
| $T_2$ | 122 ± 4 | 115 ± 1 | 100 ± 4 |
| p-value | <0.01 | <0.01 | NA |
| $T_3$ | 107 ± 2 | 108 ± 6 | 100 ± 2 |
| p-value | 0.01 | 0.04 | NA |

The nitrogen content of $T_2$ seeds from one event of SR05004 was significantly decreased compared to the nitrogen content of corresponding control seeds. As presented in Table 7, the nitrogen content was decreased to 74% in seeds from event −02 compared to the nitrogen content in control seeds.

TABLE 7

| | Total nitrogen content (% control) of $T_2$ and $T_3$ seeds from SR05004 events | | |
|---|---|---|---|
| | Event -01 | Event -02 | Control |
| $T_2$ | 93 ± 4 | 74 ± 2 | 100 ± 5 |
| p-value | 0.12 | <0.01 | NA |
| $T_3$ | 101 ± 1 | 87 ± 6 | 100 ± 3 |
| p-value | 0.73 | 0.01 | NA |

The carbon content of $T_3$ seeds from two events of SR05004 was significantly increased compared to the carbon content of corresponding control seeds. As presented in Table 6, the carbon content was increased to 107% and 108% in seeds from events −01 and −02, respectively, compared to the carbon content in control seeds.

The nitrogen content of $T_3$ seeds from one event of SR05004 was significantly decreased compared to the nitrogen content of corresponding control seeds. As presented in Table 7, the nitrogen content was decreased to 87% in seeds from event −02 compared to the nitrogen content in control seeds.

$T_3$ seeds from SR05004 events analyzed for carbon and nitrogen content were collected from one $T_2$ plant from each event.

The segregation of Finale™ resistance in $T_2$ plants from events −01 and −02 of SR05004 was a 3:1 ratio of resistant to sensitive.

There were no observable or statistically significant differences between $T_2$ SR05004 and control plants in germination, onset of flowering, rosette area, fertility, seed size, and general morphology/architecture.

Example 7

Results for SR05005 Events $T_2$ and $T_3$ seeds from two events of SR05005 containing Ceres cDNA ID 2997404 were analyzed for total carbon and nitrogen content as described in Example 2.

The carbon content of $T_2$ seeds from two events of SR05005 was significantly increased compared to the carbon content of corresponding control seeds. As presented in Table 8, the carbon content was increased to 114% and 105% in seeds from events −01 and −04, respectively, compared to the carbon content in control seeds.

TABLE 8

| | Total carbon content (% control) of $T_2$ and $T_3$ seeds from SR05005 events | | |
|---|---|---|---|
| | Event -01 | Event -04 | Control |
| $T_2$ | 114 ± 1 | 105 ± 2 | 100 ± 2 |
| p-value | <0.01 | 0.05 | NA |
| $T_3$ | 104 ± 1 | 105 ± 2 | 100 ± 2 |
| p-value | 0.02 | 0.03 | NA |

The nitrogen content of $T_2$ seeds from two events of SR05005 was significantly decreased compared to the nitrogen content of corresponding control seeds. As presented in Table 9, the nitrogen content was decreased to 85% and 84% in seeds from events −01 and −04, respectively, compared to the nitrogen content in control seeds.

TABLE 9

| | Total nitrogen content (% control) of $T_2$ and $T_3$ seeds from SR05005 events | | |
|---|---|---|---|
| | Event -01 | Event -04 | Control |
| $T_2$ | 85 ± 4 | 84 ± 2 | 100 ± 4 |
| p-value | 0.01 | <0.01 | NA |
| $T_3$ | 92 ± 2 | 95 ± 2 | 100 ± 4 |
| p-value | 0.04 | 0.16 | NA |

The carbon content of $T_3$ seeds from two events of SR05005 was significantly increased compared to the carbon content of corresponding control seeds. As presented in Table 8, the carbon content was increased to 104% and 105% in seeds from events −01 and −04, respectively, compared to the carbon content in control seeds.

The nitrogen content of $T_3$ seeds from one event of SR05005 was significantly decreased compared to the nitrogen content of corresponding control seeds. As presented in Table 9, the nitrogen content was decreased to 92% in seeds from event −01 compared to the nitrogen content in control seeds.

$T_3$ seeds from SR05005 events analyzed for carbon and nitrogen content were collected from one $T_2$ plant from each event.

The segregation ratio of Finale™ resistance in $T_2$ plants from events −01 and −04 of SR05005 was 3:1 resistant to sensitive.

There were no observable or statistically significant differences between $T_2$ SR05005 and control plants in germination, onset of flowering, rosette area, fertility, seed size, and general morphology/architecture.

Example 8

Results for ME06182 Events $T_2$ and $T_3$ seeds from two events of ME06182 containing Ceres cDNA ID 4904707 were analyzed for total carbon and nitrogen content as described in Example 2.

The carbon content of $T_2$ seeds from two events of ME06182 was significantly increased compared to the carbon content of corresponding control seeds. As presented in Table 10, the carbon content was increased to 104% in seeds from events −02 and −03 compared to the carbon content in control seeds.

TABLE 10

| | Total carbon content (% control) of $T_2$ and $T_3$ seeds from ME06182 events | | |
|---|---|---|---|
| | Event -02 | Event -03 | Control |
| $T_2$ | 104 ± 2 | 104 ± 1 | 100 ± 1 |
| p-value | 0.02 | <0.01 | NA |
| $T_3$ | 105 ± 1 | 106 ± 2 | 100 ± 1 |
| p-value | <0.01 | <0.01 | NA |

The nitrogen content of $T_2$ seeds from two events of ME06182 was significantly decreased compared to the nitrogen content of corresponding control seeds. As presented in Table 11, the nitrogen content was decreased to 77% and 87% in seeds from events −02 and −03, respectively, compared to the nitrogen content in control seeds.

TABLE 11

| Total nitrogen content (% control) of $T_2$ and $T_3$ seeds from ME06182 events | | | |
|---|---|---|---|
| | Event -02 | Event -03 | Control |
| $T_2$ | 77 ± 2 | 87 ± 2 | 100 ± 3 |
| p-value | <0.01 | <0.01 | NA |
| $T_3$ | 94 ± 2 | 98 ± 2 | 100 ± 2 |
| p-value | 0.03 | 0.28 | NA |

The carbon content of $T_3$ seeds from two events of ME06182 was significantly increased compared to the carbon content of corresponding control seeds. As presented in Table 10, the carbon content was increased to 105% and 106% in seeds from events −02 and −03, respectively, compared to the carbon content in control seeds.

The nitrogen content of $T_3$ seeds from one event of ME06182 was significantly decreased compared to the nitrogen content of corresponding control seeds. As presented in Table 11, the nitrogen content was decreased to 94% in seeds from event −02 compared to the nitrogen content in control seeds.

$T_3$ seeds from ME06182 events analyzed for carbon and nitrogen content were collected from one $T_2$ plant from each event.

The segregation of Finale™ resistance in $T_2$ plants from events −02 and −03 of ME06182 was a 3:1 ratio of resistant to sensitive.

There were no observable or statistically significant differences between $T_2$ ME06182 and control plants in germination, onset of flowering, rosette area, fertility, and general morphology/architecture.

Example 9

Results for ME08125 Events $T_2$ and $T_3$ seeds from two events of ME08125 containing Ceres cDNA ID 5669462 were analyzed for total carbon and nitrogen content as described in Example 2.

The carbon content of $T_2$ seeds from two events of ME08125 was significantly increased compared to the carbon content of corresponding control seeds. As presented in Table 12, the carbon content was increased to 104% in seeds from events −03 and −04 compared to the carbon content in control seeds.

TABLE 12

| Total carbon content (% control) of $T_2$ and $T_3$ seeds from ME08125 events | | | |
|---|---|---|---|
| | Event -03 | Event -04 | Control |
| $T_2$ | 104 ± 1 | 104 ± 1 | 100 ± 1 |
| p-value | <0.01 | 0.02 | NA |
| $T_3$ | 105 ± 1 | 103 ± 1 | 100 ± 1 |
| p-value | <0.01 | 0.04 | NA |

The nitrogen content of $T_2$ seeds from two events of ME08125 was significantly increased compared to the nitrogen content of corresponding control seeds. As presented in Table 13, the nitrogen content was increased to 116% and 112% in seeds from events −03 and −04, respectively, compared to the nitrogen content in control seeds.

TABLE 13

| Total nitrogen content (% control) of $T_2$ and $T_3$ seeds from ME08125 events | | | |
|---|---|---|---|
| | Event -03 | Event -04 | Control |
| $T_2$ | 116 ± 2 | 112 ± 3 | 100 ± 2 |
| p-value | <0.01 | <0.01 | NA |
| $T_3$ | 101 ± 2 | 103 ± 3 | 100 ± 1 |
| p-value | 0.56 | 0.13 | NA |

The carbon content of $T_3$ seeds from two events of ME08125 was significantly increased compared to the carbon content of corresponding control seeds. As presented in Table 12, the carbon content was increased to 105% and 103% in seeds from events −03 and −04, respectively, compared to the carbon content in control seeds.

The nitrogen content of $T_3$ seeds from two events of ME08125 was not observed to differ significantly from the nitrogen content of corresponding control seeds (Table 13).

$T_3$ seeds from ME08125 events analyzed for carbon and nitrogen content were collected from one $T_2$ plant from each event.

The segregation of Finale™ resistance in $T_2$ plants from events −03 and −04 of ME08125 was a 3:1 ratio of resistant to sensitive.

There were no observable or statistically significant differences between $T_2$ ME08125 and control plants in germination, onset of flowering, rosette area, fertility, and general morphology/architecture.

Example 10

Determination of Functional Homolog and/or Ortholog Sequences

A subject sequence was considered a functional homolog or ortholog of a query sequence if the subject and query sequences encoded proteins having a similar function and/or activity. A process known as Reciprocal BLAST (Rivera et al., *Proc. Natl. Acad. Sci.* USA, 95:6239-6244 (1998)) was used to identify potential functional homolog and/or ortholog sequences from databases consisting of all available public and proprietary peptide sequences, including NR from NCBI and peptide translations from Ceres clones.

Before starting a Reciprocal BLAST process, a specific query polypeptide was searched against all peptides from its source species using BLAST in order to identify polypeptides having sequence identity of 80% or greater to the query polypeptide and an alignment length of 85% or greater along the shorter sequence in the alignment. The query polypeptide and any of the aforementioned identified polypeptides were designated as a cluster.

The main Reciprocal BLAST process consists of two rounds of BLAST searches; forward search and reverse search. In the forward search step, a query polypeptide sequence, "polypeptide A," from source species SA was BLASTed against all protein sequences from a species of interest. Top hits were determined using an E-value cutoff of 10-5 and an identity cutoff of 35%. Among the top hits, the sequence having the lowest E-value was designated as the best hit, and considered a potential functional homolog or ortholog. Any other top hit that had a sequence identity of 80% or greater to the best hit or to the original query polypeptide was considered a potential functional homolog or ortholog as well. This process was repeated for all species of interest.

In the reverse search round, the top hits identified in the forward search from all species were BLASTed against all protein sequences from the source species SA. A top hit from the forward search that returned a polypeptide from the aforementioned cluster as its best hit was also considered as a potential functional homolog or ortholog.

Functional homologs and/or orthologs were identified by manual inspection of potential functional homolog and/or ortholog sequences. Representative functional homologs and/or orthologs for SEQ ID NO:2, SEQ ID NO:22, SEQ ID NO:36, SEQ ID NO:40, SEQ ID NO:55, SEQ ID NO:67, and SEQ ID NO:83 are shown in FIGS. 1-7, respectively. The percent identities of functional homologs and/or orthologs to SEQ ID NO:2, SEQ ID NO:22, SEQ ID NO:36, SEQ ID NO:40, SEQ ID NO:55, SEQ ID NO:67, and SEQ ID NO:83 are shown below in Tables 14-20, respectively.

TABLE 14

Percent identity to Ceres cDNA ID 3080447 (SEQ ID NO: 2)

| Designation | Species | SEQ ID NO: | % Identity | e-value |
|---|---|---|---|---|
| gi\|57283317 | *Populus tremula* × *Populus tremuloides* | 3 | 74.9 | 0 |
| CeresClone: 1545993 | *Zea mays* | 4 | 67.3 | 0 |
| gi\|34911556 | *Oryza sativa* subsp. *japonica* | 5 | 65.8 | 0 |
| gi\|3005576 | *Glycine max* | 6 | 61.3 | 0 |
| gi\|37999150 | *Physcomitrella patens* | 7 | 61 | 0 |
| gi\|37999148 | *Physcomitrella patens* | 8 | 60.6 | 0 |
| gi\|37999154 | *Physcomitrella patens* | 9 | 60.4 | 0 |
| gi\|9931082 | *Brassica napus* | 10 | 60 | 0 |
| gi\|39573544 | *Prunus persica* | 11 | 59.9 | 0 |
| gi\|38636547 | *Prunus persica* | 12 | 59.7 | 0 |
| gi\|13539545 | *Lotus japonicus* | 13 | 59.7 | 0 |
| gi\|15990600 | *Triticum aestivum* | 14 | 59.3 | 0 |
| gi\|4731146 | *Hordeum vulgare* subsp. *vulgare* | 15 | 59.3 | 0 |
| gi\|1680655 | *Hordeum vulgare* subsp. *vulgare* | 16 | 59.2 | 0 |
| gi\|9858859 | *Triticum aestivum* | 17 | 59 | 0 |
| gi\|13345827 | *Triticum aestivum* | 18 | 58.8 | 0 |
| gi\|4731148 | *Hordeum vulgare* subsp. *vulgare* | 19 | 58.8 | 0 |
| gi\|37999156 | *Physcomitrella patens* | 20 | 58.7 | 0 |

TABLE 15

Percent identity to Ceres cDNA ID 1828694 (SEQ ID NO: 22)

| Designation | Species | SEQ ID NO: | % Identity | e-value |
|---|---|---|---|---|
| gi\|57283313 | *Populus tremula* × *Populus tremuloides* | 24 | 81.4 | 0 |
| gi\|2065194 | *Lycopersicon esculentum* | 23 | 81.4 | 0 |
| gi\|31322044 | *Lotus japonicus* | 25 | 80.7 | 0 |
| gi\|50910611 | *Oryza sativa* subsp. *japonica* | 26 | 79.9 | 0 |
| gi\|50428339 | *Camellia sinensis* | 27 | 79.3 | 0 |
| gi\|15705368 | *Oryza sativa* | 28 | 77.3 | 0 |
| gi\|52550773 | *Oryza sativa* subsp. *japonica* | 29 | 77.1 | 0 |
| gi\|22001520 | *Lycopersicon esculentum* | 30 | 76.8 | 0 |
| gi\|50926368 | *Oryza sativa* subsp. *japonica* | 31 | 76.7 | 0 |
| gi\|38684027 | *Triticum aestivum* | 32 | 75.7 | 0 |
| gi\|11066960 | *Brassica napus* | 33 | 75.2 | 0 |
| gi\|50910607 | *Oryza sativa* subsp. *japonica* | 34 | 72.7 | 0 |

TABLE 16

Percent identity to Ceres cDNA ID 3086062 (SEQ ID NO: 36)

| Designation | Species | SEQ ID NO: | % Identity | e-value |
|---|---|---|---|---|
| CeresClone: 1002997 | *Arabidopsis thaliana* | 37 | 83.2 | 0 |
| gi\|47900739 | *Solanum demissum* | 38 | 50.2 | 0 |

TABLE 17

Percent identity to Ceres cDNA ID 3091277 (SEQ ID NO: 40)

| Designation | Species | SEQ ID NO: | % Identity | e-value |
|---|---|---|---|---|
| gi\|50912139 | *Oryza sativa* subsp. *japonica* | 41 | 63.5 | 0 |
| gi\|50911647 | *Oryza sativa* subsp. *japonica* | 42 | 61.4 | 0 |
| gi\|54290524 | *Oryza sativa* subsp. *japonica* | 43 | 51.2 | 0 |
| gi\|48675345 | *Prunus persica* | 48 | 41.4 | 3E−100 |
| gi\|47717628 | *Triticum aestivum* | 51 | 38.8 | 2.6E−101 |
| gi\|9581817 | *Nicotiana plumbaginifolia* | 52 | 38.8 | 1.9E−98 |
| gi\|28273094 | *Nicotiana tabacum* | 53 | 38.4 | 8.1E−98 |

TABLE 18

Percent identity to Ceres cDNA ID 2997404 (SEQ ID NO: 55)

| Designation | Species | SEQ ID NO: | % Identity | e-value |
|---|---|---|---|---|
| gi\|15391731 | *Cucumis sativus* | 56 | 36.2 | 2.1E−58 |
| CeresClone: 1144139 | *Arabidopsis thaliana* | 57 | 81.9 | 0 |
| gi\|54291818 | *Oryza sativa* subsp. *japonica* | 58 | 42.5 | 1.3E−81 |
| gi\|34905798 | *Oryza sativa* subsp. *japonica* | 59 | 42.8 | 1.8E−75 |
| gi\|47900739 | *Solanum demissum* | 60 | 46.7 | 5.8E−104 |
| gi\|15391731_T | Artificial Sequence | 61 | 34.43 | 3.70E−64 |
| CeresClone: 1144139_T | Artificial Sequence | 62 | 80.55 | 1.60E−189 |
| gi\|54291818_T | Artificial Sequence | 63 | 39.73 | 2.30E−87 |
| gi\|34905798_T | Artificial Sequence | 64 | 39.81 | 3.20E−81 |
| gi\|47900739_T | Artificial Sequence | 65 | 45.35 | 1.00E−109 |

TABLE 19

Percent identity to Ceres cDNA ID 4904707 (SEQ ID NO: 67)

| Designation | Species | SEQ ID NO: | % Identity | e-value |
|---|---|---|---|---|
| gi\|28393251 | *Arabidopsis thaliana* | 68 | 91 | 8.9E−210 |
| gi\|21554196 | *Arabidopsis thaliana* | 69 | 90.6 | 1.1E−209 |
| CeresClone: 20959 | *Arabidopsis thaliana* | 70 | 90.6 | 1.1E−209 |
| gi\|31376371 | *Arabidopsis thaliana* | 71 | 85 | 6.2E−202 |
| CeresClone: 526395 | *Glycine max* | 72 | 73.6 | 2.2E−174 |
| gi\|21069018 | *Avicennia marina* | 73 | 71.8 | 2.3E−172 |
| gi\|8571474 | *Atriplex hortensis* | 74 | 71.7 | 2.8E−167 |
| gi\|50933631 | *Oryza sativa* subsp. *japonica* | 75 | 70.8 | 1.5E−168 |
| gi\|53749423 | *Oryza sativa* subsp. *japonica* | 76 | 69.1 | 1.2E−164 |
| gi\|4584852 | *Lycopersicon esculentum* | 77 | 69 | 1.9E−166 |

TABLE 19-continued

| Percent identity to Ceres cDNA ID 4904707 (SEQ ID NO: 67) | | | | |
|---|---|---|---|---|
| Designation | Species | SEQ ID NO: | % Identity | e-value |
| gi\|16215723 | *Hordeum vulgare* subsp. *vulgare* | 78 | 66.7 | 2.1E−162 |
| gi\|4584848 | *Lycopersicon esculentum* | 79 | 66.7 | 3E−161 |
| gi\|4584850 | *Lycopersicon esculentum* | 80 | 65.2 | 1.4E−158 |
| gi\|21069016 | *Avicennia marina* | 81 | 65.1 | 1.7E−158 |

TABLE 20

| Percent identity to Ceres cDNA ID 5669462 (SEQ ID NO: 83) | | | | |
|---|---|---|---|---|
| Designation | Species | SEQ ID NO: | % Identity | e-value |
| gi\|21594026 | *Arabidopsis thaliana* | 84 | 94.9 | 1.5E−134 |
| CeresClone: 6495 | *Arabidopsis thaliana* | 85 | 94.9 | 1.5E−134 |
| gi\|9758358 | *Arabidopsis thaliana* | 86 | 94.5 | 1.1E−133 |
| CeresClone: 967151 | *Brassica napus* | 87 | 85.1 | 8.7E−116 |
| CeresClone: 214246 | *Zea mays* | 88 | 76.6 | 1.8E−85 |

TABLE 20-continued

| Percent identity to Ceres cDNA ID 5669462 (SEQ ID NO: 83) | | | | |
|---|---|---|---|---|
| Designation | Species | SEQ ID NO: | % Identity | e-value |
| CeresClone: 257290 | *Zea mays* | 89 | 76.6 | 2.3E−85 |
| CeresClone: 341958 | *Zea mays* | 90 | 76.6 | 2.3E−85 |
| CeresClone: 686561 | *Triticum aestivum* | 91 | 75.1 | 1.2E−84 |
| gi\|50918343 | *Oryza sativa* subsp. *japonica* | 92 | 72.1 | 8.3E−88 |

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of increasing the level of carbon in a plant, said method comprising introducing into a plant cell an exogenous nucleic acid comprising a nucleotide sequence encoding a polypeptide having 90 percent or greater sequence identity to the amino acid sequence set forth in SEQ ID NO:2, wherein said polypeptide has nitrate transporter activity, and growing said plant cell into a plant, wherein the plant expresses said nucleotide sequence and has an increased level of carbon as compared to the corresponding level in a control plant that does not comprise said nucleic acid.

2. The method of claim 1, wherein said exogenous nucleic acid is operably linked to a regulatory region.

3. The method of claim 2, wherein said regulatory region is a promoter selected from the group consisting of YP0092, PT0676, PT0708, PT0613, PT0672, PT0678, PT0688, PT0837, the napin promoter, the Arcelin-5 promoter, the phaseolin gene promoter, the soybean trypsin inhibitor promoter, the ACP promoter, the stearoyl-ACP desaturase gene, the soybean α' subunit of β-conglycinin promoter, the oleosin promoter, the 15 kD zein promoter, the 16 kD zein promoter, the 19 kD zein promoter, the 22 kD zein promoter, the 27 kD zein promoter, the Osgt-1 promoter, the beta-amylase gene promoter, and the barley hordein gene promoter.

4. A method of producing a plant, said method comprising growing a plant comprising an exogenous nucleic acid comprising a nucleotide sequence encoding a polypeptide having 90 percent or greater sequence identity to the amino acid sequence set forth in SEQ ID NO:2, wherein said polypeptide has nitrate transporter activity, and wherein said plant expresses said nucleotide sequence and has an increased level of carbon as compared to the corresponding level in a control plant that does not comprise said nucleic acid.

5. A plant produced according to the method of any one of claims 1, 2, 3, or 4.

6. The method of claim 1, wherein said plant produces seeds, and wherein said seeds comprise and express said exogenous nucleic acid and have an increased level of carbon as compared to seeds of a control plant that do not comprise said nucleic acid.

7. The method of claim 1, wherein the vegetative tissue of said plant comprises and expresses said exogenous nucleic acid and has an increased level of carbon as compared to the vegetative tissue of a control plant that does not comprise said nucleic acid.

8. The method of claim 4, wherein said plant produces seeds, and wherein said seeds comprise and express said exogenous nucleic acid and have an increased level of carbon as compared to seeds of a control plant that do not comprise said nucleic acid.

9. The method of claim 4, wherein the vegetative tissue of said plant comprises and expresses said exogenous nucleic acid and has an increased level of carbon as compared to vegetative tissue of a control plant that does not comprise said nucleic acid.

10. The method of claim 4, wherein said exogenous nucleic acid is operably linked to a regulatory region.

11. The method of claim 10, wherein said regulatory region is a promoter selected from the group consisting of YP0092, PT0676, PT0708, PT0613, PT0672, PT0678, PT0688, PT0837, the napin promoter, the Arcelin-5 promoter, the phaseolin gene promoter, the soybean trypsin inhibitor promoter, the ACP promoter, the stearoyl-ACP desaturase gene, the soybean α' subunit of β-conglycinin promoter, the oleosin promoter, the 15 kD zein promoter, the 16 kD zein promoter, the 19 kD zein promoter, the 22 kD zein promoter, the 27 kD zein promoter, the Osgt-1 promoter, the beta-amylase gene promoter, and the barley hordein gene promoter.

* * * * *

SEQUENCE LISTING

```
<160> NUMBER OF SEQ ID NOS: 100

<210> SEQ ID NO 1
<211> LENGTH: 1509
<212> TYPE: DNA
<213> ORGANISM: Arabidopsis thaliana
<220> FEATURE:
<221> NAME/KEY: misc_feature
<222> LOCATION: (1)..(1509)
<223> OTHER INFORMATION: Ceres CDNA ID no. 3080447
<220> FEATURE:
<221> NAME/KEY: CDS
<222> LOCATION: (1)..(1506)
<223> OTHER INFORMATION: Referenced by SEQ ID NO: 2

<400> SEQUENCE: 1

atggaggtcg aaggcaaagg aggagaagct ggaaccacca ccacaaccgc acctcggagg      60

ttcgcacttc cggtggacgc ggagaacaaa gcaacaactt tccgactatt ctcagtcgct     120

aaacctcaca tgagagcttt ccatctctca tggtttcaat tcttttgctg cttcgtctcc     180

actttcgcag ctccgcctct cctccctgtt atccgtgaaa atcttaacct caccgccacc     240

gacatcggaa acgccggaat agcctctgtc tccggcgctg ttttcgctcg tatcgtcatg     300

ggcacggcat gtgatctttt cggtccacgt ctagcctccg ccgctttgac gctctccacc     360

gctcccgccg tctatttcac cgccgggata aagtctccga tcgggtttat catggtgaga     420

ttcttcgccg gattctctct cgccactttc gtctcgactc agttctggat gagctccatg     480

ttctctggac ccgtcgtggg ttcggctaac ggaatcgccg ccgggtgggg taacctcgga     540

ggaggcgcga cgcagctgat catgcccatc gtgttctcgt tgattcgtaa tatgggagcc     600
```

-continued

```
accaagttca ccgcgtggag gatcgctttt ttcatccccg gtctctttca gactctctct    660

gctttcgccg ttctcttgtt cggtcaggat cttcctgatg gagattattg ggcgatgcat    720

aaatctggag agagggagaa agatgatgtg gggaaagtga tatctaatgg aatcaaaaac    780

tataggggat ggataacagc attagcatat ggctattgtt ttggagtaga gcttaccatt    840

gacaacatca tcgcagaata tttcttcgat agattccatt taaagctcca gacagcaggg    900

attatagcag cgagttttgg actagccaat tttttcgcta gacctggagg aggaattttc    960

tctgatttta tgtcgagacg gtttgggatg agaggaaggt tgtgggcttg gtggattgtg   1020

caaacatcag gaggtgtatt atgcgcatgt cttggccaga tttcttcctt gacagtgtct   1080

ataattgtta tgcttgtctt ctctgtattc gtccaagccg cttgtggact tacctttggc   1140

gttgttccct ttatttctag aagatctctt ggggtggtat cgggaatgac tggtgcggga   1200

ggcaatgtag gcgcggtctt aacacagttg atattcttca aggatcgac atacacgaga    1260

gagacgggta taactctaat gggggtaatg tcaatcgcat gttcattacc aatatgcttg   1320

atttactttc cgcaatgggg aggtatgttt tgtggaccct cttccaaaaa agtaactgaa   1380

gaagactatt atctcgccga atggaacgat gaagagaaag aaaagaactt acatatcgga   1440

agccaaaaat ttgcggaaac cagcattagc gaaagaggtc gagccacaac gactcatccc   1500

caaacttga                                                           1509
```

<210> SEQ ID NO 2
<211> LENGTH: 502
<212> TYPE: PRT
<213> ORGANISM: Arabidopsis thaliana
<220> FEATURE:
<221> NAME/KEY: misc_feature
<222> LOCATION: (50)..(412)
<223> OTHER INFORMATION: Pfam Name: MFS_1; Pfam Description: Major
      Facilitator Superfamily

<400> SEQUENCE: 2

```
Met Glu Val Glu Gly Lys Gly Gly Glu Ala Gly Thr Thr Thr Thr Thr
1               5                   10                  15

Ala Pro Arg Arg Phe Ala Leu Pro Val Asp Ala Glu Asn Lys Ala Thr
            20                  25                  30

Thr Phe Arg Leu Phe Ser Val Ala Lys Pro His Met Arg Ala Phe His
        35                  40                  45

Leu Ser Trp Phe Gln Phe Phe Cys Cys Phe Val Ser Thr Phe Ala Ala
    50                  55                  60

Pro Pro Leu Leu Pro Val Ile Arg Glu Asn Leu Asn Leu Thr Ala Thr
65                  70                  75                  80

Asp Ile Gly Asn Ala Gly Ile Ala Ser Val Ser Gly Ala Val Phe Ala
                85                  90                  95

Arg Ile Val Met Gly Thr Ala Cys Asp Leu Phe Gly Pro Arg Leu Ala
            100                 105                 110

Ser Ala Ala Leu Thr Leu Ser Thr Ala Pro Ala Val Tyr Phe Thr Ala
        115                 120                 125

Gly Ile Lys Ser Pro Ile Gly Phe Ile Met Val Arg Phe Phe Ala Gly
    130                 135                 140

Phe Ser Leu Ala Thr Phe Val Ser Thr Gln Phe Trp Met Ser Ser Met
145                 150                 155                 160

Phe Ser Gly Pro Val Val Gly Ser Ala Asn Gly Ile Ala Ala Gly Trp
                165                 170                 175

Gly Asn Leu Gly Gly Gly Ala Thr Gln Leu Ile Met Pro Ile Val Phe
```

```
            180                 185                 190

Ser Leu Ile Arg Asn Met Gly Ala Thr Lys Phe Thr Ala Trp Arg Ile
        195                 200                 205

Ala Phe Phe Ile Pro Gly Leu Phe Gln Thr Leu Ser Ala Phe Ala Val
    210                 215                 220

Leu Leu Phe Gly Gln Asp Leu Pro Asp Gly Asp Tyr Trp Ala Met His
225                 230                 235                 240

Lys Ser Gly Glu Arg Glu Lys Asp Asp Val Gly Lys Val Ile Ser Asn
                245                 250                 255

Gly Ile Lys Asn Tyr Arg Gly Trp Ile Thr Ala Leu Ala Tyr Gly Tyr
            260                 265                 270

Cys Phe Gly Val Glu Leu Thr Ile Asp Asn Ile Ile Ala Glu Tyr Phe
        275                 280                 285

Phe Asp Arg Phe His Leu Lys Leu Gln Thr Ala Gly Ile Ile Ala Ala
    290                 295                 300

Ser Phe Gly Leu Ala Asn Phe Phe Ala Arg Pro Gly Gly Gly Ile Phe
305                 310                 315                 320

Ser Asp Phe Met Ser Arg Arg Phe Gly Met Arg Gly Arg Leu Trp Ala
                325                 330                 335

Trp Trp Ile Val Gln Thr Ser Gly Gly Val Leu Cys Ala Cys Leu Gly
            340                 345                 350

Gln Ile Ser Ser Leu Thr Val Ser Ile Ile Val Met Leu Val Phe Ser
        355                 360                 365

Val Phe Val Gln Ala Ala Cys Gly Leu Thr Phe Gly Val Val Pro Phe
    370                 375                 380

Ile Ser Arg Arg Ser Leu Gly Val Val Ser Gly Met Thr Gly Ala Gly
385                 390                 395                 400

Gly Asn Val Gly Ala Val Leu Thr Gln Leu Ile Phe Phe Lys Gly Ser
                405                 410                 415

Thr Tyr Thr Arg Glu Thr Gly Ile Thr Leu Met Gly Val Met Ser Ile
            420                 425                 430

Ala Cys Ser Leu Pro Ile Cys Leu Ile Tyr Phe Pro Gln Trp Gly Gly
        435                 440                 445

Met Phe Cys Gly Pro Ser Ser Lys Lys Val Thr Glu Glu Asp Tyr Tyr
    450                 455                 460

Leu Ala Glu Trp Asn Asp Glu Glu Lys Glu Lys Asn Leu His Ile Gly
465                 470                 475                 480

Ser Gln Lys Phe Ala Glu Thr Ser Ile Ser Glu Arg Gly Arg Ala Thr
                485                 490                 495

Thr Thr His Pro Gln Thr


<210> SEQ ID NO 3
<211> LENGTH: 508
<212> TYPE: PRT
<213> ORGANISM: Populus tremula x Populus tremuloides
<220> FEATURE:
<221> NAME/KEY: misc_feature
<222> LOCATION: (1)..(508)
<223> OTHER INFORMATION: Public GI no. 57283317

<400> SEQUENCE: 3

Met Glu Ile Glu Gly Gln Ala Thr Val Lys Glu Ser Gln Pro Pro Lys
1               5                   10                  15

Phe Ala Leu Pro Val Asp Ser Glu His Lys Ala Thr Glu Phe Arg Leu
            20                  25                  30
```

-continued

```
Phe Ser Val Ala Ala Pro His Met Arg Ala Phe His Leu Ser Trp Val
        35                  40                  45

Ser Phe Phe Ala Cys Phe Val Ser Ser Phe Ala Ala Pro Pro Leu Leu
    50                  55                  60

Pro Ile Ile Arg Asp Asn Leu Asn Leu Thr Ala Ser Asp Ile Gly Asn
65                  70                  75                  80

Ala Gly Ile Ala Ser Val Ser Gly Ala Val Phe Ala Arg Val Ala Met
                85                  90                  95

Gly Thr Ala Cys Asp Leu Phe Gly Pro Arg Leu Ala Ser Ala Ser Leu
            100                 105                 110

Ile Leu Leu Thr Ala Pro Ala Val Tyr Phe Thr Ser Met Ala Ser Ser
        115                 120                 125

Ser Thr Ser Phe Leu Leu Val Arg Phe Phe Thr Gly Phe Ser Leu Ala
    130                 135                 140

Thr Phe Val Ser Thr Gln Phe Trp Met Ser Ser Met Phe Ser Ala Pro
145                 150                 155                 160

Val Val Gly Thr Ala Asn Gly Val Ala Gly Gly Trp Gly Asn Leu Gly
                165                 170                 175

Gly Gly Ala Thr Gln Leu Ile Met Pro Leu Val Phe Gly Leu Ile Arg
            180                 185                 190

Asp Ile Gly Ala Ile Lys Phe Thr Ala Trp Arg Ile Ala Phe Phe Ile
        195                 200                 205

Pro Ala Leu Phe Gln Thr Leu Ser Ala Phe Ala Val Leu Ile Phe Gly
    210                 215                 220

Lys Asp Leu Pro Asp Gly Asn Phe Arg Arg Leu Gln Lys Ala Gly Asp
225                 230                 235                 240

Lys Thr Lys Asp Lys Phe Ser Asn Val Phe Tyr His Gly Ile Lys Asn
                245                 250                 255

Tyr Arg Gly Trp Ile Leu Ala Leu Ser Tyr Gly Tyr Cys Phe Gly Val
            260                 265                 270

Glu Leu Thr Ile Asp Asn Ile Val Ala Glu Tyr Phe Tyr Asp Arg Phe
        275                 280                 285

Asp Leu Lys Leu His Thr Ala Gly Met Ile Ala Ala Ser Phe Gly Leu
    290                 295                 300

Ala Asn Ile Val Ser Arg Pro Gly Gly Gly Met Ile Ser Asp Ala Val
305                 310                 315                 320

Gly Lys Arg Phe Gly Met Arg Gly Lys Leu Trp Ala Leu Trp Val Val
                325                 330                 335

Gln Thr Leu Gly Gly Val Phe Cys Ile Ile Leu Gly Arg Val Gly Ser
            340                 345                 350

Leu Gly Ala Ser Ile Val Val Met Ile Val Phe Phe Leu Phe Cys Gln
        355                 360                 365

Ala Ala Cys Gly Leu Thr Phe Gly Val Val Pro Phe Val Ser Arg Arg
    370                 375                 380

Ser Leu Gly Leu Ile Ser Gly Met Thr Gly Gly Gly Gly Asn Val Gly
385                 390                 395                 400

Ala Val Leu Thr Gln Leu Ile Phe Phe Arg Gly Ser Lys Tyr Ser Lys
                405                 410                 415

Glu Arg Gly Ile Met Leu Met Gly Val Met Ile Ile Cys Cys Thr Leu
            420                 425                 430

Pro Ile Cys Leu Ile His Phe Pro Gln Trp Gly Gly Met Phe Cys Gly
        435                 440                 445

Pro Ser Ser Thr Lys Ile Ala Thr Glu Glu Asp Tyr Tyr Leu Ser Glu
```

-continued

```
    450                 455                 460

Trp Asn Ser Glu Glu Lys Glu Lys Gly Leu His Leu Ser Ser Leu Lys
465                 470                 475                 480

Phe Ala Asp Asn Ser Arg Ser Glu Arg Gly Arg Lys Glu Asp Ser Glu
                485                 490                 495

Thr Arg Pro Val Asp Glu Thr Leu Ser Thr Lys Val
            500                 505


<210> SEQ ID NO 4
<211> LENGTH: 520
<212> TYPE: PRT
<213> ORGANISM: Zea mays
<220> FEATURE:
<221> NAME/KEY: misc_feature
<222> LOCATION: (1)..(520)
<223> OTHER INFORMATION: Ceres CLONE ID no. 1545993

<400> SEQUENCE: 4

Met Ala Glu Gly Glu Phe Lys Pro Ala Ala Met Gln Val Glu Ala Pro
1               5                   10                  15

Ala Glu Ala Ala Ala Ala Pro Ser Lys Pro Arg Phe Arg Met Pro Val
            20                  25                  30

Asp Ser Asp Asn Lys Ala Thr Glu Phe Trp Leu Phe Ser Phe Ala Arg
        35                  40                  45

Pro His Met Ser Ala Phe His Met Ser Trp Phe Ser Phe Phe Cys Cys
    50                  55                  60

Phe Leu Ser Thr Phe Ala Ala Pro Pro Leu Leu Pro Leu Ile Arg Asp
65                  70                  75                  80

Thr Leu Gly Leu Thr Ala Thr Asp Ile Gly Asn Ala Gly Ile Ala Ser
                85                  90                  95

Val Ser Gly Ala Val Phe Ala Arg Val Ala Met Gly Thr Ala Cys Asp
            100                 105                 110

Leu Val Gly Pro Arg Leu Ala Ser Ala Ala Ile Ile Leu Leu Thr Thr
        115                 120                 125

Pro Ala Val Tyr Tyr Ser Ala Val Ile Asp Ser Ala Ser Ser Tyr Leu
    130                 135                 140

Leu Val Arg Phe Phe Thr Gly Phe Ser Leu Ala Ser Phe Val Ser Thr
145                 150                 155                 160

Gln Phe Trp Met Ser Ser Met Phe Ser Pro Pro Lys Val Gly Leu Ala
                165                 170                 175

Asn Gly Val Ala Gly Gly Trp Gly Asn Leu Gly Gly Gly Ala Val Gln
            180                 185                 190

Leu Ile Met Pro Leu Val Phe Glu Ala Ile Arg Lys Ala Gly Ala Thr
        195                 200                 205

Pro Phe Thr Ala Trp Arg Val Ala Phe Phe Val Pro Gly Leu Leu Gln
    210                 215                 220

Thr Leu Ser Ala Val Ala Val Leu Ala Phe Gly Gln Asp Met Pro Asp
225                 230                 235                 240

Gly Asn Tyr Arg Lys Leu His Arg Ser Gly Asp Met His Lys Asp Ser
                245                 250                 255

Phe Gly Asn Val Leu Arg His Ala Val Thr Asn Tyr Arg Ala Trp Ile
            260                 265                 270

Leu Ala Leu Thr Tyr Gly Tyr Cys Phe Gly Val Glu Leu Ala Val Asp
        275                 280                 285

Asn Ile Val Ala Gln Tyr Phe Tyr Asp Arg Phe Gly Val Lys Leu Ser
    290                 295                 300
```

```
Thr Ala Gly Phe Ile Ala Ala Ser Phe Gly Met Ala Asn Ile Val Ser
305                 310                 315                 320

Arg Pro Gly Gly Gly Leu Leu Ser Asp Trp Leu Ser Ser Arg Phe Gly
                325                 330                 335

Met Arg Gly Arg Leu Trp Gly Leu Trp Val Val Gln Thr Ile Gly Gly
            340                 345                 350

Val Leu Cys Val Val Leu Gly Ala Val Asp Tyr Ser Phe Ala Ala Ser
        355                 360                 365

Val Ala Val Met Ile Leu Phe Ser Met Phe Val Gln Ala Ala Cys Gly
    370                 375                 380

Leu Thr Phe Gly Ile Val Pro Phe Val Ser Arg Arg Ser Leu Gly Leu
385                 390                 395                 400

Ile Ser Gly Met Thr Gly Gly Gly Gly Asn Val Gly Ala Val Leu Thr
                405                 410                 415

Gln Leu Ile Phe Phe His Gly Ser Lys Tyr Lys Thr Glu Thr Gly Ile
            420                 425                 430

Lys Tyr Met Gly Phe Met Ile Ile Ala Cys Thr Leu Pro Ile Thr Leu
        435                 440                 445

Ile Tyr Phe Pro Gln Trp Gly Gly Met Phe Leu Gly Pro Arg Pro Gly
    450                 455                 460

Ala Thr Ala Glu Asp Tyr Tyr Asn Arg Glu Trp Thr Ala His Glu Cys
465                 470                 475                 480

Asp Lys Gly Phe Asn Thr Ala Ser Val Arg Phe Ala Glu Asn Ser Val
                485                 490                 495

Arg Glu Gly Gly Arg Ser Gly Ser Gln Ser Lys His Thr Thr Val Pro
            500                 505                 510

Val Glu Ser Ser Pro Ala Asp Val
        515                 520
```

```
<210> SEQ ID NO 5
<211> LENGTH: 516
<212> TYPE: PRT
<213> ORGANISM: Oryza sativa (japonica cultivar-group)
<220> FEATURE:
<221> NAME/KEY: misc_feature
<222> LOCATION: (1)..(516)
<223> OTHER INFORMATION: Public GI no. 34911556

<400> SEQUENCE: 5

Met Glu Ala Lys Pro Val Ala Met Glu Val Glu Gly Val Glu Ala Ala
1               5                   10                  15

Gly Gly Lys Pro Arg Phe Arg Met Pro Val Asp Ser Asp Leu Lys Ala
            20                  25                  30

Thr Glu Phe Trp Leu Phe Ser Phe Ala Arg Pro His Met Ala Ser Phe
        35                  40                  45

His Met Ala Trp Phe Ser Phe Phe Cys Cys Phe Val Ser Thr Phe Ala
    50                  55                  60

Ala Pro Pro Leu Leu Pro Leu Ile Arg Asp Thr Leu Gly Leu Thr Ala
65                  70                  75                  80

Thr Asp Ile Gly Asn Ala Gly Ile Ala Ser Val Ser Gly Ala Val Phe
                85                  90                  95

Ala Arg Leu Ala Met Gly Thr Ala Cys Asp Leu Val Gly Pro Arg Leu
            100                 105                 110

Ala Ser Ala Ser Leu Ile Leu Leu Thr Thr Pro Ala Val Tyr Cys Ser
        115                 120                 125
```

-continued

```
Ser Ile Ile Gln Ser Pro Ser Gly Tyr Leu Leu Val Arg Phe Phe Thr
    130                 135                 140

Gly Ile Ser Leu Ala Ser Phe Val Ser Ala Gln Phe Trp Met Ser Ser
145                 150                 155                 160

Met Phe Ser Ala Pro Lys Val Gly Leu Ala Asn Gly Val Ala Gly Gly
                165                 170                 175

Trp Gly Asn Leu Gly Gly Gly Ala Val Gln Leu Leu Met Pro Leu Val
            180                 185                 190

Tyr Glu Ala Ile His Lys Ile Gly Ser Thr Pro Phe Thr Ala Trp Arg
        195                 200                 205

Ile Ala Phe Phe Ile Pro Gly Leu Met Gln Thr Phe Ser Ala Ile Ala
    210                 215                 220

Val Leu Ala Phe Gly Gln Asp Met Pro Gly Gly Asn Tyr Gly Lys Leu
225                 230                 235                 240

His Lys Thr Gly Asp Met His Lys Asp Ser Phe Gly Asn Val Leu Arg
                245                 250                 255

His Ala Leu Thr Asn Tyr Arg Gly Trp Ile Leu Ala Leu Thr Tyr Gly
            260                 265                 270

Tyr Ser Phe Gly Val Glu Leu Thr Ile Asp Asn Val Val His Gln Tyr
        275                 280                 285

Phe Tyr Asp Arg Phe Asp Val Asn Leu Gln Thr Ala Gly Leu Ile Ala
    290                 295                 300

Ala Ser Phe Gly Met Ala Asn Ile Ile Ser Arg Pro Gly Gly Gly Leu
305                 310                 315                 320

Leu Ser Asp Trp Leu Ser Ser Arg Tyr Gly Met Arg Gly Arg Leu Trp
                325                 330                 335

Gly Leu Trp Thr Val Gln Thr Ile Gly Gly Val Leu Cys Val Val Leu
            340                 345                 350

Gly Ile Val Asp Phe Ser Phe Ala Ala Ser Val Ala Val Met Val Leu
        355                 360                 365

Phe Ser Phe Phe Val Gln Ala Ala Cys Gly Leu Thr Phe Gly Ile Val
    370                 375                 380

Pro Phe Val Ser Arg Arg Ser Leu Gly Leu Ile Ser Gly Met Thr Gly
385                 390                 395                 400

Gly Gly Gly Asn Val Gly Ala Val Leu Thr Gln Tyr Ile Phe Phe His
                405                 410                 415

Gly Thr Lys Tyr Lys Thr Glu Thr Gly Ile Lys Tyr Met Gly Leu Met
            420                 425                 430

Ile Ile Ala Cys Thr Leu Pro Val Met Leu Ile Tyr Phe Pro Gln Trp
        435                 440                 445

Gly Gly Met Leu Val Gly Pro Arg Lys Gly Ala Thr Ala Glu Glu Tyr
    450                 455                 460

Tyr Ser Arg Glu Trp Ser Asp His Glu Arg Glu Lys Gly Phe Asn Ala
465                 470                 475                 480

Ala Ser Val Arg Phe Ala Glu Asn Ser Val Arg Glu Gly Gly Arg Ser
                485                 490                 495

Ser Ala Asn Gly Gly Gln Pro Arg His Thr Val Pro Val Asp Ala Ser
            500                 505                 510

Pro Ala Gly Val
        515
```

<210> SEQ ID NO 6
<211> LENGTH: 530
<212> TYPE: PRT

-continued

<213> ORGANISM: Glycine max
<220> FEATURE:
<221> NAME/KEY: misc_feature
<222> LOCATION: (1)..(530)
<223> OTHER INFORMATION: Public GI no. 3005576

<400> SEQUENCE: 6

Met Ala Glu Ile Glu Gly Ser Pro Gly Ser Ser Met His Gly Val Thr
1               5                   10                  15

Gly Arg Glu Gln Thr Phe Val Ala Ser Val Ala Ser Pro Ile Val Pro
            20                  25                  30

Thr Asp Thr Thr Ala Lys Phe Ala Leu Pro Val Asp Ser Glu His Lys
        35                  40                  45

Ala Lys Val Phe Lys Leu Phe Ser Leu Ala Asn Pro His Met Arg Thr
    50                  55                  60

Phe His Leu Ser Trp Ile Ser Phe Phe Thr Cys Phe Val Ser Thr Phe
65                  70                  75                  80

Ala Ala Ala Pro Leu Val Pro Ile Ile Arg Asp Asn Leu Asn Leu Thr
                85                  90                  95

Lys Ser Asp Ile Gly Asn Ala Gly Val Ala Ser Val Ser Gly Ser Ile
            100                 105                 110

Phe Ser Arg Leu Ala Met Gly Ala Val Cys Asp Met Leu Gly Pro Arg
        115                 120                 125

Tyr Gly Cys Ala Phe Leu Ile Met Leu Ser Ala Pro Thr Val Phe Cys
    130                 135                 140

Met Ser Phe Val Lys Asp Ala Ala Gly Tyr Ile Ala Val Arg Phe Leu
145                 150                 155                 160

Ile Gly Phe Ser Leu Ala Thr Phe Val Ser Cys Gln Tyr Trp Met Ser
                165                 170                 175

Thr Met Phe Asn Ser Lys Ile Ile Gly Leu Ala Asn Gly Thr Ala Ala
            180                 185                 190

Gly Trp Gly Asn Met Gly Gly Gly Ala Thr Gln Leu Ile Met Pro Leu
        195                 200                 205

Val Tyr Glu Leu Ile Arg Arg Ala Gly Ala Thr Pro Phe Thr Ala Trp
    210                 215                 220

Arg Ile Ala Phe Phe Val Pro Gly Phe Met His Val Ile Met Gly Ile
225                 230                 235                 240

Leu Val Leu Thr Leu Gly Gln Asp Leu Pro Asp Gly Asn Leu Gly Ala
                245                 250                 255

Leu Arg Lys Lys Gly Asp Val Ala Lys Asp Lys Phe Ser Lys Val Leu
            260                 265                 270

Trp Tyr Ala Ile Thr Asn Tyr Arg Thr Trp Ile Phe Ala Leu Leu Tyr
        275                 280                 285

Gly Tyr Ser Met Gly Val Glu Leu Thr Thr Asp Asn Val Ile Ala Glu
    290                 295                 300

Tyr Phe Tyr Asp Arg Phe Asn Leu Lys Leu His Thr Ala Gly Ile Ile
305                 310                 315                 320

Ala Ala Ser Phe Gly Met Ala Asn Leu Val Ala Arg Pro Phe Gly Gly
                325                 330                 335

Tyr Ala Ser Asp Val Ala Ala Arg Leu Phe Gly Met Arg Gly Arg Leu
            340                 345                 350

Trp Thr Leu Trp Ile Leu Gln Thr Leu Gly Gly Val Phe Cys Ile Trp
        355                 360                 365

Leu Gly Arg Ala Asn Ser Leu Pro Ile Ala Val Leu Ala Met Ile Leu
    370                 375                 380

```
Phe Ser Ile Gly Ala Gln Ala Ala Cys Gly Ala Thr Phe Gly Ile Ile
385                 390                 395                 400

Pro Phe Ile Ser Arg Arg Ser Leu Gly Ile Ile Ser Gly Leu Thr Gly
                405                 410                 415

Ala Gly Gly Asn Phe Gly Ser Gly Leu Thr Gln Leu Val Phe Phe Ser
            420                 425                 430

Thr Ser Lys Phe Ser Thr Ala Thr Gly Leu Ser Leu Met Gly Val Met
        435                 440                 445

Ile Val Ala Cys Thr Leu Pro Val Ser Val Val His Phe Pro Gln Trp
    450                 455                 460

Gly Ser Met Phe Leu Pro Pro Ser Lys Asp Val Ser Lys Ser Thr Glu
465                 470                 475                 480

Glu Phe Tyr Tyr Thr Ser Glu Trp Asn Glu Glu Glu Lys Gln Lys Gly
                485                 490                 495

Leu His Gln Gln Ser Leu Lys Phe Ala Glu Asn Ser Arg Ser Glu Arg
            500                 505                 510

Gly Lys Arg Val Ala Ser Ala Pro Thr Pro Pro Asn Ala Thr Pro Thr
        515                 520                 525

His Val
    530


<210> SEQ ID NO 7
<211> LENGTH: 547
<212> TYPE: PRT
<213> ORGANISM: Physcomitrella patens
<220> FEATURE:
<221> NAME/KEY: misc_feature
<222> LOCATION: (1)..(547)
<223> OTHER INFORMATION: Public GI no. 37999150

<400> SEQUENCE: 7

Met Ala Asp Leu Ser Ser Ser Ala Val Gly Asp Arg Asn Ala Lys Gly
1               5                   10                  15

Asp Pro Gly Ser Ser Met His Gly Val Thr Gly Lys Glu Ala Leu Tyr
            20                  25                  30

Ala Phe Ser Leu His Asp Gly Asp Lys Met Asn Tyr Asp Pro Asp Ala
        35                  40                  45

Lys Phe Ala Leu Pro Val Asp Ser Glu His Lys Ala Thr Thr Met Arg
    50                  55                  60

Ile His Ser Phe Ser Arg Pro His Met Leu Thr Phe His Leu Ser Trp
65                  70                  75                  80

Phe Ser Phe Phe Thr Cys Phe Met Ser Thr Phe Ala Ala Pro Pro Leu
                85                  90                  95

Ile Pro Val Ile Arg Asp Asn Leu Asn Leu Asn Lys Glu Asp Ile Gly
            100                 105                 110

His Ala Ala Ile Ala Ser Val Thr Gly Ser Ile Leu Ser Arg Leu Leu
        115                 120                 125

Met Gly Ser Leu Cys Asp Met Ile Gly Pro Arg Tyr Gly Cys Ala Phe
    130                 135                 140

Leu Val Met Ile Ile Ser Pro Ala Val Tyr Ala Met Ala Val Val Asp
145                 150                 155                 160

Ser Ala Ala Gly Phe Thr Ala Val Arg Phe Phe Val Gly Phe Ser Leu
                165                 170                 175

Ala Thr Phe Val Ser Cys Gln Tyr Trp Met Ser Ser Met Phe Asn Gly
            180                 185                 190
```

-continued

```
Lys Ile Val Gly Thr Ala Asn Gly Ile Ala Ala Gly Trp Gly Asn Leu
        195                 200                 205

Gly Gly Gly Ala Thr Gln Met Ile Met Pro Leu Val Tyr Ala Leu Ile
    210                 215                 220

Lys Asp Ser Phe His Ser Pro Ser Tyr Thr Ala Trp Arg Leu Ala Phe
225                 230                 235                 240

Phe Leu Pro Gly Val Met His Thr Val Ile Gly Leu Leu Val Leu Phe
                245                 250                 255

Leu Gly Gln Asp Leu Pro Asp Gly Asn Phe Lys Glu Leu Gln Glu Gln
            260                 265                 270

Gly Thr Lys Pro Lys Asp Ser Phe Lys Lys Val Phe Ile Asn Ala Ile
        275                 280                 285

Thr Asn Tyr Arg Thr Trp Ile Phe Leu Ile Thr Tyr Gly Tyr Cys Phe
    290                 295                 300

Gly Val Glu Leu Thr Val Asp Asn Ile Ile Ala Glu Tyr Phe Tyr Asp
305                 310                 315                 320

Arg Phe Gly Leu Ser Leu Ser Thr Ala Gly Ile Ile Ala Ser Ser Phe
                325                 330                 335

Gly Leu Met Asn Ile Phe Ser Arg Pro Leu Gly Gly Ile Leu Ser Asp
            340                 345                 350

Val Val Ala Arg Arg Tyr Gly Met Gln Gly Arg Leu Trp Asn Leu Trp
        355                 360                 365

Ile Ile Gln Thr Leu Gly Gly Val Phe Cys Ile Val Leu Gly Lys Thr
    370                 375                 380

Ala Ala Leu Gly Pro Ala Ile Gly Val Met Ile Val Phe Ser Phe Phe
385                 390                 395                 400

Val Gln Ala Ala Cys Gly Ala Thr Phe Gly Val Ile Pro Phe Val Ser
                405                 410                 415

Arg Arg Ser Leu Gly Val Ile Ser Gly Phe Thr Gly Ala Gly Gly Asn
            420                 425                 430

Val Gly Ala Val Leu Thr Gln Thr Ile Phe Phe Thr Gln Ala Thr Tyr
        435                 440                 445

His Thr Glu Val Gly Ile Glu Asn Met Gly Ile Met Ile Ile Cys Cys
    450                 455                 460

Thr Ala Leu Val Leu Phe Val Trp Phe Pro Gln Trp Gly Ser Met Phe
465                 470                 475                 480

Phe Lys Ser Ser Arg Met Thr Glu Glu Asp Tyr Tyr Ala Ser Glu Tyr
                485                 490                 495

Ser Glu Gly Glu Gln Asp Gln Gly Leu His Gln Ala Ser Leu Lys Phe
            500                 505                 510

Ala Glu Asn Ala Lys Ser Glu Arg Gly Arg Ser Lys Gly Ser Lys Ser
        515                 520                 525

Pro Pro Glu Asn Gly Lys Pro Asp Gly Leu Lys Gly Ile Lys Glu Gly
    530                 535                 540

Ala Glu Val
545
```

<210> SEQ ID NO 8
<211> LENGTH: 548
<212> TYPE: PRT
<213> ORGANISM: Physcomitrella patens
<220> FEATURE:
<221> NAME/KEY: misc_feature
<222> LOCATION: (1)..(548)
<223> OTHER INFORMATION: Public GI no. 37999148

```
<400> SEQUENCE: 8

Met Ala Asp Gln Ser Ser Ser Ala Val Gly Asp Arg Asn Ala Lys Gly
1               5                   10                  15

Asp Pro Gly Ser Ser Met His Gly Val Thr Gly Lys Glu Ala Leu Tyr
            20                  25                  30

Ala Phe Ser Leu His Glu Gly Asp Lys Met Asn His Asp Pro Asp Ala
        35                  40                  45

Lys Lys Phe Ala Leu Pro Val Asp Ser Glu His Lys Ala Thr Thr Met
    50                  55                  60

Arg Ile Tyr Ser Phe Ala Arg Pro His Met Leu Thr Phe His Leu Ser
65                  70                  75                  80

Trp Phe Ser Phe Phe Thr Cys Phe Leu Ser Thr Phe Ala Ala Pro Pro
                85                  90                  95

Leu Ile Pro Val Ile Arg Asp Asn Leu Asn Leu Thr Lys Glu Asp Ile
            100                 105                 110

Gly His Ala Ala Ile Ala Ser Val Ser Gly Ser Ile Leu Ser Arg Leu
        115                 120                 125

Leu Met Gly Ser Ile Cys Asp Leu Ile Gly Pro Arg Tyr Gly Cys Ala
    130                 135                 140

Phe Leu Val Met Ile Ile Ser Pro Ala Val Tyr Ala Met Ala Ser Val
145                 150                 155                 160

Glu Thr Ala Ala Gly Phe Thr Ala Val Arg Phe Phe Ile Gly Phe Ser
                165                 170                 175

Leu Ala Thr Phe Val Ser Cys Gln Tyr Trp Met Ser Ser Met Phe Asn
            180                 185                 190

Gly Lys Ile Val Gly Thr Ala Asn Gly Ile Ala Ala Gly Trp Gly Asn
        195                 200                 205

Leu Gly Gly Gly Ala Thr Gln Leu Ile Met Pro Leu Val Tyr Ala Leu
    210                 215                 220

Ile Lys Asp Ser Phe Lys Ser Pro Ser Tyr Thr Ala Trp Arg Leu Ser
225                 230                 235                 240

Phe Phe Leu Pro Gly Val Met His Thr Val Ile Gly Leu Met Val Leu
                245                 250                 255

Phe Leu Gly Gln Asp Leu Pro Asp Gly Asn Phe Lys Glu Leu Gln Glu
            260                 265                 270

Gln Gly Thr Lys Val Lys Asp Ser Phe Arg Lys Val Phe Phe Asn Ala
        275                 280                 285

Val Thr Asn Tyr Arg Thr Trp Ile Phe Leu Ile Thr Tyr Gly Tyr Cys
    290                 295                 300

Phe Gly Val Glu Leu Thr Val Asp Asn Ile Ile Ala Glu Tyr Phe Tyr
305                 310                 315                 320

Asp Arg Phe Gly Leu Ser Leu Ser Ser Ala Gly Ile Ile Ala Ser Ser
                325                 330                 335

Phe Gly Phe Met Asn Ile Val Ser Arg Pro Leu Gly Gly Ile Leu Ser
            340                 345                 350

Asp Val Val Ala Arg Arg Tyr Gly Met Gln Gly Arg Leu Trp Asn Leu
        355                 360                 365

Trp Ile Ile Gln Thr Leu Gly Gly Val Phe Cys Ile Val Leu Gly Lys
    370                 375                 380

Thr Ala Ala Leu Gly Pro Ala Ile Gly Val Met Ile Val Phe Ser Phe
385                 390                 395                 400

Phe Val Gln Ala Ala Cys Gly Ala Thr Phe Gly Val Ile Pro Phe Val
                405                 410                 415
```

```
Ser Arg Arg Ser Leu Gly Val Ile Ser Gly Phe Thr Gly Ala Gly Gly
            420                 425                 430

Asn Val Gly Ala Val Leu Thr Gln Thr Ile Phe Phe Thr Gln Ala Thr
        435                 440                 445

Tyr His Thr Glu Val Gly Ile Glu Asn Met Gly Ile Met Ile Ile Cys
    450                 455                 460

Cys Thr Ala Leu Val Leu Phe Val Trp Phe Pro Gln Trp Gly Ser Met
465                 470                 475                 480

Phe Phe Lys Ser Ser Arg Met Thr Glu Glu Asp Tyr Tyr Ala Ser Glu
                485                 490                 495

Tyr Ser Glu Gly Glu Gln Asp Gln Gly Leu His Gln Ala Ser Leu Lys
            500                 505                 510

Phe Ala Glu Asn Ala Lys Ser Glu Arg Gly Arg Ser Lys Gly Ser Lys
        515                 520                 525

Ser Pro Pro Glu Asp Gly Lys Pro Asp Gly Leu Lys Gly Ile Lys Glu
    530                 535                 540

Gly Ala Glu Val
545
```

<210> SEQ ID NO 9
<211> LENGTH: 548
<212> TYPE: PRT
<213> ORGANISM: Physcomitrella patens
<220> FEATURE:
<221> NAME/KEY: misc_feature
<222> LOCATION: (1)..(548)
<223> OTHER INFORMATION: Public GI no. 37999154

<400> SEQUENCE: 9

```
Met Ala Asp Gln Ser Ala Ser Gly Val Gly Asn Lys Asn Ala Lys Gly
1               5                   10                  15

Asp Pro Gly Thr Ser Met His Gly Val Thr Gly Lys Glu Pro Val Tyr
            20                  25                  30

Ala Phe Ser Val Leu Gln Ala Ala Lys Ala Lys Pro Asp Pro Asp Ala
        35                  40                  45

Ala Lys Phe Ala Leu Pro Val Asp Ser Glu His Lys Ala Thr Thr Met
    50                  55                  60

Arg Ile Tyr Ser Phe Arg Ala Pro His Met Leu Thr Phe His Leu Ser
65                  70                  75                  80

Trp Phe Ser Phe Phe Thr Cys Phe Leu Ser Thr Phe Ala Ala Pro Pro
                85                  90                  95

Leu Ile Pro Val Ile Arg Asp Asn Leu Asn Leu Asp Lys Gly Asp Ile
            100                 105                 110

Gly His Ala Ala Ile Ala Ser Val Ser Gly Ser Ile Leu Ser Arg Leu
        115                 120                 125

Leu Met Gly Ser Ile Cys Asp Leu Ile Gly Pro Arg Tyr Gly Cys Ala
    130                 135                 140

Phe Leu Val Met Ile Ile Ser Pro Ala Val Tyr Ala Met Ala Ser Val
145                 150                 155                 160

Glu Thr Ala Ala Gly Phe Thr Ala Val Arg Phe Phe Ile Gly Phe Ser
                165                 170                 175

Leu Ala Thr Phe Val Ser Cys Gln Tyr Trp Met Ser Ser Met Phe Asn
            180                 185                 190

Gly Lys Ile Val Gly Thr Ala Asn Gly Ile Ala Ala Gly Trp Gly Asn
        195                 200                 205
```

-continued

```
Leu Gly Gly Gly Ala Thr Gln Leu Ile Met Pro Leu Val Tyr Ala Leu
    210                 215                 220

Ile Lys Asp Ser Phe Lys Ser Pro Ser Phe Thr Ala Trp Arg Leu Ala
225                 230                 235                 240

Phe Phe Leu Pro Gly Val Met His Thr Thr Ile Gly Leu Met Val Leu
                245                 250                 255

Phe Leu Gly Gln Asp Leu Pro Asp Gly Asn Phe Lys Glu Leu Glu Ala
            260                 265                 270

Gln Gly Thr Lys Ala Lys Asp Ser Phe Arg Lys Val Phe Val Asn Ala
        275                 280                 285

Val Thr Asn Tyr Arg Thr Trp Ile Leu Leu Ile Thr Tyr Gly Tyr Cys
    290                 295                 300

Phe Gly Val Glu Leu Thr Val Asp Asn Ile Ile Ala Glu Tyr Phe His
305                 310                 315                 320

Asp Arg Phe Asn Leu Ser Leu Ser Ser Ala Gly Ile Ile Ala Ser Ser
                325                 330                 335

Phe Gly Phe Met Asn Ile Val Ser Arg Pro Leu Gly Gly Ile Leu Ser
            340                 345                 350

Asp Ile Val Ala Val Arg Phe Gly Met Arg Gly Arg Leu Trp Asn Leu
        355                 360                 365

Trp Ile Ile Gln Thr Leu Gly Gly Val Phe Cys Ile Ile Leu Gly Lys
    370                 375                 380

Thr Ala Ala Leu Gly Pro Ala Ile Gly Val Met Ile Val Phe Ser Phe
385                 390                 395                 400

Phe Val Gln Ala Ala Cys Gly Ala Thr Phe Gly Val Ile Pro Phe Val
                405                 410                 415

Ser Arg Arg Ser Leu Gly Val Ile Ser Gly Phe Thr Gly Ala Gly Gly
            420                 425                 430

Asn Leu Gly Ala Val Met Thr Gln Thr Ile Phe Phe Thr Gln Ala Thr
        435                 440                 445

Tyr His Thr Glu Val Gly Ile Glu Tyr Met Gly Ile Met Ile Ile Cys
    450                 455                 460

Val Thr Ala Leu Val Leu Phe Val Trp Phe Pro Gln Trp Gly Gly Met
465                 470                 475                 480

Val Phe Pro Ser Ser Lys Met Ser Glu Glu Asp Tyr Tyr Ala Ser Glu
                485                 490                 495

Tyr Ser Glu Gly Glu Gln Asp Gln Gly Met His Glu Ala Ser Met Lys
            500                 505                 510

Phe Ala Glu Asn Ser Lys Ser Glu Arg Gly Arg Arg Lys Gly Ser Asn
        515                 520                 525

Ser Pro Pro Gln Asp Ala Lys Pro Asp Gly Leu Lys Gly Ile Lys Glu
    530                 535                 540

Gly Ala Glu Val
545


<210> SEQ ID NO 10
<211> LENGTH: 530
<212> TYPE: PRT
<213> ORGANISM: Brassica napus
<220> FEATURE:
<221> NAME/KEY: misc_feature
<222> LOCATION: (1)..(530)
<223> OTHER INFORMATION: Public GI no. 9931082

<400> SEQUENCE: 10

Met Gly Asp Ser Thr Gly Glu Pro Gly Ser Ser Met His Gly Val Thr
```

-continued

```
1               5                   10                  15

Gly Arg Glu Gln Thr Phe Ala Phe Ser Val Ala Ser Pro Ile Val Pro
            20                  25                  30

Thr Asp Lys Thr Ala Lys Phe Asp Leu Pro Val Asp Ser Glu His Lys
        35                  40                  45

Ala Thr Val Phe Lys Leu Phe Ser Phe Ala Lys Pro His Met Arg Thr
    50                  55                  60

Phe His Leu Ser Trp Ile Ser Phe Ser Thr Cys Phe Val Ser Thr Phe
65                  70                  75                  80

Ala Ala Ala Pro Leu Val Pro Ile Ile Arg Glu Asn Leu Asn Leu Thr
                85                  90                  95

Lys Gln Asp Ile Gly Asn Ala Gly Val Ala Ser Val Ser Gly Ser Ile
            100                 105                 110

Phe Ser Arg Leu Val Met Gly Ala Val Cys Asp Leu Leu Gly Pro Arg
        115                 120                 125

Tyr Gly Cys Ala Phe Leu Val Met Leu Ser Ala Pro Thr Val Phe Ser
    130                 135                 140

Met Ser Phe Val Ser Gly Ala Ala Gly Phe Ile Thr Val Arg Phe Met
145                 150                 155                 160

Ile Gly Phe Cys Leu Ala Thr Phe Val Ser Cys Gln Tyr Gly Met Ser
                165                 170                 175

Thr Met Phe Asn Ser Gln Ile Ile Gly Leu Val Asn Gly Thr Ala Ala
            180                 185                 190

Gly Trp Gly Asn Met Gly Gly Gly Ile Thr Gln Leu Leu Met Pro Val
        195                 200                 205

Val Tyr Glu Ile Ile Arg Arg Cys Gly Ala Thr Ala Phe Thr Ala Trp
    210                 215                 220

Arg Leu Ala Phe Phe Val Pro Gly Trp Leu His Ile Ile Met Gly Val
225                 230                 235                 240

Leu Val Leu Asn Leu Gly Gln Asp Leu Pro Asp Gly Asn Arg Ser Ala
                245                 250                 255

Leu Glu Lys Lys Gly Glu Val Ala Lys Asp Lys Phe Gly Lys Ile Met
            260                 265                 270

Trp Tyr Ala Val Thr Asn Tyr Arg Thr Trp Ile Phe Val Leu Leu Tyr
        275                 280                 285

Gly Tyr Ser Met Gly Val Glu Leu Ser Thr Asp Asn Val Ile Ala Glu
    290                 295                 300

Tyr Phe Phe Asp Arg Phe His Leu Lys Leu His Thr Ala Gly Ile Ile
305                 310                 315                 320

Ala Ala Cys Phe Gly Met Ala Asn Phe Phe Ala Arg Pro Ala Gly Gly
                325                 330                 335

Tyr Ala Ser Asp Leu Ala Ala Lys Tyr Phe Gly Met Arg Gly Arg Leu
            340                 345                 350

Trp Ala Leu Trp Ile Ile Gln Thr Ala Gly Gly Val Phe Cys Val Trp
        355                 360                 365

Leu Gly Arg Ala Asn Thr Leu Val Thr Ala Val Val Ala Met Val Leu
    370                 375                 380

Phe Ser Leu Gly Ala Gln Ala Ala Cys Gly Ala Thr Phe Ala Ile Val
385                 390                 395                 400

Pro Phe Val Ser Arg Arg Ala Leu Gly Ile Ile Ser Gly Leu Thr Gly
                405                 410                 415

Ala Gly Gly Asn Phe Gly Ser Gly Leu Thr Gln Leu Ile Phe Phe Ser
            420                 425                 430
```

```
Thr Ser Arg Phe Thr Thr Glu Gln Gly Leu Thr Trp Met Gly Val Met
        435                 440                 445

Ile Val Ala Cys Thr Leu Pro Val Thr Leu Ile His Phe Pro Gln Trp
    450                 455                 460

Gly Ser Met Phe Leu Pro Pro Ser Thr Asp Pro Val Lys Gly Pro Lys
465                 470                 475                 480

Glu His Tyr Tyr Ala Ser Glu Trp Asn Glu Gln Glu Lys Glu Lys Asn
                485                 490                 495

Met His Gln Gly Ser Leu Arg Phe Ala Lys Asn Ala Lys Ser Glu Gly
            500                 505                 510

Gly Arg Arg Val Arg Ser Ala Ala Thr Pro Pro Glu Asn Thr Pro Asn
        515                 520                 525

Asn Val
    530


<210> SEQ ID NO 11
<211> LENGTH: 530
<212> TYPE: PRT
<213> ORGANISM: Prunus persica
<220> FEATURE:
<221> NAME/KEY: misc_feature
<222> LOCATION: (1)..(530)
<223> OTHER INFORMATION: Public GI no. 39573544

<400> SEQUENCE: 11

Met Ala Glu Val Glu Gly Glu Pro Gly Ser Ser Met His Gly Val Thr
1               5                   10                  15

Gly Arg Glu Gln Thr Phe Ala Phe Ser Val Ala Ser Pro Ile Val Pro
            20                  25                  30

Thr Asp Pro Thr Ala Lys Phe Asp Leu Pro Val Asp Ser Glu His Lys
        35                  40                  45

Ala Lys Val Phe Lys Ile Phe Ser Leu Ala Asn Pro His Met Arg Thr
    50                  55                  60

Phe His Leu Ser Trp Ile Ser Phe Phe Thr Cys Phe Val Ser Thr Phe
65                  70                  75                  80

Ala Ala Ala Pro Leu Val Pro Ile Ile Arg Asp Asn Leu Asn Leu Thr
                85                  90                  95

Lys Gln Asp Ile Gly Asn Ala Gly Val Ala Ser Val Ser Gly Ser Ile
            100                 105                 110

Phe Ser Arg Leu Val Met Gly Ala Val Cys Asp Leu Leu Gly Pro Arg
        115                 120                 125

Tyr Gly Cys Ala Phe Leu Ile Met Leu Ser Ala Pro Thr Val Phe Cys
    130                 135                 140

Met Ser Phe Val Ser Asp Ala Gly Gly Tyr Leu Ala Val Arg Phe Met
145                 150                 155                 160

Ile Gly Phe Ser Leu Ala Thr Phe Val Ser Cys Gln Tyr Trp Met Ser
                165                 170                 175

Thr Met Phe Asn Ser Lys Ile Ile Gly Leu Val Asn Gly Thr Ala Ala
            180                 185                 190

Gly Trp Gly Asn Met Gly Gly Gly Ala Thr Gln Leu Leu Met Pro Leu
        195                 200                 205

Val Phe Asp Ile Ile Gly Arg Val Gly Ala Thr Pro Phe Thr Ala Trp
    210                 215                 220

Arg Ile Ala Phe Phe Ile Pro Gly Trp Leu His Val Ile Met Gly Ile
225                 230                 235                 240
```

-continued

```
Met Val Leu Thr Leu Gly Gln Asp Leu Pro Asp Gly Asn Leu Ala Ala
                245                 250                 255

Leu Gln Lys Lys Gly Asp Val Ala Lys Asp Gln Phe Ser Lys Val Leu
            260                 265                 270

Trp His Ala Ile Thr Asn Tyr Arg Thr Trp Ile Phe Val Leu Leu Tyr
        275                 280                 285

Gly Tyr Ser Met Gly Val Glu Leu Ser Ile Asp Asn Val Ile Ala Glu
    290                 295                 300

Tyr Phe Tyr Asp Arg Phe Asn Leu Lys Leu His Thr Ala Gly Ile Ile
305                 310                 315                 320

Ala Ala Ala Phe Gly Met Ala Asn Ile Val Ala Arg Pro Phe Gly Gly
                325                 330                 335

Phe Ala Ser Asp Arg Ala Ala Arg Tyr Phe Gly Met Arg Gly Arg Leu
            340                 345                 350

Trp Thr Leu Trp Ile Leu Gln Thr Leu Gly Gly Val Phe Cys Ile Trp
        355                 360                 365

Leu Gly Arg Ala Asn Ser Leu Pro Ile Ala Val Phe Ala Met Ile Leu
    370                 375                 380

Phe Ser Val Gly Ala Gln Ala Ala Cys Gly Ala Thr Phe Gly Val Ile
385                 390                 395                 400

Pro Phe Ile Ser Arg Arg Ser Leu Gly Ile Ile Ser Gly Leu Thr Gly
                405                 410                 415

Ala Gly Gly Asn Phe Gly Ser Gly Leu Thr Gln Leu Val Phe Phe Ser
            420                 425                 430

Ser Ala Ala Phe Ser Thr Ala Thr Gly Leu Ser Leu Met Gly Val Met
        435                 440                 445

Ile Val Cys Cys Thr Leu Pro Val Thr Leu Val His Phe Pro Gln Trp
    450                 455                 460

Gly Ser Met Phe Leu Pro Pro Ser Lys Asp Val Val Lys Ser Thr Glu
465                 470                 475                 480

Glu Phe Tyr Tyr Gly Ala Glu Trp Asn Glu Glu Glu Lys Gln Lys Gly
                485                 490                 495

Leu His Gln Gln Ser Leu Arg Phe Ala Glu Asn Ser Arg Ser Glu Arg
            500                 505                 510

Gly Arg Arg Val Ala Ser Ala Pro Thr Pro Pro Asn Thr Thr Pro Ser
        515                 520                 525

His Val
    530
```

<210> SEQ ID NO 12
<211> LENGTH: 530
<212> TYPE: PRT
<213> ORGANISM: Prunus persica
<220> FEATURE:
<221> NAME/KEY: misc_feature
<222> LOCATION: (1)..(530)
<223> OTHER INFORMATION: Public GI no. 38636547

<400> SEQUENCE: 12

```
Met Ala Glu Val Glu Gly Glu Pro Gly Ser Ser Met His Gly Val Thr
1               5                   10                  15

Gly Arg Glu Gln Thr Phe Ala Phe Ser Val Ala Ser Pro Ile Val Pro
            20                  25                  30

Thr Asp Pro Thr Ala Lys Phe Asp Leu Pro Val Asp Ser Glu His Lys
        35                  40                  45

Ala Lys Val Phe Lys Ile Phe Ser Leu Ala Asn Pro His Met Arg Thr
```

-continued

```
    50                  55                  60

Phe His Leu Ser Trp Ile Ser Phe Phe Thr Cys Phe Val Ser Thr Phe
65                  70                  75                  80

Ala Ala Ala Pro Leu Val Pro Ile Ile Arg Asp Asn Leu Asn Leu Thr
                85                  90                  95

Lys Gln Asp Ile Gly Asn Ala Gly Val Ala Ser Val Ser Gly Ser Ile
            100                 105                 110

Phe Ser Arg Leu Val Met Gly Ala Val Cys Asp Leu Leu Gly Pro Arg
        115                 120                 125

Tyr Gly Cys Ala Phe Leu Ile Met Leu Ser Ala Pro Thr Val Phe Cys
    130                 135                 140

Met Ser Phe Val Ser Asp Ala Gly Gly Tyr Leu Ala Val Arg Phe Met
145                 150                 155                 160

Ile Gly Phe Ser Leu Ala Thr Phe Val Ser Cys Gln Tyr Trp Met Ser
                165                 170                 175

Thr Met Phe Asn Ser Lys Ile Ile Gly Leu Val Asn Gly Thr Ala Ala
            180                 185                 190

Gly Trp Gly Asn Met Gly Gly Gly Ala Thr Gln Leu Leu Met Pro Leu
        195                 200                 205

Val Phe Asp Ile Ile Gly Arg Val Gly Ala Thr Pro Phe Thr Ala Trp
    210                 215                 220

Arg Ile Ala Phe Phe Ile Pro Gly Trp Leu His Val Ile Met Gly Ile
225                 230                 235                 240

Met Val Leu Thr Leu Gly Gln Asp Leu Pro Asp Gly Asn Leu Ala Ala
                245                 250                 255

Leu Gln Lys Lys Gly Asp Val Ala Lys Asp Gln Phe Ser Lys Val Leu
            260                 265                 270

Trp His Ala Val Thr Asn Tyr Arg Thr Trp Ile Phe Val Leu Leu Tyr
        275                 280                 285

Gly Tyr Ser Met Gly Val Glu Leu Ser Thr Asp Asn Val Ile Ala Glu
    290                 295                 300

Tyr Phe Tyr Asp Arg Phe Asn Leu Lys Leu His Thr Ala Gly Ile Ile
305                 310                 315                 320

Ala Ala Thr Phe Gly Met Ala Asn Leu Val Ala Arg Pro Phe Gly Gly
                325                 330                 335

Phe Ala Ser Asp Arg Ala Ala Arg Tyr Phe Gly Met Arg Gly Arg Leu
            340                 345                 350

Trp Thr Leu Trp Ile Leu Gln Thr Leu Gly Gly Val Phe Cys Ile Trp
        355                 360                 365

Leu Gly Arg Ala Asn Ser Leu Pro Ile Ala Val Phe Ala Met Ile Leu
    370                 375                 380

Phe Ser Val Gly Ala Gln Ala Ala Cys Gly Ala Thr Phe Gly Val Ile
385                 390                 395                 400

Pro Phe Ile Ser Arg Arg Ser Leu Gly Ile Ile Ser Gly Leu Thr Gly
                405                 410                 415

Ala Gly Gly Asn Phe Gly Ser Gly Leu Thr Gln Leu Val Phe Phe Ser
            420                 425                 430

Ser Ser Ala Phe Ser Thr Ala Thr Gly Leu Ser Leu Met Gly Val Met
        435                 440                 445

Ile Val Cys Cys Thr Leu Pro Val Thr Leu Val His Phe Pro Gln Trp
    450                 455                 460

Gly Ser Met Phe Leu Pro Pro Ser Lys Asp Val Val Lys Ser Thr Glu
465                 470                 475                 480
```

```
Glu Phe Tyr Tyr Gly Ala Glu Trp Asn Glu Glu Glu Lys Gln Lys Gly
                485                 490                 495

Leu His Gln Gln Ser Leu Arg Phe Ala Glu Asn Ser Arg Ser Glu Arg
            500                 505                 510

Gly Arg Arg Val Ala Ser Ala Pro Thr Pro Pro Asn Thr Thr Pro Ser
        515                 520                 525

His Val
    530


<210> SEQ ID NO 13
<211> LENGTH: 530
<212> TYPE: PRT
<213> ORGANISM: Lotus corniculatus var. japonicus
<220> FEATURE:
<221> NAME/KEY: misc_feature
<222> LOCATION: (1)..(530)
<223> OTHER INFORMATION: Public GI no. 13539545

<400> SEQUENCE: 13

Met Val Glu Ile Glu Gly Ser Pro Gly Thr Ser Met His Gly Val Thr
1               5                   10                  15

Gly Arg Glu Gln Thr Phe Ile Ser Ser Val Ser Ser Pro Met Val Pro
            20                  25                  30

Thr Asp Thr Thr Ala Lys Phe Asp Leu Pro Val Asp Ser Gln His Lys
        35                  40                  45

Ala Lys Val Phe Lys Leu Phe Ser Leu Ala Asn Pro His Met Thr Thr
    50                  55                  60

Phe His Leu Ser Trp Ile Ser Phe Phe Thr Cys Phe Val Ser Thr Phe
65                  70                  75                  80

Ala Ala Ala Pro Leu Val Pro Ile Ile Arg Asp Asn Leu Asn Leu Thr
                85                  90                  95

Lys Ser Asp Ile Gly Asn Ala Gly Val Ala Ser Val Ser Gly Ser Ile
            100                 105                 110

Phe Ser Arg Leu Thr Met Gly Val Ile Cys Asp Leu Leu Gly Pro Arg
        115                 120                 125

Tyr Gly Cys Ala Phe Leu Ile Met Leu Ser Ala Pro Thr Val Phe Cys
    130                 135                 140

Met Ser Phe Val Asn Asp Ala Ala Gly Tyr Ile Val Val Arg Phe Met
145                 150                 155                 160

Ile Gly Phe Ser Leu Ala Thr Phe Val Ser Cys Gln Tyr Trp Met Ser
                165                 170                 175

Thr Met Phe Asn Ser Lys Ile Ile Gly Leu Val Asn Gly Thr Ala Ala
            180                 185                 190

Gly Trp Gly Asn Met Gly Gly Gly Ala Thr Gln Leu Ile Met Pro Ile
        195                 200                 205

Val Tyr Glu Leu Ile Arg Arg Ala Gly Ser Thr Gly Phe Thr Ala Trp
    210                 215                 220

Arg Ile Ala Phe Phe Ile Pro Gly Phe Met His Val Phe Met Gly Ile
225                 230                 235                 240

Leu Val Leu Thr Leu Gly Gln Asp Leu Pro Asp Gly Asn Leu Ser Ala
                245                 250                 255

Leu Gln Lys Lys Gly Asp Val Ala Lys Asp Lys Phe Ser Lys Val Leu
            260                 265                 270

Trp Tyr Ala Ile Thr Asn Tyr Arg Thr Trp Ile Phe Ala Leu Leu Tyr
        275                 280                 285
```

```
Gly Tyr Ser Met Gly Val Glu Leu Thr Thr Asp Asn Val Ile Ala Glu
    290                 295                 300

Tyr Phe Tyr Asp Arg Phe Asn Leu Lys Leu His Thr Val Gly Ile Ile
305                 310                 315                 320

Ala Ala Ser Phe Gly Met Ala Asn Leu Val Ala Arg Pro Phe Gly Gly
                325                 330                 335

Tyr Val Ser Asp Val Ala Ala Arg Leu Phe Gly Met Arg Gly Arg Leu
            340                 345                 350

Trp Thr Leu Trp Ile Leu Gln Thr Leu Gly Gly Val Phe Cys Ile Trp
        355                 360                 365

Leu Gly Arg Ala Asn Ser Leu Pro Ile Ala Val Leu Ala Met Ile Leu
    370                 375                 380

Phe Ser Val Gly Ala Gln Ala Ala Cys Gly Ala Thr Phe Gly Ile Ile
385                 390                 395                 400

Pro Phe Ile Ser Lys Arg Ser Leu Gly Ile Ile Ser Gly Leu Thr Gly
                405                 410                 415

Ala Gly Gly Asn Phe Gly Ser Gly Leu Thr Gln Leu Val Phe Phe Ser
            420                 425                 430

Thr Ser Arg Phe Ser Thr Gly Ala Gly Leu Ser Trp Met Gly Val Met
        435                 440                 445

Ile Val Gly Cys Thr Leu Pro Val Thr Leu Val His Phe Pro Gln Trp
    450                 455                 460

Gly Ser Met Phe Leu Pro Pro Ser Lys Asp Ile Asn Lys Ser Ser Glu
465                 470                 475                 480

Glu His Tyr Tyr Thr Ala Glu Trp Asp Glu Glu Glu Arg Lys Lys Gly
                485                 490                 495

Leu His Ser Gln Ser Leu Lys Phe Ala Glu Asn Ser Arg Ser Glu Arg
            500                 505                 510

Gly Lys Arg Val Ser Ser Ala Pro Thr Pro Pro Asn Thr Thr Pro Thr
        515                 520                 525

His Val
    530


<210> SEQ ID NO 14
<211> LENGTH: 507
<212> TYPE: PRT
<213> ORGANISM: Triticum aestivum
<220> FEATURE:
<221> NAME/KEY: misc_feature
<222> LOCATION: (1)..(507)
<223> OTHER INFORMATION: Public GI no. 15990600

<400> SEQUENCE: 14

Met Glu Val Glu Ser Ser Ala His Gly Asp Ala Ala Ala Ser Lys Phe
1               5                   10                  15

Thr Leu Pro Val Asp Ser Glu His Lys Ala Lys Ser Phe Arg Leu Phe
            20                  25                  30

Ser Phe Ala Asn Pro His Met Arg Thr Phe His Leu Ser Trp Ile Ser
        35                  40                  45

Phe Phe Thr Cys Phe Val Ser Thr Phe Ala Ala Ala Pro Leu Val Pro
    50                  55                  60

Ile Ile Arg Asp Asn Leu Asn Leu Ala Lys Ala Asp Ile Gly Asn Ala
65                  70                  75                  80

Gly Val Ala Ser Val Ser Gly Ser Ile Phe Ser Arg Leu Ala Met Gly
                85                  90                  95

Ala Val Cys Asp Leu Leu Gly Pro Arg Tyr Gly Cys Ala Phe Leu Val
```

```
            100                 105                 110

Met Leu Ser Ala Pro Thr Val Phe Cys Met Ala Val Ile Asp Asp Ala
        115                 120                 125

Ser Gly Tyr Ile Ala Val Arg Phe Leu Ile Gly Phe Ser Leu Ala Ala
    130                 135                 140

Phe Val Ser Cys Gln Tyr Trp Met Ser Thr Met Phe Asn Ser Lys Ile
145                 150                 155                 160

Ile Gly Thr Val Asn Gly Leu Ala Ala Gly Trp Gly Asn Met Gly Gly
                165                 170                 175

Gly Ala Thr Gln Leu Ile Met Pro Leu Val Phe His Ala Ile Gln Lys
            180                 185                 190

Cys Gly Ala Thr Pro Phe Val Ala Trp Arg Ile Ala Tyr Phe Val Pro
        195                 200                 205

Gly Met Met His Ile Val Met Gly Leu Leu Val Leu Thr Met Gly Gln
    210                 215                 220

Asp Leu Pro Asp Gly Asn Leu Ala Ser Leu Gln Lys Lys Gly Asp Met
225                 230                 235                 240

Ala Lys Asp Lys Phe Ser Lys Val Leu Trp Gly Ala Val Thr Asn Tyr
                245                 250                 255

Arg Thr Trp Ile Phe Val Leu Leu Tyr Gly Tyr Cys Met Gly Val Glu
            260                 265                 270

Leu Thr Thr Asp Asn Val Ile Ala Glu Tyr Tyr Tyr Asp His Phe His
        275                 280                 285

Leu His Leu Arg Ala Ala Gly Thr Ile Ala Ala Cys Phe Gly Met Ala
    290                 295                 300

Asn Ile Val Ala Arg Pro Met Gly Gly Tyr Leu Ser Asp Leu Gly Ala
305                 310                 315                 320

Arg Tyr Phe Gly Met Arg Ala Arg Leu Trp Asn Ile Trp Ile Leu Gln
                325                 330                 335

Thr Ala Gly Gly Ala Phe Cys Ile Trp Leu Gly Arg Ala Ser Ala Leu
            340                 345                 350

Pro Ala Ser Val Thr Ala Met Val Leu Phe Ser Ile Cys Ala Gln Ala
        355                 360                 365

Ala Cys Gly Ala Val Phe Gly Val Ala Pro Phe Val Ser Arg Arg Ser
    370                 375                 380

Leu Gly Ile Ile Ser Gly Leu Thr Gly Ala Gly Gly Asn Val Gly Ala
385                 390                 395                 400

Gly Leu Thr Gln Leu Leu Phe Phe Thr Ser Ser Gln Tyr Ser Thr Gly
                405                 410                 415

Arg Gly Leu Glu Tyr Met Gly Ile Met Ile Met Ala Cys Thr Leu Pro
            420                 425                 430

Ile Thr Leu Val His Phe Pro Gln Trp Gly Ser Met Phe Phe Pro Ala
        435                 440                 445

Ser Ala Asp Ala Thr Glu Glu Glu Tyr Tyr Ala Ser Glu Trp Ser Glu
    450                 455                 460

Glu Glu Lys Gly Lys Gly Leu His Ile Ala Gly Gln Lys Phe Ala Glu
465                 470                 475                 480

Asn Ser Arg Ser Glu Arg Gly Arg Arg Asn Val Ile Leu Ala Thr Ser
                485                 490                 495

Ala Thr Pro Pro Asn Asn Thr Pro Gln His Val
            500                 505
```

<210> SEQ ID NO 15

<211> LENGTH: 506
<212> TYPE: PRT
<213> ORGANISM: Hordeum vulgare
<220> FEATURE:
<221> NAME/KEY: misc_feature
<222> LOCATION: (1)..(506)
<223> OTHER INFORMATION: Public GI no. 4731146

<400> SEQUENCE: 15

```
Met Glu Val Glu Ala Gly Ala His Gly Asp Thr Ala Ala Ser Lys Phe
1               5                   10                  15

Thr Leu Pro Val Asp Ser Glu His Lys Ala Lys Ser Phe Arg Leu Phe
            20                  25                  30

Ser Phe Ala Asn Pro His Met Arg Thr Phe His Leu Ser Trp Ile Ser
        35                  40                  45

Phe Phe Thr Cys Phe Val Ser Thr Phe Ala Ala Ala Pro Leu Val Pro
    50                  55                  60

Ile Ile Arg Asp Asn Leu Asn Leu Ala Lys Ala Asp Ile Gly Asn Ala
65                  70                  75                  80

Gly Val Ala Ser Val Ser Gly Ser Ile Phe Ser Arg Leu Ala Met Gly
                85                  90                  95

Ala Ile Cys Asp Leu Leu Gly Pro Arg Tyr Gly Cys Ala Phe Leu Val
            100                 105                 110

Met Leu Ser Ala Pro Thr Val Phe Cys Met Ala Val Ile Asp Asp Ala
        115                 120                 125

Ser Gly Tyr Ile Ala Val Arg Phe Leu Ile Gly Phe Ser Leu Ala Thr
    130                 135                 140

Phe Val Ser Cys Gln Tyr Trp Met Ser Thr Met Phe Asn Ser Lys Ile
145                 150                 155                 160

Ile Gly Thr Val Asn Gly Leu Ala Ala Gly Trp Gly Asn Met Gly Gly
                165                 170                 175

Gly Ala Thr Gln Leu Ile Met Pro Leu Val Phe His Ala Ile Gln Lys
            180                 185                 190

Cys Gly Ala Thr Pro Phe Val Ala Trp Arg Ile Ala Tyr Phe Val Pro
        195                 200                 205

Gly Met Met His Ile Val Met Gly Leu Leu Val Leu Thr Met Gly Gln
    210                 215                 220

Asp Leu Pro Asp Gly Asn Leu Ala Ser Leu Gln Lys Arg Gly Asp Met
225                 230                 235                 240

Ala Lys Asp Lys Phe Ser Lys Val Leu Trp Gly Ala Val Thr Asn Tyr
                245                 250                 255

Arg Thr Trp Ile Phe Val Leu Leu Tyr Gly Tyr Cys Met Gly Val Glu
            260                 265                 270

Leu Thr Thr Asp Asn Val Ile Ala Glu Tyr Tyr Phe Asp His Phe His
        275                 280                 285

Leu Asp Leu Arg Ala Ala Gly Thr Ile Ala Ala Cys Phe Gly Met Ala
    290                 295                 300

Asn Ile Val Ala Arg Pro Met Gly Gly Tyr Leu Ser Asp Leu Gly Ala
305                 310                 315                 320

Arg Tyr Phe Gly Met Arg Ala Leu Trp Asn Ile Trp Ile Leu Gln Thr
                325                 330                 335

Ala Gly Gly Ala Phe Cys Ile Trp Leu Gly Arg Ala Ser Ala Leu Pro
            340                 345                 350

Ala Ser Val Thr Ala Met Val Leu Phe Ser Ile Cys Ala Gln Ala Ala
        355                 360                 365
```

```
Cys Gly Ala Ile Phe Gly Val Ala Pro Phe Val Ser Arg Arg Ser Leu
    370                 375                 380

Gly Ile Ile Ser Gly Leu Thr Gly Ala Gly Gly Asn Val Gly Ala Gly
385                 390                 395                 400

Leu Thr Gln Leu Leu Phe Phe Thr Ser Ser Gln Tyr Ser Thr Gly Arg
                405                 410                 415

Gly Leu Glu Tyr Met Gly Ile Met Ile Met Ala Cys Thr Leu Pro Val
            420                 425                 430

Ala Leu Val His Phe Pro Gln Trp Gly Ser Met Phe Phe Pro Ala Ser
        435                 440                 445

Ala Asp Ala Thr Glu Glu Glu Tyr Tyr Ala Ser Glu Trp Ser Glu Glu
    450                 455                 460

Glu Lys Gly Lys Gly Leu His Ile Ala Gly Gln Lys Phe Ala Glu Asn
465                 470                 475                 480

Ser Arg Ser Glu Arg Gly Arg Arg Asn Val Ile Phe Ala Thr Ser Ala
                485                 490                 495

Thr Pro Pro Asn Asn Thr Pro Gln Gln Val
            500                 505


<210> SEQ ID NO 16
<211> LENGTH: 507
<212> TYPE: PRT
<213> ORGANISM: Lycopersicon esculentum
<220> FEATURE:
<221> NAME/KEY: misc_feature
<222> LOCATION: (1)..(507)
<223> OTHER INFORMATION: Public GI no. 1680655

<400> SEQUENCE: 16

Met Glu Val Glu Ala Gly Ala His Gly Asp Thr Ala Ala Ser Lys Phe
1               5                   10                  15

Thr Leu Pro Val Asp Ser Glu His Lys Ala Lys Ser Phe Arg Leu Phe
            20                  25                  30

Ser Phe Ala Asn Pro His Met Arg Thr Phe His Leu Ser Trp Ile Ser
        35                  40                  45

Phe Phe Thr Cys Phe Ile Ser Thr Phe Ala Ala Ala Pro Leu Val Pro
    50                  55                  60

Ile Ile Arg Asp Asn Leu Asn Leu Ala Lys Ala Asp Ile Gly Asn Ala
65                  70                  75                  80

Gly Val Ala Ser Val Ser Gly Ser Ile Phe Ser Arg Leu Ala Met Gly
                85                  90                  95

Ala Ile Cys Asp Leu Leu Gly Pro Arg Tyr Gly Cys Ala Phe Leu Val
            100                 105                 110

Met Leu Ser Ala Pro Thr Val Phe Cys Met Ala Val Ile Asp Asp Ala
        115                 120                 125

Ser Gly Tyr Ile Ala Val Arg Phe Leu Ile Gly Phe Ser Leu Ala Thr
    130                 135                 140

Phe Val Ser Cys Gln Tyr Trp Met Ser Thr Met Phe Asn Ser Lys Ile
145                 150                 155                 160

Ile Gly Thr Val Asn Gly Leu Ala Ala Gly Trp Gly Asn Met Gly Gly
                165                 170                 175

Gly Ala Thr Gln Leu Ile Met Pro Leu Val Phe His Ala Ile Gln Lys
            180                 185                 190

Cys Gly Ala Thr Pro Phe Val Ala Trp Arg Ile Ala Tyr Phe Val Pro
        195                 200                 205

Gly Met Met His Ile Val Met Gly Leu Leu Val Leu Thr Met Gly Gln
```

-continued

```
    210                 215                 220

Asp Leu Pro Asp Gly Asn Leu Ala Ser Leu Gln Lys Lys Gly Asp Met
225                 230                 235                 240

Ala Lys Asp Lys Phe Ser Lys Val Leu Trp Gly Ala Val Thr Asn Tyr
                245                 250                 255

Arg Thr Trp Ile Phe Val Leu Leu Tyr Gly Tyr Cys Met Gly Val Glu
            260                 265                 270

Leu Thr Thr Asp Asn Val Ile Ala Glu Tyr Tyr Phe Asp His Phe His
        275                 280                 285

Leu Asp Leu Arg Ala Ala Gly Thr Ile Ala Ala Cys Phe Gly Met Ala
    290                 295                 300

Asn Ile Val Ala Arg Pro Thr Gly Gly Tyr Leu Ser Asp Leu Gly Ala
305                 310                 315                 320

Arg Tyr Phe Gly Met Arg Ala Arg Leu Trp Asn Ile Trp Ile Leu Gln
                325                 330                 335

Thr Ala Gly Gly Ala Phe Cys Ile Trp Leu Gly Arg Ala Ser Ala Leu
            340                 345                 350

Pro Ala Ser Val Thr Ala Met Val Leu Phe Ser Ile Cys Ala Gln Ala
        355                 360                 365

Ala Cys Gly Ala Ile Phe Gly Val Ala Pro Phe Val Ser Arg Arg Ser
    370                 375                 380

Leu Gly Ile Ile Ser Gly Leu Thr Gly Ala Gly Gly Asn Val Gly Ala
385                 390                 395                 400

Gly Leu Thr Gln Leu Leu Phe Phe Thr Ser Ser Gln Tyr Ser Thr Gly
                405                 410                 415

Arg Gly Leu Glu Tyr Met Gly Ile Met Ile Met Ala Cys Thr Leu Pro
            420                 425                 430

Val Ala Leu Val His Phe Pro Gln Trp Gly Ser Met Phe Phe Pro Ala
        435                 440                 445

Ser Ala Asp Ala Thr Glu Glu Glu Tyr Tyr Ala Ser Glu Trp Ser Glu
    450                 455                 460

Glu Glu Lys Ala Lys Gly Leu His Ile Ala Gly Gln Lys Phe Ala Glu
465                 470                 475                 480

Asn Ser Arg Ser Glu Arg Gly Arg Arg Asn Val Ile Leu Ala Thr Ser
                485                 490                 495

Ala Thr Pro Pro Asn Asn Thr Pro Gln His Val
            500                 505


<210> SEQ ID NO 17
<211> LENGTH: 507
<212> TYPE: PRT
<213> ORGANISM: Triticum aestivum
<220> FEATURE:
<221> NAME/KEY: misc_feature
<222> LOCATION: (1)..(507)
<223> OTHER INFORMATION: Public GI no. 9858859

<400> SEQUENCE: 17

Met Glu Val Glu Ala Ser Ala His Gly Asp Thr Ala Ala Ser Lys Phe
1               5                   10                  15

Thr Leu Pro Val Asp Ser Glu His Lys Ala Lys Ser Phe Arg Leu Phe
            20                  25                  30

Ser Phe Ala Asn Pro His Met Arg Thr Phe His Leu Ser Trp Ile Ser
        35                  40                  45

Phe Phe Thr Cys Phe Val Ser Thr Phe Ala Ala Ala Pro Leu Val Pro
    50                  55                  60
```

-continued

```
Ile Ile Arg Asp Asn Leu Asn Leu Ala Lys Ala Asp Ile Gly Asn Ala
65                  70                  75                  80

Gly Val Ala Ser Val Ser Gly Ser Ile Phe Ser Arg Leu Ala Met Gly
                85                  90                  95

Ala Ile Cys Asp Leu Leu Gly Pro Arg Tyr Gly Cys Ala Phe Leu Val
            100                 105                 110

Met Leu Ser Ala Pro Thr Val Phe Cys Met Ala Ala Ile Asp Asp Ala
        115                 120                 125

Ser Gly Tyr Ile Ala Val Arg Phe Leu Ile Gly Phe Ser Leu Ala Thr
    130                 135                 140

Phe Val Ser Cys Gln Tyr Trp Met Ser Thr Met Phe Asn Ser Lys Ile
145                 150                 155                 160

Ile Gly Thr Val Asn Gly Leu Ala Ala Gly Trp Gly Asn Met Gly Gly
                165                 170                 175

Gly Ala Thr Gln Leu Ile Met Pro Leu Val Phe His Ala Ile Gln Lys
            180                 185                 190

Cys Gly Ala Thr Pro Phe Val Ala Trp Arg Ile Ala Tyr Phe Val Pro
        195                 200                 205

Gly Met Met His Ile Val Met Gly Leu Leu Val Leu Thr Met Gly Gln
    210                 215                 220

Asp Leu Pro Asp Gly Asn Leu Ala Ser Leu Gln Lys Lys Gly Asp Met
225                 230                 235                 240

Ala Lys Asp Lys Phe Ser Lys Val Leu Trp Gly Ala Val Thr Asn Tyr
                245                 250                 255

Arg Thr Trp Ile Phe Val Leu Leu Tyr Gly Tyr Cys Met Gly Val Glu
            260                 265                 270

Leu Thr Thr Asp Asn Val Ile Ala Glu Tyr Tyr Tyr Asp His Phe His
        275                 280                 285

Leu Asp Leu Arg Ala Ala Gly Thr Ile Ala Ala Cys Phe Gly Met Ala
    290                 295                 300

Asn Ile Val Ala Arg Pro Met Gly Gly Tyr Leu Ser Asp Leu Gly Ala
305                 310                 315                 320

Arg Tyr Phe Gly Met Arg Ala Arg Leu Trp Asn Ile Trp Ile Leu Gln
                325                 330                 335

Thr Ala Gly Gly Ala Phe Cys Ile Trp Leu Gly Arg Ala Ser Ala Leu
            340                 345                 350

Pro Ala Ser Val Thr Ala Met Val Leu Phe Ser Ile Cys Ala Gln Ala
        355                 360                 365

Ala Cys Gly Ala Val Phe Gly Val Ala Pro Phe Val Ser Arg Arg Ser
    370                 375                 380

Leu Gly Ile Ile Ser Gly Leu Thr Gly Ala Gly Gly Asn Val Gly Ala
385                 390                 395                 400

Gly Leu Thr Gln Leu Leu Phe Phe Thr Ser Ser Gln Tyr Ser Thr Gly
                405                 410                 415

Arg Gly Leu Glu Tyr Met Gly Ile Met Ile Met Ala Cys Thr Leu Pro
            420                 425                 430

Val Ala Leu Val His Phe Pro Gln Trp Gly Ser Met Phe Phe Pro Ala
        435                 440                 445

Ser Ala Asp Ala Thr Glu Glu Glu Tyr Tyr Ala Ser Glu Trp Ser Glu
    450                 455                 460

Glu Glu Lys Gly Lys Gly Leu His Ile Thr Gly Gln Lys Phe Ala Glu
465                 470                 475                 480
```

```
Asn Ser Arg Ser Glu Arg Gly Arg Arg Asn Val Ile Leu Ala Thr Ser
                485                 490                 495

Ala Thr Pro Pro Asn Asn Thr Pro Gln His Val
            500                 505


<210> SEQ ID NO 18
<211> LENGTH: 507
<212> TYPE: PRT
<213> ORGANISM: Triticum aestivum
<220> FEATURE:
<221> NAME/KEY: misc_feature
<222> LOCATION: (1)..(507)
<223> OTHER INFORMATION: Public GI no. 13345827

<400> SEQUENCE: 18

Met Glu Val Gln Ala Gly Ser His Ala Asp Ala Ala Ala Ser Lys Phe
1               5                   10                  15

Thr Leu Pro Val Asp Ser Glu His Lys Ala Lys Ser Phe Arg Leu Phe
            20                  25                  30

Ser Phe Ala Asn Pro His Met Arg Thr Phe His Leu Ser Trp Ile Ser
        35                  40                  45

Phe Phe Thr Cys Phe Val Ser Thr Phe Ala Ala Ala Pro Leu Val Pro
    50                  55                  60

Ile Ile Arg Asp Asn Leu Asn Leu Ala Lys Ala Asp Ile Gly Asn Ala
65                  70                  75                  80

Gly Val Ala Ser Val Ser Gly Ser Ile Phe Ser Arg Leu Ala Met Gly
                85                  90                  95

Ala Ile Cys Asp Leu Leu Gly Pro Arg Tyr Gly Cys Ala Phe Leu Val
            100                 105                 110

Met Leu Ser Ala Pro Thr Val Phe Cys Met Ala Val Ile Asp Asp Ala
        115                 120                 125

Ser Gly Tyr Ile Ala Val Arg Phe Leu Ile Gly Phe Ser Leu Ala Thr
    130                 135                 140

Phe Val Ser Cys Gln Tyr Trp Met Ser Thr Met Phe Asn Ser Lys Ile
145                 150                 155                 160

Ile Gly Thr Val Asn Gly Leu Ala Ala Gly Trp Gly Asn Met Gly Gly
                165                 170                 175

Gly Ala Thr Gln Leu Ile Met Pro Leu Val Phe His Ala Ile Gln Lys
            180                 185                 190

Cys Gly Ala Thr Pro Phe Val Ala Trp Arg Ile Ala Tyr Phe Val Pro
        195                 200                 205

Gly Met Met His Ile Val Met Gly Leu Leu Val Leu Thr Met Gly Gln
    210                 215                 220

Asp Leu Pro Asp Gly Asn Leu Ala Ser Leu Gln Lys Lys Gly Asp Met
225                 230                 235                 240

Ala Lys Asp Lys Phe Ser Lys Val Leu Trp Gly Ala Val Thr Asn Tyr
                245                 250                 255

Arg Thr Trp Ile Phe Val Leu Leu Tyr Gly Tyr Cys Met Gly Val Glu
            260                 265                 270

Leu Thr Thr Asp Asn Val Ile Ala Glu Tyr Tyr Tyr Asp His Phe His
        275                 280                 285

Leu Asp Leu Arg Ala Ala Gly Thr Ile Ala Ala Cys Phe Gly Met Ala
    290                 295                 300

Asn Ile Val Ala Arg Pro Met Gly Gly Tyr Leu Ser Asp Leu Gly Ala
305                 310                 315                 320

Arg Tyr Phe Gly Met Arg Ala Arg Leu Trp Asn Ile Trp Ile Leu Gln
```

-continued

```
                325                 330                 335

Thr Ala Gly Gly Ala Phe Cys Ile Trp Leu Gly Arg Ala Ser Ala Leu
            340                 345                 350

Pro Ala Ser Val Thr Ala Met Val Leu Phe Ser Ile Cys Ala Gln Ala
        355                 360                 365

Ala Cys Gly Ala Val Phe Gly Val Ala Pro Phe Val Ser Arg Arg Ser
    370                 375                 380

Leu Gly Ile Ile Ser Gly Leu Thr Gly Ala Gly Gly Asn Val Gly Ala
385                 390                 395                 400

Gly Leu Thr Gln Leu Leu Phe Phe Thr Ser Ser Gln Tyr Ser Thr Gly
                405                 410                 415

Arg Gly Leu Glu Tyr Met Gly Ile Met Ile Met Ala Cys Thr Leu Pro
            420                 425                 430

Val Ala Leu Val His Phe Pro Gln Trp Gly Ser Met Phe Phe Pro Ala
        435                 440                 445

Ser Ala Asp Ala Thr Glu Glu Glu Tyr Tyr Ala Ser Glu Trp Ser Glu
    450                 455                 460

Glu Glu Lys Asn Lys Gly Leu His Ile Ala Gly Gln Lys Phe Ala Glu
465                 470                 475                 480

Asn Ser Arg Ser Glu Arg Gly Arg Arg Asn Val Ile Leu Ala Thr Ser
                485                 490                 495

Ala Thr Pro Pro Asn Asn Thr Pro Gln His Val
            500                 505


<210> SEQ ID NO 19
<211> LENGTH: 507
<212> TYPE: PRT
<213> ORGANISM: Hordeum vulgare
<220> FEATURE:
<221> NAME/KEY: misc_feature
<222> LOCATION: (1)..(507)
<223> OTHER INFORMATION: Public GI no. 4731148

<400> SEQUENCE: 19

Met Glu Val Glu Ala Gly Ala His Gly Asp Ala Ala Ala Ser Lys Phe
1               5                   10                  15

Thr Leu Pro Val Asp Ser Glu His Lys Ala Lys Ser Phe Arg Leu Phe
            20                  25                  30

Ser Phe Ala Asn Pro His Met Arg Thr Phe His Leu Ser Trp Ile Ser
        35                  40                  45

Phe Phe Thr Cys Phe Val Ser Thr Phe Ala Ala Ala Pro Leu Val Pro
    50                  55                  60

Ile Ile Arg Asp Asn Leu Asn Leu Ala Lys Ala Asp Ile Gly Asn Ala
65                  70                  75                  80

Gly Val Ala Ser Val Ser Gly Ser Ile Phe Ser Arg Leu Ala Met Gly
                85                  90                  95

Ala Ile Cys Asp Leu Leu Gly Pro Arg Tyr Gly Cys Ala Phe Leu Val
            100                 105                 110

Met Leu Ser Ala Pro Thr Val Phe Cys Met Ala Val Ile Asp Asp Ala
        115                 120                 125

Ser Gly Tyr Ile Ala Val Arg Phe Leu Ile Gly Phe Ser Leu Ala Thr
    130                 135                 140

Phe Val Ser Cys Gln Tyr Trp Met Ser Thr Met Phe Asn Ser Lys Ile
145                 150                 155                 160

Ile Gly Thr Val Asn Gly Leu Ala Ala Gly Trp Gly Asn Met Gly Gly
                165                 170                 175
```

```
Gly Ala Thr Gln Leu Ile Met Pro Leu Val Phe His Ala Ile Gln Lys
            180                 185                 190

Cys Gly Ala Thr Pro Phe Val Ala Trp Arg Ile Ala Tyr Phe Val Pro
        195                 200                 205

Gly Met Met His Ile Val Met Gly Leu Leu Val Leu Thr Met Gly Gln
    210                 215                 220

Asp Leu Pro Asp Gly Asn Leu Ala Ser Leu Gln Lys Lys Gly Asp Met
225                 230                 235                 240

Ala Lys Asp Lys Phe Ser Lys Val Leu Trp Gly Ala Val Thr Asn Tyr
                245                 250                 255

Arg Thr Trp Ile Phe Val Leu Leu Tyr Gly Tyr Cys Met Gly Val Glu
            260                 265                 270

Leu Thr Thr Gly Asn Val Ile Ala Glu Tyr Tyr Phe Asp His Phe His
        275                 280                 285

Leu Asn Leu Arg Ala Ala Gly Thr Ile Ala Ala Cys Phe Gly Met Ala
    290                 295                 300

Asn Ile Val Ala Arg Pro Met Gly Gly Tyr Leu Ser Asp Leu Gly Ala
305                 310                 315                 320

Arg Tyr Phe Gly Met Arg Ala Arg Leu Trp Asn Ile Trp Ile Leu Gln
                325                 330                 335

Thr Ala Gly Gly Ala Phe Cys Ile Trp Leu Gly Arg Ala Ser Ala Leu
            340                 345                 350

Pro Ala Ser Val Thr Ala Met Val Leu Phe Ser Ile Cys Ala Gln Ala
        355                 360                 365

Ala Cys Gly Ala Ile Phe Gly Val Glu Pro Phe Val Ser Arg Arg Ser
    370                 375                 380

Leu Gly Ile Ile Ser Gly Leu Thr Gly Ala Gly Gly Asn Val Gly Ala
385                 390                 395                 400

Gly Leu Thr Gln Leu Leu Phe Phe Thr Ser Ser Gln Tyr Ser Thr Gly
                405                 410                 415

Arg Gly Leu Glu Tyr Met Gly Ile Met Ile Met Ala Cys Thr Leu Pro
            420                 425                 430

Val Ala Leu Val His Phe Pro Gln Trp Gly Ser Met Phe Leu Ala Ala
        435                 440                 445

Ser Ala Asp Ala Thr Glu Glu Glu Tyr Tyr Ala Ser Glu Trp Ser Glu
    450                 455                 460

Glu Glu Lys Ser Lys Gly Leu His Ile Ala Gly Gln Lys Phe Ala Glu
465                 470                 475                 480

Asn Ser Arg Ser Glu Arg Gly Arg Arg Asn Val Ile Leu Ala Thr Ser
                485                 490                 495

Ala Thr Pro Pro Asn Asn Thr Pro Leu His Val
            500                 505
```

<210> SEQ ID NO 20
<211> LENGTH: 517
<212> TYPE: PRT
<213> ORGANISM: Physcomitrella patens
<220> FEATURE:
<221> NAME/KEY: misc_feature
<222> LOCATION: (1)..(517)
<223> OTHER INFORMATION: Public GI no. 37999156

<400> SEQUENCE: 20

```
Met Ala Asp Gln Ser Arg Ala Asn Ala Thr Asp Glu Ile Val Phe Arg
1               5                   10                  15
```

-continued

```
Leu Pro Val Asp Ser Glu His Lys Ala Lys Thr Leu His Ile Phe Ser
            20                  25                  30

Phe Ala Lys Pro His Met Arg Ala Phe His Leu Ser Trp Ile Ser Phe
        35                  40                  45

Phe Thr Ser Phe Leu Ser Thr Phe Ala Ala Pro Pro Leu Ile Pro Val
    50                  55                  60

Ile Arg Asp Asn Leu Asn Leu Thr Lys Thr Asp Ile Gly Gln Ala Ser
65                  70                  75                  80

Ile Ala Ser Val Ser Gly Ala Val Leu Ser Arg Leu Met Met Gly Thr
                85                  90                  95

Val Cys Asp Ile Val Gly Pro Arg Tyr Gly Ser Ala Phe Leu Ile Met
            100                 105                 110

Ile Asn Ala Pro Ala Val Phe Ser Met Ala Val Val Asp Asp Pro Ala
        115                 120                 125

Gly Phe Leu Ile Cys Arg Phe Phe Ile Gly Phe Ser Leu Ala Thr Phe
    130                 135                 140

Val Ser Cys Glu Phe Trp Val Thr Asn Met Phe Thr Thr Lys Ile Val
145                 150                 155                 160

Gly Thr Ala Asn Gly Leu Ala Ala Gly Trp Gly Asn Leu Gly Gly Gly
                165                 170                 175

Ala Thr Gln Ile Ile Met Pro Leu Ile Phe Leu Trp Ile Arg Asp Ser
            180                 185                 190

Phe His His Pro Ser Phe Met Ala Trp Arg Leu Ala Phe Phe Leu Pro
        195                 200                 205

Gly Thr Val His Ile Phe Val Gly Leu Leu Ile Leu Phe Leu Gly Gln
    210                 215                 220

Asp Leu Pro Asp Gly Asn Asp Thr Thr His Leu His Arg Gln Asn Asp
225                 230                 235                 240

Val Lys Asp Ser Phe Asn Lys Val Leu Tyr Phe Ala Val Thr Ser Pro
                245                 250                 255

Arg Thr Trp Ile Phe Phe Ile Ile Tyr Gly Tyr Ser Phe Gly Val Glu
            260                 265                 270

Leu Thr Val Asp Asn Ile Ile Ala Glu Tyr Phe Tyr Asp Arg Phe Asp
        275                 280                 285

Leu Asn Leu Asn Thr Ala Gly Val Ile Ala Ser Ala Phe Gly Phe Met
    290                 295                 300

Asn Ile Phe Ser Arg Pro Ala Gly Gly Tyr Leu Ser Asp Tyr Ile Gly
305                 310                 315                 320

Arg Arg Phe Gly Met Arg Gly Arg Leu Trp Ile Leu Trp Ile Val Gln
                325                 330                 335

Ser Leu Gly Gly Val Phe Cys Ile Leu Leu Gly Leu Met Thr Asp Leu
            340                 345                 350

Ser Ala Ala Ile Ala Ala Met Ile Val Phe Ser Ile Phe Val Gln Ala
        355                 360                 365

Ala Cys Gly Thr Ala Phe Gly Ile Ile Pro Phe Ile Ser Arg Arg Ser
    370                 375                 380

Leu Gly Met Val Ile Gly Leu Thr Ala Ala Gly Gly Asn Ile Gly Ser
385                 390                 395                 400

Val Val Thr Gln Ala Leu Phe Phe Thr Ser Ser Ser Tyr His Thr Glu
                405                 410                 415

Val Gly Leu Ile Tyr Met Gly Val Met Ile Leu Cys Cys Thr Met Leu
            420                 425                 430

Val Thr Leu Ile Trp Phe Pro Gln Trp Gly Ser Met Phe Phe Pro Ala
```

-continued

```
        435                 440                 445

Arg Lys Ser Ala Thr Glu Glu Asp Tyr Tyr Val Ser Glu Trp Thr Ala
    450                 455                 460

Glu Glu Gln Gly His Gly Leu His Leu Ala Ser Leu Lys Phe Ala Val
465                 470                 475                 480

Asn Ala Arg Ser Glu Arg Gly Arg His Gly Ser Ser Ser Ser Arg Asp
                485                 490                 495

Pro Glu Gly Asp His Pro Thr Ala Asp Gly Ile Gly Leu Ser Leu Trp
            500                 505                 510

Lys Ser Tyr Ser His
        515
```

<210> SEQ ID NO 21
<211> LENGTH: 1545
<212> TYPE: DNA
<213> ORGANISM: Arabidopsis thaliana
<220> FEATURE:
<221> NAME/KEY: misc_feature
<222> LOCATION: (1)..(1545)
<223> OTHER INFORMATION: Ceres CDNA ID no. 1828694
<220> FEATURE:
<221> NAME/KEY: CDS
<222> LOCATION: (1)..(1542)
<223> OTHER INFORMATION: Referenced by SEQ ID NO: 22

<400> SEQUENCE: 21

```
atggacaccg caaccaccac atgctctgcc gtagatctat ctgccctcct atcctcttct     60

tctaactcaa catcttccct cgccgcggca acctttttat gttcccaaat ttcaaacatc    120

tccaacaaac tctccgacac aacttatgcc gtcgacaaca cgtatctcct cttctccgcc    180

taccttgtct ttgccatgca gctcggtttc gctatgcttt gtgctggatc agtccgagcc    240

aagaacacta tgaacatcat gcttaccaat gtccttgatg ctgccgctgg agccatctct    300

tactacctct tcggattcgc attcgccttt ggtacacctt ccaacggatt catcggtcgc    360

caccatagct tcttcgcttt aagctcttac cctgaacgcc ccggctccga cttcagcttt    420

ttcctctacc aatgggcttt tgccatagcc gcggccggaa tcactagcgg ttccatcgcc    480

gagcggacgc aattcgttgc ttaccttatc tactctactt tcttgaccgg ttttgtttac    540

ccgacagtct cgcactggtt ctggtcaagt gatggatggg ctagcgcgtc ccggtctgac    600

aacaatctct tgtttggctc aggtgctatt gatttcgcag gttcaggagt tgttcacatg    660

gtaggtggaa ttgccggttt atgtggagcg ttagttgaag gaccaagaat aggtagattt    720

gaccggtcag gccggtccgt ggctttacgt ggtcacagtg catcccttgt cgtgcttggt    780

accttcttgt tgtggtttgg atggtatggg tttaaccctg gttccttttt aaccattctt    840

aaaggctacg acaagtctcg gccatattat ggtcaatgga gcgctgtagg tcgcaccgcg    900

gtcaccacaa cgctttctgg ctgcaccgct gcgttgacta ctctattcag taaacggctt    960

ttagcaggtc attggaacgt tattgacgta tgcaacggac ttctaggcgg ctttgcagct   1020

ataacctccg gatgtgccgt ggtggagccg tgggctgcta tagtatgtgg ctttgtggca   1080

tcatgggttt taatcggatt taacttgctt gccaagaaac ttaaatatga tgacccactc   1140

gaggctgctc agctccacgg tggatgtgga gcatggggat taatctttac cgggctgttc   1200

gcaaggaaag aatacgttaa cgagatttac tccggtgata ggccttacgg actgttcatg   1260

ggcgggggag aaaaactgct cgccgcgcag atcgttcaga tcattgtgat catcgggtgg   1320

gtgacggtaa ctatgggacc gttgttttat gggttacata agatgaatct tttgaggata   1380
```

-continued

```
tcagcagaag atgagatggc tggaatggac atgacacgtc atggaggatt tgcttacgca   1440

tacaatgacg aagacgacgt gtcgactaaa ccatggggtc atttcgctgg aagagtggag   1500

cctacaagcc ggagctcgac tcctacaccg accttgactg tttga                   1545


<210> SEQ ID NO 22
<211> LENGTH: 514
<212> TYPE: PRT
<213> ORGANISM: Arabidopsis thaliana
<220> FEATURE:
<221> NAME/KEY: misc_feature
<222> LOCATION: (53)..(479)
<223> OTHER INFORMATION: Pfam Name: Ammonium_transp; Pfam Description:
      Ammonium Transporter Family

<400> SEQUENCE: 22

Met Asp Thr Ala Thr Thr Thr Cys Ser Ala Val Asp Leu Ser Ala Leu
1               5                   10                  15

Leu Ser Ser Ser Ser Asn Ser Thr Ser Ser Leu Ala Ala Ala Thr Phe
            20                  25                  30

Leu Cys Ser Gln Ile Ser Asn Ile Ser Asn Lys Leu Ser Asp Thr Thr
        35                  40                  45

Tyr Ala Val Asp Asn Thr Tyr Leu Leu Phe Ser Ala Tyr Leu Val Phe
    50                  55                  60

Ala Met Gln Leu Gly Phe Ala Met Leu Cys Ala Gly Ser Val Arg Ala
65                  70                  75                  80

Lys Asn Thr Met Asn Ile Met Leu Thr Asn Val Leu Asp Ala Ala Ala
                85                  90                  95

Gly Ala Ile Ser Tyr Tyr Leu Phe Gly Phe Ala Phe Ala Phe Gly Thr
            100                 105                 110

Pro Ser Asn Gly Phe Ile Gly Arg His His Ser Phe Phe Ala Leu Ser
        115                 120                 125

Ser Tyr Pro Glu Arg Pro Gly Ser Asp Phe Ser Phe Phe Leu Tyr Gln
    130                 135                 140

Trp Ala Phe Ala Ile Ala Ala Ala Gly Ile Thr Ser Gly Ser Ile Ala
145                 150                 155                 160

Glu Arg Thr Gln Phe Val Ala Tyr Leu Ile Tyr Ser Thr Phe Leu Thr
                165                 170                 175

Gly Phe Val Tyr Pro Thr Val Ser His Trp Phe Trp Ser Ser Asp Gly
            180                 185                 190

Trp Ala Ser Ala Ser Arg Ser Asp Asn Asn Leu Leu Phe Gly Ser Gly
        195                 200                 205

Ala Ile Asp Phe Ala Gly Ser Gly Val Val His Met Val Gly Gly Ile
    210                 215                 220

Ala Gly Leu Cys Gly Ala Leu Val Glu Gly Pro Arg Ile Gly Arg Phe
225                 230                 235                 240

Asp Arg Ser Gly Arg Ser Val Ala Leu Arg Gly His Ser Ala Ser Leu
                245                 250                 255

Val Val Leu Gly Thr Phe Leu Leu Trp Phe Gly Trp Tyr Gly Phe Asn
            260                 265                 270

Pro Gly Ser Phe Leu Thr Ile Leu Lys Gly Tyr Asp Lys Ser Arg Pro
        275                 280                 285

Tyr Tyr Gly Gln Trp Ser Ala Val Gly Arg Thr Ala Val Thr Thr Thr
    290                 295                 300

Leu Ser Gly Cys Thr Ala Ala Leu Thr Thr Leu Phe Ser Lys Arg Leu
305                 310                 315                 320
```

```
Leu Ala Gly His Trp Asn Val Ile Asp Val Cys Asn Gly Leu Leu Gly
                325                 330                 335

Gly Phe Ala Ala Ile Thr Ser Gly Cys Ala Val Val Glu Pro Trp Ala
            340                 345                 350

Ala Ile Val Cys Gly Phe Val Ala Ser Trp Val Leu Ile Gly Phe Asn
        355                 360                 365

Leu Leu Ala Lys Lys Leu Lys Tyr Asp Asp Pro Leu Glu Ala Ala Gln
    370                 375                 380

Leu His Gly Gly Cys Gly Ala Trp Gly Leu Ile Phe Thr Gly Leu Phe
385                 390                 395                 400

Ala Arg Lys Glu Tyr Val Asn Glu Ile Tyr Ser Gly Asp Arg Pro Tyr
                405                 410                 415

Gly Leu Phe Met Gly Gly Gly Glu Lys Leu Leu Ala Ala Gln Ile Val
            420                 425                 430

Gln Ile Ile Val Ile Ile Gly Trp Val Thr Val Thr Met Gly Pro Leu
        435                 440                 445

Phe Tyr Gly Leu His Lys Met Asn Leu Leu Arg Ile Ser Ala Glu Asp
    450                 455                 460

Glu Met Ala Gly Met Asp Met Thr Arg His Gly Gly Phe Ala Tyr Ala
465                 470                 475                 480

Tyr Asn Asp Glu Asp Asp Val Ser Thr Lys Pro Trp Gly His Phe Ala
                485                 490                 495

Gly Arg Val Glu Pro Thr Ser Arg Ser Ser Thr Pro Thr Pro Thr Leu
            500                 505                 510

Thr Val


<210> SEQ ID NO 23
<211> LENGTH: 514
<212> TYPE: PRT
<213> ORGANISM: Lycopersicon esculentum
<220> FEATURE:
<221> NAME/KEY: misc_feature
<222> LOCATION: (1)..(514)
<223> OTHER INFORMATION: Public GI no. 2065194

<400> SEQUENCE: 23

Met Ala Ser Ala Met Thr Cys Ser Ala Ala Glu Leu Phe Pro His Leu
1               5                   10                  15

Gly Ser Ser Ala Asn Ala Thr Ala Ala Ala Glu Phe Ile Cys Ser Arg
            20                  25                  30

Phe Ser Ala Val Ser Glu Tyr Leu Thr Asn Thr Thr Tyr Ala Val Asp
        35                  40                  45

Thr Thr Tyr Leu Leu Phe Ser Ala Tyr Leu Val Phe Ala Met Gln Leu
    50                  55                  60

Gly Phe Ala Met Leu Cys Ala Gly Ser Val Arg Ala Lys Asn Thr Met
65                  70                  75                  80

Asn Ile Met Leu Thr Asn Val Leu Asp Ala Ala Ala Gly Gly Phe Ser
                85                  90                  95

Tyr Tyr Leu Phe Gly Phe Ala Phe Ala Phe Gly Ala Pro Ser Asn Gly
            100                 105                 110

Phe Ile Gly Lys His Phe Phe Gly Leu Lys Glu Phe Pro Ser Gln Ala
        115                 120                 125

Phe Asp Tyr Ser Tyr Phe Leu Tyr Gln Trp Ala Phe Ala Ile Ala Ala
    130                 135                 140

Ala Gly Ile Thr Ser Gly Ser Ile Ala Glu Arg Thr Gln Phe Val Ala
145                 150                 155                 160
```

-continued

```
Tyr Leu Ile Tyr Ser Ser Phe Leu Thr Gly Phe Val Tyr Pro Ile Val
                165                 170                 175

Ser His Trp Phe Trp Ser Gly Asp Gly Trp Ala Ser Ala Ser Lys Thr
            180                 185                 190

Asp Gly Asn Leu Leu Leu Arg Phe Gly Val Ile Asp Phe Ala Gly Ser
        195                 200                 205

Gly Val Val His Met Val Gly Gly Ile Ala Gly Leu Trp Gly Ala Phe
    210                 215                 220

Ile Glu Gly Pro Arg Ile Gly Arg Phe Asp Arg Ser Gly Arg Ser Val
225                 230                 235                 240

Ala Leu Arg Gly His Ser Ala Ser Leu Val Val Leu Gly Thr Phe Leu
                245                 250                 255

Leu Trp Phe Gly Trp Tyr Gly Phe Asn Pro Gly Ser Phe Leu Thr Ile
            260                 265                 270

Leu Lys Ser Tyr Asp His Thr Ile Arg Gly Thr Tyr Tyr Gly Gln Trp
        275                 280                 285

Ser Ala Ile Gly Arg Thr Ala Val Thr Thr Thr Leu Ala Gly Cys Thr
    290                 295                 300

Ala Ala Leu Thr Thr Leu Phe Cys Lys Arg Leu Leu Val Ala His Trp
305                 310                 315                 320

Asn Val Val Asp Val Cys Asn Gly Leu Leu Gly Gly Phe Ala Ala Ile
                325                 330                 335

Thr Ser Gly Cys Ala Val Val Glu Pro Trp Ala Ala Ile Val Cys Gly
            340                 345                 350

Phe Ile Ala Ala Trp Val Leu Ile Gly Phe Asn Ala Leu Ala Ala Lys
        355                 360                 365

Leu Lys Tyr Asp Asp Pro Leu Glu Ala Ala Gln Leu His Gly Gly Cys
    370                 375                 380

Gly Ser Trp Gly Ile Ile Phe Thr Gly Leu Phe Ala Lys Lys Glu Tyr
385                 390                 395                 400

Val Asn Glu Val Tyr Pro Gly Phe Pro Asn Arg Pro Tyr Gly Leu Phe
                405                 410                 415

Met Gly Gly Gly Gly Lys Leu Leu Gly Ala Gln Val Ile Gln Val Val
            420                 425                 430

Val Ile Ile Gly Trp Val Ser Val Thr Met Gly Pro Leu Phe Tyr Leu
        435                 440                 445

Leu His Lys Phe Lys Leu Leu Arg Ile Ser Arg Asp Asp Glu Thr Ala
    450                 455                 460

Gly Met Asp Leu Thr Arg His Gly Gly Phe Ala Tyr Ile Tyr His Asp
465                 470                 475                 480

Glu Asp Glu Gly Ser Ser Met Pro Gly Phe Lys Met Thr Arg Val Glu
                485                 490                 495

Pro Thr Asn Thr Ser Thr Pro Asp His Gln Asn Arg Ser Val Asn Val
            500                 505                 510

Val Val
```

<210> SEQ ID NO 24
<211> LENGTH: 507
<212> TYPE: PRT
<213> ORGANISM: Populus tremula x Populus tremuloides
<220> FEATURE:
<221> NAME/KEY: misc_feature
<222> LOCATION: (1)..(507)
<223> OTHER INFORMATION: Public GI no. 57283313

<400> SEQUENCE: 24

```
Met Ala Cys Ser Ala Ser Asp Leu Ala Pro Leu Leu Ser Ser Thr Val
1               5                   10                  15

Asn Ser Thr Glu Ala Ala Thr Tyr Leu Cys Ser Gln Phe Thr Ser Ile
            20                  25                  30

Ser Asn His Leu Ser Asp Thr Ser Tyr Ala Val Asn Asn Thr Tyr Leu
        35                  40                  45

Leu Phe Ser Ala Tyr Leu Val Phe Ala Met Gln Leu Gly Phe Ala Met
    50                  55                  60

Leu Cys Ala Gly Ser Val Arg Ala Lys Asn Thr Met Asn Ile Met Leu
65                  70                  75                  80

Thr Asn Val Leu Asp Ala Ala Ala Gly Gly Leu Ser Tyr Tyr Leu Phe
                85                  90                  95

Gly Tyr Ala Phe Ala Phe Gly Ser Pro Ser Asn Gly Phe Ile Gly Arg
            100                 105                 110

His Phe Phe Gly Leu Gly Asp Phe Pro Ser Pro Gln Ala Asp Tyr Ser
        115                 120                 125

Phe Phe Leu Tyr Gln Trp Ala Phe Ala Ile Ala Ala Ala Gly Ile Thr
    130                 135                 140

Ser Gly Ser Ile Ala Glu Arg Thr Gln Phe Val Ala Tyr Leu Ile Tyr
145                 150                 155                 160

Ser Thr Phe Leu Thr Gly Phe Val Tyr Pro Val Val Ser His Trp Leu
                165                 170                 175

Trp Ser Gly Asp Gly Trp Ala Asn Pro Ala Lys Ser Asp Asn Asn Leu
            180                 185                 190

Leu Phe Gly Ser Gly Ala Ile Asp Phe Ala Gly Ser Gly Val Val His
        195                 200                 205

Met Val Gly Gly Ile Ala Gly Leu Trp Gly Ala Leu Ile Glu Gly Pro
    210                 215                 220

Arg Ile Gly Arg Phe Asp His Asn Gly Arg Ser Val Ala Leu Arg Gly
225                 230                 235                 240

His Ser Ala Ser Leu Val Val Leu Gly Ser Phe Leu Leu Trp Phe Gly
                245                 250                 255

Trp Tyr Gly Phe Asn Pro Gly Ser Phe Leu Ile Ile Leu Lys Ser Tyr
            260                 265                 270

Gly Gly Gly Ala Gly Gly Tyr Tyr Gly Gln Trp Ser Ala Val Gly Arg
        275                 280                 285

Thr Ala Val Thr Thr Thr Leu Ala Gly Ser Thr Ala Ala Leu Thr Thr
    290                 295                 300

Leu Phe Gly Lys Arg Leu Leu Ser Gly His Trp Asn Val Ile Asp Val
305                 310                 315                 320

Cys Asn Gly Leu Leu Arg Gly Phe Ala Ala Ile Thr Ala Gly Cys Ser
                325                 330                 335

Val Val Glu Pro Trp Ala Ala Ile Ile Cys Gly Phe Val Ala Ala Trp
            340                 345                 350

Val Leu Ile Gly Cys Asn Lys Leu Ala Glu Lys Leu Gln Tyr Asp Asp
        355                 360                 365

Pro Leu Glu Ala Ala Gln Leu His Gly Gly Cys Gly Met Trp Gly Leu
    370                 375                 380

Leu Phe Thr Gly Leu Phe Ala Lys Lys Ala Tyr Val Asn Glu Val Tyr
385                 390                 395                 400

Ser Asn Lys Pro Gly Arg Pro Tyr Gly Leu Phe Met Gly Gly Gly Gly
                405                 410                 415
```

```
Lys Leu Leu Ala Ala Gln Ile Ile Glu Ile Leu Val Ile Val Gly Trp
            420                 425                 430

Val Ser Ala Thr Met Gly Pro Leu Phe Tyr Gly Leu His Lys Leu Lys
        435                 440                 445

Leu Leu Arg Ile Ser Ser Glu Asp Glu Met Ala Gly Met Asp Leu Thr
    450                 455                 460

Arg His Gly Gly Phe Ala Tyr Ala Tyr Asp Ala Glu Asp Asp Val Ser
465                 470                 475                 480

Gly Lys Pro Ser Phe Met Met Arg Lys Val Leu Pro Ala Asn Asn Thr
                485                 490                 495

Thr Pro Asn Glu Asn Ser Pro Ser Ile Asn Val
            500                 505


<210> SEQ ID NO 25
<211> LENGTH: 518
<212> TYPE: PRT
<213> ORGANISM: Lotus japonicus
<220> FEATURE:
<221> NAME/KEY: misc_feature
<222> LOCATION: (1)..(518)
<223> OTHER INFORMATION: Public GI no. 31322044

<400> SEQUENCE: 25

Met Ala Ser Leu Ser Cys Ser Ala Thr Asp Leu Ala Pro Leu Leu Thr
1               5                   10                  15

Ala Thr Thr Asn Ala Thr Ala Thr Ala Ala Ala Thr Tyr Leu Cys Asn
            20                  25                  30

Gln Leu Asp Thr Ile Ser Arg Lys Leu Ser Asp Thr Thr Tyr Ala Val
        35                  40                  45

Asp Asn Thr Tyr Leu Leu Phe Ser Ala Tyr Leu Val Phe Ala Met Gln
    50                  55                  60

Leu Gly Phe Ala Met Leu Cys Ala Gly Ser Val Arg Ala Lys Asn Thr
65                  70                  75                  80

Met Asn Ile Met Leu Thr Asn Val Leu Asp Ala Ala Ala Gly Gly Leu
                85                  90                  95

Ser Tyr Tyr Leu Phe Gly Phe Ala Phe Ala Phe Gly Ala Pro Ser Asn
            100                 105                 110

Gly Phe Ile Gly Arg His Phe Phe Gly Leu Lys His Tyr Pro Ser Pro
        115                 120                 125

Thr Tyr Asp Tyr Ser Phe Phe Leu Tyr Gln Trp Ala Phe Ala Ile Ala
    130                 135                 140

Ala Ala Gly Ile Thr Ser Gly Ser Ile Ala Glu Arg Thr Gln Phe Val
145                 150                 155                 160

Ala Tyr Leu Ile Tyr Ser Ser Phe Leu Thr Gly Phe Val Tyr Pro Val
                165                 170                 175

Val Ser His Trp Leu Trp Ser Ser Asp Gly Trp Ala Ser Pro Thr Arg
            180                 185                 190

Thr Thr Gly Ser Leu Leu Phe Gly Ser Gly Ala Ile Asp Phe Ala Gly
        195                 200                 205

Ser Gly Val Val His Met Val Gly Gly Ile Ala Gly Leu Trp Gly Ala
    210                 215                 220

Phe Ile Glu Gly Pro Arg Ile Gly Arg Phe Asp Arg Thr Gly Arg Ser
225                 230                 235                 240

Val Ala Leu Arg Gly His Ser Ala Ser Leu Val Val Leu Gly Ser Phe
                245                 250                 255
```

-continued

```
Leu Leu Trp Phe Gly Trp Tyr Gly Phe Asn Pro Gly Ser Phe Leu Thr
            260                 265                 270

Ile Ala Lys Ala Tyr Gly Asn Asn Gly Glu Asn Gly Asn Tyr Tyr Gly
        275                 280                 285

Gln Trp Ser Ala Ile Gly Arg Thr Ala Val Thr Thr Thr Leu Ala Gly
    290                 295                 300

Cys Thr Ala Ala Leu Thr Thr Leu Phe Ser Lys Arg Leu Leu Glu Gly
305                 310                 315                 320

His Trp Lys Val Leu Asp Val Cys Asn Gly Leu Leu Gly Gly Phe Ala
                325                 330                 335

Ala Ile Thr Ser Gly Cys Ser Val Val Glu Pro Trp Pro Ala Ile Val
            340                 345                 350

Cys Gly Phe Val Ala Ala Trp Val Leu Ile Gly Leu Asn Leu Val Ala
        355                 360                 365

Ala Lys Met Lys Tyr Asp Asp Pro Leu Glu Ala Ala Gln Leu His Gly
    370                 375                 380

Gly Cys Gly Ala Trp Gly Val Leu Phe Thr Gly Leu Phe Ala Lys Gly
385                 390                 395                 400

Glu Tyr Val Ala Glu Val Tyr Gly Ser Ala Gly Arg Pro Tyr Gly Leu
                405                 410                 415

Leu Met Gly Gly Gly Gly Lys Leu Leu Ala Ala Gln Val Ile Glu Ile
            420                 425                 430

Leu Val Val Cys Gly Trp Val Thr Ala Thr Met Gly Pro Leu Phe Tyr
        435                 440                 445

Gly Leu His Lys Thr Lys Leu Leu Arg Ile Ser Glu Asp Asp Glu Thr
    450                 455                 460

Ala Gly Met Asp Leu Thr Arg His Gly Gly Phe Ala Tyr Ala Tyr His
465                 470                 475                 480

Asp Asp Asp Asp Val Ser Thr Lys Arg Gly Val Met Met Ser Arg Ile
                485                 490                 495

Gly Pro Gly Ser Ser Ser Pro Ser Thr Met Asn Thr Pro Ala Ala Ser
            500                 505                 510

Ala Ala Ala Asn Asp Cys
        515


<210> SEQ ID NO 26
<211> LENGTH: 496
<212> TYPE: PRT
<213> ORGANISM: Oryza sativa (japonica cultivar-group)
<220> FEATURE:
<221> NAME/KEY: misc_feature
<222> LOCATION: (1)..(496)
<223> OTHER INFORMATION: Public GI no. 50910611

<400> SEQUENCE: 26

Met Ala Thr Cys Ala Asp Thr Leu Gly Pro Leu Leu Gly Thr Ala Ala
1               5                   10                  15

Ala Asn Ala Thr Asp Tyr Leu Cys Asn Gln Phe Ala Asp Thr Thr Ser
            20                  25                  30

Ala Val Asp Ser Thr Tyr Leu Leu Phe Ser Ala Tyr Leu Val Phe Ala
        35                  40                  45

Met Gln Leu Gly Phe Ala Met Leu Cys Ala Gly Ser Val Arg Ala Lys
    50                  55                  60

Asn Thr Met Asn Ile Met Leu Thr Asn Val Leu Asp Ala Ala Ala Gly
65                  70                  75                  80

Ala Leu Phe Tyr Tyr Leu Phe Gly Phe Ala Phe Ala Phe Gly Ala Pro
```

-continued

```
                85                  90                  95

Ser Asn Gly Phe Ile Gly Lys His Phe Phe Gly Leu Lys Gln Val Pro
            100                 105                 110

Gln Val Gly Phe Asp Tyr Ser Phe Phe Leu Phe Gln Trp Ala Phe Ala
        115                 120                 125

Ile Ala Ala Ala Gly Ile Thr Ser Gly Ser Ile Ala Glu Arg Thr Gln
    130                 135                 140

Phe Val Ala Tyr Leu Ile Tyr Ser Ala Phe Leu Thr Gly Phe Val Tyr
145                 150                 155                 160

Pro Val Val Ser His Trp Ile Trp Ser Ala Asp Gly Trp Ala Ser Ala
                165                 170                 175

Ser Arg Thr Ser Gly Ser Leu Leu Phe Gly Ser Gly Val Ile Asp Phe
            180                 185                 190

Ala Gly Ser Gly Val Val His Met Val Gly Gly Val Ala Gly Leu Trp
        195                 200                 205

Gly Ala Leu Ile Glu Gly Pro Arg Ile Gly Arg Phe Asp His Ala Gly
    210                 215                 220

Arg Ser Val Ala Leu Arg Gly His Ser Ala Ser Leu Val Val Leu Gly
225                 230                 235                 240

Ser Phe Leu Leu Trp Phe Gly Trp Tyr Gly Phe Asn Pro Gly Ser Phe
                245                 250                 255

Leu Thr Ile Leu Lys Ser Tyr Gly Pro Pro Gly Ser Ile His Gly Gln
            260                 265                 270

Trp Ser Ala Val Gly Arg Thr Ala Val Thr Thr Thr Leu Ala Gly Ser
        275                 280                 285

Thr Ala Ala Leu Thr Thr Leu Phe Gly Lys Arg Leu Gln Thr Gly His
    290                 295                 300

Trp Asn Val Ile Asp Val Cys Asn Gly Leu Leu Gly Gly Phe Ala Ala
305                 310                 315                 320

Ile Thr Ala Gly Cys Ser Val Val Asp Pro Trp Ala Ala Ile Ile Cys
                325                 330                 335

Gly Phe Val Ser Ala Trp Val Leu Ile Gly Leu Asn Ala Leu Ala Ala
            340                 345                 350

Arg Leu Lys Phe Asp Asp Pro Leu Glu Ala Ala Gln Leu His Gly Gly
        355                 360                 365

Cys Gly Ala Trp Gly Val Ile Phe Thr Ala Leu Phe Ala Arg Lys Glu
    370                 375                 380

Tyr Val Asp Gln Ile Phe Gly Gln Pro Gly Arg Pro Tyr Gly Leu Phe
385                 390                 395                 400

Met Gly Gly Gly Gly Arg Leu Leu Gly Ala His Ile Val Val Ile Leu
                405                 410                 415

Val Ile Ala Ala Trp Val Ser Phe Thr Met Ala Pro Leu Phe Leu Val
            420                 425                 430

Leu Asn Lys Leu Gly Leu Leu Arg Ile Ser Ala Glu Asp Glu Met Ala
        435                 440                 445

Gly Met Asp Gln Thr Arg His Gly Gly Phe Ala Tyr Ala Tyr His Asp
    450                 455                 460

Asp Asp Ala Ser Gly Lys Pro Asp Arg Ser Val Gly Gly Phe Met Leu
465                 470                 475                 480

Lys Ser Ala His Gly Thr Gln Val Ala Ala Glu Met Gly Gly His Val
                485                 490                 495
```

<210> SEQ ID NO 27

<211> LENGTH: 513
<212> TYPE: PRT
<213> ORGANISM: Camellia sinensis var. sinensis
<220> FEATURE:
<221> NAME/KEY: misc_feature
<222> LOCATION: (1)..(513)
<223> OTHER INFORMATION: Public GI no. 50428339

<400> SEQUENCE: 27

```
Met Ala Ser Thr Leu Gly Cys Ser Ala Thr Asp Leu Val Pro His Leu
1               5                   10                  15

Thr Gly Val Asn Asn Ala Thr Ala Val Ala Asp Phe Ile Cys Gly Arg
            20                  25                  30

Leu Asp Ala Val Ser Thr Lys Leu Ser Asp Thr Thr Tyr Ala Val Asp
        35                  40                  45

Thr Thr Tyr Leu Leu Phe Ser Ala Tyr Leu Val Phe Ala Met Gln Leu
    50                  55                  60

Gly Phe Ala Met Leu Cys Ala Gly Ser Val Arg Ala Lys Asn Thr Met
65                  70                  75                  80

Asn Ile Met Leu Thr Asn Val Leu Asp Ala Ala Ala Gly Gly Leu Ser
                85                  90                  95

Tyr Tyr Leu Phe Gly Phe Ala Phe Ala Phe Gly Ser Gly Ser Arg Ser
            100                 105                 110

Asn Ala Phe Ile Gly His Tyr Ser Phe Ala Leu Thr Gly Val Pro Ser
        115                 120                 125

Ala Thr His Asp Tyr Ser Phe Phe Leu Tyr Gln Trp Ala Phe Ala Ile
    130                 135                 140

Ala Ala Ala Gly Ile Thr Ser Gly Ser Ile Ala Glu Arg Thr Gln Phe
145                 150                 155                 160

Val Ala Tyr Leu Ile Tyr Ser Ser Phe Leu Thr Ala Phe Val Tyr Pro
                165                 170                 175

Ile Val Ser His Trp Val Trp Ser Gly Asp Gly Trp Leu Ser Ala Ser
            180                 185                 190

Arg Thr Ser Gly Ala Leu Leu Phe Ser Ser Gly Ala Ile Asp Phe Ala
        195                 200                 205

Gly Ser Gly Val Val His Met Val Gly Gly Ile Ala Gly Leu Trp Gly
    210                 215                 220

Ala Leu Ile Glu Gly Pro Arg Ile Gly Arg Phe Asp Arg Ser Gly Arg
225                 230                 235                 240

Ser Val Ala Leu Arg Gly His Ser Ala Ser Leu Val Val Leu Gly Ser
                245                 250                 255

Phe Leu Leu Trp Phe Gly Trp Tyr Gly Phe Asn Pro Gly Ser Phe Leu
            260                 265                 270

Thr Ile Leu Lys Ser Tyr Gly Thr Ala Gly Thr Tyr Tyr Gly Gln Trp
        275                 280                 285

Ser Ala Val Gly Arg Thr Ala Val Thr Thr Thr Leu Ala Gly Cys Thr
    290                 295                 300

Ala Ala Leu Thr Thr Leu Phe Gly Lys Arg Leu Leu Asp Gly His Trp
305                 310                 315                 320

Asn Val Val Asp Val Cys Asn Gly Leu Leu Gly Gly Phe Ala Ala Ile
                325                 330                 335

Thr Ser Gly Cys Ser Val Val Glu Pro Trp Ala Ala Ile Val Cys Gly
            340                 345                 350

Phe Val Ser Ala Trp Val Leu Ile Gly Cys Asn Lys Val Ala Glu Lys
        355                 360                 365
```

-continued

```
Leu Lys Tyr Asp Asp Pro Leu Glu Ala Ala Gln Leu His Gly Gly Cys
    370                 375                 380

Gly Ser Trp Gly Ile Leu Phe Thr Gly Leu Phe Ala Lys Lys Lys Tyr
385                 390                 395                 400

Val Asp Glu Val Tyr Ser Ala Gly Arg Pro Tyr Gly Leu Phe Met Gly
                405                 410                 415

Gly Gly Gly Lys Leu Leu Ala Ala Gln Leu Ile Glu Ile Leu Val Ile
            420                 425                 430

Phe Gly Trp Val Ser Val Thr Met Gly Pro Leu Phe Tyr Gly Leu Lys
        435                 440                 445

Lys Leu Lys Leu Leu Arg Ile Ser Arg Glu Asp Glu Met Ala Gly Met
    450                 455                 460

Asp Leu Thr Arg His Gly Gly Phe Ala Tyr Ile Tyr Arg Asp Glu Asp
465                 470                 475                 480

Asp Leu Ala Asn Arg Pro Gly Phe Met Met Arg Lys Val Glu Pro Gln
                485                 490                 495

Asn Ser Ser Pro Thr Pro Asp His Asn Ser Ser Ser Pro Ala Glu Ala
            500                 505                 510

Val


<210> SEQ ID NO 28
<211> LENGTH: 532
<212> TYPE: PRT
<213> ORGANISM: Oryza sativa
<220> FEATURE:
<221> NAME/KEY: misc_feature
<222> LOCATION: (1)..(532)
<223> OTHER INFORMATION: Public GI no. 15705368

<400> SEQUENCE: 28

Met Ala Thr Cys Ala Ala Asp Leu Ala Pro Leu Leu Gly Pro Val Ala
1               5                   10                  15

Ala Asn Ala Thr Asp Tyr Leu Cys Asn Arg Phe Ala Asp Thr Thr Ser
            20                  25                  30

Ala Val Asp Ala Thr Tyr Leu Leu Phe Ser Ala Tyr Leu Val Phe Ala
        35                  40                  45

Met Gln Leu Gly Phe Ala Met Leu Cys Ala Gly Ser Val Arg Ala Lys
    50                  55                  60

Asn Thr Met Asn Ile Met Leu Thr Asn Val Leu Asp Ala Ala Ala Gly
65                  70                  75                  80

Ala Leu Phe Tyr Tyr Leu Phe Gly Phe Ala Phe Ala Phe Gly Thr Pro
                85                  90                  95

Ser Asn Gly Phe Ile Gly Lys Gln Phe Phe Gly Leu Lys His Met Pro
            100                 105                 110

Gln Thr Gly Phe Asp Tyr Asp Phe Phe Leu Phe Gln Trp Ala Phe Ala
        115                 120                 125

Ile Ala Ala Ala Gly Ile Thr Ser Gly Ser Ile Ala Glu Arg Thr Gln
    130                 135                 140

Phe Val Ala Tyr Leu Ile Tyr Ser Ala Phe Leu Thr Gly Phe Val Tyr
145                 150                 155                 160

Pro Val Val Ser His Trp Ile Trp Ser Ala Asp Gly Trp Ala Ser Ala
                165                 170                 175

Ser Arg Thr Ser Gly Pro Leu Leu Phe Gly Ser Gly Val Ile Asp Phe
            180                 185                 190

Ala Gly Ser Gly Val Val His Met Val Gly Gly Val Ala Gly Leu Trp
        195                 200                 205
```

```
Gly Ala Leu Ile Glu Gly Pro Arg Ile Gly Arg Phe Asp His Ala Gly
    210                 215                 220

Arg Ser Val Ala Leu Lys Gly His Ser Ala Ser Leu Val Val Leu Gly
225                 230                 235                 240

Thr Phe Leu Leu Trp Phe Gly Trp Tyr Gly Phe Asn Pro Gly Ser Phe
                245                 250                 255

Thr Thr Ile Leu Lys Thr Tyr Gly Pro Ala Gly Gly Ile Asn Gly Gln
            260                 265                 270

Trp Ser Gly Val Gly Arg Thr Ala Val Thr Thr Thr Leu Ala Gly Ser
        275                 280                 285

Val Ala Ala Leu Thr Thr Leu Phe Gly Lys Arg Leu Gln Thr Gly His
    290                 295                 300

Trp Asn Val Val Asp Val Cys Asn Gly Leu Leu Gly Gly Phe Ala Ala
305                 310                 315                 320

Ile Thr Ala Gly Cys Ser Val Val Asp Pro Trp Ala Ala Ile Ile Cys
                325                 330                 335

Gly Phe Val Ser Ala Trp Val Leu Ile Gly Leu Asn Ala Leu Ala Ala
            340                 345                 350

Arg Leu Lys Phe Asp Asp Pro Leu Glu Ala Ala Gln Leu His Gly Gly
        355                 360                 365

Cys Gly Ala Trp Gly Ile Leu Phe Thr Ala Leu Phe Ala Arg Gln Lys
    370                 375                 380

Tyr Val Glu Glu Ile Tyr Gly Ala Gly Arg Pro Tyr Gly Leu Phe Met
385                 390                 395                 400

Gly Gly Gly Gly Lys Leu Leu Ala Ala His Val Ile Gln Ile Leu Val
                405                 410                 415

Ile Phe Gly Trp Val Ser Cys Thr Met Gly Pro Leu Phe Tyr Gly Leu
            420                 425                 430

Lys Lys Leu Gly Leu Leu Arg Ile Ser Ala Glu Asp Glu Thr Ser Gly
        435                 440                 445

Met Asp Leu Thr Arg His Gly Gly Phe Ala Tyr Val Tyr His Asp Glu
    450                 455                 460

Asp Glu His Asp Lys Ser Gly Val Gly Gly Phe Met Leu Arg Ser Ala
465                 470                 475                 480

Gln Thr Arg Val Glu Pro Ala Ala Ala Gly Cys Leu Gln Gln Gln Gln
                485                 490                 495

Pro Ser Val Thr Asn Pro Glu Arg Thr Thr Ser Gln Arg Arg Lys Lys
            500                 505                 510

Ser Arg Val Ser Leu Pro Leu Arg Ser Arg Ser Ser Arg His Lys Phe
        515                 520                 525

Asp Pro His Ile
    530


<210> SEQ ID NO 29
<211> LENGTH: 532
<212> TYPE: PRT
<213> ORGANISM: Oryza sativa (japonica cultivar-group)
<220> FEATURE:
<221> NAME/KEY: misc_feature
<222> LOCATION: (1)..(532)
<223> OTHER INFORMATION: Public GI no. 52550773

<400> SEQUENCE: 29

Met Ala Thr Cys Ala Ala Asp Leu Ala Pro Leu Leu Gly Pro Val Ala
1               5                   10                  15
```

-continued

```
Ala Asn Ala Thr Asp Tyr Leu Cys Asn Arg Phe Ala Asp Thr Thr Ser
            20                  25                  30

Ala Val Asp Ala Thr Tyr Leu Leu Phe Ser Ala Tyr Leu Val Phe Ala
        35                  40                  45

Met Gln Leu Gly Phe Ala Met Leu Cys Ala Gly Ser Val Arg Ala Lys
    50                  55                  60

Asn Thr Met Asn Ile Met Leu Thr Asn Val Leu Asp Ala Ala Ala Gly
65                  70                  75                  80

Ala Leu Phe Tyr Tyr Leu Phe Gly Phe Ala Phe Ala Phe Gly Thr Pro
                85                  90                  95

Ser Asn Gly Phe Ile Gly Lys Gln Phe Phe Gly Leu Lys His Met Pro
            100                 105                 110

Gln Thr Gly Phe Asp Tyr Asp Phe Phe Leu Phe Gln Trp Ala Phe Ala
        115                 120                 125

Ile Ala Ala Ala Gly Ile Thr Ser Gly Ser Ile Ala Glu Arg Thr Gln
    130                 135                 140

Phe Val Ala Tyr Leu Ile Tyr Ser Ala Phe Leu Thr Gly Phe Val Tyr
145                 150                 155                 160

Pro Val Val Ser His Trp Ile Trp Ser Ala Asp Gly Trp Ala Ser Ala
                165                 170                 175

Ser Arg Thr Ser Gly Pro Leu Leu Phe Gly Ser Gly Val Ile Asp Phe
            180                 185                 190

Ala Gly Ser Gly Val Val His Met Val Gly Gly Val Ala Gly Leu Trp
        195                 200                 205

Gly Ala Leu Ile Glu Gly Pro Arg Ile Gly Arg Phe Asp His Ala Gly
    210                 215                 220

Arg Ser Val Ala Leu Lys Gly His Ser Ala Ser Leu Val Val Leu Gly
225                 230                 235                 240

Thr Phe Leu Leu Trp Phe Gly Trp Tyr Gly Phe Asn Pro Gly Ser Ser
                245                 250                 255

Thr Thr Ile Leu Lys Thr Tyr Gly Pro Ala Gly Gly Ile Asn Gly Gln
            260                 265                 270

Trp Ser Gly Val Gly Arg Thr Ala Val Thr Thr Thr Leu Ala Gly Ser
        275                 280                 285

Val Ala Ala Leu Thr Thr Leu Phe Gly Lys Arg Leu Gln Thr Gly His
    290                 295                 300

Trp Asn Val Val Asp Val Cys Asn Gly Leu Leu Gly Gly Phe Ala Ala
305                 310                 315                 320

Ile Thr Ala Gly Cys Ser Val Val Asp Pro Trp Ala Ala Ile Ile Cys
                325                 330                 335

Gly Phe Val Ser Ala Trp Val Leu Ile Gly Leu Asn Ala Leu Ala Ala
            340                 345                 350

Arg Leu Lys Phe Asp Asp Pro Leu Glu Ala Ala Gln Leu His Gly Gly
        355                 360                 365

Cys Gly Ala Trp Gly Ile Leu Phe Thr Ala Leu Phe Ala Arg Gln Lys
    370                 375                 380

Tyr Val Glu Glu Ile Tyr Gly Ala Gly Arg Pro Tyr Gly Leu Phe Met
385                 390                 395                 400

Gly Gly Gly Gly Lys Leu Leu Ala Ala His Val Ile Gln Ile Leu Val
                405                 410                 415

Ile Phe Gly Trp Val Ser Cys Thr Met Gly Pro Leu Phe Tyr Gly Leu
            420                 425                 430

Lys Lys Leu Gly Leu Leu Arg Ile Ser Ala Glu Asp Glu Thr Ser Gly
```

```
        435                 440                 445

Met Asp Leu Thr Arg His Gly Gly Phe Ala Tyr Val Tyr His Asp Glu
    450                 455                 460

Asp Glu His Asp Lys Ser Gly Val Gly Gly Phe Met Leu Arg Ser Ala
465                 470                 475                 480

Gln Thr Arg Val Glu Pro Ala Ala Ala Gly Cys Leu Gln Gln Gln Gln
                485                 490                 495

Pro Ser Val Thr Asn Pro Glu Arg Thr Thr Ser Gln Arg Arg Lys Lys
            500                 505                 510

Ser Arg Val Ser Leu Pro Leu Arg Ser Arg Ser Ser Arg His Lys Phe
        515                 520                 525

Asp Pro His Ile
    530


<210> SEQ ID NO 30
<211> LENGTH: 488
<212> TYPE: PRT
<213> ORGANISM: Lycopersicon esculentum
<220> FEATURE:
<221> NAME/KEY: misc_feature
<222> LOCATION: (1)..(488)
<223> OTHER INFORMATION: Public GI no. 22001520

<400> SEQUENCE: 30

Met Ala Cys Ser Val Asp Thr Leu Ala Pro Phe Leu Gly Pro Asn Thr
1               5                   10                  15

Thr Asn Ala Val Ala Ala Ala Ser Tyr Ile Cys Asn Gln Phe Ser Gly
            20                  25                  30

Val Ser Asp Arg Phe Val Asp Thr Gly Tyr Ala Ile Asp Ser Thr Tyr
        35                  40                  45

Leu Leu Phe Ser Ala Tyr Leu Val Phe Ser Met Gln Leu Gly Phe Ala
    50                  55                  60

Met Leu Leu Ala Gly Ser Val Arg Asn Thr Met Asn Ile Met Leu Thr
65                  70                  75                  80

Asn Val Leu Asp Ala Ala Ala Gly Gly Leu Phe Tyr Tyr Leu Phe Gly
                85                  90                  95

Phe Ala Phe Ala Leu Gly Gly Pro Ser Asn Gly Phe Ile Gly Arg His
            100                 105                 110

Phe Phe Gly Leu Lys Glu Ile Pro Ser Asn Ser Phe Asp Tyr Met Asn
        115                 120                 125

Phe Leu Tyr Gln Trp Ala Phe Ala Ile Ala Ala Ala Gly Ile Thr Ser
    130                 135                 140

Gly Ser Ile Ala Glu Arg Thr Gln Phe Val Ala Tyr Leu Ile Tyr Ser
145                 150                 155                 160

Ser Phe Leu Thr Gly Phe Val Tyr Pro Val Val Ser His Trp Phe Trp
                165                 170                 175

Thr Pro Asp Gly Trp Ala Ser Pro Thr Asn Ser Asn Leu Leu Phe Gly
            180                 185                 190

Ser Gly Val Ile Asp Phe Ala Gly Ser Gly Val Val His Met Val Gly
        195                 200                 205

Gly Ile Ala Gly Phe Tyr Gly Ala Leu Ile Glu Gly Pro Arg Ile Gly
    210                 215                 220

Arg Tyr Asp His Thr Gly Arg Ser Val Ala Leu Arg Gly His Ser Ala
225                 230                 235                 240

Ser Leu Val Val Leu Gly Thr Phe Leu Leu Trp Phe Gly Trp Tyr Gly
                245                 250                 255
```

```
Phe Asn Pro Gly Ser Phe Asn Lys Ile Leu Val Thr Tyr Gly Ala Ser
            260                 265                 270

Gly Gly Tyr Tyr Gly Gln Trp Ser Ala Val Gly Arg Thr Ala Val Thr
        275                 280                 285

Thr Thr Leu Ala Gly Cys Thr Ala Ala Leu Thr Thr Leu Phe Gly Lys
    290                 295                 300

Arg Ile Leu Ser Gly His Trp Asn Val Thr Asp Val Cys Asn Gly Leu
305                 310                 315                 320

Leu Gly Gly Phe Ala Ala Ile Thr Ala Gly Cys Ser Val Val Glu Pro
                325                 330                 335

Trp Ala Ala Ile Ile Cys Gly Phe Val Ala Ala Leu Val Leu Ile Gly
            340                 345                 350

Phe Asn Met Leu Ala Glu Lys Phe Lys Tyr Asp Asp Pro Leu Glu Ala
        355                 360                 365

Ala Gln Leu His Gly Gly Cys Gly Ala Trp Gly Ile Ile Phe Thr Gly
    370                 375                 380

Leu Phe Ala Lys Gly Glu Phe Val Asp Gln Val Tyr Pro Gly Lys Pro
385                 390                 395                 400

Gly Arg Pro His Gly Leu Phe Met Gly Gly Gly Gly Lys Leu Leu Gly
                405                 410                 415

Ala His Ile Ile Gln Ile Leu Val Ile Ile Gly Trp Val Ser Ala Thr
            420                 425                 430

Met Gly Pro Leu Phe Tyr Ile Leu His Lys Phe Lys Leu Leu Arg Ile
        435                 440                 445

Ser Ser Glu Asp Glu Met Ala Gly Met Asp Leu Thr Arg His Gly Gly
    450                 455                 460

Phe Ala Tyr Tyr His Glu Glu Asp Pro Lys Leu Gly Met Gln Met Arg
465                 470                 475                 480

Arg Ile Glu Pro Thr Thr Ser Thr
                485


<210> SEQ ID NO 31
<211> LENGTH: 498
<212> TYPE: PRT
<213> ORGANISM: Oryza sativa (japonica cultivar-group)
<220> FEATURE:
<221> NAME/KEY: misc_feature
<222> LOCATION: (1)..(498)
<223> OTHER INFORMATION: Public GI no. 50926368

<400> SEQUENCE: 31

Met Ala Thr Cys Ala Ala Asp Leu Ala Pro Leu Leu Gly Pro Val Ala
1               5                   10                  15

Ala Asn Ala Thr Asp Tyr Leu Cys Asn Arg Phe Ala Asp Thr Thr Ser
            20                  25                  30

Ala Val Asp Ala Thr Tyr Leu Leu Phe Ser Ala Tyr Leu Val Phe Ala
        35                  40                  45

Met Gln Leu Gly Phe Ala Met Leu Cys Ala Gly Ser Val Arg Ala Lys
    50                  55                  60

Asn Thr Met Asn Ile Met Leu Thr Asn Val Leu Asp Ala Ala Ala Gly
65                  70                  75                  80

Ala Leu Phe Tyr Tyr Leu Phe Gly Phe Ala Phe Ala Phe Gly Thr Pro
                85                  90                  95

Ser Asn Gly Phe Ile Gly Lys Gln Phe Phe Gly Leu Lys His Met Pro
            100                 105                 110
```

-continued

```
Gln Thr Gly Phe Asp Tyr Asp Phe Phe Leu Phe Gln Trp Ala Phe Ala
        115                 120                 125

Ile Ala Ala Ala Gly Ile Thr Ser Gly Ser Ile Ala Glu Arg Thr Gln
    130                 135                 140

Phe Val Ala Tyr Leu Ile Tyr Ser Ala Phe Leu Thr Gly Phe Val Tyr
145                 150                 155                 160

Pro Val Val Ser His Trp Ile Trp Ser Ala Asp Gly Trp Ala Ser Ala
                165                 170                 175

Ser Arg Thr Ser Gly Pro Leu Leu Phe Gly Ser Gly Val Ile Asp Phe
            180                 185                 190

Ala Gly Ser Gly Val Val His Met Val Gly Gly Val Ala Gly Leu Trp
        195                 200                 205

Gly Ala Leu Ile Glu Gly Pro Arg Ile Gly Arg Phe Asp His Ala Gly
    210                 215                 220

Arg Ser Val Ala Leu Lys Gly His Ser Ala Ser Leu Val Val Leu Gly
225                 230                 235                 240

Thr Phe Leu Leu Trp Phe Gly Trp Tyr Gly Phe Asn Pro Gly Ser Phe
                245                 250                 255

Thr Thr Ile Leu Lys Thr Tyr Gly Pro Ala Gly Gly Ile Asn Gly Gln
            260                 265                 270

Trp Ser Gly Val Gly Arg Thr Ala Val Thr Thr Thr Leu Ala Gly Ser
        275                 280                 285

Val Ala Ala Leu Thr Thr Leu Phe Gly Lys Arg Leu Gln Thr Gly His
    290                 295                 300

Trp Asn Val Val Asp Val Cys Asn Gly Leu Leu Gly Gly Phe Ala Ala
305                 310                 315                 320

Ile Thr Ala Gly Cys Ser Val Val Asp Pro Trp Ala Ala Ile Ile Cys
                325                 330                 335

Gly Phe Val Ser Ala Trp Val Leu Ile Gly Leu Asn Ala Leu Ala Ala
            340                 345                 350

Arg Leu Lys Phe Asp Asp Pro Leu Glu Ala Ala Gln Leu His Gly Gly
        355                 360                 365

Cys Gly Ala Trp Gly Ile Leu Phe Thr Ala Leu Phe Ala Arg Gln Lys
    370                 375                 380

Tyr Val Glu Glu Ile Tyr Gly Ala Gly Arg Pro Tyr Gly Leu Phe Met
385                 390                 395                 400

Gly Gly Gly Gly Lys Leu Leu Ala Ala His Val Ile Gln Ile Leu Val
                405                 410                 415

Ile Phe Gly Trp Val Ser Cys Thr Met Gly Pro Leu Phe Tyr Gly Leu
            420                 425                 430

Lys Lys Leu Gly Leu Leu Arg Ile Ser Ala Glu Asp Glu Thr Ser Gly
        435                 440                 445

Met Asp Leu Thr Arg His Gly Gly Phe Ala Tyr Val Tyr His Asp Glu
    450                 455                 460

Asp Glu His Asp Lys Ser Gly Val Gly Gly Phe Met Leu Arg Ser Ala
465                 470                 475                 480

Gln Thr Arg Val Glu Pro Ala Ala Ala Ala Ala Ser Asn Ser Asn Asn
                485                 490                 495

Gln Val
```

<210> SEQ ID NO 32
<211> LENGTH: 494
<212> TYPE: PRT
<213> ORGANISM: Triticum aestivum

```
<220> FEATURE:
<221> NAME/KEY: misc_feature
<222> LOCATION: (1)..(494)
<223> OTHER INFORMATION: Public GI no. 38684027

<400> SEQUENCE: 32

Met Ser Ala Thr Cys Ala Ala Asp Leu Gly Pro Leu Leu Gly Ala Ala
1               5                   10                  15

Ala Ala Asn Ala Thr Asp Tyr Leu Cys Asn Arg Phe Ala Asp Thr Thr
            20                  25                  30

Ser Ala Val Asp Ser Thr Tyr Leu Leu Phe Ser Ala Tyr Leu Val Phe
        35                  40                  45

Ala Met Gln Leu Gly Phe Ala Met Leu Cys Ala Gly Ser Val Arg Ala
    50                  55                  60

Lys Asn Thr Met Asn Ile Met Leu Thr Asn Val Leu Asp Ala Ala Ala
65                  70                  75                  80

Gly Ala Leu Phe Tyr Tyr Leu Phe Gly Phe Ala Phe Ala Phe Gly Thr
                85                  90                  95

Pro Ser Asn Gly Phe Ile Gly Lys His Phe Phe Gly Leu Lys Asp Met
            100                 105                 110

Pro Gln Thr Gly Phe Asp Tyr Ser Phe Phe Leu Phe Gln Trp Ala Phe
        115                 120                 125

Ala Val Ala Ala Ala Gly Ile Thr Ser Gly Ser Ile Ala Glu Arg Thr
    130                 135                 140

Gln Phe Val Ala Tyr Leu Ile Tyr Ser Ala Phe Leu Thr Gly Phe Val
145                 150                 155                 160

Tyr Pro Val Val Ser His Trp Ile Trp Ser Val Asp Gly Trp Ala Ser
                165                 170                 175

Ala Ala Arg Thr Ser Gly Pro Leu Leu Phe Lys Ser Gly Val Ile Asp
            180                 185                 190

Phe Ala Gly Ser Gly Val Val His Met Val Gly Gly Ile Ala Gly Phe
        195                 200                 205

Trp Gly Ala Leu Ile Glu Gly Pro Arg Ile Gly Arg Phe Asp His Ala
    210                 215                 220

Gly Arg Ser Val Ala Leu Lys Gly His Ser Ala Ser Leu Val Val Leu
225                 230                 235                 240

Gly Thr Phe Leu Leu Trp Phe Gly Trp Tyr Gly Phe Asn Pro Gly Ser
                245                 250                 255

Phe Val Thr Ile Leu Lys Ser Tyr Gly Pro Pro Gly Ser Ile Asn Gly
            260                 265                 270

Gln Trp Ser Gly Val Gly Arg Thr Ala Val Thr Thr Thr Leu Ala Gly
        275                 280                 285

Ser Val Ala Ala Leu Thr Thr Leu Phe Gly Lys Arg Leu Gln Thr Gly
    290                 295                 300

His Trp Asn Val Val Asp Val Cys Asn Gly Leu Leu Gly Gly Phe Ala
305                 310                 315                 320

Ala Ile Thr Ala Gly Cys Ser Val Val Asp Pro Trp Ala Ala Val Ile
                325                 330                 335

Cys Gly Phe Val Ser Ala Trp Val Leu Ile Gly Leu Asn Ala Leu Ala
            340                 345                 350

Gly Arg Leu Lys Tyr Asp Asp Pro Leu Glu Ala Ala Gln Leu His Gly
        355                 360                 365

Gly Cys Gly Ala Trp Gly Ile Ile Phe Thr Ala Leu Phe Ala Lys Lys
    370                 375                 380
```

-continued

```
Gln Tyr Val Glu Glu Ile Tyr Gly Ala Gly Arg Pro Tyr Gly Leu Phe
385                 390                 395                 400

Leu Gly Gly Gly Gly Arg Leu Leu Ala Ala His Ile Val Gln Ile Leu
                405                 410                 415

Ala Ile Ala Gly Phe Val Ser Cys Thr Met Gly Pro Leu Phe Leu Ala
            420                 425                 430

Leu Lys Lys Leu Gly Leu Leu Arg Ile Ser Ala Glu Asp Glu Met Ala
        435                 440                 445

Gly Met Asp Leu Thr Arg His Gly Gly Phe Ala Tyr Val Tyr His Asp
    450                 455                 460

Asp Asp Glu His Asp Lys Ser Val Gly Gly Phe Met Leu Arg Ser Ala
465                 470                 475                 480

Gln Thr Arg Val Glu Pro Ala Ala Ala Ala Asn Ser Gln Val
                485                 490


<210> SEQ ID NO 33
<211> LENGTH: 519
<212> TYPE: PRT
<213> ORGANISM: Brassica napus
<220> FEATURE:
<221> NAME/KEY: misc_feature
<222> LOCATION: (1)..(519)
<223> OTHER INFORMATION: Public GI no. 11066960

<400> SEQUENCE: 33

Met Ser Gly Ala Ile Thr Cys Ser Ala Ala Asp Leu Ala Thr Leu Leu
1               5                   10                  15

Gly Pro Asn Ala Thr Ala Ala Ala Asp Tyr Ile Cys Gly Gln Leu Gly
            20                  25                  30

Thr Val Asn Asn Lys Phe Thr Asp Ala Ala Phe Ala Ile Asp Asn Thr
        35                  40                  45

Tyr Leu Leu Phe Ser Ala Tyr Leu Val Phe Ala Met Gln Leu Gly Phe
    50                  55                  60

Ala Met Leu Cys Ala Gly Ser Val Arg Ala Lys Asn Thr Met Asn Ile
65                  70                  75                  80

Met Leu Thr Asn Val Leu Asp Ala Ala Ala Gly Gly Phe Phe Tyr Tyr
                85                  90                  95

Leu Phe Gly Tyr Ala Phe Ala Phe Gly Gly Ser Ser Glu Gly Phe Ile
            100                 105                 110

Gly Arg His Asn Phe Ala Leu Arg Asp Phe Pro Thr Pro Thr Ala Asp
        115                 120                 125

Tyr Ser Phe Phe Leu Tyr Gln Trp Ala Phe Ala Ile Ala Ala Ala Gly
    130                 135                 140

Ile Thr Ser Gly Ser Ile Ala Glu Arg Thr Gln Phe Val Ala Tyr Leu
145                 150                 155                 160

Ile Tyr Ser Ser Phe Leu Thr Gly Phe Val Tyr Pro Val Val Ser His
                165                 170                 175

Trp Phe Trp Ser Pro Asp Gly Trp Ala Ser Pro Phe Arg Ser Ala Asp
            180                 185                 190

Asp Arg Leu Phe Ser Thr Gly Ala Ile Asp Phe Ala Gly Ser Gly Val
        195                 200                 205

Val His Met Val Gly Gly Ile Ala Gly Leu Trp Gly Ala Leu Ile Glu
    210                 215                 220

Gly Pro Arg Arg Gly Arg Phe Glu Lys Gly Gly Arg Ala Ile Ala Leu
225                 230                 235                 240

Arg Gly His Ser Ala Ser Leu Val Val Leu Gly Thr Phe Leu Leu Trp
```

```
                245                 250                 255

Phe Gly Trp Tyr Gly Phe Asn Pro Gly Ser Phe Thr Lys Ile Leu Val
            260                 265                 270

Pro Tyr Asn Ser Gly Ser Asn Tyr Gly Gln Trp Ser Gly Ile Gly Arg
        275                 280                 285

Thr Ala Val Asn Thr Thr Leu Ser Gly Cys Thr Ala Ala Leu Thr Thr
    290                 295                 300

Leu Phe Gly Lys Arg Leu Leu Ser Gly His Trp Asn Val Thr Asp Val
305                 310                 315                 320

Cys Asn Gly Leu Leu Gly Gly Phe Ala Ala Ile Thr Ala Gly Cys Ser
                325                 330                 335

Val Val Glu Pro Trp Ala Ala Ile Val Cys Gly Phe Met Thr Ser Leu
            340                 345                 350

Val Leu Ile Gly Cys Asn Lys Leu Ala Glu Leu Val Gln Tyr Gly Asp
        355                 360                 365

Pro Leu Glu Ala Ala Gln Leu His Gly Gly Cys Gly Ala Trp Gly Leu
    370                 375                 380

Ile Phe Val Gly Leu Phe Ala Lys Glu Lys Tyr Leu Asn Glu Val Tyr
385                 390                 395                 400

Gly Ala Thr Pro Gly Arg Pro Tyr Gly Leu Phe Met Gly Gly Gly Gly
                405                 410                 415

Lys Leu Leu Gly Ala Gln Leu Val Gln Ile Leu Val Ile Val Gly Trp
            420                 425                 430

Val Ser Ala Thr Met Gly Thr Leu Phe Phe Ile Leu Lys Arg Leu Asn
        435                 440                 445

Leu Leu Arg Ile Ser Glu Gln His Glu Met Gln Gly Met Asp Met Thr
    450                 455                 460

Arg His Gly Gly Phe Ala Tyr Ile Tyr His Asp Asn Asp Asp Glu Ser
465                 470                 475                 480

His Arg Val Asp Pro Gly Ser Pro Phe Pro Arg Ser Ala Leu Pro Leu
                485                 490                 495

Ala Phe Asn Phe Gln Leu Phe Gly Asn Leu Leu Pro Phe Lys Tyr Cys
            500                 505                 510

Leu Gly Phe Gly Phe Glu Ile
        515


<210> SEQ ID NO 34
<211> LENGTH: 498
<212> TYPE: PRT
<213> ORGANISM: Oryza sativa (japonica cultivar-group)
<220> FEATURE:
<221> NAME/KEY: misc_feature
<222> LOCATION: (1)..(498)
<223> OTHER INFORMATION: Public GI no. 50910607

<400> SEQUENCE: 34

Met Ala Thr Cys Leu Asp Ser Leu Gly Pro Leu Leu Gly Gly Ala Ala
1               5                   10                  15

Asn Ser Thr Asp Ala Ala Asn Tyr Ile Cys Asn Arg Phe Thr Asp Thr
            20                  25                  30

Ser Ser Ala Val Asp Ala Thr Tyr Leu Leu Phe Ser Ala Tyr Leu Val
        35                  40                  45

Phe Ala Met Gln Leu Gly Phe Ala Met Leu Cys Ala Gly Ser Val Arg
    50                  55                  60

Ala Lys Asn Ser Met Asn Ile Met Leu Thr Asn Val Leu Asp Ala Ala
65                  70                  75                  80
```

-continued

```
Ala Gly Ala Leu Phe Tyr Tyr Leu Phe Gly Phe Ala Phe Ala Phe Gly
                85                  90                  95

Thr Pro Ser Lys Gly Phe Ile Gly Lys Gln Phe Phe Gly Leu Lys His
            100                 105                 110

Met Pro Gln Thr Gly Tyr Asp Tyr Asp Phe Phe Leu Phe Gln Trp Ala
        115                 120                 125

Phe Ala Ile Ala Ala Ala Gly Ile Thr Ser Gly Ser Ile Ala Glu Arg
    130                 135                 140

Thr Arg Phe Ser Ala Tyr Leu Ile Tyr Ser Ala Phe Leu Thr Gly Phe
145                 150                 155                 160

Val Tyr Pro Val Val Ser His Trp Phe Trp Ser Thr Asp Gly Trp Ala
                165                 170                 175

Ser Ala Gly Arg Leu Thr Gly Pro Leu Leu Phe Lys Ser Gly Val Ile
            180                 185                 190

Asp Phe Ala Gly Ser Gly Val Val His Leu Val Gly Gly Ile Ala Gly
        195                 200                 205

Leu Trp Gly Ala Phe Ile Glu Gly Pro Arg Ile Gly Arg Phe Asp Ala
    210                 215                 220

Ala Gly Arg Thr Val Ala Met Lys Gly His Ser Ala Ser Leu Val Val
225                 230                 235                 240

Leu Gly Thr Phe Leu Leu Trp Phe Gly Trp Phe Gly Phe Asn Pro Gly
                245                 250                 255

Ser Phe Thr Thr Ile Ser Lys Ile Tyr Gly Glu Ser Gly Thr Ile Asp
            260                 265                 270

Gly Gln Trp Ser Ala Val Gly Arg Thr Ala Val Thr Thr Ser Leu Ala
        275                 280                 285

Gly Ser Val Ala Ala Leu Thr Thr Leu Tyr Gly Lys Arg Trp Leu Thr
    290                 295                 300

Gly His Trp Asn Val Thr Asp Val Cys Asn Gly Leu Leu Gly Gly Phe
305                 310                 315                 320

Ala Ala Ile Thr Ala Gly Cys Ser Val Val Asp Pro Trp Ala Ser Val
                325                 330                 335

Ile Cys Gly Phe Val Ser Ala Trp Val Leu Ile Gly Cys Asn Lys Leu
            340                 345                 350

Ser Leu Ile Leu Lys Phe Asp Asp Pro Leu Glu Ala Thr Gln Leu His
        355                 360                 365

Ala Gly Cys Gly Ala Trp Gly Ile Ile Phe Thr Ala Leu Phe Ala Arg
    370                 375                 380

Arg Glu Tyr Val Glu Leu Ile Tyr Gly Val Pro Gly Arg Pro Tyr Gly
385                 390                 395                 400

Leu Phe Met Gly Gly Gly Gly Arg Leu Leu Ala Ala His Ile Val Gln
                405                 410                 415

Ile Leu Val Ile Val Gly Trp Val Ser Ala Thr Met Gly Thr Leu Phe
            420                 425                 430

Tyr Val Leu His Arg Phe Gly Leu Leu Arg Val Ser Pro Ala Thr Glu
        435                 440                 445

Met Glu Gly Met Asp Pro Thr Cys His Gly Gly Phe Gly Tyr Val Asp
    450                 455                 460

Glu Asp Glu Gly Glu Arg Arg Val Arg Ala Lys Ser Ala Ala Glu Thr
465                 470                 475                 480

Ala Arg Val Glu Pro Arg Lys Ser Pro Glu Gln Ala Ala Ala Gly Gln
                485                 490                 495
```

Phe Val

<210> SEQ ID NO 35
<211> LENGTH: 1674
<212> TYPE: DNA
<213> ORGANISM: Arabidopsis thaliana
<220> FEATURE:
<221> NAME/KEY: misc_feature
<222> LOCATION: (1)..(1674)
<223> OTHER INFORMATION: Ceres CDNA ID no. 3086062
<220> FEATURE:
<221> NAME/KEY: CDS
<222> LOCATION: (1)..(1671)
<223> OTHER INFORMATION: Referenced by SEQ ID NO: 36

<400> SEQUENCE: 35

```
atgtctggtt cagtttcccg cgatgcagaa gctctgaagt cagcagattc tagcaccaga     60
cgctctggcg gcaggatcac cttcccgttt atgatagtaa cgttgttcgg cctaacatta    120
gctacgttgg gatggttaca gaacttgatt gtctacctga tcgaagagta caacatgaag    180
agcatcgcag ctgcgaagat tctcaacatt ttcagtggtt ttacctttat gttccctgcc    240
attggagcca ttgcagcgga ttctttcttc ggaacaattc ctgttatctt ggtttcatca    300
ttcatttctc tagtgggcgt agttctgctg gctctaacga ctttgtttga ctctttaaga    360
ccccaagcct gcgaaacagc atcaagctta tgccaagccc ctacgaacat ccagctcggt    420
gtcctttaca cagcaataac tctaggctgt gtgggagcag gtgggctgcg gtttaccttg    480
gccaccgctg gtgcgaacca gtatgaaaaa gctaaagacc aaggcagctt tttcaactgg    540
tttttcttca catggtatct agctgcctct ataagtgcaa cagccattgt ctacgccgaa    600
gaaaacatca gctggagttt cgggtttggt ctgtgtgtag ctgctaatct gtttggcttg    660
atagttttca tcttggggaa aagattctac aagcatgaca agcctttggg aagtcccttc    720
acaagtttac ttcgtgtcat ctttgttgcc atacgtaaaa gaaaagctgt ggtttccacc    780
aacgagaaag actaccacag tgaatcaaag aaagcgccta caaagagttt caggttcttt    840
aaccgggcag cattgaaaca gaatgatgag gttaatgcag acggcacaat tcacaatcaa    900
tggagactat gcagcgttca acaagtagaa gatttcaaag cagtcataag aatcatccct    960
cttgtgttag ctatattatt cttgagcact ccaatcgcga tgcagctagg attaacagta   1020
cttcagggtc tggtgatgga ccggagactt ggccctcact tcaagatccc tgcaggctct   1080
ctccaagtca taacacttct ctccacttgc ctatttatca tagtcaacga tcggtttctc   1140
tacccatttt accaaaaact aaccgggaag ttccccacac cgattcaaag ggtgggaata   1200
ggccacgttt tcaacattct aagcatggct gtgactgcca tagttgaagc aaagcgattg   1260
aagatagtac agaaaggtca ttttctcgga tcatcatctg ttgctgacat gtcagtcttg   1320
tggttattcc ctcctctagt catagtagga atcggagagg ccttccattt cccagggaat   1380
gtagctctgt gctatcaaga gtttccagag tctatgcgaa gtactgcgac atcaataacc   1440
tcggtgttga ttgggatatg tttctacaca agcactgctt tgatcgacct gattcagaag   1500
accactgcat ggttaccaga tgatattaac catggaagag ttgacaatgt ttactggatt   1560
ttagtcatag gaggagtctt gaatcttggc tatttccttg tgtgttcttg gttttataaa   1620
tacagaaacc tcgagaatgc tgatcatgaa caagatgcaa atgtctctca ctaa         1674
```

<210> SEQ ID NO 36
<211> LENGTH: 557
<212> TYPE: PRT
<213> ORGANISM: Arabidopsis thaliana

```
<220> FEATURE:
<221> NAME/KEY: misc_feature
<222> LOCATION: (93)..(484)
<223> OTHER INFORMATION: Pfam Name: PTR2; Pfam Description: POT family

<400> SEQUENCE: 36

Met Ser Gly Ser Val Ser Arg Asp Ala Glu Ala Leu Lys Ser Ala Asp
1               5                   10                  15

Ser Ser Thr Arg Arg Ser Gly Gly Arg Ile Thr Phe Pro Phe Met Ile
            20                  25                  30

Val Thr Leu Phe Gly Leu Thr Leu Ala Thr Leu Gly Trp Leu Gln Asn
        35                  40                  45

Leu Ile Val Tyr Leu Ile Glu Glu Tyr Asn Met Lys Ser Ile Ala Ala
    50                  55                  60

Ala Lys Ile Leu Asn Ile Phe Ser Gly Phe Thr Phe Met Phe Pro Ala
65                  70                  75                  80

Ile Gly Ala Ile Ala Ala Asp Ser Phe Phe Gly Thr Ile Pro Val Ile
                85                  90                  95

Leu Val Ser Ser Phe Ile Ser Leu Val Gly Val Val Leu Leu Ala Leu
            100                 105                 110

Thr Thr Leu Phe Asp Ser Leu Arg Pro Gln Ala Cys Glu Thr Ala Ser
        115                 120                 125

Ser Leu Cys Gln Ala Pro Thr Asn Ile Gln Leu Gly Val Leu Tyr Thr
    130                 135                 140

Ala Ile Thr Leu Gly Cys Val Gly Ala Gly Gly Leu Arg Phe Thr Leu
145                 150                 155                 160

Ala Thr Ala Gly Ala Asn Gln Tyr Glu Lys Ala Lys Asp Gln Gly Ser
                165                 170                 175

Phe Phe Asn Trp Phe Phe Phe Thr Trp Tyr Leu Ala Ala Ser Ile Ser
            180                 185                 190

Ala Thr Ala Ile Val Tyr Ala Glu Glu Asn Ile Ser Trp Ser Phe Gly
        195                 200                 205

Phe Gly Leu Cys Val Ala Ala Asn Leu Phe Gly Leu Ile Val Phe Ile
    210                 215                 220

Leu Gly Lys Arg Phe Tyr Lys His Asp Lys Pro Leu Gly Ser Pro Phe
225                 230                 235                 240

Thr Ser Leu Leu Arg Val Ile Phe Val Ala Ile Arg Lys Arg Lys Ala
                245                 250                 255

Val Val Ser Thr Asn Glu Lys Asp Tyr His Ser Glu Ser Lys Lys Ala
            260                 265                 270

Pro Thr Lys Ser Phe Arg Phe Phe Asn Arg Ala Ala Leu Lys Gln Asn
        275                 280                 285

Asp Glu Val Asn Ala Asp Gly Thr Ile His Asn Gln Trp Arg Leu Cys
    290                 295                 300

Ser Val Gln Gln Val Glu Asp Phe Lys Ala Val Ile Arg Ile Ile Pro
305                 310                 315                 320

Leu Val Leu Ala Ile Leu Phe Leu Ser Thr Pro Ile Ala Met Gln Leu
                325                 330                 335

Gly Leu Thr Val Leu Gln Gly Leu Val Met Asp Arg Arg Leu Gly Pro
            340                 345                 350

His Phe Lys Ile Pro Ala Gly Ser Leu Gln Val Ile Thr Leu Leu Ser
        355                 360                 365

Thr Cys Leu Phe Ile Ile Val Asn Asp Arg Phe Leu Tyr Pro Phe Tyr
    370                 375                 380
```

-continued

```
Gln Lys Leu Thr Gly Lys Phe Pro Thr Pro Ile Gln Arg Val Gly Ile
385                 390                 395                 400

Gly His Val Phe Asn Ile Leu Ser Met Ala Val Thr Ala Ile Val Glu
                405                 410                 415

Ala Lys Arg Leu Lys Ile Val Gln Lys Gly His Phe Leu Gly Ser Ser
            420                 425                 430

Ser Val Ala Asp Met Ser Val Leu Trp Leu Phe Pro Pro Leu Val Ile
        435                 440                 445

Val Gly Ile Gly Glu Ala Phe His Phe Pro Gly Asn Val Ala Leu Cys
    450                 455                 460

Tyr Gln Glu Phe Pro Glu Ser Met Arg Ser Thr Ala Thr Ser Ile Thr
465                 470                 475                 480

Ser Val Leu Ile Gly Ile Cys Phe Tyr Thr Ser Thr Ala Leu Ile Asp
                485                 490                 495

Leu Ile Gln Lys Thr Thr Ala Trp Leu Pro Asp Asp Ile Asn His Gly
            500                 505                 510

Arg Val Asp Asn Val Tyr Trp Ile Leu Val Ile Gly Gly Val Leu Asn
        515                 520                 525

Leu Gly Tyr Phe Leu Val Cys Ser Trp Phe Tyr Lys Tyr Arg Asn Leu
    530                 535                 540

Glu Asn Ala Asp His Glu Gln Asp Ala Asn Val Ser His
545                 550                 555


<210> SEQ ID NO 37
<211> LENGTH: 558
<212> TYPE: PRT
<213> ORGANISM: Arabidopsis thaliana
<220> FEATURE:
<221> NAME/KEY: misc_feature
<222> LOCATION: (1)..(558)
<223> OTHER INFORMATION: Ceres CLONE ID no. 1002997

<400> SEQUENCE: 37

Met Ala Ser Ser Val Thr Gly Asp Ala Glu Thr Ala Ile Ser Ala Asp
1               5                   10                  15

Ser Ser Thr Lys Arg Arg Gly Gly Gly Trp Ile Thr Phe Pro Phe Met
            20                  25                  30

Ile Ala Thr Leu Leu Gly Leu Thr Ile Ala Ala Trp Gly Trp Leu Leu
        35                  40                  45

Asn Leu Ile Val Tyr Leu Ile Glu Glu Phe Asn Val Lys Ser Ile Ala
    50                  55                  60

Ala Ala Gln Ile Ala Asn Ile Val Ser Gly Cys Ile Cys Met Val Pro
65                  70                  75                  80

Ala Val Ala Ala Ile Ala Ser Asp Ser Phe Phe Gly Thr Ile Pro Val
                85                  90                  95

Ile Ser Val Ser Ala Phe Ile Ser Leu Met Gly Val Ala Leu Leu Thr
            100                 105                 110

Leu Thr Ala Ser Leu Asp Thr Leu Arg Pro Arg Pro Cys Glu Thr Ala
        115                 120                 125

Ser Ile Leu Cys Gln Ser Pro Ser Lys Thr Gln Leu Gly Val Leu Tyr
    130                 135                 140

Thr Ala Ile Thr Leu Ala Ser Ile Gly Thr Gly Gly Thr Arg Phe Thr
145                 150                 155                 160

Leu Ala Thr Ala Gly Ala Asn Gln Tyr Glu Lys Thr Lys Asp Gln Gly
                165                 170                 175

Ser Phe Phe Asn Trp Phe Phe Phe Thr Thr Tyr Leu Ala Gly Ala Ile
```

```
            180                 185                 190

Ser Ala Thr Ala Ile Val Tyr Thr Glu Asp Asn Ile Ser Trp Thr Leu
        195                 200                 205

Gly Phe Gly Leu Ser Val Ala Ala Asn Phe Phe Ser Phe Leu Val Phe
    210                 215                 220

Val Ser Gly Lys Arg Phe Tyr Lys His Asp Lys Pro Leu Gly Ser Pro
225                 230                 235                 240

Phe Thr Ser Leu Leu Cys Val Ile Phe Ala Ala Leu Arg Lys Arg Lys
                245                 250                 255

Ala Val Val Ser Thr Asn Glu Lys Asp Tyr His Asn Glu Ser Ile Thr
            260                 265                 270

Met Pro Thr Lys Ser Phe Arg Phe Phe Asn Arg Ala Ala Leu Lys Gln
        275                 280                 285

Glu Asp Glu Val Lys Pro Asp Gly Thr Ile Arg Asn Pro Trp Arg Leu
    290                 295                 300

Cys Ser Val Gln Gln Val Glu Asp Phe Lys Ala Val Ile Arg Ile Ile
305                 310                 315                 320

Pro Leu Ala Leu Ala Thr Ile Phe Leu Ser Thr Pro Ile Ala Met Gln
                325                 330                 335

Leu Ser Leu Thr Val Leu Gln Gly Leu Val Met Asp Arg Arg Leu Gly
            340                 345                 350

Pro Ser Phe Lys Ile Pro Ala Gly Ser Leu Gln Val Ile Thr Leu Leu
        355                 360                 365

Ser Thr Cys Leu Phe Ile Ile Val Asn Asp Arg Val Leu Tyr Pro Phe
    370                 375                 380

Tyr Gln Lys Leu Thr Gly Lys His Leu Thr Pro Leu Gln Arg Val Gly
385                 390                 395                 400

Ile Gly His Ala Phe Asn Ile Leu Ser Met Ala Val Thr Ala Ile Val
                405                 410                 415

Glu Ala Lys Arg Leu Lys Ile Val Gln Lys Gly His Phe Leu Gly Ser
            420                 425                 430

Ser Ser Val Ala Asp Met Ser Val Leu Trp Leu Phe Pro Pro Leu Val
        435                 440                 445

Ile Val Gly Ile Gly Glu Ala Phe His Phe Pro Gly Asn Val Ala Leu
    450                 455                 460

Cys Tyr Gln Glu Phe Pro Glu Ser Met Arg Ser Thr Ala Thr Ser Ile
465                 470                 475                 480

Thr Ser Val Val Ile Gly Ile Cys Phe Tyr Thr Ser Thr Ala Leu Ile
                485                 490                 495

Asp Leu Ile Gln Arg Thr Thr Ala Trp Leu Pro Asp Asp Ile Asn His
            500                 505                 510

Gly Arg Val Asp Asn Val Tyr Trp Ile Leu Val Ile Gly Gly Val Leu
        515                 520                 525

Asn Leu Gly Tyr Phe Leu Val Cys Ser Trp Leu Tyr Arg Tyr Arg Asn
    530                 535                 540

Leu Lys Asp Asp Asp His Lys Gln Ala Ala Asn Val Ser His
545                 550                 555
```

<210> SEQ ID NO 38
<211> LENGTH: 567
<212> TYPE: PRT
<213> ORGANISM: Solanum demissum
<220> FEATURE:
<221> NAME/KEY: misc_feature
<222> LOCATION: (1)..(567)

<223> OTHER INFORMATION: Public GI no. 47900739

<400> SEQUENCE: 38

```
Met Glu Ser Ser Val Arg Gly Val Asp Glu Ala Ala Ile Met Lys Ser
1               5                   10                  15

Ser Thr Arg Arg Lys Asn Gly Gly Trp Ile Thr Phe Pro Phe Ile Ile
            20                  25                  30

Val Ser Ala Thr Met Ala Gly Leu Ser Leu Ala Ser Gly Gly Trp Thr
        35                  40                  45

Ser Asn Leu Ile Val Tyr Leu Ile Asp Glu Phe Asn Met Lys Ser Ile
    50                  55                  60

Lys Thr Ala Lys Val Tyr Asn Val Ile Asn Gly Cys Thr Thr Leu Phe
65                  70                  75                  80

Pro Ile Val Gly Gly Ile Leu Ala Asp Ser Tyr Leu Gly Ser Phe Ser
                85                  90                  95

Val Ile Trp Phe Ser Ser Leu Ile Ser Ala Leu Gly Ile Leu Leu Leu
            100                 105                 110

Leu Phe Thr Ser Ala Ile Asp Val Leu Arg Pro Pro Pro Cys Asp Asp
        115                 120                 125

Gly Ser Ser Leu Cys Thr Ser Pro Ser Thr His Gln Tyr Ala Val Leu
    130                 135                 140

Tyr Val Ala Leu Ala Leu Ala Ser Leu Gly Val Ala Gly Thr Arg Phe
145                 150                 155                 160

Ile Ile Ala Pro Met Gly Ala Asn Gln Phe Asp Lys Pro Lys His Gln
                165                 170                 175

Ala Ile Phe Phe Asn Trp Tyr Ile Phe Ala Phe Tyr Met Ser Phe Ala
            180                 185                 190

Ile Ser Thr Thr Val Ile Val Tyr Val Glu Asp Asn Val Ser Trp Ser
        195                 200                 205

Trp Gly Tyr Gly Ile Ser Met Ala Phe Asn Ile Leu Gly Leu Ala Met
    210                 215                 220

Phe Leu Ile Gly Lys Arg Phe Tyr Cys Asp Val Lys Glu Gln Gly Gly
225                 230                 235                 240

Ser Pro Phe Val Asn Leu Ala Arg Val Ile Val Val Ala Ile Gln Lys
                245                 250                 255

Trp Arg Val Pro Leu Ser Glu Gln Thr Gln His Tyr Tyr His Asp Pro
            260                 265                 270

Ser Asp Thr Thr Thr Thr Leu Thr Ile Thr Gln Ile Pro Thr Lys Ser
        275                 280                 285

Phe Lys Phe Leu Asn Cys Ala Ala Phe Ile Thr Glu Gly Asp Thr Lys
    290                 295                 300

Pro Asp Gly Ser Ile Ser Asn Pro Trp Arg Leu Cys Thr Val Gln Gln
305                 310                 315                 320

Val Glu Asp Leu Lys Ser Leu Ile Lys Leu Phe Pro Leu Trp Ala Ser
                325                 330                 335

Gly Phe Leu Ile Ser Thr Gln Leu Val Ile Gln Ala Ser Leu Leu Ile
            340                 345                 350

Leu Gln Ala Leu Lys Met Asp Arg His Met Gly Pro His Phe Glu Ile
        355                 360                 365

Pro Ala Gly Ser Met Leu Val Phe Ile Leu Leu Phe Thr Cys Ile Ala
    370                 375                 380

Ile Phe Ile Ile Asp Arg Phe Leu Tyr Pro Phe Leu Ala Lys Tyr Thr
385                 390                 395                 400
```

-continued

```
Thr Phe Ser Leu Thr Pro Leu Gln Arg Ile Gly Ile Gly His Val Ile
                405                 410                 415

Thr Ile Ile Ser Met Ala Val Ser Ala Leu Val Glu Ser Arg Arg Leu
            420                 425                 430

Arg Ile Val Arg Thr His Lys Leu Gln Gly Gln Asn Asn Asp Ile Val
        435                 440                 445

Pro Met Ser Val Phe Trp Leu Val Pro Gln Leu Ala Leu Asn Gly Ile
    450                 455                 460

Gly Glu Gly Phe His Phe Pro Gly His Ile Ala Phe Tyr Tyr Gln Glu
465                 470                 475                 480

Phe Pro Thr Ser Leu Lys Ser Thr Ser Thr Ala Met Val Ala Leu Phe
                485                 490                 495

Ile Gly Ile Ala His Tyr Leu Gly Asn Thr Leu Ile Asp Leu Val Gln
            500                 505                 510

Arg Leu Ser Gly Trp Leu Pro Asp Asn Ile Asn Lys Gly Arg Thr Asp
        515                 520                 525

Asn Val Phe Trp Leu Cys Cys Ile Leu Gly Ser Ala Asn Phe Met Tyr
    530                 535                 540

Tyr Val Val Cys Ala Ser Leu Tyr Lys Tyr Lys Asn Val Asp Asn Lys
545                 550                 555                 560

Ser Asn Ile Ala Pro Ser Lys
                565
```

<210> SEQ ID NO 39
<211> LENGTH: 1799
<212> TYPE: DNA
<213> ORGANISM: Arabidopsis thaliana
<220> FEATURE:
<221> NAME/KEY: misc_feature
<222> LOCATION: (1)..(1799)
<223> OTHER INFORMATION: Ceres CDNA ID no. 3091277
<220> FEATURE:
<221> NAME/KEY: CDS
<222> LOCATION: (1)..(1767)
<223> OTHER INFORMATION: Referenced by SEQ ID NO: 40

<400> SEQUENCE: 39

```
atggatcaaa aagttagaca gtttgaggtt tgcactcaag acggtagcgt tgatcgtcac      60

ggcaatccag ctatccgagc taataccggc aaatggctca ctgctattct cattctagtg     120

aatcaaggac tagctacgct tgcgttcttc ggtgtaggag tgaatttggt tctgtttctg     180

actcgagtga tgggacaaga caatgcagaa gcggctaata atgttagtaa atggacagga     240

actgtctata tcttctcttt gcttggtgct ttcctcagtg actcttattg ggacgttac     300

aagacttgtg ctatctttca agcaagtttc gttgcagggt tgatgatgtt atctttatct     360

actggtgcgt tattgcttga accaagtggt tgtggagttg aagattcgcc gtgtaagcct     420

cattcgacgt ttaagacggt tctgttttat ctgtcggtgt atctaatcgc gttagggtat     480

ggtggttatc agccgaacat agctactttt ggagctgatc agtttgatgc ggaggattcc     540

gttgaaggac actcgaaaat cgcgtttttc agttactttt acttggctct gaatcttgga     600

tcgctcttct caaatactgt cttgggttac tttgaggatc aaggggaatg gccgcttgga     660

ttttgggcgt ctgctggctc tgcttttgcg gggttagtgc ttttcttgat tggcacgcca     720

aagtaccgac actttacgcc tagagagagt ccttggtcta gattctgcca agtgttggtt     780

gctgcaacaa gaaaggctaa gattgatgtg caccatgaag agttgaatct ctatgattct     840

gagactcaat acactggaga taagaagatt cttcatacca aaggcttcag attcttggat     900
```

-continued

```
agagctgcta ttgttacacc tgatgatgag gctgagaaag tagagagcgg atcgaaatac    960

gatccatgga ggctctgctc ggtgactcaa gtcgaagaag tgaaatgtgt attaagactc   1020

ttaccaatct ggctctgcac catcctctac tctgtggttt tcacccaaat ggcttcactg   1080

ttcgttgtgc aaggagcagc gatgaagaca aacatcaaaa acttccggat tccagcttca   1140

agcatgtcta gtttcgacat tctcagtgtc gccttcttca tcttcgcata caggcggttt   1200

cttgatccac tctttgcaag acttaacaaa acagaacgca acaaaggtct cactgagctt   1260

cagaggatgg ggattgggct tgtgattgcg ataatggcga tgatttccgc aggaatcgta   1320

gagatacaca gactgaaaaa taaggaaccg gaaagtgcta cttcgatctc aagctccagc   1380

actttgagca ttttttggca agtacctcag tacatgttga taggtgcatc agaagtgttc   1440

atgtacgttg gtcaactcga gttcttcaac agccaagcac caaccgggct aaagagcttt   1500

gcaagcgcgc tatgtatggc ttcaatatct cttgggaact atgtaagcag tttgttagtt   1560

tccattgtca tgaagatctc tacaacagat gatgtgcatg gctggattcc tgaaaatctc   1620

aacaaaggac acttggagag attctacttc cttttagctg gtctaaccgc tgctgatttc   1680

gtggtttact tgatttgtgc caaatggtac aagtatatta aatctgaagc aagtttctct   1740

gagtccgtaa ctgaagagga ggaagtctga aatgctgcag tctcgagccg atcgttcac    1799
```

<210> SEQ ID NO 40
<211> LENGTH: 589
<212> TYPE: PRT
<213> ORGANISM: Arabidopsis thaliana
<220> FEATURE:
<221> NAME/KEY: misc_feature
<222> LOCATION: (100)..(509)
<223> OTHER INFORMATION: Pfam Name: PTR2; Pfam Description: POT family

<400> SEQUENCE: 40

```
Met Asp Gln Lys Val Arg Gln Phe Glu Val Cys Thr Gln Asp Gly Ser
1               5                   10                  15

Val Asp Arg His Gly Asn Pro Ala Ile Arg Ala Asn Thr Gly Lys Trp
            20                  25                  30

Leu Thr Ala Ile Leu Ile Leu Val Asn Gln Gly Leu Ala Thr Leu Ala
        35                  40                  45

Phe Phe Gly Val Gly Val Asn Leu Val Leu Phe Leu Thr Arg Val Met
    50                  55                  60

Gly Gln Asp Asn Ala Glu Ala Ala Asn Asn Val Ser Lys Trp Thr Gly
65                  70                  75                  80

Thr Val Tyr Ile Phe Ser Leu Leu Gly Ala Phe Leu Ser Asp Ser Tyr
                85                  90                  95

Trp Gly Arg Tyr Lys Thr Cys Ala Ile Phe Gln Ala Ser Phe Val Ala
            100                 105                 110

Gly Leu Met Met Leu Ser Leu Ser Thr Gly Ala Leu Leu Leu Glu Pro
        115                 120                 125

Ser Gly Cys Gly Val Glu Asp Ser Pro Cys Lys Pro His Ser Thr Phe
    130                 135                 140

Lys Thr Val Leu Phe Tyr Leu Ser Val Tyr Leu Ile Ala Leu Gly Tyr
145                 150                 155                 160

Gly Gly Tyr Gln Pro Asn Ile Ala Thr Phe Gly Ala Asp Gln Phe Asp
                165                 170                 175

Ala Glu Asp Ser Val Glu Gly His Ser Lys Ile Ala Phe Phe Ser Tyr
            180                 185                 190

Phe Tyr Leu Ala Leu Asn Leu Gly Ser Leu Phe Ser Asn Thr Val Leu
```

-continued

```
        195                 200                 205

Gly Tyr Phe Glu Asp Gln Gly Glu Trp Pro Leu Gly Phe Trp Ala Ser
    210                 215                 220

Ala Gly Ser Ala Phe Ala Gly Leu Val Leu Phe Leu Ile Gly Thr Pro
225                 230                 235                 240

Lys Tyr Arg His Phe Thr Pro Arg Glu Ser Pro Trp Ser Arg Phe Cys
                245                 250                 255

Gln Val Leu Val Ala Ala Thr Arg Lys Ala Lys Ile Asp Val His His
            260                 265                 270

Glu Glu Leu Asn Leu Tyr Asp Ser Glu Thr Gln Tyr Thr Gly Asp Lys
        275                 280                 285

Lys Ile Leu His Thr Lys Gly Phe Arg Phe Leu Asp Arg Ala Ala Ile
    290                 295                 300

Val Thr Pro Asp Asp Glu Ala Glu Lys Val Glu Ser Gly Ser Lys Tyr
305                 310                 315                 320

Asp Pro Trp Arg Leu Cys Ser Val Thr Gln Val Glu Glu Val Lys Cys
                325                 330                 335

Val Leu Arg Leu Leu Pro Ile Trp Leu Cys Thr Ile Leu Tyr Ser Val
            340                 345                 350

Val Phe Thr Gln Met Ala Ser Leu Phe Val Val Gln Gly Ala Ala Met
        355                 360                 365

Lys Thr Asn Ile Lys Asn Phe Arg Ile Pro Ala Ser Ser Met Ser Ser
    370                 375                 380

Phe Asp Ile Leu Ser Val Ala Phe Phe Ile Phe Ala Tyr Arg Arg Phe
385                 390                 395                 400

Leu Asp Pro Leu Phe Ala Arg Leu Asn Lys Thr Glu Arg Asn Lys Gly
                405                 410                 415

Leu Thr Glu Leu Gln Arg Met Gly Ile Gly Leu Val Ile Ala Ile Met
            420                 425                 430

Ala Met Ile Ser Ala Gly Ile Val Glu Ile His Arg Leu Lys Asn Lys
        435                 440                 445

Glu Pro Glu Ser Ala Thr Ser Ile Ser Ser Ser Ser Thr Leu Ser Ile
    450                 455                 460

Phe Trp Gln Val Pro Gln Tyr Met Leu Ile Gly Ala Ser Glu Val Phe
465                 470                 475                 480

Met Tyr Val Gly Gln Leu Glu Phe Phe Asn Ser Gln Ala Pro Thr Gly
                485                 490                 495

Leu Lys Ser Phe Ala Ser Ala Leu Cys Met Ala Ser Ile Ser Leu Gly
            500                 505                 510

Asn Tyr Val Ser Ser Leu Leu Val Ser Ile Val Met Lys Ile Ser Thr
        515                 520                 525

Thr Asp Asp Val His Gly Trp Ile Pro Glu Asn Leu Asn Lys Gly His
    530                 535                 540

Leu Glu Arg Phe Tyr Phe Leu Leu Ala Gly Leu Thr Ala Ala Asp Phe
545                 550                 555                 560

Val Val Tyr Leu Ile Cys Ala Lys Trp Tyr Lys Tyr Ile Lys Ser Glu
                565                 570                 575

Ala Ser Phe Ser Glu Ser Val Thr Glu Glu Glu Val
            580                 585


<210> SEQ ID NO 41
<211> LENGTH: 584
<212> TYPE: PRT
<213> ORGANISM: Oryza sativa (japonica cultivar-group)
```

-continued

<220> FEATURE:
<221> NAME/KEY: misc_feature
<222> LOCATION: (1)..(584)
<223> OTHER INFORMATION: Public GI no. 50912139

<400> SEQUENCE: 41

```
Met Ala Pro Thr Ala Val Asp Ser Lys Arg Ile Ser Asp Ile Thr Glu
1               5                   10                  15

Asp Gly Ser Met Asp Arg Arg Gly Asn Pro Ala Val Lys Ala Lys Thr
            20                  25                  30

Gly Asn Trp Arg Ser Ser Ile Leu Leu Leu Val Asn Tyr Gly Leu Val
        35                  40                  45

Thr Cys Ala Phe Phe Gly Val Gly Val Asn Leu Val Val Phe Leu Arg
    50                  55                  60

Arg Val Leu His Gln Asp Asn Ala Glu Ala Ala Asn Ser Ile Ser Lys
65                  70                  75                  80

Trp Thr Gly Thr Val Tyr Ile Phe Ser Leu Ile Gly Ala Phe Met Ser
                85                  90                  95

Asp Ser Tyr Trp Gly Arg Tyr Ile Thr Cys Ala Ile Phe Gln Met Ile
            100                 105                 110

Tyr Val Thr Gly Leu Val Ile Leu Ser Leu Ala Ser Trp Phe Leu Leu
        115                 120                 125

Val Lys Pro Thr Gly Cys Gly Ala Ala Gly Glu His Cys Asp Ala Pro
    130                 135                 140

Ser Ser Ala Gly Val Ala Leu Phe Tyr Leu Ser Thr Tyr Met Ile Ala
145                 150                 155                 160

Phe Gly Asn Gly Gly Tyr Gln Pro Ser Ile Ala Thr Phe Gly Ser Asp
                165                 170                 175

Gln Phe Asp Glu Thr Asp Pro Arg Glu Ala Arg Ser Lys Val Ala Phe
            180                 185                 190

Phe Ser Tyr Phe Tyr Leu Ala Leu Asn Val Gly Ser Leu Phe Ser Asn
        195                 200                 205

Thr Val Leu Val Tyr Tyr Glu Asp Glu Gly Arg Trp Val Met Gly Phe
    210                 215                 220

Trp Val Ser Ala Ala Ala Ala Ala Met Ala Leu Val Leu Phe Leu Leu
225                 230                 235                 240

Gly Thr Pro Asn Tyr Arg His Phe Lys Pro Thr Gly Asn Pro Leu Thr
                245                 250                 255

Arg Ile Ala Gln Val Phe Val Ala Ala Phe Arg Lys Trp Arg Ala Glu
            260                 265                 270

Val Pro Arg Ser Glu Leu Leu His Glu Val Asp Gly Asp Glu Ser Gln
        275                 280                 285

Ile Ala Gly Ile Arg Lys Ile Leu His Ser Asp Gln Ile Arg Phe Leu
    290                 295                 300

Asp Lys Ala Ala Thr Val Thr Glu Glu Asp Tyr Cys Thr Pro Glu Asn
305                 310                 315                 320

Met Gln Asp Pro Trp Arg Leu Cys Thr Val Thr Gln Val Glu Glu Val
                325                 330                 335

Lys Cys Ile Leu Lys Met Leu Pro Ile Trp Leu Cys Thr Ile Val Tyr
            340                 345                 350

Ser Val Val Phe Thr Gln Met Ala Ser Leu Phe Val Glu Gln Gly Thr
        355                 360                 365

Thr Met Asn Thr Asn Ile Gly Ser Phe His Val Pro Ala Ala Ser Met
    370                 375                 380
```

```
Ser Val Phe Asp Ile Leu Ser Val Leu Ala Phe Ile Ala Ile Tyr Arg
385                 390                 395                 400

Arg Val Leu Val Pro Val Met Ser Arg Leu Ser Gly Asn Pro Gln Gly
                405                 410                 415

Leu Thr Glu Leu Gln Arg Met Gly Val Gly Leu Val Val Gly Met Ala
            420                 425                 430

Ala Met Val Val Ala Gly Val Val Glu Val Glu Arg Leu Lys Arg Val
        435                 440                 445

Gly Ala Pro Asp Gln Pro Ser Ser Leu Ser Val Leu Trp Gln Val Pro
    450                 455                 460

Gln Tyr Ala Leu Ile Gly Ala Ser Glu Val Phe Met Tyr Val Gly Gln
465                 470                 475                 480

Leu Glu Phe Phe Asn Gly Gln Ala Pro Asp Gly Val Lys Ser Phe Gly
                485                 490                 495

Ser Ser Leu Cys Met Ala Ser Ile Ser Leu Gly Asn Tyr Val Ser Ile
            500                 505                 510

Met Leu Val Ser Val Val Thr Ser Leu Thr Ala Gly Asp Arg Arg Pro
        515                 520                 525

Gly Trp Ile Pro Gly Asn Leu Asn Ser Gly His Leu Asp Arg Phe Tyr
    530                 535                 540

Phe Leu Leu Ala Ala Leu Ser Leu Val Asp Leu Ala Val Tyr Val Ala
545                 550                 555                 560

Cys Ala Val Trp Tyr Lys Gly Ile Lys Leu Asp Ser Asn Glu Glu Lys
                565                 570                 575

Ala Asn Lys Ile Thr Val His Val
            580


<210> SEQ ID NO 42
<211> LENGTH: 610
<212> TYPE: PRT
<213> ORGANISM: Oryza sativa (japonica cultivar-group)
<220> FEATURE:
<221> NAME/KEY: misc_feature
<222> LOCATION: (1)..(610)
<223> OTHER INFORMATION: Public GI no. 50911647

<400> SEQUENCE: 42

Met Ser Gly Asn Asp Gly Asp Met Lys Met Arg Val Ile Val Val Glu
1               5                   10                  15

Gly Asp Glu Thr Ser Asn Ala Pro Lys Asp Val Cys Cys Glu Tyr Thr
            20                  25                  30

Leu Asp Gly Ser Val Asp Ile Lys Gly Ser Pro Ala Val Lys Gly Lys
        35                  40                  45

Ser Gly Gly Trp Leu Ala Gly Gly Leu Ile Leu Leu Asn Gln Gly Leu
    50                  55                  60

Ala Thr Leu Ala Phe Phe Gly Val Asn Val Asn Leu Val Leu Phe Leu
65                  70                  75                  80

Thr Arg Val Leu Gln Gln Ser Asn Gly Asp Ala Ala Asn Asn Val Ser
                85                  90                  95

Lys Trp Thr Gly Thr Val Tyr Met Phe Ser Leu Ile Gly Ala Phe Leu
            100                 105                 110

Ser Asp Ser Tyr Trp Gly Arg Tyr Lys Thr Cys Ala Ile Phe Gln Ala
        115                 120                 125

Ile Phe Val Leu Gly Leu Ala Leu Leu Ser Leu Ser Ser Arg Leu Tyr
    130                 135                 140

Leu Ile Arg Pro Val Gly Cys Gly Thr Glu His Val Pro Cys Glu Pro
```

-continued

```
145                 150                 155                 160

His Ser Gly Ala Glu Leu Gly Ile Phe Tyr Ile Ala Leu Tyr Met Ile
                165                 170                 175

Ala Phe Gly Asn Gly Gly Tyr Gln Pro Asn Val Ala Thr Phe Gly Ala
            180                 185                 190

Asp Gln Phe Asp Gly Glu Asp Pro Ala Glu Ser His Ser Lys Val Ser
        195                 200                 205

Phe Phe Ser Tyr Phe Tyr Leu Ala Leu Asn Leu Gly Ser Leu Phe Ser
    210                 215                 220

Asn Thr Phe Leu Ser Phe Leu Glu Asp Glu Gly Asn Trp Ala Leu Gly
225                 230                 235                 240

Phe Trp Val Ser Thr Ala Ala Ala Ala Thr Ala Leu Leu Leu Phe Leu
                245                 250                 255

Gly Gly Thr Leu Arg Tyr Arg Tyr Ile Arg Pro Ser Gly Asn Pro Val
            260                 265                 270

Gly Arg Ile Phe Gln Val Ala Phe Ala Ala Cys Arg Asn Trp Lys Ala
        275                 280                 285

Gly Glu Ser Pro Gly Ala Val Thr Leu Tyr Glu Ser Asp Glu Lys Ala
    290                 295                 300

Asp Ser Gly Gly Arg Lys Leu Leu His Thr Glu Gly Phe Arg Phe Leu
305                 310                 315                 320

Asp Arg Ala Ala Val Val Gly Ala Asn Pro Lys Leu Gly Thr Cys Thr
                325                 330                 335

Gln Pro Arg Asp Pro Trp Lys Leu Cys Thr Val Thr Gln Val Glu Glu
            340                 345                 350

Val Lys Ser Ile Leu Arg Leu Leu Pro Ile Trp Leu Cys Thr Ile Leu
        355                 360                 365

Tyr Ser Val Val Phe Thr Gln Met Ala Ser Leu Phe Val Val Gln Gly
    370                 375                 380

Ala Ala Met Arg Arg Thr Thr Arg Phe Pro Gly Phe Ser Val Pro Pro
385                 390                 395                 400

Ser Ser Met Ser Ala Phe Asp Ile Leu Thr Val Ala Thr Thr Ile Phe
                405                 410                 415

Leu Tyr Arg Arg Ala Val Cys Pro Leu Val Ser Arg Leu Thr Gly Arg
            420                 425                 430

His Thr Gly Pro Thr Glu Leu Gln Arg Met Gly Leu Gly Leu Val Leu
        435                 440                 445

Gly Ala Met Ala Met Ala Thr Ala Gly Thr Val Glu His Phe Arg Lys
    450                 455                 460

Ala Gly Ala Thr Thr Ala Met Ser Ser Asp Leu His Ile Met Trp Gln
465                 470                 475                 480

Val Pro Gln Tyr Ala Leu Ile Gly Val Ser Glu Val Met Met Tyr Val
                485                 490                 495

Gly Gln Leu Glu Phe Phe Asn Gly Glu Met Pro Asp Ala Leu Lys Ser
            500                 505                 510

Phe Gly Ser Ala Leu Cys Met Met Ser Met Ser Leu Gly Asn Tyr Phe
        515                 520                 525

Ser Asp Val Ile Val Ser Ala Val Thr Lys Ala Thr Ala Val Arg Gly
    530                 535                 540

Arg Pro Gly Trp Ile Pro Ala Asp Leu Asn Glu Gly His Leu Asp Lys
545                 550                 555                 560

Phe Phe Phe Leu Leu Ala Val Leu Ala Val Ala Asp Phe Ala Val Tyr
                565                 570                 575
```

```
Leu Val Cys Ala Ser Arg Tyr Arg Ser Gly Thr Val Asp Val Asp Arg
            580                 585                 590

Ser Asp Gly Glu Glu Glu Asp Gly Val Ala Gly Arg Gln Met Ala Ala
        595                 600                 605

Thr Val
    610
```

<210> SEQ ID NO 43
<211> LENGTH: 606
<212> TYPE: PRT
<213> ORGANISM: Oryza sativa (japonica cultivar-group)
<220> FEATURE:
<221> NAME/KEY: misc_feature
<222> LOCATION: (1)..(606)
<223> OTHER INFORMATION: Public GI no. 54290524

<400> SEQUENCE: 43

```
Met Glu Asp Val Glu Ser Val Gly Ser Cys Ser Pro Cys Asn Ser Met
1               5                   10                  15

Ile Tyr Asn Glu Ser Phe Val His Thr Glu Asp Gln Thr Gln His Phe
            20                  25                  30

Gln Gly Ser Pro Glu Leu Lys Thr Ser Arg Gly Lys Met Thr Met Ala
        35                  40                  45

Leu Leu Leu Ala Leu Leu Asp Asp Ala Val Ser Tyr Val Leu Ala Asn
    50                  55                  60

Phe Ala Phe Phe Gly Val Ala Val Gly Leu Val Val Phe Leu Arg Gln
65                  70                  75                  80

Val Leu His Gln Glu Asn Ala Glu Ala Ala Asn Ser Val Ser Met Trp
                85                  90                  95

Met Gly Thr Val Tyr Ile Phe Ser Leu Phe Cys Ala Phe Leu Ser Asp
            100                 105                 110

Ser Tyr Met Gly Arg Tyr Ile Thr Cys Ile Met Phe Gln Phe Ile Phe
        115                 120                 125

Ile Val Gly Leu Met Leu Leu Ser Leu Leu Ser Trp Phe Leu Leu Val
    130                 135                 140

Glu Pro Pro Gly Cys Gly Asp Gly Gly Gly Leu Arg Gln Cys Ala Ala
145                 150                 155                 160

Pro Ser Arg Arg Gly Val Ala Val Phe Tyr Leu Ser Ile Tyr Met Ala
                165                 170                 175

Ala Phe Gly Asn Gly Gly Tyr Gln Pro Ser Val Ala Thr Phe Gly Ala
            180                 185                 190

Asp Gln Phe Asp Asp Ala Asp Pro Gly Glu Arg Arg Arg Lys Gln Ala
        195                 200                 205

Phe Phe Cys Leu Phe Tyr Leu Ser Leu Asn Val Gly Ser Leu Phe Tyr
    210                 215                 220

Asn Ser Val Leu Val Phe Phe Glu Asp Arg Gly Arg Trp Val Ala Gly
225                 230                 235                 240

Phe Trp Val Ser Thr Ala Ala Ala Ala Leu Ala Leu Ala Leu Phe Leu
                245                 250                 255

Leu Gly Thr Pro Arg Tyr Arg Arg Val Arg Pro Ala Gly Asn Pro Leu
            260                 265                 270

Thr Arg Ile Ala Gln Val Phe Val Ala Ala Tyr Arg Lys Arg His Ile
        275                 280                 285

Val Pro Pro Pro Gly Asp His Leu His Glu Val Asp Gly Glu Gly Ser
    290                 295                 300
```

-continued

```
Ala Ile Arg Gly Val Gly Lys Leu Ala His Ser Asp Gln Leu Arg Phe
305                 310                 315                 320

Leu Asp Lys Ala Ala Thr Ala Thr Glu Glu Asp Tyr His Asp Gly Asn
                325                 330                 335

Ala Lys Asn Pro Trp Arg Leu Cys Thr Val Thr Gln Val Glu Glu Ala
            340                 345                 350

Lys Cys Val Val Ser Met Val Pro Ile Trp Ile Cys Ser Ile Val Tyr
        355                 360                 365

Ser Val Glu Phe Thr Gln Met Ser Ser Leu Phe Val Glu Gln Gly Ala
    370                 375                 380

Ala Met Asp Thr Asp Ile Leu Gly Leu Phe Asn Ala Pro Ala Ala Ser
385                 390                 395                 400

Met Ser Val Phe Asp Val Ala Gly Val Leu Ala Thr Leu Ala Phe Ser
                405                 410                 415

His Tyr Val Leu Val Pro Ala Ala Ala Arg Leu Thr Lys Asn Pro Arg
            420                 425                 430

Gly Val Gly Glu Leu Lys Arg Met Gly Ala Gly Leu Val Ile Ala Leu
        435                 440                 445

Leu Gly Met Val Ala Ala Ala Val Val Glu Val His Arg Arg Arg Arg
    450                 455                 460

Ser Gly Ala Gly Gly Arg Ala Met Ser Val Leu Trp Gln Ala Pro Gln
465                 470                 475                 480

Tyr Ala Val Met Gly Ala Ser Glu Val Phe Val Tyr Val Gly Gln Leu
                485                 490                 495

Glu Phe Phe Asn Val Gln Ser Pro Glu Gly Val Lys Ser Leu Gly Ser
            500                 505                 510

Ser Leu Cys Met Ala Ser Ile Ser Leu Gly Asn Tyr Ala Ser Met Val
        515                 520                 525

Met Val Ser Ala Ile Ser Gly Val Ala Ser Arg Arg Arg Thr Gly Gly
    530                 535                 540

Gly Thr Ala Gly Trp Ile Leu Ala Glu Leu Asp Arg Gly His Leu Asp
545                 550                 555                 560

Arg Ser Phe Ile Thr Leu Ala Val Leu Ser Ala Val Asp Leu Val Val
                565                 570                 575

Phe Ile Val Phe Ala Arg Leu Phe Lys Gly Ile Glu Pro Glu Val Glu
            580                 585                 590

Gly Ile Ser Ser Ser Pro Gln Asp Asp His Ile Tyr Ile Val
        595                 600                 605
```

<210> SEQ ID NO 44
<211> LENGTH: 579
<212> TYPE: PRT
<213> ORGANISM: Hordeum vulgare
<220> FEATURE:
<221> NAME/KEY: misc_feature
<222> LOCATION: (1)..(579)
<223> OTHER INFORMATION: Public GI no. 2655098

<400> SEQUENCE: 44

```
Met Gly Glu Val Ala Ala Glu Met Tyr Thr Gln Asp Gly Thr Val Asp
1               5                   10                  15

Ile Lys Gly Asn Pro Ala Leu Lys Lys Asp Thr Gly Asn Trp Arg Ala
            20                  25                  30

Cys Pro Tyr Ile Leu Ala Asn Glu Cys Cys Glu Arg Leu Ala Tyr Tyr
        35                  40                  45

Gly Met Ser Thr Asn Leu Val Asn Phe Met Lys Asp Arg Met Gly Met
```

-continued

```
    50                  55                  60

Ala Asn Ala Ala Ala Ala Asn Asn Val Thr Asn Trp Gly Gly Thr Cys
65                  70                  75                  80

Tyr Ile Thr Pro Leu Ile Gly Ala Phe Leu Ala Asp Ala Tyr Leu Gly
                85                  90                  95

Arg Phe Trp Thr Ile Ala Ser Phe Met Ile Ile Tyr Ile Phe Gly Leu
            100                 105                 110

Gly Leu Leu Thr Met Ala Thr Ser Val His Gly Leu Val Pro Ala Cys
        115                 120                 125

Ala Ser Lys Gly Val Cys Asp Pro Thr Pro Gly Gln Ser Ala Ala Val
    130                 135                 140

Phe Ile Ala Leu Tyr Leu Ile Ala Leu Gly Thr Gly Gly Ile Lys Pro
145                 150                 155                 160

Cys Val Ser Ser Phe Gly Ala Asp Gln Phe Asp Glu His Asp Asp Val
                165                 170                 175

Glu Arg Lys Ser Lys Ser Ser Phe Phe Asn Trp Phe Tyr Phe Ser Ile
            180                 185                 190

Asn Ile Gly Ala Leu Val Ala Ser Ser Val Leu Val Tyr Val Gln Thr
        195                 200                 205

His Val Gly Trp Ser Trp Gly Phe Gly Ile Pro Ala Val Val Met Ala
    210                 215                 220

Ile Ala Val Gly Ser Phe Phe Val Gly Thr Ser Leu Tyr Arg His Gln
225                 230                 235                 240

Arg Pro Gly Gly Ser Pro Leu Thr Arg Ile Ala Gln Val Leu Val Ala
                245                 250                 255

Ala Thr Arg Lys Leu Gly Val Ala Val Asp Gly Ser Ala Leu Tyr Glu
            260                 265                 270

Thr Ala Asp Lys Glu Ser Gly Ile Glu Gly Ser Arg Lys Leu Glu His
        275                 280                 285

Thr Arg Gln Phe Arg Phe Leu Asp Lys Ala Ala Val Glu Thr His Ala
    290                 295                 300

Asp Arg Thr Ala Ala Ala Pro Ser Pro Trp Arg Leu Cys Thr Val Thr
305                 310                 315                 320

Gln Val Glu Glu Leu Lys Ser Val Val Arg Leu Leu Pro Ile Trp Ala
                325                 330                 335

Ser Gly Ile Val Phe Ala Thr Val Tyr Gly Gln Met Ser Thr Met Phe
            340                 345                 350

Val Leu Gln Gly Asn Thr Leu Asp Ala Ser Met Gly Pro Lys Phe Lys
        355                 360                 365

Ile Pro Ser Ala Ser Leu Ser Ile Phe Asp Thr Leu Ser Val Ile Ala
    370                 375                 380

Trp Val Pro Val Tyr Asp Arg Ile Leu Val Pro Ala Val Arg Ser Val
385                 390                 395                 400

Thr Gly Arg Pro Arg Gly Phe Thr Gln Leu Gln Arg Met Gly Ile Gly
                405                 410                 415

Leu Val Val Ser Met Phe Ala Met Leu Ala Ala Gly Val Leu Glu Leu
            420                 425                 430

Val Arg Leu Arg Thr Ile Ala Gln His Gly Leu Tyr Gly Glu Lys Asp
        435                 440                 445

Val Val Pro Ile Ser Ile Phe Trp Gln Val Pro Gln Tyr Phe Ile Ile
    450                 455                 460

Gly Cys Ala Glu Val Phe Thr Phe Val Gly Gln Leu Glu Phe Phe Tyr
465                 470                 475                 480
```

```
Asp Gln Ala Pro Asp Ala Met Arg Ser Met Cys Ser Ala Leu Ser Leu
                485                 490                 495

Thr Thr Val Ala Leu Gly Asn Tyr Leu Ser Thr Leu Leu Val Thr Val
            500                 505                 510

Val Ala Lys Val Thr Thr Arg Gly Gly Lys Gln Gly Trp Ile Pro Asp
        515                 520                 525

Asn Leu Asn Val Gly His Leu Asp Tyr Phe Phe Trp Leu Leu Ala Ala
    530                 535                 540

Leu Ser Leu Val Asn Phe Ala Val Tyr Leu Leu Ile Ala Ser Trp Tyr
545                 550                 555                 560

Thr Tyr Lys Lys Thr Ala Gly Asp Ser Pro Asp Ala Lys Gly Gly Ala
                565                 570                 575

His Asp Gln


<210> SEQ ID NO 45
<211> LENGTH: 584
<212> TYPE: PRT
<213> ORGANISM: Vicia faba
<220> FEATURE:
<221> NAME/KEY: misc_feature
<222> LOCATION: (1)..(584)
<223> OTHER INFORMATION: Public GI no. 31088360

<400> SEQUENCE: 45

Met Gly Ser Val Glu Asp Asp Ser Ser Arg Leu Glu Glu Ala Leu Ile
1               5                   10                  15

Gln Asp Glu Glu Ser Lys Leu Tyr Thr Gly Asp Gly Ser Val Asp Phe
            20                  25                  30

Lys Gly Arg Pro Val Leu Lys Lys Asn Thr Gly Asn Trp Lys Ala Cys
        35                  40                  45

Pro Phe Ile Leu Gly Asn Glu Cys Cys Glu Arg Leu Ala Tyr Tyr Gly
    50                  55                  60

Ile Ala Thr Asn Leu Val Lys Pro Ile Leu Leu Ala Lys Leu His Glu
65                  70                  75                  80

Gly Asn Val Ser Ala Ala Arg Asn Val Thr Thr Trp Gln Gly Thr Cys
                85                  90                  95

Tyr Leu Ala Pro Leu Ile Gly Ala Val Leu Ala Asp Ser Tyr Trp Gly
            100                 105                 110

Arg Tyr Trp Thr Ile Ala Ile Phe Ser Met Ile Tyr Phe Ile Gly Met
        115                 120                 125

Gly Thr Leu Thr Leu Ser Ala Ser Ile Pro Ala Leu Lys Pro Ala Glu
    130                 135                 140

Cys Leu Gly Ala Val Cys Pro Pro Ala Thr Pro Ala Gln Tyr Ala Val
145                 150                 155                 160

Phe Phe Ile Gly Leu Tyr Leu Ile Ala Leu Gly Thr Gly Gly Ile Lys
                165                 170                 175

Pro Cys Val Ser Ser Phe Gly Ala Asp Gln Phe Asp Asp Thr Asp Ser
            180                 185                 190

Arg Glu Arg Val Lys Lys Gly Ser Phe Phe Asn Trp Phe Tyr Phe Ser
        195                 200                 205

Ile Asn Ile Gly Ala Leu Ile Ser Ser Ser Phe Ile Val Trp Ile Gln
    210                 215                 220

Glu Asn Ala Gly Trp Gly Leu Gly Phe Gly Ile Pro Ala Leu Phe Met
225                 230                 235                 240

Gly Leu Ala Ile Gly Ser Phe Phe Leu Gly Thr Pro Leu Tyr Arg Phe
```

-continued

```
                245                 250                 255

Gln Lys Pro Gly Gly Ser Pro Leu Thr Arg Met Cys Gln Val Val Ala
            260                 265                 270

Ala Ser Phe Arg Lys Arg Asn Leu Thr Val Pro Glu Asp Ser Ser Leu
        275                 280                 285

Leu Tyr Glu Thr Pro Asp Lys Ser Ser Ala Ile Glu Gly Ser Arg Lys
    290                 295                 300

Leu Gln His Ser Asp Glu Leu Arg Cys Leu Asp Arg Ala Ala Val Ile
305                 310                 315                 320

Ser Asp Asp Glu Arg Lys Arg Gly Asp Tyr Ser Asn Leu Trp Arg Leu
                325                 330                 335

Cys Thr Val Thr Gln Val Glu Glu Leu Lys Ile Leu Ile Arg Met Phe
            340                 345                 350

Pro Val Trp Ala Thr Gly Ile Val Phe Ser Ala Val Tyr Ala Gln Met
        355                 360                 365

Ser Thr Met Phe Val Glu Gln Gly Thr Met Met Asp Thr Ser Val Gly
    370                 375                 380

Ser Phe Lys Ile Pro Ala Ala Ser Leu Ser Thr Phe Asp Val Ile Ser
385                 390                 395                 400

Val Ile Phe Trp Val Pro Val Tyr Asp Arg Phe Ile Val Pro Ile Ala
                405                 410                 415

Arg Lys Phe Thr Gly Lys Glu Arg Gly Phe Ser Glu Leu Gln Arg Met
            420                 425                 430

Gly Ile Gly Leu Phe Ile Ser Val Leu Cys Met Ser Ala Ala Ala Ile
        435                 440                 445

Val Glu Ile Lys Arg Leu Gln Leu Ala Lys Glu Leu Asp Leu Val Asp
    450                 455                 460

Lys Ala Val Pro Val Pro Leu Thr Ile Phe Leu Gln Ile Pro Gln Tyr
465                 470                 475                 480

Phe Leu Leu Gly Ala Ala Glu Val Phe Thr Phe Val Gly Gln Leu Glu
                485                 490                 495

Phe Phe Tyr Asp Gln Ser Pro Asp Ala Met Arg Ser Leu Cys Ser Ala
            500                 505                 510

Leu Ser Leu Leu Thr Thr Ser Leu Gly Asn Tyr Leu Ser Ser Phe Ile
        515                 520                 525

Leu Thr Val Val Leu Tyr Phe Thr Thr Arg Gly Gly Asn Pro Gly Trp
    530                 535                 540

Ile Pro Asp Asn Leu Asn Lys Gly His Leu Asp Tyr Phe Ser Gly Leu
545                 550                 555                 560

Ala Gly Leu Ser Phe Leu Asn Met Phe Leu Tyr Ile Val Ala Ala Lys
                565                 570                 575

Arg Tyr Lys Ser Lys Lys Ala Ser
            580


<210> SEQ ID NO 46
<211> LENGTH: 580
<212> TYPE: PRT
<213> ORGANISM: Lycopersicon esculentum
<220> FEATURE:
<221> NAME/KEY: misc_feature
<222> LOCATION: (1)..(580)
<223> OTHER INFORMATION: Public GI no. 4102839

<400> SEQUENCE: 46

Met Lys Tyr Leu Phe Ser Lys Asn Gly Gly Leu Leu Glu Asp Glu Asn
1               5                   10                  15
```

-continued

```
Ser Gly Leu Tyr Thr Arg Asp Gly Ser Val Asp Ile Lys Gly Asn Pro
            20                  25                  30

Val Leu Lys Ser Glu Thr Gly Asn Trp Arg Ala Cys Pro Phe Ile Leu
        35                  40                  45

Gly Asn Glu Cys Cys Glu Arg Leu Ala Tyr Tyr Gly Ile Ala Ala Asn
    50                  55                  60

Leu Val Thr Tyr Leu Thr Lys Lys Leu His Glu Gly Asn Val Ser Ala
65                  70                  75                  80

Ala Arg Asn Val Thr Thr Trp Gln Gly Thr Cys Tyr Ile Thr Pro Leu
                85                  90                  95

Ile Gly Ala Val Leu Ala Asp Ala Tyr Trp Gly Arg Tyr Trp Thr Ile
            100                 105                 110

Ala Thr Phe Ser Thr Ile Tyr Phe Ile Gly Met Cys Thr Leu Thr Leu
        115                 120                 125

Ser Ala Ser Val Pro Ala Phe Lys Pro Pro Gln Cys Val Gly Ser Val
    130                 135                 140

Cys Pro Ser Ala Ser Pro Ala Gln Tyr Ala Ile Phe Phe Phe Gly Leu
145                 150                 155                 160

Tyr Leu Ile Ala Leu Gly Thr Gly Gly Ile Lys Pro Cys Val Ser Ser
                165                 170                 175

Phe Gly Ala Asp Gln Phe Asp Asp Thr Asp Pro Lys Glu Arg Val Lys
            180                 185                 190

Lys Gly Ser Phe Phe Asn Trp Phe Tyr Phe Ser Ile Asn Ile Gly Ala
        195                 200                 205

Leu Ile Ser Ser Ser Leu Ile Val Trp Ile Gln Glu Asn Ala Gly Trp
    210                 215                 220

Gly Leu Gly Phe Gly Ile Pro Ala Val Phe Met Gly Ile Ala Ile Ala
225                 230                 235                 240

Ser Phe Phe Phe Gly Thr Pro Leu Tyr Arg Phe Gln Lys Pro Gly Gly
                245                 250                 255

Ser Pro Leu Thr Arg Met Cys Gln Val Leu Val Ala Val Phe His Lys
            260                 265                 270

Trp Asn Leu Ser Val Pro Asp Asp Ser Thr Leu Leu Tyr Glu Thr Pro
        275                 280                 285

Asp Lys Ser Ser Ala Ile Glu Gly Ser Arg Lys Leu Leu His Thr Asp
    290                 295                 300

Glu Leu Arg Cys Leu Asp Lys Ala Ala Val Val Ser Asp Asn Glu Leu
305                 310                 315                 320

Thr Thr Gly Asp Tyr Ser Asn Ala Trp Arg Leu Cys Thr Val Thr Gln
                325                 330                 335

Val Glu Glu Leu Lys Ile Leu Ile Arg Met Phe Pro Ile Trp Ala Thr
            340                 345                 350

Gly Ile Val Phe Ser Ala Val Tyr Ala Gln Met Ser Thr Met Phe Val
        355                 360                 365

Glu Gln Gly Met Val Met Asp Thr Ala Val Gly Ser Phe Lys Ile Pro
    370                 375                 380

Ala Ala Ser Leu Ser Thr Phe Asp Thr Ile Ser Val Ile Val Trp Val
385                 390                 395                 400

Pro Val Tyr Asp Lys Ile Leu Val Pro Ile Ala Arg Arg Phe Thr Gly
                405                 410                 415

Ile Glu Arg Gly Phe Ser Glu Leu Gln Arg Met Gly Ile Gly Leu Phe
            420                 425                 430
```

-continued

```
Leu Ser Met Leu Cys Met Ser Ala Ala Ala Ile Val Glu Ile Arg Arg
        435                 440                 445

Leu Gln Leu Ala Arg Asp Leu Gly Leu Val Asp Glu Ala Val Ser Val
    450                 455                 460

Pro Leu Ser Ile Phe Trp Gln Ile Pro Gln Tyr Phe Ile Leu Gly Ala
465                 470                 475                 480

Ala Glu Ile Phe Thr Phe Ile Gly Gln Leu Glu Phe Phe Tyr Asp Gln
                485                 490                 495

Ser Pro Asp Ala Met Arg Ser Leu Cys Ser Ala Leu Ser Leu Leu Thr
            500                 505                 510

Thr Ala Leu Gly Asn Tyr Leu Ser Ser Phe Ile Leu Thr Val Val Thr
        515                 520                 525

Ser Ile Thr Thr Arg Gly Gly Lys Pro Gly Trp Ile Pro Asn Asn Leu
    530                 535                 540

Asn Gly Gly His Leu Asp Tyr Phe Phe Trp Leu Leu Ala Ala Leu Ser
545                 550                 555                 560

Phe Phe Asn Leu Val Ile Tyr Val Phe Leu Cys Gln Met Tyr Lys Ser
                565                 570                 575

Lys Lys Ala Ser
            580


<210> SEQ ID NO 47
<211> LENGTH: 559
<212> TYPE: PRT
<213> ORGANISM: Prunus dulcis
<220> FEATURE:
<221> NAME/KEY: misc_feature
<222> LOCATION: (1)..(559)
<223> OTHER INFORMATION: Public GI no. 6635838
<220> FEATURE:
<221> NAME/KEY: misc_feature
<222> LOCATION: (46)..(46)
<223> OTHER INFORMATION: Xaa is any aa, unknown, or other

<400> SEQUENCE: 47

Met Gly Ser Leu Glu Glu Glu Arg Ser Leu Leu Glu Asp Gly Leu Ile
1               5                   10                  15

Gln Asp Glu Thr Asn Gly Leu Tyr Thr Gly Asp Gly Ser Val Asp Ile
            20                  25                  30

Thr Gly Lys Pro Val Leu Lys Gln Ser Thr Gly Asn Trp Xaa Ala Cys
        35                  40                  45

Pro Phe Ile Leu Gly Thr Glu Cys Cys Glu Arg Leu Ala Phe Tyr Gly
    50                  55                  60

Ile Ser Thr Asn Leu Val Thr Tyr Leu Thr His Lys Leu His Glu Gly
65                  70                  75                  80

Asn Val Ser Ala Ala Arg Asn Val Thr Thr Trp Ser Gly Thr Cys Tyr
                85                  90                  95

Leu Thr Pro Leu Ile Gly Ala Val Leu Ala Asp Ala Tyr Trp Gly Arg
            100                 105                 110

Tyr Trp Thr Ile Ala Ile Phe Ser Thr Ile Tyr Phe Ile Gly Met Cys
        115                 120                 125

Thr Leu Thr Ile Ser Ala Ser Val Pro Ala Leu Lys Pro Pro Gln Cys
    130                 135                 140

Val Asp Ser Val Cys Pro Ser Ala Ser Pro Ala Gln Tyr Gly Val Phe
145                 150                 155                 160

Phe Phe Gly Leu Tyr Leu Ile Ala Leu Arg Thr Gly Gly Ile Lys Pro
                165                 170                 175
```

```
Cys Val Ser Ser Phe Gly Ala Asp Gln Phe Asp Asp Thr Asp Ser Arg
            180                 185                 190

Glu Arg Val Lys Lys Gly Ser Phe Phe Asn Trp Phe Tyr Phe Ser Ile
        195                 200                 205

Asn Ile Gly Ala Leu Val Ser Ser Thr Leu Ile Val Trp Val Gln Asp
    210                 215                 220

Asn Ala Gly Trp Gly Leu Gly Phe Gly Ile Pro Ala Leu Phe Met Gly
225                 230                 235                 240

Ile Ala Ile Val Ser Phe Phe Ser Gly Thr Pro Leu Tyr Arg Phe Gln
                245                 250                 255

Lys Pro Gly Gly Ser Pro Leu Thr Arg Met Cys Gln Val Leu Val Ala
            260                 265                 270

Ser Phe Arg Lys Trp Asn Leu Asp Val Pro Arg Asp Ser Ser Leu Leu
        275                 280                 285

Tyr Glu Thr Gln Asp Lys Gly Ser Ala Ile Lys Gly Ser Arg Lys Leu
    290                 295                 300

Glu His Ser Asp Glu Leu Asn Cys Leu Asp Lys Ala Ala Val Ile Ser
305                 310                 315                 320

Glu Thr Glu Thr Lys Thr Gly Asp Phe Ser Asn Pro Trp Arg Ile Cys
                325                 330                 335

Thr Val Thr Gln Val Glu Glu Leu Lys Ile Leu Ile Arg Met Phe Pro
            340                 345                 350

Ile Trp Ala Thr Gly Ile Val Phe Ser Ala Val Tyr Ala Gln Met Ala
        355                 360                 365

Thr Met Phe Val Glu Gln Gly Met Met Met Asp Thr Ser Val Gly Ser
    370                 375                 380

Phe Thr Ile Pro Pro Ala Ser Leu Ser Ser Phe Asp Val Ile Ser Val
385                 390                 395                 400

Ile Phe Trp Val Pro Ile Tyr Asp Arg Phe Ile Val Pro Ile Ala Arg
                405                 410                 415

Lys Phe Thr Gly Lys Glu Arg Gly Phe Ser Glu Leu Gln Arg Met Gly
            420                 425                 430

Ile Gly Leu Phe Leu Ser Val Leu Cys Met Ser Ala Ala Ala Val Val
        435                 440                 445

Glu Met Lys Arg Leu Gln Leu Ala Thr Glu Leu Gly Leu Val Asp Lys
    450                 455                 460

Glu Val Ala Val Pro Leu Ser Ile Phe Trp Gln Ile Pro Gln Tyr Phe
465                 470                 475                 480

Leu Leu Gly Ala Ala Glu Ile Phe Thr Phe Ile Gly Gln Leu Glu Phe
                485                 490                 495

Phe Tyr Asp Gln Ser Ser Asp Ala Met Arg Ser Leu Cys Ser Ala Leu
            500                 505                 510

Ser Ala Ser Asp Asp Phe Ile Gly Lys Leu Ser Glu Leu Phe Asp Ser
        515                 520                 525

Asp Ile Val Thr Tyr Phe Thr Thr Gln Gly Gly Lys Ala Gly Trp Ile
    530                 535                 540

Pro Asp Asn Leu Asn Asp Gly His Leu Asp Tyr Phe Ser Gly Ser
545                 550                 555
```

<210> SEQ ID NO 48
<211> LENGTH: 594
<212> TYPE: PRT
<213> ORGANISM: Prunus persica
<220> FEATURE:
<221> NAME/KEY: misc_feature
<222> LOCATION: (1)..(594)
<223> OTHER INFORMATION: Public GI no. 48675345

<400> SEQUENCE: 48

```
Met Ser Asn Cys Thr Leu Pro Glu Thr Gln Glu Lys Leu Thr Leu Pro
1               5                   10                  15

Asp Ala Trp Asp Phe Lys Gly Arg Pro Ala Glu Arg Ser Lys Thr Gly
            20                  25                  30

Gly Trp Thr Ala Ala Ala Met Ile Leu Gly Gly Glu Ala Cys Glu Arg
        35                  40                  45

Leu Thr Thr Leu Gly Ile Ala Val Asn Leu Val Thr Tyr Leu Thr Gly
    50                  55                  60

Thr Met His Leu Gly Asn Ala Thr Ser Ala Asn Thr Val Thr Asn Phe
65                  70                  75                  80

Leu Gly Thr Ser Phe Met Leu Cys Leu Leu Gly Gly Phe Val Ala Asp
                85                  90                  95

Thr Phe Leu Gly Arg Tyr Leu Thr Ile Ala Ile Phe Ala Thr Phe Gln
            100                 105                 110

Ala Met Gly Val Thr Ile Leu Thr Ile Ser Thr Thr Ile Pro Ser Leu
        115                 120                 125

Arg Pro Pro Lys Cys Thr Ser Asp Thr Ser Thr Pro Cys Ile Pro Ala
    130                 135                 140

Ser Gly Lys Gln Leu Met Val Leu Tyr Ile Ala Leu Tyr Leu Thr Ala
145                 150                 155                 160

Leu Gly Thr Gly Gly Leu Lys Ser Ser Val Ser Gly Phe Gly Ser Asp
                165                 170                 175

Gln Phe Asp Glu Ser Asp Lys Gln Glu Arg Arg Gln Met Thr Asn Phe
            180                 185                 190

Phe Asn Trp Phe Phe Phe Phe Ile Ser Ile Gly Ser Leu Ala Ala Val
        195                 200                 205

Thr Val Leu Val Tyr Ile Gln Asp Asn Leu Gly Arg Gln Trp Gly Tyr
    210                 215                 220

Gly Ile Cys Val Cys Ala Ile Val Leu Gly Leu Ile Val Phe Leu Ser
225                 230                 235                 240

Gly Thr Arg Arg Tyr Arg Phe Lys Lys Leu Val Gly Ser Pro Leu Thr
                245                 250                 255

Gln Ile Ser Gly Val Cys Val Ala Ala Trp Arg Lys Arg Asn Met Glu
            260                 265                 270

Leu Pro Ser Asp Met Ser Phe Leu Tyr Asn Val Asp Asp Ile Asp Asp
        275                 280                 285

Gly Leu Lys Lys Lys Lys Lys Gln Lys Leu Pro His Ser Lys Gln Phe
    290                 295                 300

Arg Phe Leu Asp Lys Ala Ala Ile Lys Glu Pro Lys Thr Thr Ser Gly
305                 310                 315                 320

Thr Ala Met Ile Ile Asn Lys Trp Ser Leu Ser Thr Leu Thr Asp Val
                325                 330                 335

Glu Glu Val Lys Leu Ile Ile Arg Met Leu Pro Ile Trp Ala Thr Thr
            340                 345                 350

Ile Met Phe Trp Thr Val Tyr Ala Gln Met Thr Thr Phe Ser Val Ser
        355                 360                 365

Gln Ala Thr Ser Met Asp Arg His Ile Gly Lys Ser Phe Gln Ile Pro
    370                 375                 380

Pro Ala Ser Leu Thr Ala Phe Phe Val Gly Ser Ile Leu Leu Thr Val
385                 390                 395                 400
```

```
Pro Val Tyr Asp Arg Leu Ile Val Pro Met Ala Arg Lys Ala Leu Glu
                405                 410                 415

Asn Pro Gln Gly Leu Thr Pro Leu Gln Arg Met Gly Val Gly Leu Val
            420                 425                 430

Phe Ser Ile Phe Ala Met Val Ala Ala Ala Leu Thr Glu Val Lys Arg
        435                 440                 445

Leu Asn Ile Ala Arg Ser His Gly Leu Thr Asp Asn Pro Thr Ala Glu
    450                 455                 460

Ile Pro Leu Ser Val Phe Trp Leu Val Pro Gln Phe Phe Phe Val Gly
465                 470                 475                 480

Ser Gly Glu Ala Phe Thr Tyr Ile Gly Gln Leu Asp Phe Phe Leu Arg
                485                 490                 495

Glu Cys Pro Lys Gly Met Lys Thr Met Ser Thr Gly Leu Phe Leu Ser
            500                 505                 510

Thr Leu Ser Leu Gly Phe Phe Phe Ser Ser Leu Leu Val Thr Ile Val
        515                 520                 525

His Lys Thr Thr Gly His Asn Lys Pro Trp Leu Ala Asp Asn Leu Asn
    530                 535                 540

Gln Gly Lys Leu Tyr Asp Phe Tyr Trp Leu Leu Ala Leu Leu Ser Ala
545                 550                 555                 560

Leu Asn Leu Val Ile Tyr Leu Phe Cys Ala Asn Trp Tyr Val Tyr Lys
                565                 570                 575

Asp Lys Arg Leu Ala Glu Glu Gly Ile Glu Leu Glu Glu Pro Glu Ile
            580                 585                 590

Cys Ala


<210> SEQ ID NO 49
<211> LENGTH: 584
<212> TYPE: PRT
<213> ORGANISM: Oryza sativa
<220> FEATURE:
<221> NAME/KEY: misc_feature
<222> LOCATION: (1)..(584)
<223> OTHER INFORMATION: Public GI no. 6409176

<400> SEQUENCE: 49

Met Asp Ser Ser Tyr Gln His Asp Lys Pro Leu Leu Asp Glu Glu Asn
1               5                   10                  15

Ser Ser Gln Val Thr Leu Glu Tyr Thr Gly Asp Gly Ser Val Cys Ile
            20                  25                  30

Arg Gly His Pro Ala Leu Arg Lys His Thr Gly Asn Trp Lys Gly Ser
        35                  40                  45

Ser Leu Ala Ile Val Phe Ser Phe Cys Ser Tyr Leu Ala Phe Thr Ser
    50                  55                  60

Ile Val Lys Asn Leu Val Ser Tyr Leu Thr Lys Val Leu His Glu Thr
65                  70                  75                  80

Asn Val Ala Ala Ala Arg Asp Val Ala Thr Trp Ser Gly Thr Ser Tyr
                85                  90                  95

Leu Ala Pro Leu Val Gly Ala Phe Leu Ala Asp Ser Tyr Leu Gly Lys
            100                 105                 110

Tyr Cys Thr Ile Leu Ile Phe Cys Thr Ile Phe Ile Ile Gly Leu Met
        115                 120                 125

Met Leu Leu Leu Ser Ala Ala Val Pro Leu Ile Ser Thr Gly Pro His
    130                 135                 140

Ser Trp Ile Ile Trp Thr Asp Pro Val Ser Ser Gln Asn Ile Ile Phe
```

-continued

```
145                 150                 155                 160

Phe Val Gly Leu Tyr Met Val Ala Leu Gly Tyr Gly Ala Gln Cys Pro
                165                 170                 175

Cys Ile Ser Ser Phe Gly Ala Asp Gln Phe Asp Asp Thr Asp Glu Asn
            180                 185                 190

Glu Arg Thr Lys Lys Ser Ser Phe Phe Asn Trp Thr Tyr Phe Val Ala
        195                 200                 205

Asn Ala Gly Ser Leu Ile Ser Gly Thr Val Ile Val Trp Val Gln Asp
    210                 215                 220

His Lys Gly Trp Ile Trp Gly Phe Thr Ile Ser Ala Leu Phe Val Tyr
225                 230                 235                 240

Leu Gly Phe Gly Thr Phe Ile Phe Gly Ser Ser Met Tyr Asp Phe Arg
                245                 250                 255

Asn Leu Glu Glu Ala Pro Leu Ala Arg Ile Cys Gln Val Val Val Ala
            260                 265                 270

Ala Ile His Lys Arg Asp Lys Asp Leu Pro Cys Asp Ser Ser Val Leu
        275                 280                 285

Tyr Glu Phe Leu Gly Gln Ser Ser Ala Ile Glu Gly Ser Arg Lys Leu
    290                 295                 300

Glu His Thr Thr Gly Leu Lys Phe Phe Asp Arg Ala Ala Met Val Thr
305                 310                 315                 320

Pro Ser Asp Phe Glu Ser Asp Gly Leu Leu Asn Thr Trp Lys Ile Cys
                325                 330                 335

Thr Val Thr Gln Val Glu Glu Leu Lys Ile Leu Ile Arg Met Phe Pro
            340                 345                 350

Val Trp Ala Thr Met Ile Leu Phe Ala Ala Val Leu Asp Asn Met Phe
        355                 360                 365

Ser Thr Phe Ile Glu Gln Gly Met Val Met Glu Lys His Ile Gly Ser
    370                 375                 380

Phe Glu Ile Pro Ala Ala Ser Phe Gln Ser Ile Asp Val Ile Ala Val
385                 390                 395                 400

Leu Ile Leu Val Pro Val Tyr Glu Arg Val Leu Val Pro Val Phe Arg
                405                 410                 415

Lys Phe Thr Gly Arg Ala Asn Gly Ile Thr Pro Leu Gln Arg Met Gly
            420                 425                 430

Ile Gly Leu Phe Phe Ser Met Leu Ser Met Val Ser Ala Ala Leu Val
        435                 440                 445

Glu Ser Asn Arg Leu Arg Ile Ala Gln Asp Glu Gly Leu Val His Arg
    450                 455                 460

Lys Val Ala Val Pro Met Ser Ile Leu Trp Gln Gly Pro Gln Tyr Phe
465                 470                 475                 480

Leu Ile Gly Val Gly Glu Val Phe Ser Asn Ile Gly Leu Thr Glu Phe
                485                 490                 495

Phe Tyr Gln Glu Ser Pro Asp Ala Met Arg Ser Leu Cys Leu Ala Phe
            500                 505                 510

Ser Leu Ala Asn Val Ser Ala Gly Ser Tyr Leu Ser Ser Phe Ile Val
        515                 520                 525

Ser Leu Val Pro Val Phe Thr Ala Arg Glu Gly Ser Pro Gly Trp Ile
    530                 535                 540

Pro Asp Asn Leu Asn Glu Gly His Leu Asp Arg Phe Phe Trp Met Met
545                 550                 555                 560

Ala Gly Leu Cys Phe Leu Asn Met Leu Ala Phe Val Phe Cys Ala Met
                565                 570                 575
```

```
Arg Tyr Lys Cys Lys Lys Ala Ser
            580


<210> SEQ ID NO 50
<211> LENGTH: 586
<212> TYPE: PRT
<213> ORGANISM: Triticum aestivum
<220> FEATURE:
<221> NAME/KEY: misc_feature
<222> LOCATION: (1)..(586)
<223> OTHER INFORMATION: Public GI no. 50059161

<400> SEQUENCE: 50

Met Asp Ser Thr Asp Gln Phe Asp Asn Ser Pro Leu Leu Asp Gly Asp
1               5                   10                  15

Gly Ser Ser Gln Glu Asn Thr Thr Glu Tyr Thr Gly Asp Gly Ser Val
            20                  25                  30

Cys Ile Ser Gly His Pro Ala Ser Arg Lys His Thr Gly Asn Trp Lys
        35                  40                  45

Ala Ser Phe Leu Ile Ile Val Cys Ser Phe Cys Cys Tyr Leu Ala Tyr
    50                  55                  60

Ser Ser Ile Gly Lys Asn Leu Val Ser Tyr Leu Thr Lys Val Leu His
65                  70                  75                  80

Glu Thr Asn Leu Asp Ala Ala Arg His Val Ala Thr Trp Gln Gly Thr
                85                  90                  95

Ser Tyr Leu Ala Pro Leu Val Gly Ala Phe Val Ala Asp Ser Tyr Leu
            100                 105                 110

Gly Lys Tyr Arg Thr Ala Leu Ile Ala Cys Lys Ile Phe Ile Ile Gly
        115                 120                 125

Met Met Met Leu Leu Leu Ser Ala Ala Leu Gln Leu Ile Ser Ala Gly
    130                 135                 140

Pro His Ala Trp Thr Val Trp Val His Leu Val Ser Ser Gln Tyr Thr
145                 150                 155                 160

Ile Phe Leu Ile Gly Leu Tyr Met Val Gly Leu Gly Tyr Gly Ala Gln
                165                 170                 175

Arg Pro Cys Val Thr Ser Phe Gly Ala Asp Gln Phe Asp Asp Thr Asp
            180                 185                 190

Tyr Val Glu Lys Thr Arg Lys Ser Ser Phe Phe Asn Trp His Tyr Phe
        195                 200                 205

Ala Ile Asn Ala Gly Ser Leu Ile Ala Gly Thr Val Ile Val Trp Val
    210                 215                 220

Gln Glu His Glu Gly Trp Leu Trp Gly Phe Thr Ile Ser Thr Leu Phe
225                 230                 235                 240

Val Thr Leu Gly Val Cys Ile Phe Phe Leu Gly Ser Ile Val Tyr Arg
                245                 250                 255

Phe Gln Lys Pro Arg Gly Ser Pro Leu Thr Arg Leu Cys Gln Val Val
            260                 265                 270

Ile Ala Ala Thr Arg Asn Phe Asp Lys Val Leu Pro Cys Asp Ser Ser
        275                 280                 285

Ala Leu Tyr Glu Phe Met Gly Gln Gly Ser Ala Ile Glu Gly Arg Arg
    290                 295                 300

Lys Leu Glu His Thr Thr Gly Leu Gly Phe Phe Asp Lys Ala Ala Ile
305                 310                 315                 320

Val Thr Leu Pro Asp Cys Glu Ser Pro Gly Gln His Asn Lys Trp Lys
                325                 330                 335
```

```
Ile Cys Thr Val Thr Gln Val Glu Glu Leu Lys Ile Leu Ile Arg Met
            340                 345                 350

Phe Pro Ile Trp Ser Ala Met Ile Leu Phe Ala Ala Val Gln Glu Gln
        355                 360                 365

Met Ser Ser Thr Phe Val Glu Gln Gly Met Ala Met Asp Lys His Ile
    370                 375                 380

Gly Ser Phe Glu Ile Pro Ser Ala Ser Phe Gln Cys Val Asp Thr Ile
385                 390                 395                 400

Thr Val Ile Val Leu Val Pro Ile Tyr Glu Arg Leu Ile Val Pro Val
                405                 410                 415

Ile Arg Lys Phe Thr Gly Arg Ala Asn Gly Ile Thr Ser Pro Gln Arg
            420                 425                 430

Ile Gly Ile Gly Leu Cys Phe Ser Met Phe Ser Met Val Ser Ala Ala
        435                 440                 445

Leu Val Glu Gly Asn Arg Leu Gln Ile Ala Gln Ala Glu Gly Leu Val
    450                 455                 460

His Arg Lys Val Ala Val Pro Met Ser Ile Met Trp Gln Gly Pro Gln
465                 470                 475                 480

Tyr Phe Leu Leu Gly Val Ala Glu Val Phe Ser Asn Ile Gly Leu Thr
                485                 490                 495

Glu Ala Phe Tyr Asp Glu Ser Pro Asp Gly Met Arg Ser Leu Cys Met
            500                 505                 510

Ala Phe Ser Leu Val Asn Met Ser Ala Gly Asn Tyr Leu Ser Ser Leu
        515                 520                 525

Ile Leu Ser Leu Val Pro Val Phe Thr Ala Arg Gly Gly Ser Pro Gly
    530                 535                 540

Trp Ile Pro Asp Asn Leu Asn Glu Gly His Leu Asp Arg Phe Tyr Leu
545                 550                 555                 560

Met Met Ala Gly Leu Ser Phe Phe Asn Ile Val Val Phe Val Phe Cys
                565                 570                 575

Ala Met Arg Tyr Lys Cys Lys Lys Ala Ser
            580                 585


<210> SEQ ID NO 51
<211> LENGTH: 586
<212> TYPE: PRT
<213> ORGANISM: Triticum aestivum
<220> FEATURE:
<221> NAME/KEY: misc_feature
<222> LOCATION: (1)..(586)
<223> OTHER INFORMATION: Public GI no. 47717628

<400> SEQUENCE: 51

Met Asp Ser Thr Asp Arg Phe Asp Lys Ser Pro Leu Leu Asp Gly Gly
1               5                   10                  15

Ser Ser Ser Gln Glu Asn Ser Thr Glu Tyr Thr Gly Asp Gly Ser Val
            20                  25                  30

Cys Thr Ser Gly His Pro Ala Ser Arg Lys His Thr Gly Asn Trp Lys
        35                  40                  45

Val Ser Ser Leu Thr Ile Val Cys Ser Phe Cys Cys Tyr Leu Ala Tyr
    50                  55                  60

Ser Ser Ile Gly Lys Asn Leu Val Ser Tyr Leu Thr Lys Val Leu Asp
65                  70                  75                  80

Glu Thr Asn Leu Asp Ala Ala Arg His Val Ala Thr Trp Gln Gly Thr
                85                  90                  95

Ser Tyr Leu Ala Pro Leu Val Gly Ala Phe Val Ala Asp Ser Tyr Leu
```

-continued

```
            100                 105                 110

Gly Lys Tyr Arg Thr Ala Leu Ile Ser Cys Thr Ile Phe Ile Met Gly
        115                 120                 125

Met Met Met Leu Leu Leu Ser Ala Ala Leu Pro Leu Ile Ser Ala Gly
    130                 135                 140

Pro His Ala Trp Thr Leu Trp Ala Asp Pro Ile Ser Ser Arg Tyr Ile
145                 150                 155                 160

Ile Phe Leu Val Gly Leu Tyr Met Val Gly Leu Gly Tyr Gly Ala Gln
                165                 170                 175

Cys Pro Cys Val Thr Ser Phe Gly Ala Asp Gln Phe Asp Asp Thr Asn
            180                 185                 190

Glu Met Glu Lys Thr Arg Lys Ser Ser Phe Phe Asn Trp His Tyr Phe
        195                 200                 205

Ser Ile Asn Ala Gly Ser Leu Ile Ala Gly Thr Val Ile Val Trp Val
    210                 215                 220

Gln Glu His Glu Gly Trp Leu Trp Gly Phe Thr Ile Ser Thr Leu Phe
225                 230                 235                 240

Val Thr Leu Gly Ile Ser Val Phe Phe Leu Gly Ser Ile Val Tyr Arg
                245                 250                 255

Phe Gln Lys Pro Gly Gly Ser Pro Leu Ala Arg Ile Trp Gln Val Val
            260                 265                 270

Val Ala Ala Ser Arg Asn Phe Asp Lys Val Leu Pro Cys Asp Ser Ser
        275                 280                 285

Ala Leu Tyr Glu Phe Ser Gly Gln Gly Ser Ala Ile Glu Gly Ser Arg
    290                 295                 300

Lys Ser Glu His Thr Ser Gly Leu Glu Phe Phe Asp Lys Ala Ala Ile
305                 310                 315                 320

Leu Thr Leu Pro Asp Cys Glu Ser Pro Gly Gln Leu Asn Lys Trp Lys
                325                 330                 335

Ile Cys Thr Val Thr Gln Val Glu Glu Leu Lys Ile Leu Ile Arg Met
            340                 345                 350

Phe Pro Ile Trp Ser Ala Met Val Leu Phe Ala Ala Val Gln Glu Gln
        355                 360                 365

Met Phe Ser Thr Phe Val Glu Gln Gly Met Thr Met Glu Lys His Val
    370                 375                 380

Gly Ser Phe Glu Ile Pro Thr Ala Ser Phe Gln Ser Ile Asp Thr Leu
385                 390                 395                 400

Thr Val Ile Met Leu Val Pro Ile Tyr Glu Arg Val Leu Val Pro Val
                405                 410                 415

Ile Arg Lys Phe Thr Gly Arg Ala Asn Gly Ile Ser Ser Pro Gln Arg
            420                 425                 430

Ile Gly Ile Gly Leu Cys Phe Ser Met Leu Ser Met Val Leu Ala Ala
        435                 440                 445

Leu Val Glu Ser Asn Arg Leu Gln Ile Ala Gln Ser Glu Gly Leu Val
    450                 455                 460

His Ser Lys Val Thr Val Pro Met Ser Ile Leu Trp Gln Gly Pro Gln
465                 470                 475                 480

Tyr Phe Leu Leu Gly Val Ala Glu Val Phe Ser Asn Ile Gly Leu Thr
                485                 490                 495

Glu Phe Phe Cys Asp Glu Ser Pro Asp Ala Met Arg Ser Leu Gly Met
            500                 505                 510

Ala Phe Ser Leu Leu Asn Ile Ser Ala Gly Asn Tyr Leu Ser Ser Phe
        515                 520                 525
```

-continued

```
Ile Leu Ser Leu Val Pro Val Phe Thr Ala Arg Gly Gly Ser Pro Gly
    530                 535                 540

Trp Ile Pro Asp Asn Leu Asn Glu Gly His Leu Asp Arg Phe Tyr Leu
545                 550                 555                 560

Met Met Ala Gly Leu Ser Leu Leu Asn Ile Phe Val Phe Val Phe Tyr
                565                 570                 575

Ala Arg Arg Tyr Lys Cys Lys Lys Ala Ser
            580                 585


<210> SEQ ID NO 52
<211> LENGTH: 590
<212> TYPE: PRT
<213> ORGANISM: Nicotiana plumbaginifolia
<220> FEATURE:
<221> NAME/KEY: misc_feature
<222> LOCATION: (1)..(590)
<223> OTHER INFORMATION: Public GI no. 9581817

<400> SEQUENCE: 52

Met Ala Leu Pro Glu Thr Gln Gln Asp Thr Lys Thr Leu Pro Asp Ala
1               5                   10                  15

Trp Asp Tyr Lys Gly Arg Pro Ala Val Arg Ser Ser Ser Gly Gly Trp
            20                  25                  30

Ser Ser Ala Ala Met Ile Leu Gly Ile Glu Ala Val Glu Arg Leu Thr
        35                  40                  45

Thr Leu Gly Ile Ala Val Asn Leu Val Thr Tyr Leu Thr Gly Thr Met
    50                  55                  60

His Leu Gly Asn Ala Ser Ser Ala Asn Asn Val Thr Asn Phe Leu Gly
65                  70                  75                  80

Thr Ser Phe Met Leu Thr Leu Leu Gly Gly Phe Val Ala Asp Thr Phe
                85                  90                  95

Leu Gly Arg Tyr Leu Thr Ile Gly Ile Phe Thr Thr Ile Gln Ala Met
            100                 105                 110

Gly Val Thr Ile Leu Thr Ile Ser Thr Ile Ile Pro Ser Leu Arg Pro
        115                 120                 125

Pro Lys Cys Ser Pro Gly Ser Ser Thr Cys Ile Pro Ala Ser Ser Lys
    130                 135                 140

Gln Leu Met Val Leu Tyr Ile Ala Leu Tyr Met Thr Ala Leu Gly Thr
145                 150                 155                 160

Gly Gly Leu Lys Ser Ser Val Ser Gly Phe Gly Ser Asp Gln Phe Asp
                165                 170                 175

Glu Thr Asp Lys Lys Glu Arg Gly Gln Met Ile Lys Phe Phe Asn Trp
            180                 185                 190

Phe Phe Phe Phe Ile Asn Val Gly Ser Leu Gly Ala Val Thr Val Leu
        195                 200                 205

Val Tyr Ile Gln Asp Asn Leu Gly Arg Glu Tyr Gly Tyr Gly Ile Cys
    210                 215                 220

Ala Cys Ala Ile Val Ile Gly Leu Val Ile Phe Leu Ser Gly Thr Arg
225                 230                 235                 240

Lys Tyr Arg Phe Lys Lys Leu Val Gly Ser Pro Leu Thr Gln Ile Ala
                245                 250                 255

Ser Val Phe Val Ala Ala Trp Asn Lys Arg His Met Asp Leu Pro Ser
            260                 265                 270

Asp Ser Thr Leu Leu Tyr Asn Ile Asp Asp Ile Pro Gly Asp Gly Asn
        275                 280                 285
```

-continued

```
Lys Lys Ala Lys Gln Arg Leu Pro His Ser Lys Glu Phe Arg Phe Leu
    290                 295                 300

Asp Lys Ala Ala Ile Lys Val Gln Asp Thr Glu Ser Ala Gly Ile Thr
305                 310                 315                 320

Val Val Asn Lys Trp Asn Leu Ser Thr Leu Thr Asp Val Glu Glu Val
                325                 330                 335

Lys Leu Val Val Arg Met Leu Pro Thr Trp Ala Thr Thr Ile Met Phe
            340                 345                 350

Trp Thr Val Tyr Ala Gln Met Thr Thr Phe Ser Val Ser Gln Ala Thr
        355                 360                 365

Thr Met Asp Arg His Ile Gly Asn Phe Glu Ile Pro Pro Ala Ser Leu
    370                 375                 380

Thr Leu Phe Phe Val Gly Ser Ile Leu Leu Thr Cys Ile Phe Tyr Asp
385                 390                 395                 400

Arg Ala Val Val Pro Val Cys Arg Arg Val Leu Asn Asn Pro His Gly
                405                 410                 415

Thr Thr Pro Leu Gln Arg Ile Ala Val Gly Leu Ile Leu Ser Ile Ile
            420                 425                 430

Ala Met Val Ala Ala Ala Leu Thr Glu Val Lys Arg Leu Asn Val Ala
        435                 440                 445

His Leu His Gly Leu Thr Asn Asp Ala Asn Ala Lys Val Pro Leu Ser
    450                 455                 460

Val Phe Trp Leu Val Pro Gln Phe Leu Leu Val Gly Ala Gly Glu Ala
465                 470                 475                 480

Phe Thr Tyr Ile Gly Gln Leu Asp Phe Phe Leu Arg Glu Cys Pro Lys
                485                 490                 495

Gly Met Lys Thr Met Ser Thr Gly Leu Phe Leu Ser Thr Leu Ser Leu
            500                 505                 510

Gly Phe Phe Val Ser Ser Ile Leu Val Thr Ile Val His Lys Val Thr
        515                 520                 525

Val Lys Asn Pro Trp Leu Ala Asp Asn Leu Asn Gln Gly Arg Leu Tyr
    530                 535                 540

Asp Phe Tyr Trp Leu Leu Ala Thr Leu Ser Val Leu Asn Leu Met Val
545                 550                 555                 560

Phe Leu Phe Ile Ser Arg Arg Tyr Val Tyr Lys Glu Lys Arg Leu Ala
                565                 570                 575

Glu Cys Gly Ile Glu Met Glu Asp Ser Glu Pro Ala Cys His
            580                 585                 590


<210> SEQ ID NO 53
<211> LENGTH: 590
<212> TYPE: PRT
<213> ORGANISM: Nicotiana tabacum
<220> FEATURE:
<221> NAME/KEY: misc_feature
<222> LOCATION: (1)..(590)
<223> OTHER INFORMATION: Public GI no. 28273094

<400> SEQUENCE: 53

Met Ala Leu Pro Glu Thr Gln Gln Asp Thr Lys Thr Leu Pro Asp Ala
1               5                   10                  15

Trp Asp Tyr Lys Gly Arg Pro Ala Val Arg Ser Ser Ser Gly Gly Trp
            20                  25                  30

Ser Ser Ala Ala Met Ile Leu Gly Ile Glu Ala Val Glu Arg Leu Thr
        35                  40                  45

Thr Leu Gly Ile Ala Val Asn Leu Val Thr Tyr Leu Thr Gly Thr Met
```

-continued

```
    50                  55                  60

His Leu Gly Asn Ala Ser Ser Ala Asn Asn Val Thr Asn Phe Leu Gly
65                  70                  75                  80

Thr Ser Phe Met Leu Thr Leu Leu Gly Gly Phe Val Ala Asp Thr Phe
                85                  90                  95

Leu Gly Arg Tyr Leu Thr Ile Gly Ile Phe Thr Thr Ile Gln Ala Met
            100                 105                 110

Gly Val Thr Ile Leu Thr Ile Ser Thr Ile Ile Pro Ser Leu Arg Pro
        115                 120                 125

Pro Lys Cys Ser Pro Gly Ser Ser Thr Cys Ile Pro Ala Ser Ser Lys
    130                 135                 140

Gln Leu Met Val Leu Tyr Ile Ala Leu Tyr Met Thr Ala Leu Gly Thr
145                 150                 155                 160

Gly Gly Leu Lys Ser Ser Val Ser Gly Phe Gly Ser Asp Gln Phe Asp
                165                 170                 175

Glu Thr Asp Lys Lys Glu Arg Gly Gln Met Ile Lys Phe Phe Asn Trp
            180                 185                 190

Phe Phe Phe Phe Ile Asn Val Gly Ser Leu Gly Ala Val Thr Val Leu
        195                 200                 205

Val Tyr Ile Gln Asp Asn Leu Gly Arg Glu Tyr Gly Tyr Gly Ile Cys
    210                 215                 220

Ala Cys Ala Ile Val Ile Gly Leu Val Ile Phe Leu Ser Gly Thr Arg
225                 230                 235                 240

Lys Tyr Arg Phe Lys Lys Leu Val Gly Ser Pro Leu Thr Gln Ile Ala
                245                 250                 255

Ser Val Phe Val Ala Ala Trp Asn Lys Arg His Met Asp Leu Pro Ser
            260                 265                 270

Asp Ser Tyr Leu Leu Tyr Asn Ile Asp Asp Ile Pro Gly Asp Gly Asn
        275                 280                 285

Lys Lys Ala Lys Gln Arg Leu Pro His Ser Lys Glu Phe Arg Phe Leu
    290                 295                 300

Asp Lys Ala Ala Ile Lys Val Gln Asp Pro Glu Ser Ala Gly Ile Thr
305                 310                 315                 320

Val Val Asn Lys Trp Asn Leu Ser Thr Leu Thr Asp Val Glu Glu Val
                325                 330                 335

Lys Leu Val Val Arg Met Leu Pro Thr Trp Ala Thr Thr Ile Met Phe
            340                 345                 350

Trp Thr Val Tyr Ala Gln Met Thr Thr Phe Ser Val Ser Gln Ala Thr
        355                 360                 365

Thr Met Asp Arg His Ile Gly Asn Phe Glu Ile Pro Pro Ala Ser Leu
    370                 375                 380

Thr Leu Phe Phe Val Gly Ser Ile Leu Leu Thr Cys Ile Phe Tyr Asp
385                 390                 395                 400

Arg Ala Val Val Pro Val Cys Arg Arg Val Leu Asn Asn Pro His Gly
                405                 410                 415

Thr Thr Pro Leu Gln Arg Ile Ala Val Gly Leu Ile Leu Ser Ile Ile
            420                 425                 430

Ala Met Val Ala Ala Ala Leu Thr Glu Val Lys Arg Leu Asn Val Ala
        435                 440                 445

His Leu His Gly Leu Thr Asn Asp Ala Asn Ala Lys Val Pro Leu Ser
    450                 455                 460

Val Phe Trp Leu Val Pro Gln Phe Leu Leu Val Gly Ala Gly Glu Ala
465                 470                 475                 480
```

```
Phe Thr Tyr Ile Gly Gln Leu Asp Phe Phe Leu Arg Glu Cys Pro Lys
                485                 490                 495

Gly Met Lys Thr Met Ser Thr Gly Leu Phe Leu Ser Thr Leu Ser Leu
            500                 505                 510

Gly Phe Phe Phe Ser Ser Ile Leu Val Thr Ile Val His Lys Val Thr
        515                 520                 525

Val Lys Asn Pro Trp Leu Ala Asp Asn Leu Asn Gln Gly Arg Leu Tyr
    530                 535                 540

Asp Phe Tyr Trp Leu Leu Ala Thr Leu Ser Val Leu Asn Leu Met Ile
545                 550                 555                 560

Phe Leu Phe Ile Ser Arg Arg Tyr Val Tyr Lys Glu Lys Arg Leu Ala
                565                 570                 575

Glu Cys Gly Ile Glu Met Glu Asp Ser Glu Pro Ala Cys His
            580                 585                 590
```

<210> SEQ ID NO 54
<211> LENGTH: 1886
<212> TYPE: DNA
<213> ORGANISM: Arabidopsis thaliana
<220> FEATURE:
<221> NAME/KEY: misc_feature
<222> LOCATION: (1)..(1886)
<223> OTHER INFORMATION: Ceres CDNA ID no. 2997404
<220> FEATURE:
<221> NAME/KEY: CDS
<222> LOCATION: (1)..(1078)
<223> OTHER INFORMATION: Referenced by SEQ ID NO: 55

<400> SEQUENCE: 54

```
atggctcgtt cagtcgacac agaagcaatg accactcgcg atccaagcag caagcgcggt     60

ggctggaaaa cgtttccatt catgatcggt tagtgtattt tatgactgtt tggtttatgt    120

ttttgaacac aaaacataga caaatgatag tgattgtaag gctctatatg gtgcagctac    180

attgttagga ctttccatag cttcattcgg atgggtgatg aacttggtcg tcttcctaat    240

taaagaattc aacatcaaga gcatcgctgc tacgcagatt tctaatattg ttaatggatg    300

tgtgagcatg tttcctgtta ttgcagccat tctagctgat tctttttttcg gaaacattcc   360

cgtcatctcc gtctctgcct tcatttcttt gcttgtaagt ctgagactta aatattctat    420

tgtcttgtgt gacacacaaa gcttactagt tgttaaacgt ttccagggca tcgttctatt    480

gaccatgatt acatctttgg actacttgag acctccaccg tgtgaaacgg ggtcaattct    540

atgccaatcg tcatcaaaac tccagctcgg aatcttgtat atagccttag ctctagtgat    600

cattggatca gctggtacgc ggtttacctt agcatccgcg ggtgcaaacc aatatgagaa    660

acctaaagaa caaggaagct tttttcaactg gtacttcctc acactctaca ctggagctat   720

tactggtgca acagcaattg tatatacaca ggaaaatgct agctggaaac ttgggttcgg    780

tctttgcgcc gtcgctaatt tgatcagttt catagttttc gtctctggca agagatacta    840

caagcatgac aaaccaatgg gaagtccctt cacaaatctg atccgcgttg tagtcgctgc    900

tacaagaaaa aggaaagctg tgatttcatc tagagaagaa gactatcacc atgggcttgg    960

aagagaaggc aagacatctt ctgcaatgcc ctccaagagc tttaggtgaa aaaacaaaaa   1020

aaacttgctt cattcatcaa acttaaaaca gaacttaaaa gagcttttac atgtgcaggt   1080

tctttaaccg tgcagcattg aaaaccgaag atgactcagt taataacaac tggaggctat   1140

gttctgttca agaagtagaa gattttaaag ccgttttccg agttctccct ctgttactag   1200

ccatcatctt cgttagtact cccatggtga cgcaaacaag cttgattata ctaaaagctc   1260
```

```
tagtcacaga ccgcggtctc gggcctcact tcaaaatccc ggccgggtcc ctccaagtca   1320

tagtaatcat cactgcatgt attgttatct taatgaacaa ttgccttgtc tatcccatgt   1380

accagaagct agcccataag ccattgacac cgcttcaaaa agtcggtata ggccacgttt   1440

tcatcatttt aagcatggcg atatccgcca ttgtggaagc aaagaggctg aaaacagtta   1500

ctaatggcca ttccatgtca gtgctatggc tggttcctcc ccttgtgata gtaggaatag   1560

gagaaacgtt ccaatttccg gcgaatattg aattattcta tagagaattc cccgagtctc   1620

tgagtagcac cgcgacttca ttgacctcag tggtgattgg aatatctttc tacctgagca   1680

cagctctgat cactctgatc cagaagacca ccaagtggtt accaaatgat attaaccatg   1740

gaagagttgg caatgtttac tggcttttag tcattgtagg agtcttgaat ttcggctatt   1800

tccttgtctg cgcttggttt tacagatata gaaacctgaa tgatgatgat gatcaggaac   1860

aagatccaaa agacgataca acctaa                                        1886
```

```
<210> SEQ ID NO 55
<211> LENGTH: 466
<212> TYPE: PRT
<213> ORGANISM: Arabidopsis thaliana
<220> FEATURE:
<221> NAME/KEY: misc_feature
<222> LOCATION: (90)..(433)
<223> OTHER INFORMATION: Pfam Name: PTR2; Pfam Description: POT family

<400> SEQUENCE: 55

Met Ala Arg Ser Val Asp Thr Glu Ala Met Thr Thr Arg Asp Pro Ser
1               5                   10                  15

Ser Lys Arg Gly Gly Trp Lys Thr Phe Pro Phe Met Ile Ala Thr Leu
            20                  25                  30

Leu Gly Leu Ser Ile Ala Ser Phe Gly Trp Val Met Asn Leu Val Val
        35                  40                  45

Phe Leu Ile Lys Glu Phe Asn Ile Lys Ser Ile Ala Ala Thr Gln Ile
    50                  55                  60

Ser Asn Ile Val Asn Gly Cys Val Ser Met Phe Pro Val Ile Ala Ala
65                  70                  75                  80

Ile Leu Ala Asp Ser Phe Phe Gly Asn Ile Pro Val Ile Ser Val Ser
                85                  90                  95

Ala Phe Ile Ser Leu Leu Gly Ile Val Leu Leu Thr Met Ile Thr Ser
            100                 105                 110

Leu Asp Tyr Leu Arg Pro Pro Pro Cys Glu Thr Gly Ser Ile Leu Cys
        115                 120                 125

Gln Ser Ser Ser Lys Leu Gln Leu Gly Ile Leu Tyr Ile Ala Leu Ala
    130                 135                 140

Leu Val Ile Ile Gly Ser Ala Gly Thr Arg Phe Thr Leu Ala Ser Ala
145                 150                 155                 160

Gly Ala Asn Gln Tyr Glu Lys Pro Lys Glu Gln Gly Ser Phe Phe Asn
                165                 170                 175

Trp Tyr Phe Leu Thr Leu Tyr Thr Gly Ala Ile Thr Gly Ala Thr Ala
            180                 185                 190

Ile Val Tyr Thr Gln Glu Asn Ala Ser Trp Lys Leu Gly Phe Gly Leu
        195                 200                 205

Cys Ala Val Ala Asn Leu Ile Ser Phe Ile Val Phe Val Ser Gly Lys
    210                 215                 220

Arg Tyr Tyr Lys His Asp Lys Pro Met Gly Ser Pro Phe Thr Asn Leu
225                 230                 235                 240
```

```
Ile Arg Val Val Val Ala Ala Thr Arg Lys Arg Lys Ala Val Ile Ser
                245                 250                 255

Ser Arg Glu Glu Asp Tyr His His Gly Leu Gly Arg Glu Gly Lys Thr
            260                 265                 270

Ser Ser Ala Met Pro Ser Lys Ser Phe Arg Phe Phe Asn Arg Ala Ala
        275                 280                 285

Leu Lys Thr Glu Asp Asp Ser Val Asn Asn Asn Trp Arg Leu Cys Ser
    290                 295                 300

Val Gln Glu Val Glu Asp Phe Lys Ala Val Phe Arg Val Leu Pro Leu
305                 310                 315                 320

Leu Leu Ala Ile Ile Phe Val Ser Thr Pro Met Val Thr Gln Thr Ser
                325                 330                 335

Leu Ile Ile Leu Lys Ala Leu Val Thr Asp Arg Gly Leu Gly Pro His
            340                 345                 350

Phe Lys Ile Pro Ala Gly Ser Leu Gln Val Ile Val Ile Ile Thr Ala
        355                 360                 365

Cys Ile Val Ile Leu Met Asn Asn Cys Leu Val Tyr Pro Met Tyr Gln
    370                 375                 380

Lys Leu Ala His Lys Pro Leu Thr Pro Leu Gln Lys Val Gly Ile Gly
385                 390                 395                 400

His Val Phe Ile Ile Leu Ser Met Ala Ile Ser Ala Ile Val Glu Ala
                405                 410                 415

Lys Arg Leu Lys Thr Val Thr Asn Gly His Ser Met Ser Val Leu Trp
            420                 425                 430

Leu His Arg Asp Phe Ile Asp Leu Ser Gly Asp Trp Asn Ile Phe Leu
        435                 440                 445

Pro Glu His Ser Ser Asp His Ser Asp Pro Glu Asp His Gln Val Val
    450                 455                 460

Thr Lys
465


<210> SEQ ID NO 56
<211> LENGTH: 604
<212> TYPE: PRT
<213> ORGANISM: Cucumis sativus
<220> FEATURE:
<221> NAME/KEY: misc_feature
<222> LOCATION: (1)..(604)
<223> OTHER INFORMATION: Public GI no. 15391731

<400> SEQUENCE: 56

Met Glu Ile Glu Ser Leu Arg Val Ser Val Asp Glu Lys Val Leu Lys
1               5                   10                  15

Asp Glu Glu Lys Asn Glu Lys Glu Glu Met Lys Met Lys Met Lys Met
            20                  25                  30

Lys Arg Lys Leu Gly Gly Val Lys Thr Met Pro Phe Ile Leu Gly Asn
        35                  40                  45

Glu Val Cys Asp Arg Phe Ala Ser Ser Gly Phe His Ser Asn Ile Ile
    50                  55                  60

Thr Tyr Leu Thr Gln Asp Leu Asn Met Pro Leu Val Pro Ala Ser Asn
65                  70                  75                  80

Ile Leu Thr Asn Phe Ala Ala Thr Ser Ser Phe Thr Ser Leu Ile Gly
                85                  90                  95

Ala Leu Ile Ala Asp Ser Phe Ala Gly Arg Phe Trp Thr Ile Thr Ile
            100                 105                 110
```

-continued

```
Ala Ser Ile Ile Tyr Glu Leu Gly Met Val Thr Ile Thr Ile Ser Ala
        115                 120                 125

Ile Leu Pro Ser Leu His Pro Pro Pro Cys Pro Thr Gln Ile Asn Cys
    130                 135                 140

Thr Gln Ala Ser Gly Thr Gln Leu Met Ile Leu Tyr Leu Ala Leu Leu
145                 150                 155                 160

Leu Thr Ser Leu Gly Ala Gly Gly Ile Arg Pro Cys Val Val Ala Phe
                165                 170                 175

Ala Ala Asp Gln Phe Asp Met Thr Lys Val Gly Ile Ala Gly Arg Thr
            180                 185                 190

Trp Asn Phe Phe Asn Trp Tyr Tyr Phe Cys Met Gly Met Ala Thr Leu
        195                 200                 205

Thr Ala Leu Thr Val Val Val Tyr Ile Gln Asp Asn Val Gly Trp Gly
    210                 215                 220

Trp Gly Phe Gly Leu Pro Thr Ile Ala Met Ala Leu Ser Val Val Ala
225                 230                 235                 240

Phe Val Val Gly Ser Pro Leu Tyr Asn Lys Leu Lys Pro Ser Gly Ser
                245                 250                 255

Pro Leu Val Arg Leu Ala Gln Val Val Val Ala Ala Phe Lys Asn Arg
            260                 265                 270

Lys Ala Val Leu Pro Asp Asp Ser Lys Leu Leu Tyr Arg Asn His Glu
        275                 280                 285

Leu Asp Ala Ala Ile Ala Ile Gln Gly Arg Leu Val His Thr Asp Gln
    290                 295                 300

Phe Lys Trp Leu Asp Lys Ala Ala Val Ile Thr Ser Pro Asp Ser Thr
305                 310                 315                 320

Ala Asn Pro Pro Asn Leu Trp Arg Leu Ala Thr Val His Arg Val Glu
                325                 330                 335

Glu Leu Lys Ser Ile Ile Arg Met Leu Pro Ile Trp Ala Ala Gly Ile
            340                 345                 350

Leu Leu Val Thr Ala Ser Ser His Gln His Ser Phe Thr Ile Gln Gln
        355                 360                 365

Ala Arg Thr Met Asn Arg His Leu Thr Pro Thr Phe Gln Ile Pro Pro
    370                 375                 380

Ala Thr Leu Ser Ile Phe Gly Ile Leu Ser Met Leu Thr Gly Leu Val
385                 390                 395                 400

Leu Tyr Asp Arg Leu Leu Val Pro Phe Ala Lys Lys Leu Thr His Asn
                405                 410                 415

Pro Ser Gly Ile Thr Cys Leu Gln Arg Met Gly Val Gly Phe Ala Ile
            420                 425                 430

Asn Ile Leu Ala Thr Leu Val Ser Ser Ile Val Glu Ile Lys Arg Lys
        435                 440                 445

Lys Val Ala Ala Asn His Gly Leu Leu Asp Asn Pro Thr Ala Thr Ile
    450                 455                 460

Pro Phe Ser Val Phe Trp Leu Val Pro Gln Phe Trp Leu His Gly Ile
465                 470                 475                 480

Ala Glu Val Phe Met Ser Val Gly His Leu Glu Phe Met Tyr Asp Gln
                485                 490                 495

Ser Pro Glu Ser Leu Arg Ser Thr Ala Thr Ala Leu Tyr Trp Leu Ala
            500                 505                 510

Ile Ser Val Gly Asn Tyr Ile Gly Thr Leu Met Val Tyr Leu Val His
        515                 520                 525

Lys Tyr Thr Gly Glu Glu His Asn Trp Leu Pro Asp Arg Asn Leu Asn
```

-continued

```
    530                 535                 540

Arg Gly Arg Leu Glu Tyr Tyr Tyr Trp Leu Val Ser Gly Ile Gln Val
545                 550                 555                 560

Met Asn Leu Val Tyr Tyr Val Ile Cys Ala Trp Phe Tyr Thr Tyr Lys
                565                 570                 575

Pro Leu Glu Glu Glu Lys Ile Asn Ile Glu Asn Lys Asp Gly Asp Gln
            580                 585                 590

Glu Trp Glu Arg Cys Glu Asp Thr Ile Lys Ile Ala
        595                 600


<210> SEQ ID NO 57
<211> LENGTH: 558
<212> TYPE: PRT
<213> ORGANISM: Arabidopsis thaliana
<220> FEATURE:
<221> NAME/KEY: misc_feature
<222> LOCATION: (1)..(558)
<223> OTHER INFORMATION: Ceres CLONE ID no. 1144139

<400> SEQUENCE: 57

Met Ala Ser Leu Val Ser Gly Asp Lys Glu Ala Gln Ile Ser Gly Asp
1               5                   10                  15

Pro Gly Ser Lys Arg Gly Gly Trp Ile Thr Phe Pro Phe Met Leu Ala
            20                  25                  30

Thr Leu Leu Gly Leu Ser Val Thr Ser Phe Gly Trp Val Met Asn Leu
        35                  40                  45

Ile Val Phe Leu Ile Glu Glu Phe Asn Ile Lys Ser Ile Ala Ala Ala
    50                  55                  60

Gln Ile Ser Asn Val Ala Asn Gly Cys Leu Ser Met Leu Pro Val Val
65                  70                  75                  80

Ala Ala Ile Leu Ala Asp Ser Phe Phe Gly Asn Ile Pro Val Ile Ala
                85                  90                  95

Ala Ser Ser Phe Ile Ser Leu Leu Gly Ile Val Leu Leu Thr Leu Ile
            100                 105                 110

Ala Ser Leu Asp Tyr Leu Arg Pro Arg Pro Cys Glu Ala Gly Ser Val
        115                 120                 125

Leu Cys Thr Pro Pro Ser Lys Leu His Leu Gly Ile Leu Tyr Thr Ala
    130                 135                 140

Leu Ala Leu Val Thr Thr Gly Ala Gly Gly Thr Arg Phe Thr Met Ala
145                 150                 155                 160

Ser Ala Gly Ala Asn Gln Tyr Glu Lys Pro Lys Glu Gln Gly Ser Phe
                165                 170                 175

Phe Asn Trp Tyr Phe Leu Thr Leu Tyr Ala Gly Ala Ile Thr Gly Ala
            180                 185                 190

Thr Ala Ile Val Tyr Ile Gln Asp Asn Ala Ser Trp Lys Leu Gly Phe
        195                 200                 205

Gly Leu Cys Ala Ala Ala Asn Leu Ile Ser Phe Ile Val Phe Val Ser
    210                 215                 220

Gly Lys Arg Tyr Tyr Lys His Asp Lys Pro Met Gly Ser Pro Phe Thr
225                 230                 235                 240

Ser Leu Ile Arg Val Val Val Ser Ala Thr Val Lys Arg Lys Ala Val
                245                 250                 255

Ile Ser Cys Asn Glu Glu Asp Tyr His His Tyr Gly Leu Glu Lys Glu
            260                 265                 270

Val Lys Thr Ser Ala Ala Met Pro Ser Lys Ser Phe Arg Phe Leu Asn
        275                 280                 285
```

```
Arg Ala Ala Leu Met Thr Lys Asp Asp Leu Asn Gln Lys Glu Gly Ser
    290                 295                 300

Val Asn Asn Ile Trp Arg Leu Cys Ser Val Gln Glu Val Glu Asp Phe
305                 310                 315                 320

Lys Ala Ile Leu Arg Val Phe Pro Leu Trp Leu Ser Ile Ile Phe Val
                325                 330                 335

Ser Thr Pro Met Val Met Gln Thr Ser Leu Ile Val Leu Gln Ala Leu
            340                 345                 350

Val Thr Asp Arg Gly Leu Gly Pro Asn Phe Lys Val Pro Ala Gly Ser
        355                 360                 365

Leu Gln Val Ile Ile Ile Ile Thr Ala Cys Ile Val Ile Ile Met Asn
    370                 375                 380

Asn Trp Leu Val Phe Pro Met Tyr Lys Lys Leu Thr His Lys Leu Leu
385                 390                 395                 400

Thr Pro Leu Gln Lys Val Gly Ile Gly Gln Val Leu Thr Ile Leu Ser
                405                 410                 415

Met Ala Leu Ser Ala Val Val Glu Ala Lys Arg Leu Lys Thr Val Glu
            420                 425                 430

Asn Gly His Pro Met Ser Val Leu Trp Leu Phe Pro Pro Leu Val Ile
        435                 440                 445

Val Gly Ile Gly Glu Ala Phe Gln Phe Pro Ala Asn Ile Glu Leu Phe
    450                 455                 460

Tyr Gly Glu Phe Pro Glu Ser Leu Arg Asn Thr Ala Thr Ser Leu Thr
465                 470                 475                 480

Ser Val Val Ile Gly Ile Ser Phe Tyr Leu Ser Thr Ala Leu Ile Asp
                485                 490                 495

Leu Ile Gln Arg Thr Thr Ala Trp Leu Pro Asn Asp Ile Asn His Gly
            500                 505                 510

Arg Val Asp Asn Val Tyr Trp Leu Leu Val Ile Gly Gly Ile Leu Asn
        515                 520                 525

Phe Gly Tyr Phe Leu Val Cys Ser Trp Val Tyr Lys Tyr Arg Asn Leu
    530                 535                 540

Lys Asp Asn Asp Gln Glu Gln Asp Pro Lys Asp Gly Thr Met
545                 550                 555


<210> SEQ ID NO 58
<211> LENGTH: 583
<212> TYPE: PRT
<213> ORGANISM: Oryza sativa (japonica cultivar-group)
<220> FEATURE:
<221> NAME/KEY: misc_feature
<222> LOCATION: (1)..(583)
<223> OTHER INFORMATION: Public GI no. 54291818

<400> SEQUENCE: 58

Met Glu Glu Glu Arg Ser Arg Ala Gly Gly Ala Ala Val Ala Val Asp
1               5                   10                  15

Gly Glu Ser Leu Arg Arg Pro Glu Glu Glu Gly Gly Arg Arg Lys Lys
            20                  25                  30

Gly Gly Trp Ile Thr Phe Pro Phe Met Ala Val Ser Leu Leu Ala Phe
        35                  40                  45

Gly Leu Ser Ser Ala Gly Ala Met Gly Asn Leu Val Val Tyr Leu Val
    50                  55                  60

Lys Glu Tyr His Val Pro Ser Val Asp Ala Ala Gln Ile Ser Thr Ile
65                  70                  75                  80
```

-continued

```
Val Ser Gly Cys Ile Ser Val Ala Pro Val Ala Gly Ala Ile Val Ala
                85                  90                  95

Asp Ala Phe Phe Gly Cys Phe Pro Val Val Ala Val Ala Met Val Phe
            100                 105                 110

Ser Val Leu Ala Leu Val Val Phe Thr Leu Thr Ala Ser Val Arg Gly
        115                 120                 125

Leu Arg Pro Ala Ala Cys Val Pro Gly Ala Thr Ala Cys Glu Ala Ala
    130                 135                 140

Thr Ala Gly Gln Met Ala Val Leu Tyr Ala Gly Val Phe Leu Leu Cys
145                 150                 155                 160

Val Ser Ser Ala Gly Ala Arg Phe Asn Gln Ala Thr Met Gly Ala Asp
                165                 170                 175

Gln Phe Asp Ala Ala Ala Asp Arg Asp Val Phe Phe Asn Trp Tyr Phe
            180                 185                 190

Ile Phe Phe Tyr Gly Ser Ala Val Leu Gly Ser Thr Val Leu Val Tyr
        195                 200                 205

Val Gln Asp Ala Val Ser Trp Glu Leu Gly Phe Gly Leu Ala Ala Thr
    210                 215                 220

Ile Ala Ala Ala Gly Leu Ala Ala Leu Leu Leu Gly Ala Arg Tyr Tyr
225                 230                 235                 240

Arg Arg Pro Ala Ala Arg Gly Ser Pro Phe Thr Gly Ile Ala Arg Val
                245                 250                 255

Val Val Ala Ala Ala Arg Lys Arg Lys Ile Asp Val Ala Ala Ala Ala
            260                 265                 270

Ala Ala Ser Gly Asp Leu Lys Phe Tyr Tyr Gly Pro Arg Ser Gly Asp
        275                 280                 285

Gly Asp Asp Asp Gly Gly Lys Pro Ser Asp Asp Asn Asn Phe Ala Pro
    290                 295                 300

Ser Asp Ser Phe Ser Phe Leu Asn Arg Ala Ala Val Ile Thr Asp Gly
305                 310                 315                 320

Asp Val Asp Ala Ala Asp Ala Ala Ala Pro Leu Arg Pro Trp Arg Val
                325                 330                 335

Cys Thr Val Arg Gln Val Glu Asp Leu Lys Ala Val Leu Arg Ile Leu
            340                 345                 350

Pro Leu Trp Ser Ser Ser Ile Phe Leu Ser Ile Ser Ile Gly Val Gln
        355                 360                 365

Leu Asn Phe Thr Val Leu Gln Ala Leu Ala Met Asp Arg Ala Ile Gly
    370                 375                 380

Arg Phe His Val Pro Ala Ala Ser Met Val Val Ser Ser Phe Val Ala
385                 390                 395                 400

Val Val Val Ser Leu Gly Leu Ile Asp Arg Ala Leu Leu Pro Leu Trp
                405                 410                 415

Arg Ala Leu Thr Gly Gly Arg Arg Ala Pro Thr Pro Leu Gln Arg Ile
            420                 425                 430

Gly Val Gly His Val Leu Thr Val Leu Ser Met Ala Ala Ser Ala Ala
        435                 440                 445

Val Glu Arg Arg Arg Leu Ala Thr Val Arg Ala His Gly Glu Ala Ala
    450                 455                 460

Arg Asp Asp Pro Ala Trp Val Ser Pro Leu Pro Ala Ala Trp Leu Val
465                 470                 475                 480

Leu Pro Phe Ala Leu Ser Gly Ala Gly Glu Ala Phe His Phe Pro Ala
                485                 490                 495

Gln Val Thr Leu Tyr Tyr Gln Glu Phe Pro Pro Ser Leu Lys Asn Thr
```

-continued

```
            500                 505                 510

Ala Ser Gly Met Val Ala Met Ile Val Ala Leu Gly Phe Tyr Leu Ser
        515                 520                 525

Thr Ala Leu Val Asp Ala Val Arg Arg Ala Thr Ala Trp Leu Pro Asp
    530                 535                 540

Asn Met Asn Ala Ser Arg Leu Glu Asn Leu Tyr Trp Leu Leu Ala Val
545                 550                 555                 560

Leu Val Ala Ile Asn Phe Gly Tyr Tyr Leu Ala Cys Ala Lys Leu Tyr
                565                 570                 575

Lys Tyr Gln Asn Phe Gly Lys
            580


<210> SEQ ID NO 59
<211> LENGTH: 543
<212> TYPE: PRT
<213> ORGANISM: Oryza sativa (japonica cultivar-group)
<220> FEATURE:
<221> NAME/KEY: misc_feature
<222> LOCATION: (1)..(543)
<223> OTHER INFORMATION: Public GI no. 34905798

<400> SEQUENCE: 59

Met Ala Met Ser Ala Thr Ser Ser Asn Leu Ile Val Tyr Leu Val His
1               5                   10                  15

Lys Tyr Asn Val Lys Ala Ile His Ala Ala Gln Ile Ser Asn Val Val
            20                  25                  30

Arg Gly Cys Met Gln Leu Ala Pro Val Leu Ala Ala Ala Leu Ser Asp
        35                  40                  45

Ala Phe Phe Gly Pro Tyr Pro Ile Ala Val Ala Gly Leu Val Phe Ser
    50                  55                  60

Leu Leu Ser Phe Val Leu Phe Thr Leu Thr Ala Ala Leu Pro Ser Leu
65                  70                  75                  80

Leu Pro Pro Pro Cys Gln Arg Gly Ala Gly Gly Gly Gly Ala Thr Ala
                85                  90                  95

Thr Ser Cys Glu Pro Pro Asn Ala Ala Gln Ser Ala Val Leu Tyr Ala
            100                 105                 110

Ala Leu Cys Leu Leu Ala Ala Gly Asn Gly Gly Thr Arg Tyr Asn Met
        115                 120                 125

Ala Ala Leu Gly Ala Asp Gln Phe Ala Gly Glu Gly Gln Pro Arg Arg
    130                 135                 140

Arg Arg Gln Gly Gly Gly Phe Phe Ser Cys Tyr Phe Ala Phe Leu Tyr
145                 150                 155                 160

Ala Ser Tyr Ala Thr Gly Asp Thr Val Leu Val Tyr Val Gln Asp Gly
                165                 170                 175

Val Ser Trp Ala Leu Gly Phe Gly Val Cys Val Ala Thr Thr Gly Leu
            180                 185                 190

Ala Leu Ala Ala Leu Leu Leu Gly Ser Arg His Tyr Arg Arg Pro Val
        195                 200                 205

Pro Lys Gly Ser Pro Phe Thr Ala Met Ala Arg Val Ala Val Ala Ala
    210                 215                 220

Ala Arg Lys Ala Thr Val Asp Leu Gly Ser Arg Val Gln Tyr Tyr His
225                 230                 235                 240

Gly Cys Asn Arg Asp Asp Ala Val Pro Arg Ala Asp Gln Ala Pro Ser
                245                 250                 255

Asp Arg Phe Arg Phe Leu Asn Arg Ala Ala Met Val Val Ala Gly Glu
            260                 265                 270
```

```
Thr Arg Glu Glu Asp Gly Ser Val Ala Lys Pro Trp Arg Leu Cys Thr
        275                 280                 285

Val Gln Gln Val Glu Asp Val Lys Ser Val Val Arg Val Leu Pro Leu
    290                 295                 300

Trp Ser Ser Gly Ile Leu Val Ser Val Thr Val Asn Ala Gln Val Ser
305                 310                 315                 320

Leu Thr Val Leu Gln Ala Leu Thr Met Asp Arg Ala Val Gly Pro Arg
                325                 330                 335

Phe Ala Val Pro Ala Ala Ser Ile Thr Val Thr Val Leu Ala Ala Phe
            340                 345                 350

Val Leu Ala Ala Ala Leu Phe Asp Arg Val Ala Ala Pro Leu Cys Ala
        355                 360                 365

Ala Ala Gly Lys Leu Ala Ile Thr Pro Leu Arg Arg Val Gly Leu Gly
    370                 375                 380

His Ala Leu Asn Val Ala Ser Met Ala Val Ala Ala Leu Val Glu Arg
385                 390                 395                 400

Arg Arg Ile Gly Ala Ala Arg Gly Arg Ala Ala Ala Ala Ala Ala Val
                405                 410                 415

Val Pro Met Ser Val Leu Trp Leu Val Pro Gln Leu Ala Leu Thr Gly
            420                 425                 430

Ala Glu Glu Ala Leu His Leu Pro Gly Asn Thr Ala Leu Phe Tyr Gly
        435                 440                 445

Glu Leu Pro Ala Ser Leu Arg Gly Thr Ala Thr Ala Met Pro Pro Leu
    450                 455                 460

Phe Ile Ala Ala Gly Ser Tyr Leu Ser Ala Ala Ala Val Asp Ala Val
465                 470                 475                 480

Lys Arg Gly Thr Thr Trp Leu Pro Asp Asp Leu Asn Ala Ser Arg Leu
                485                 490                 495

Asp Cys Val Tyr Trp Thr Leu Ala Val Leu Ala Ala Val Asn Leu Gly
            500                 505                 510

Tyr Phe Leu Leu Cys Ala Thr Thr Tyr Lys Tyr Asn Asn Tyr Gly Gly
        515                 520                 525

Asp Asp Gly Asn Val Lys Ala Gln Thr Gln Thr Asp Asp Val Ser
    530                 535                 540


<210> SEQ ID NO 60
<211> LENGTH: 567
<212> TYPE: PRT
<213> ORGANISM: Solanum demissum
<220> FEATURE:
<221> NAME/KEY: misc_feature
<222> LOCATION: (1)..(567)
<223> OTHER INFORMATION: Public GI no. 47900739

<400> SEQUENCE: 60

Met Glu Ser Ser Val Arg Gly Val Asp Glu Ala Ala Ile Met Lys Ser
1               5                   10                  15

Ser Thr Arg Arg Lys Asn Gly Gly Trp Ile Thr Phe Pro Phe Ile Ile
            20                  25                  30

Val Ser Ala Thr Met Ala Gly Leu Ser Leu Ala Ser Gly Gly Trp Thr
        35                  40                  45

Ser Asn Leu Ile Val Tyr Leu Ile Asp Glu Phe Asn Met Lys Ser Ile
    50                  55                  60

Lys Thr Ala Lys Val Tyr Asn Val Ile Asn Gly Cys Thr Thr Leu Phe
65                  70                  75                  80
```

-continued

```
Pro Ile Val Gly Gly Ile Leu Ala Asp Ser Tyr Leu Gly Ser Phe Ser
                85                  90                  95

Val Ile Trp Phe Ser Ser Leu Ile Ser Ala Leu Gly Ile Leu Leu Leu
            100                 105                 110

Leu Phe Thr Ser Ala Ile Asp Val Leu Arg Pro Pro Pro Cys Asp Asp
        115                 120                 125

Gly Ser Ser Leu Cys Thr Ser Pro Ser Thr His Gln Tyr Ala Val Leu
    130                 135                 140

Tyr Val Ala Leu Ala Leu Ala Ser Leu Gly Val Ala Gly Thr Arg Phe
145                 150                 155                 160

Ile Ile Ala Pro Met Gly Ala Asn Gln Phe Asp Lys Pro Lys His Gln
                165                 170                 175

Ala Ile Phe Phe Asn Trp Tyr Ile Phe Ala Phe Tyr Met Ser Phe Ala
            180                 185                 190

Ile Ser Thr Thr Val Ile Val Tyr Val Glu Asp Asn Val Ser Trp Ser
        195                 200                 205

Trp Gly Tyr Gly Ile Ser Met Ala Phe Asn Ile Leu Gly Leu Ala Met
    210                 215                 220

Phe Leu Ile Gly Lys Arg Phe Tyr Cys Asp Val Lys Glu Gln Gly Gly
225                 230                 235                 240

Ser Pro Phe Val Asn Leu Ala Arg Val Ile Val Val Ala Ile Gln Lys
                245                 250                 255

Trp Arg Val Pro Leu Ser Glu Gln Thr Gln His Tyr Tyr His Asp Pro
            260                 265                 270

Ser Asp Thr Thr Thr Thr Leu Thr Ile Thr Gln Ile Pro Thr Lys Ser
        275                 280                 285

Phe Lys Phe Leu Asn Cys Ala Ala Phe Ile Thr Glu Gly Asp Thr Lys
    290                 295                 300

Pro Asp Gly Ser Ile Ser Asn Pro Trp Arg Leu Cys Thr Val Gln Gln
305                 310                 315                 320

Val Glu Asp Leu Lys Ser Leu Ile Lys Leu Phe Pro Leu Trp Ala Ser
                325                 330                 335

Gly Phe Leu Ile Ser Thr Gln Leu Val Ile Gln Ala Ser Leu Leu Ile
            340                 345                 350

Leu Gln Ala Leu Lys Met Asp Arg His Met Gly Pro His Phe Glu Ile
        355                 360                 365

Pro Ala Gly Ser Met Leu Val Phe Ile Leu Leu Phe Thr Cys Ile Ala
    370                 375                 380

Ile Phe Ile Ile Asp Arg Phe Leu Tyr Pro Phe Leu Ala Lys Tyr Thr
385                 390                 395                 400

Thr Phe Ser Leu Thr Pro Leu Gln Arg Ile Gly Ile Gly His Val Ile
                405                 410                 415

Thr Ile Ile Ser Met Ala Val Ser Ala Leu Val Glu Ser Arg Arg Leu
            420                 425                 430

Arg Ile Val Arg Thr His Lys Leu Gln Gly Gln Asn Asn Asp Ile Val
        435                 440                 445

Pro Met Ser Val Phe Trp Leu Val Pro Gln Leu Ala Leu Asn Gly Ile
    450                 455                 460

Gly Glu Gly Phe His Phe Pro Gly His Ile Ala Phe Tyr Tyr Gln Glu
465                 470                 475                 480

Phe Pro Thr Ser Leu Lys Ser Thr Ser Thr Ala Met Val Ala Leu Phe
                485                 490                 495

Ile Gly Ile Ala His Tyr Leu Gly Asn Thr Leu Ile Asp Leu Val Gln
```

```
            500                 505                 510

Arg Leu Ser Gly Trp Leu Pro Asp Asn Ile Asn Lys Gly Arg Thr Asp
        515                 520                 525

Asn Val Phe Trp Leu Cys Cys Ile Leu Gly Ser Ala Asn Phe Met Tyr
    530                 535                 540

Tyr Val Val Cys Ala Ser Leu Tyr Lys Tyr Lys Asn Val Asp Asn Lys
545                 550                 555                 560

Ser Asn Ile Ala Pro Ser Lys
                565


<210> SEQ ID NO 61
<211> LENGTH: 477
<212> TYPE: PRT
<213> ORGANISM: Artificial Sequence
<220> FEATURE:
<221> NAME/KEY: misc_feature
<222> LOCATION: (1)..(477)
<223> OTHER INFORMATION: Public GI no. 15391731_T
<220> FEATURE:
<221> NAME/KEY: misc_feature
<222> LOCATION: (1)..(477)
<223> OTHER INFORMATION: Truncated portion of Public GI no. 15391731

<400> SEQUENCE: 61

Met Glu Ile Glu Ser Leu Arg Val Ser Val Asp Glu Lys Val Leu Lys
1               5                   10                  15

Asp Glu Glu Lys Asn Glu Lys Glu Glu Met Lys Met Lys Met Lys Met
            20                  25                  30

Lys Arg Lys Leu Gly Gly Val Lys Thr Met Pro Phe Ile Leu Gly Asn
        35                  40                  45

Glu Val Cys Asp Arg Phe Ala Ser Ser Gly Phe His Ser Asn Ile Ile
    50                  55                  60

Thr Tyr Leu Thr Gln Asp Leu Asn Met Pro Leu Val Pro Ala Ser Asn
65                  70                  75                  80

Ile Leu Thr Asn Phe Ala Ala Thr Ser Ser Phe Thr Ser Leu Ile Gly
                85                  90                  95

Ala Leu Ile Ala Asp Ser Phe Ala Gly Arg Phe Trp Thr Ile Thr Ile
            100                 105                 110

Ala Ser Ile Ile Tyr Glu Leu Gly Met Val Thr Ile Thr Ile Ser Ala
        115                 120                 125

Ile Leu Pro Ser Leu His Pro Pro Pro Cys Pro Thr Gln Ile Asn Cys
    130                 135                 140

Thr Gln Ala Ser Gly Thr Gln Leu Met Ile Leu Tyr Leu Ala Leu Leu
145                 150                 155                 160

Leu Thr Ser Leu Gly Ala Gly Gly Ile Arg Pro Cys Val Val Ala Phe
                165                 170                 175

Ala Ala Asp Gln Phe Asp Met Thr Lys Val Gly Ile Ala Gly Arg Thr
            180                 185                 190

Trp Asn Phe Phe Asn Trp Tyr Tyr Phe Cys Met Gly Met Ala Thr Leu
        195                 200                 205

Thr Ala Leu Thr Val Val Val Tyr Ile Gln Asp Asn Val Gly Trp Gly
    210                 215                 220

Trp Gly Phe Gly Leu Pro Thr Ile Ala Met Ala Leu Ser Val Val Ala
225                 230                 235                 240

Phe Val Val Gly Ser Pro Leu Tyr Asn Lys Leu Lys Pro Ser Gly Ser
                245                 250                 255

Pro Leu Val Arg Leu Ala Gln Val Val Val Ala Ala Phe Lys Asn Arg
```

```
            260                 265                 270

Lys Ala Val Leu Pro Asp Asp Ser Lys Leu Leu Tyr Arg Asn His Glu
        275                 280                 285

Leu Asp Ala Ala Ile Ala Ile Gln Gly Arg Leu Val His Thr Asp Gln
    290                 295                 300

Phe Lys Trp Leu Asp Lys Ala Ala Val Ile Thr Ser Pro Asp Ser Thr
305                 310                 315                 320

Ala Asn Pro Pro Asn Leu Trp Arg Leu Ala Thr Val His Arg Val Glu
                325                 330                 335

Glu Leu Lys Ser Ile Ile Arg Met Leu Pro Ile Trp Ala Ala Gly Ile
            340                 345                 350

Leu Leu Val Thr Ala Ser Ser His Gln His Ser Phe Thr Ile Gln Gln
        355                 360                 365

Ala Arg Thr Met Asn Arg His Leu Thr Pro Thr Phe Gln Ile Pro Pro
    370                 375                 380

Ala Thr Leu Ser Ile Phe Gly Ile Leu Ser Met Leu Thr Gly Leu Val
385                 390                 395                 400

Leu Tyr Asp Arg Leu Leu Val Pro Phe Ala Lys Lys Leu Thr His Asn
                405                 410                 415

Pro Ser Gly Ile Thr Cys Leu Gln Arg Met Gly Val Gly Phe Ala Ile
            420                 425                 430

Asn Ile Leu Ala Thr Leu Val Ser Ser Ile Val Glu Ile Lys Arg Lys
        435                 440                 445

Lys Val Ala Ala Asn His Gly Leu Leu Asp Asn Pro Thr Ala Thr Ile
    450                 455                 460

Pro Phe Ser Val Phe Trp Leu Val Pro Gln Phe Trp Leu
465                 470                 475


<210> SEQ ID NO 62
<211> LENGTH: 448
<212> TYPE: PRT
<213> ORGANISM: Artificial Sequence
<220> FEATURE:
<221> NAME/KEY: misc_feature
<222> LOCATION: (1)..(448)
<223> OTHER INFORMATION: Ceres CLONE ID no. 1144139_T
<220> FEATURE:
<221> NAME/KEY: misc_feature
<222> LOCATION: (1)..(448)
<223> OTHER INFORMATION: Homolog of Ceres CLONE ID no. 1144139

<400> SEQUENCE: 62

Met Ala Ser Leu Val Ser Gly Asp Lys Glu Ala Gln Ile Ser Gly Asp
1               5                   10                  15

Pro Gly Ser Lys Arg Gly Gly Trp Ile Thr Phe Pro Phe Met Leu Ala
            20                  25                  30

Thr Leu Leu Gly Leu Ser Val Thr Ser Phe Gly Trp Val Met Asn Leu
        35                  40                  45

Ile Val Phe Leu Ile Glu Glu Phe Asn Ile Lys Ser Ile Ala Ala Ala
    50                  55                  60

Gln Ile Ser Asn Val Ala Asn Gly Cys Leu Ser Met Leu Pro Val Val
65                  70                  75                  80

Ala Ala Ile Leu Ala Asp Ser Phe Phe Gly Asn Ile Pro Val Ile Ala
                85                  90                  95

Ala Ser Ser Phe Ile Ser Leu Leu Gly Ile Val Leu Leu Thr Leu Ile
            100                 105                 110

Ala Ser Leu Asp Tyr Leu Arg Pro Arg Pro Cys Glu Ala Gly Ser Val
```

```
        115                 120                 125

Leu Cys Thr Pro Pro Ser Lys Leu His Leu Gly Ile Leu Tyr Thr Ala
    130                 135                 140

Leu Ala Leu Val Thr Thr Gly Ala Gly Gly Thr Arg Phe Thr Met Ala
145                 150                 155                 160

Ser Ala Gly Ala Asn Gln Tyr Glu Lys Pro Lys Glu Gln Gly Ser Phe
                165                 170                 175

Phe Asn Trp Tyr Phe Leu Thr Leu Tyr Ala Gly Ala Ile Thr Gly Ala
            180                 185                 190

Thr Ala Ile Val Tyr Ile Gln Asp Asn Ala Ser Trp Lys Leu Gly Phe
        195                 200                 205

Gly Leu Cys Ala Ala Ala Asn Leu Ile Ser Phe Ile Val Phe Val Ser
    210                 215                 220

Gly Lys Arg Tyr Tyr Lys His Asp Lys Pro Met Gly Ser Pro Phe Thr
225                 230                 235                 240

Ser Leu Ile Arg Val Val Val Ser Ala Thr Val Lys Arg Lys Ala Val
                245                 250                 255

Ile Ser Cys Asn Glu Glu Asp Tyr His His Tyr Gly Leu Glu Lys Glu
            260                 265                 270

Val Lys Thr Ser Ala Ala Met Pro Ser Lys Ser Phe Arg Phe Leu Asn
        275                 280                 285

Arg Ala Ala Leu Met Thr Lys Asp Asp Leu Asn Gln Lys Glu Gly Ser
    290                 295                 300

Val Asn Asn Ile Trp Arg Leu Cys Ser Val Gln Glu Val Glu Asp Phe
305                 310                 315                 320

Lys Ala Ile Leu Arg Val Phe Pro Leu Trp Leu Ser Ile Ile Phe Val
                325                 330                 335

Ser Thr Pro Met Val Met Gln Thr Ser Leu Ile Val Leu Gln Ala Leu
            340                 345                 350

Val Thr Asp Arg Gly Leu Gly Pro Asn Phe Lys Val Pro Ala Gly Ser
        355                 360                 365

Leu Gln Val Ile Ile Ile Ile Thr Ala Cys Ile Val Ile Ile Met Asn
    370                 375                 380

Asn Trp Leu Val Phe Pro Met Tyr Lys Lys Leu Thr His Lys Leu Leu
385                 390                 395                 400

Thr Pro Leu Gln Lys Val Gly Ile Gly Gln Val Leu Thr Ile Leu Ser
                405                 410                 415

Met Ala Leu Ser Ala Val Val Glu Ala Lys Arg Leu Lys Thr Val Glu
            420                 425                 430

Asn Gly His Pro Met Ser Val Leu Trp Leu Phe Pro Pro Leu Val Ile
        435                 440                 445
```

```
<210> SEQ ID NO 63
<211> LENGTH: 485
<212> TYPE: PRT
<213> ORGANISM: Artificial Sequence
<220> FEATURE:
<221> NAME/KEY: misc_feature
<222> LOCATION: (1)..(485)
<223> OTHER INFORMATION: Public GI no. 54291818_T
<220> FEATURE:
<221> NAME/KEY: misc_feature
<222> LOCATION: (1)..(485)
<223> OTHER INFORMATION: Homolog of Public GI no. 54291818

<400> SEQUENCE: 63

Met Glu Glu Glu Arg Ser Arg Ala Gly Gly Ala Ala Val Ala Val Asp
```

-continued

```
1               5                   10                  15

Gly Glu Ser Leu Arg Arg Pro Glu Glu Glu Gly Gly Arg Arg Lys Lys
            20                  25                  30

Gly Gly Trp Ile Thr Phe Pro Phe Met Ala Val Ser Leu Leu Ala Phe
        35                  40                  45

Gly Leu Ser Ser Ala Gly Ala Met Gly Asn Leu Val Val Tyr Leu Val
    50                  55                  60

Lys Glu Tyr His Val Pro Ser Val Asp Ala Ala Gln Ile Ser Thr Ile
65                  70                  75                  80

Val Ser Gly Cys Ile Ser Val Ala Pro Val Ala Gly Ala Ile Val Ala
                85                  90                  95

Asp Ala Phe Phe Gly Cys Phe Pro Val Val Ala Val Ala Met Val Phe
            100                 105                 110

Ser Val Leu Ala Leu Val Val Phe Thr Leu Thr Ala Ser Val Arg Gly
        115                 120                 125

Leu Arg Pro Ala Ala Cys Val Pro Gly Ala Thr Ala Cys Glu Ala Ala
    130                 135                 140

Thr Ala Gly Gln Met Ala Val Leu Tyr Ala Gly Val Phe Leu Leu Cys
145                 150                 155                 160

Val Ser Ser Ala Gly Ala Arg Phe Asn Gln Ala Thr Met Gly Ala Asp
                165                 170                 175

Gln Phe Asp Ala Ala Ala Asp Arg Asp Val Phe Phe Asn Trp Tyr Phe
            180                 185                 190

Ile Phe Phe Tyr Gly Ser Ala Val Leu Gly Ser Thr Val Leu Val Tyr
        195                 200                 205

Val Gln Asp Ala Val Ser Trp Glu Leu Gly Phe Gly Leu Ala Ala Thr
    210                 215                 220

Ile Ala Ala Ala Gly Leu Ala Ala Leu Leu Leu Gly Ala Arg Tyr Tyr
225                 230                 235                 240

Arg Arg Pro Ala Ala Arg Gly Ser Pro Phe Thr Gly Ile Ala Arg Val
                245                 250                 255

Val Val Ala Ala Ala Arg Lys Arg Lys Ile Asp Val Ala Ala Ala Ala
            260                 265                 270

Ala Ala Ser Gly Asp Leu Lys Phe Tyr Tyr Gly Pro Arg Ser Gly Asp
        275                 280                 285

Gly Asp Asp Asp Gly Gly Lys Pro Ser Asp Asp Asn Asn Phe Ala Pro
    290                 295                 300

Ser Asp Ser Phe Ser Phe Leu Asn Arg Ala Ala Val Ile Thr Asp Gly
305                 310                 315                 320

Asp Val Asp Ala Ala Asp Ala Ala Ala Pro Leu Arg Pro Trp Arg Val
                325                 330                 335

Cys Thr Val Arg Gln Val Glu Asp Leu Lys Ala Val Leu Arg Ile Leu
            340                 345                 350

Pro Leu Trp Ser Ser Ser Ile Phe Leu Ser Ile Ser Ile Gly Val Gln
        355                 360                 365

Leu Asn Phe Thr Val Leu Gln Ala Leu Ala Met Asp Arg Ala Ile Gly
    370                 375                 380

Arg Phe His Val Pro Ala Ala Ser Met Val Val Ser Ser Phe Val Ala
385                 390                 395                 400

Val Val Val Ser Leu Gly Leu Ile Asp Arg Ala Leu Leu Pro Leu Trp
                405                 410                 415

Arg Ala Leu Thr Gly Gly Arg Arg Ala Pro Thr Pro Leu Gln Arg Ile
            420                 425                 430
```

```
Gly Val Gly His Val Leu Thr Val Leu Ser Met Ala Ala Ser Ala Ala
        435                 440                 445

Val Glu Arg Arg Arg Leu Ala Thr Val Arg Ala His Gly Glu Ala Ala
    450                 455                 460

Arg Asp Asp Pro Ala Trp Val Ser Pro Leu Pro Ala Ala Trp Leu Val
465                 470                 475                 480

Leu Pro Phe Ala Leu
                485


<210> SEQ ID NO 64
<211> LENGTH: 430
<212> TYPE: PRT
<213> ORGANISM: Artificial Sequence
<220> FEATURE:
<221> NAME/KEY: misc_feature
<222> LOCATION: (1)..(430)
<223> OTHER INFORMATION: Public GI no. 34905798_T
<220> FEATURE:
<221> NAME/KEY: misc_feature
<222> LOCATION: (1)..(430)
<223> OTHER INFORMATION: Homolog of Public GI no. 34905798

<400> SEQUENCE: 64

Met Ala Met Ser Ala Thr Ser Ser Asn Leu Ile Val Tyr Leu Val His
1               5                   10                  15

Lys Tyr Asn Val Lys Ala Ile His Ala Ala Gln Ile Ser Asn Val Val
            20                  25                  30

Arg Gly Cys Met Gln Leu Ala Pro Val Leu Ala Ala Ala Leu Ser Asp
        35                  40                  45

Ala Phe Phe Gly Pro Tyr Pro Ile Ala Val Ala Gly Leu Val Phe Ser
    50                  55                  60

Leu Leu Ser Phe Val Leu Phe Thr Leu Thr Ala Ala Leu Pro Ser Leu
65                  70                  75                  80

Leu Pro Pro Pro Cys Gln Arg Gly Ala Gly Gly Gly Gly Ala Thr Ala
                85                  90                  95

Thr Ser Cys Glu Pro Pro Asn Ala Ala Gln Ser Ala Val Leu Tyr Ala
            100                 105                 110

Ala Leu Cys Leu Leu Ala Ala Gly Asn Gly Gly Thr Arg Tyr Asn Met
        115                 120                 125

Ala Ala Leu Gly Ala Asp Gln Phe Ala Gly Glu Gly Gln Pro Arg Arg
    130                 135                 140

Arg Arg Gln Gly Gly Gly Phe Phe Ser Cys Tyr Phe Ala Phe Leu Tyr
145                 150                 155                 160

Ala Ser Tyr Ala Thr Gly Asp Thr Val Leu Val Tyr Val Gln Asp Gly
                165                 170                 175

Val Ser Trp Ala Leu Gly Phe Gly Val Cys Val Ala Thr Thr Gly Leu
            180                 185                 190

Ala Leu Ala Ala Leu Leu Leu Gly Ser Arg His Tyr Arg Arg Pro Val
        195                 200                 205

Pro Lys Gly Ser Pro Phe Thr Ala Met Ala Arg Val Ala Val Ala Ala
    210                 215                 220

Ala Arg Lys Ala Thr Val Asp Leu Gly Ser Arg Val Gln Tyr Tyr His
225                 230                 235                 240

Gly Cys Asn Arg Asp Asp Ala Val Pro Arg Ala Asp Gln Ala Pro Ser
                245                 250                 255

Asp Arg Phe Arg Phe Leu Asn Arg Ala Ala Met Val Val Ala Gly Glu
            260                 265                 270
```

```
Thr Arg Glu Glu Asp Gly Ser Val Ala Lys Pro Trp Arg Leu Cys Thr
        275                 280                 285

Val Gln Gln Val Glu Asp Val Lys Ser Val Val Arg Val Leu Pro Leu
    290                 295                 300

Trp Ser Ser Gly Ile Leu Val Ser Val Thr Val Asn Ala Gln Val Ser
305                 310                 315                 320

Leu Thr Val Leu Gln Ala Leu Thr Met Asp Arg Ala Val Gly Pro Arg
                325                 330                 335

Phe Ala Val Pro Ala Ala Ser Ile Thr Val Thr Val Leu Ala Ala Phe
            340                 345                 350

Val Leu Ala Ala Ala Leu Phe Asp Arg Val Ala Ala Pro Leu Cys Ala
        355                 360                 365

Ala Ala Gly Lys Leu Ala Ile Thr Pro Leu Arg Arg Val Gly Leu Gly
    370                 375                 380

His Ala Leu Asn Val Ala Ser Met Ala Val Ala Ala Leu Val Glu Arg
385                 390                 395                 400

Arg Arg Ile Gly Ala Ala Arg Gly Arg Ala Ala Ala Ala Ala Ala Val
                405                 410                 415

Val Pro Met Ser Val Leu Trp Leu Val Pro Gln Leu Ala Leu
            420                 425                 430


<210> SEQ ID NO 65
<211> LENGTH: 461
<212> TYPE: PRT
<213> ORGANISM: Artificial Sequence
<220> FEATURE:
<221> NAME/KEY: misc_feature
<222> LOCATION: (1)..(461)
<223> OTHER INFORMATION: Public GI no. 47900739_T
<220> FEATURE:
<221> NAME/KEY: misc_feature
<222> LOCATION: (1)..(461)
<223> OTHER INFORMATION: Homolog of Public GI no. 47900739

<400> SEQUENCE: 65

Met Glu Ser Ser Val Arg Gly Val Asp Glu Ala Ala Ile Met Lys Ser
1               5                   10                  15

Ser Thr Arg Arg Lys Asn Gly Gly Trp Ile Thr Phe Pro Phe Ile Ile
            20                  25                  30

Val Ser Ala Thr Met Ala Gly Leu Ser Leu Ala Ser Gly Gly Trp Thr
        35                  40                  45

Ser Asn Leu Ile Val Tyr Leu Ile Asp Glu Phe Asn Met Lys Ser Ile
    50                  55                  60

Lys Thr Ala Lys Val Tyr Asn Val Ile Asn Gly Cys Thr Thr Leu Phe
65                  70                  75                  80

Pro Ile Val Gly Gly Ile Leu Ala Asp Ser Tyr Leu Gly Ser Phe Ser
                85                  90                  95

Val Ile Trp Phe Ser Ser Leu Ile Ser Ala Leu Gly Ile Leu Leu Leu
            100                 105                 110

Leu Phe Thr Ser Ala Ile Asp Val Leu Arg Pro Pro Pro Cys Asp Asp
        115                 120                 125

Gly Ser Ser Leu Cys Thr Ser Pro Ser Thr His Gln Tyr Ala Val Leu
    130                 135                 140

Tyr Val Ala Leu Ala Leu Ala Ser Leu Gly Val Ala Gly Thr Arg Phe
145                 150                 155                 160

Ile Ile Ala Pro Met Gly Ala Asn Gln Phe Asp Lys Pro Lys His Gln
                165                 170                 175
```

```
Ala Ile Phe Phe Asn Trp Tyr Ile Phe Ala Phe Tyr Met Ser Phe Ala
            180                 185                 190

Ile Ser Thr Thr Val Ile Val Tyr Val Glu Asp Asn Val Ser Trp Ser
        195                 200                 205

Trp Gly Tyr Gly Ile Ser Met Ala Phe Asn Ile Leu Gly Leu Ala Met
    210                 215                 220

Phe Leu Ile Gly Lys Arg Phe Tyr Cys Asp Val Lys Glu Gln Gly Gly
225                 230                 235                 240

Ser Pro Phe Val Asn Leu Ala Arg Val Ile Val Val Ala Ile Gln Lys
                245                 250                 255

Trp Arg Val Pro Leu Ser Glu Gln Thr Gln His Tyr Tyr His Asp Pro
            260                 265                 270

Ser Asp Thr Thr Thr Thr Leu Thr Ile Thr Gln Ile Pro Thr Lys Ser
        275                 280                 285

Phe Lys Phe Leu Asn Cys Ala Ala Phe Ile Thr Glu Gly Asp Thr Lys
    290                 295                 300

Pro Asp Gly Ser Ile Ser Asn Pro Trp Arg Leu Cys Thr Val Gln Gln
305                 310                 315                 320

Val Glu Asp Leu Lys Ser Leu Ile Lys Leu Phe Pro Leu Trp Ala Ser
                325                 330                 335

Gly Phe Leu Ile Ser Thr Gln Leu Val Ile Gln Ala Ser Leu Leu Ile
            340                 345                 350

Leu Gln Ala Leu Lys Met Asp Arg His Met Gly Pro His Phe Glu Ile
        355                 360                 365

Pro Ala Gly Ser Met Leu Val Phe Ile Leu Leu Phe Thr Cys Ile Ala
    370                 375                 380

Ile Phe Ile Ile Asp Arg Phe Leu Tyr Pro Phe Leu Ala Lys Tyr Thr
385                 390                 395                 400

Thr Phe Ser Leu Thr Pro Leu Gln Arg Ile Gly Ile Gly His Val Ile
                405                 410                 415

Thr Ile Ile Ser Met Ala Val Ser Ala Leu Val Glu Ser Arg Arg Leu
            420                 425                 430

Arg Ile Val Arg Thr His Lys Leu Gln Gly Gln Asn Asn Asp Ile Val
        435                 440                 445

Pro Met Ser Val Phe Trp Leu Val Pro Gln Leu Ala Leu
    450                 455                 460
```

<210> SEQ ID NO 66
<211> LENGTH: 1329
<212> TYPE: DNA
<213> ORGANISM: Arabidopsis thaliana
<220> FEATURE:
<221> NAME/KEY: misc_feature
<222> LOCATION: (1)..(1329)
<223> OTHER INFORMATION: Ceres CDNA ID no. 4904707
<220> FEATURE:
<221> NAME/KEY: CDS
<222> LOCATION: (1)..(1326)
<223> OTHER INFORMATION: Referenced by SEQ ID NO: 67

<400> SEQUENCE: 66

```
atgaccgcca ccgaagctaa gaatcgcaaa atcaatgtcg gagatggaga tgacgttgtt     60

gatatcgaaa tccctgacac tgctcatcaa attagcagcg attcatggtt tcaggtggcg    120

ttcgttttga ccaccggtat aaacagcgcg tatgtgttgg gatattcagg aacaattatg    180

gttcctttag gttggattgg tggtgtggtt ggtcttctta ttgctactgc aatctctctt    240
```

-continued

```
tatgcaaaca ctctaatagc taagcttcat gagtttggtg gcagaagaca cattcgctat    300

agagaccttg ctggattcat ttacggtagg aaggcttatc atcttacatg ggattgcaa    360

tatgttaatc ttttcatgat taattgtgga ttcattatcc tagctggttc cgccttaaag    420

gctgtttatg tgcttttcag ggatgatcat accatgaaac tacctcattt tatagccatt    480

gctggtttga tttgtgcgat tttcgctatt gggattcctc atttatcggc tcttggggtc    540

tggcttggag tttcgacctt cctcagtctc atctatattg ttgtggcaat cgtgctatcg    600

gttagagatg gagtaaaaac accttcaaga gattacgaga tacaaggatc atcattgagc    660

aaacttttta ccatcacagg agcagccgca aatctggttt tcgcattcaa caccgggatg    720

cttccagaaa ttcaggcaac agtgaggcaa ccagttgtta aaaacatgat gaaggctcta    780

tactttcaat tcacagcggg tgttttaccg atgtacgcag ttacattcat cggatattgg    840

gcttatggat cctcaacctc gacctatcta ctaaacagtg ttaatggccc actctgggtc    900

aaagcccttg ctaacgtctc tgctatcctt caatctgtta tctctttgca catatttgcg    960

agtccaacat atgagtacat ggacacaaag tatgggatca aaggaaaccc atttgcgata   1020

aagaacctgc tgtttaggat catggcgaga ggcgggtaca tagcggtaag cacgcttatc   1080

tcagcgctgt tgccgttcct cggtgacttc atgagcctaa ctggtgcagt gagcacattc   1140

cctctcacat tcattctagc caaccacatg tactataagg caaagaacaa taagctgaat   1200

gctatgcaaa agctatggca ttggcttaac gttgtcttct ttagtttgat gtctgttgct   1260

gcagccattg cagctgtcag actcatcgcc gttgattcca aaaatttcca tgtttttgca   1320

gatttgtaa                                                            1329
```

```
<210> SEQ ID NO 67
<211> LENGTH: 442
<212> TYPE: PRT
<213> ORGANISM: Arabidopsis thaliana
<220> FEATURE:
<221> NAME/KEY: misc_feature
<222> LOCATION: (32)..(428)
<223> OTHER INFORMATION: Pfam Name: Aa_trans; Pfam Description:
      Transmembrane amino acid transporter protein

<400> SEQUENCE: 67

Met Thr Ala Thr Glu Ala Lys Asn Arg Lys Ile Asn Val Gly Asp Gly
1               5                   10                  15

Asp Asp Val Val Asp Ile Glu Ile Pro Asp Thr Ala His Gln Ile Ser
            20                  25                  30

Ser Asp Ser Trp Phe Gln Val Ala Phe Val Leu Thr Thr Gly Ile Asn
        35                  40                  45

Ser Ala Tyr Val Leu Gly Tyr Ser Gly Thr Ile Met Val Pro Leu Gly
    50                  55                  60

Trp Ile Gly Gly Val Val Gly Leu Leu Ile Ala Thr Ala Ile Ser Leu
65                  70                  75                  80

Tyr Ala Asn Thr Leu Ile Ala Lys Leu His Glu Phe Gly Gly Arg Arg
                85                  90                  95

His Ile Arg Tyr Arg Asp Leu Ala Gly Phe Ile Tyr Gly Arg Lys Ala
            100                 105                 110

Tyr His Leu Thr Trp Gly Leu Gln Tyr Val Asn Leu Phe Met Ile Asn
        115                 120                 125

Cys Gly Phe Ile Ile Leu Ala Gly Ser Ala Leu Lys Ala Val Tyr Val
    130                 135                 140

Leu Phe Arg Asp Asp His Thr Met Lys Leu Pro His Phe Ile Ala Ile
```

```
145                 150                 155                 160

Ala Gly Leu Ile Cys Ala Ile Phe Ala Ile Gly Ile Pro His Leu Ser
                165                 170                 175

Ala Leu Gly Val Trp Leu Gly Val Ser Thr Phe Leu Ser Leu Ile Tyr
            180                 185                 190

Ile Val Val Ala Ile Val Leu Ser Val Arg Asp Gly Val Lys Thr Pro
        195                 200                 205

Ser Arg Asp Tyr Glu Ile Gln Gly Ser Ser Leu Ser Lys Leu Phe Thr
    210                 215                 220

Ile Thr Gly Ala Ala Ala Asn Leu Val Phe Ala Phe Asn Thr Gly Met
225                 230                 235                 240

Leu Pro Glu Ile Gln Ala Thr Val Arg Gln Pro Val Val Lys Asn Met
                245                 250                 255

Met Lys Ala Leu Tyr Phe Gln Phe Thr Ala Gly Val Leu Pro Met Tyr
            260                 265                 270

Ala Val Thr Phe Ile Gly Tyr Trp Ala Tyr Gly Ser Ser Thr Ser Thr
        275                 280                 285

Tyr Leu Leu Asn Ser Val Asn Gly Pro Leu Trp Val Lys Ala Leu Ala
    290                 295                 300

Asn Val Ser Ala Ile Leu Gln Ser Val Ile Ser Leu His Ile Phe Ala
305                 310                 315                 320

Ser Pro Thr Tyr Glu Tyr Met Asp Thr Lys Tyr Gly Ile Lys Gly Asn
                325                 330                 335

Pro Phe Ala Ile Lys Asn Leu Leu Phe Arg Ile Met Ala Arg Gly Gly
            340                 345                 350

Tyr Ile Ala Val Ser Thr Leu Ile Ser Ala Leu Leu Pro Phe Leu Gly
        355                 360                 365

Asp Phe Met Ser Leu Thr Gly Ala Val Ser Thr Phe Pro Leu Thr Phe
    370                 375                 380

Ile Leu Ala Asn His Met Tyr Tyr Lys Ala Lys Asn Asn Lys Leu Asn
385                 390                 395                 400

Ala Met Gln Lys Leu Trp His Trp Leu Asn Val Val Phe Phe Ser Leu
                405                 410                 415

Met Ser Val Ala Ala Ala Ile Ala Ala Val Arg Leu Ile Ala Val Asp
            420                 425                 430

Ser Lys Asn Phe His Val Phe Ala Asp Leu
        435                 440


<210> SEQ ID NO 68
<211> LENGTH: 436
<212> TYPE: PRT
<213> ORGANISM: Arabidopsis thaliana
<220> FEATURE:
<221> NAME/KEY: misc_feature
<222> LOCATION: (1)..(436)
<223> OTHER INFORMATION: Public GI no. 28393251

<400> SEQUENCE: 68

Met Asn Ser Lys Asn Arg Ile Asn Asn Val Gly Glu Gly Val Asp Ile
1               5                   10                  15

Glu Ile Pro Asp Thr Ala His Gln Ile Ser Ser Asp Ser Trp Phe Gln
            20                  25                  30

Ala Ala Phe Val Leu Thr Thr Ser Ile Asn Ser Ala Tyr Val Leu Gly
        35                  40                  45

Tyr Ser Gly Thr Val Met Val Pro Leu Gly Trp Ile Gly Gly Val Val
    50                  55                  60
```

-continued

```
Gly Leu Ile Leu Ala Thr Ala Ile Ser Leu Tyr Ala Asn Thr Leu Val
65                  70                  75                  80

Ala Lys Leu His Glu Phe Gly Gly Lys Arg His Ile Arg Tyr Arg Asp
                85                  90                  95

Leu Ala Gly Phe Ile Tyr Gly Arg Lys Ala Tyr Cys Leu Thr Trp Val
            100                 105                 110

Leu Gln Tyr Val Asn Leu Phe Met Ile Asn Cys Gly Phe Ile Ile Leu
        115                 120                 125

Ala Gly Ser Ala Leu Lys Ala Val Tyr Val Leu Phe Arg Asp Asp His
    130                 135                 140

Ala Met Lys Leu Pro His Phe Ile Ala Ile Ala Gly Leu Ile Cys Ala
145                 150                 155                 160

Val Phe Ala Ile Gly Ile Pro His Leu Ser Ala Leu Gly Ile Trp Leu
                165                 170                 175

Ala Val Ser Thr Ile Leu Ser Leu Ile Tyr Ile Val Val Ala Ile Val
            180                 185                 190

Leu Ser Val Lys Asp Gly Val Lys Ala Pro Ser Arg Asp Tyr Glu Ile
        195                 200                 205

Gln Gly Ser Pro Leu Ser Lys Leu Phe Thr Ile Thr Gly Ala Ala Ala
    210                 215                 220

Thr Leu Val Phe Val Phe Asn Thr Gly Met Leu Pro Glu Ile Gln Ala
225                 230                 235                 240

Thr Val Lys Gln Pro Val Val Lys Asn Met Met Lys Ala Leu Tyr Phe
                245                 250                 255

Gln Phe Thr Val Gly Val Leu Pro Met Phe Ala Val Val Phe Ile Gly
            260                 265                 270

Tyr Trp Ala Tyr Gly Ser Ser Thr Ser Pro Tyr Leu Leu Asn Asn Val
        275                 280                 285

Asn Gly Pro Leu Trp Val Lys Ala Leu Ala Asn Ile Ser Ala Ile Leu
    290                 295                 300

Gln Ser Val Ile Ser Leu His Ile Phe Ala Ser Pro Thr Tyr Glu Tyr
305                 310                 315                 320

Met Asp Thr Lys Phe Gly Ile Lys Gly Asn Pro Leu Ala Leu Lys Asn
                325                 330                 335

Leu Leu Phe Arg Ile Met Ala Arg Gly Gly Tyr Ile Ala Val Ser Thr
            340                 345                 350

Leu Leu Ser Ala Leu Leu Pro Phe Leu Gly Asp Phe Met Ser Leu Thr
        355                 360                 365

Gly Ala Val Ser Thr Phe Pro Leu Thr Phe Ile Leu Ala Asn His Met
    370                 375                 380

Tyr Tyr Lys Ala Lys Asn Asn Lys Leu Asn Thr Leu Gln Lys Leu Cys
385                 390                 395                 400

His Trp Leu Asn Val Val Phe Phe Ser Leu Met Ser Val Ala Ala Ala
                405                 410                 415

Ile Ala Ala Leu Arg Leu Ile Ala Leu Asp Ser Lys Asn Phe His Val
            420                 425                 430

Phe Ala Asp Leu
        435
```

<210> SEQ ID NO 69
<211> LENGTH: 436
<212> TYPE: PRT
<213> ORGANISM: Arabidopsis thaliana
<220> FEATURE:

<221> NAME/KEY: misc_feature
<222> LOCATION: (1)..(436)
<223> OTHER INFORMATION: Public GI no. 21554196

<400> SEQUENCE: 69

```
Met Asn Ser Lys Asn Arg Ile Asn Asn Val Gly Glu Asp Val Asp Ile
1               5                   10                  15

Glu Ile Pro Asp Thr Ala His Gln Ile Ser Ser Asp Ser Trp Phe Gln
            20                  25                  30

Ala Ala Phe Val Leu Thr Thr Ser Ile Asn Ser Ala Tyr Val Leu Gly
        35                  40                  45

Tyr Ser Gly Thr Val Met Val Pro Leu Gly Trp Ile Gly Gly Val Val
    50                  55                  60

Gly Leu Ile Leu Ala Thr Ala Ile Ser Leu Tyr Ala Asn Thr Leu Val
65                  70                  75                  80

Ala Lys Leu His Glu Phe Gly Gly Lys Arg His Ile Arg Tyr Arg Asp
                85                  90                  95

Leu Ala Gly Phe Ile Tyr Gly Arg Lys Ala Tyr Cys Leu Thr Trp Val
            100                 105                 110

Leu Gln Tyr Val Asn Phe Phe Met Ile Asn Cys Gly Phe Ile Ile Leu
        115                 120                 125

Ala Gly Ser Ala Leu Lys Ala Val Tyr Val Leu Phe Arg Asp Asp His
    130                 135                 140

Ala Met Lys Leu Pro His Phe Ile Ala Ile Ala Gly Leu Ile Cys Ala
145                 150                 155                 160

Val Phe Ala Ile Gly Ile Pro His Leu Ser Ala Leu Gly Ile Trp Leu
                165                 170                 175

Ala Val Ser Thr Ile Leu Ser Leu Ile Tyr Ile Val Val Ala Ile Val
            180                 185                 190

Leu Ser Val Lys Asp Gly Val Lys Ala Pro Ser Arg Asp Tyr Glu Ile
        195                 200                 205

Gln Gly Ser Pro Leu Ser Lys Leu Phe Thr Ile Thr Gly Ala Ala Ala
    210                 215                 220

Thr Leu Val Phe Val Phe Asn Thr Gly Met Leu Pro Glu Ile Gln Ala
225                 230                 235                 240

Thr Val Lys Gln Pro Val Val Lys Asn Met Met Lys Ala Leu Tyr Phe
                245                 250                 255

Gln Phe Thr Val Gly Val Leu Pro Met Phe Ala Val Val Phe Ile Gly
            260                 265                 270

Tyr Trp Ala Tyr Gly Ser Ser Thr Ser Pro Tyr Leu Leu Asn Asn Val
        275                 280                 285

Asn Gly Pro Leu Trp Val Lys Ala Leu Ala Asn Ile Ser Ala Ile Leu
    290                 295                 300

Gln Ser Val Ile Ser Leu His Ile Phe Ala Ser Pro Thr Tyr Glu Tyr
305                 310                 315                 320

Met Asp Thr Lys Phe Gly Ile Lys Gly Asn Pro Leu Ala Leu Lys Asn
                325                 330                 335

Leu Leu Phe Arg Ile Met Ala Arg Gly Gly Tyr Ile Ala Val Ser Thr
            340                 345                 350

Leu Leu Ser Ala Leu Leu Pro Phe Leu Gly Asp Phe Met Ser Leu Thr
        355                 360                 365

Gly Ala Val Ser Thr Phe Pro Leu Thr Phe Ile Leu Ala Asn His Met
    370                 375                 380

Tyr Tyr Lys Ala Lys Asn Asn Lys Leu Ser Thr Leu Gln Lys Leu Trp
```

```
385                 390                 395                 400

His Trp Leu Asn Val Val Phe Phe Ser Leu Met Ser Val Ala Ala Ala
                405                 410                 415

Ile Ala Ala Leu Arg Leu Ile Ala Ile Asp Ser Lys Asn Phe His Val
            420                 425                 430

Phe Ala Asp Leu
        435


<210> SEQ ID NO 70
<211> LENGTH: 436
<212> TYPE: PRT
<213> ORGANISM: Arabidopsis thaliana
<220> FEATURE:
<221> NAME/KEY: misc_feature
<222> LOCATION: (1)..(436)
<223> OTHER INFORMATION: Ceres CLONE ID no. 20959

<400> SEQUENCE: 70

Met Asn Ser Lys Asn Arg Ile Asn Asn Val Gly Glu Asp Val Asp Ile
1               5                   10                  15

Glu Ile Pro Asp Thr Ala His Gln Ile Ser Ser Asp Ser Trp Phe Gln
            20                  25                  30

Ala Ala Phe Val Leu Thr Thr Ser Ile Asn Ser Ala Tyr Val Leu Gly
        35                  40                  45

Tyr Ser Gly Thr Val Met Val Pro Leu Gly Trp Ile Gly Gly Val Val
    50                  55                  60

Gly Leu Ile Leu Ala Thr Ala Ile Ser Leu Tyr Ala Asn Thr Leu Val
65                  70                  75                  80

Ala Lys Leu His Glu Phe Gly Gly Lys Arg His Ile Arg Tyr Arg Asp
                85                  90                  95

Leu Ala Gly Phe Ile Tyr Gly Arg Lys Ala Tyr Cys Leu Thr Trp Val
            100                 105                 110

Leu Gln Tyr Val Asn Phe Phe Met Ile Asn Cys Gly Phe Ile Ile Leu
        115                 120                 125

Ala Gly Ser Ala Leu Lys Ala Val Tyr Val Leu Phe Arg Asp Asp His
    130                 135                 140

Ala Met Lys Leu Pro His Phe Ile Ala Ile Ala Gly Leu Ile Cys Ala
145                 150                 155                 160

Val Phe Ala Ile Gly Ile Pro His Leu Ser Ala Leu Gly Ile Trp Leu
                165                 170                 175

Ala Val Ser Thr Ile Leu Ser Leu Ile Tyr Ile Val Val Ala Ile Val
            180                 185                 190

Leu Ser Val Lys Asp Gly Val Lys Ala Pro Ser Arg Asp Tyr Glu Ile
        195                 200                 205

Gln Gly Ser Pro Leu Ser Lys Leu Phe Thr Ile Thr Gly Ala Ala Ala
    210                 215                 220

Thr Leu Val Phe Val Phe Asn Thr Gly Met Leu Pro Glu Ile Gln Ala
225                 230                 235                 240

Thr Val Lys Gln Pro Val Val Lys Asn Met Met Lys Ala Leu Tyr Phe
                245                 250                 255

Gln Phe Thr Val Gly Val Leu Pro Met Phe Ala Val Val Phe Ile Gly
            260                 265                 270

Tyr Trp Ala Tyr Gly Ser Ser Thr Ser Pro Tyr Leu Leu Asn Asn Val
        275                 280                 285

Asn Gly Pro Leu Trp Val Lys Ala Leu Ala Asn Ile Ser Ala Ile Leu
    290                 295                 300
```

```
Gln Ser Val Ile Ser Leu His Ile Phe Ala Ser Pro Thr Tyr Glu Tyr
305                 310                 315                 320

Met Asp Thr Lys Phe Gly Ile Lys Gly Asn Pro Leu Ala Leu Lys Asn
                325                 330                 335

Leu Leu Phe Arg Ile Met Ala Arg Gly Gly Tyr Ile Ala Val Ser Thr
            340                 345                 350

Leu Leu Ser Ala Leu Leu Pro Phe Leu Gly Asp Phe Met Ser Leu Thr
        355                 360                 365

Gly Ala Val Ser Thr Phe Pro Leu Thr Phe Ile Leu Ala Asn His Met
    370                 375                 380

Tyr Tyr Lys Ala Lys Asn Asn Lys Leu Ser Thr Leu Gln Lys Leu Trp
385                 390                 395                 400

His Trp Leu Asn Val Val Phe Phe Ser Leu Met Ser Val Ala Ala Ala
                405                 410                 415

Ile Ala Ala Leu Arg Leu Ile Ala Ile Asp Ser Lys Asn Phe His Val
            420                 425                 430

Phe Ala Asp Leu
        435


<210> SEQ ID NO 71
<211> LENGTH: 439
<212> TYPE: PRT
<213> ORGANISM: Arabidopsis thaliana
<220> FEATURE:
<221> NAME/KEY: misc_feature
<222> LOCATION: (1)..(439)
<223> OTHER INFORMATION: Public GI no. 31376371

<400> SEQUENCE: 71

Met Asp Thr Ser Glu Ala Arg Asn Arg Lys Val Val Ala Val Glu Gln
1               5                   10                  15

Phe Asp Leu Glu Val Pro Glu Thr Ala His Gln Ile Ser Ser Asp Ser
            20                  25                  30

Trp Phe Gln Val Ala Phe Val Leu Thr Thr Gly Ile Asn Ser Ala Tyr
        35                  40                  45

Val Leu Gly Tyr Ser Gly Thr Val Met Val Pro Leu Gly Trp Ile Gly
    50                  55                  60

Gly Val Val Gly Leu Ile Leu Ala Thr Ala Ile Ser Leu Tyr Ala Asn
65                  70                  75                  80

Thr Leu Ile Ala Lys Leu His Glu Phe Gly Gly Lys Arg His Ile Arg
                85                  90                  95

Tyr Arg Asp Leu Ala Gly Phe Ile Tyr Gly Lys Lys Met Tyr Arg Val
            100                 105                 110

Thr Trp Gly Leu Gln Tyr Val Asn Leu Phe Met Ile Asn Cys Gly Phe
        115                 120                 125

Ile Ile Leu Ala Gly Ser Ala Leu Lys Ala Val Tyr Val Leu Phe Arg
    130                 135                 140

Asp Asp Ser Leu Met Lys Leu Pro His Phe Ile Ala Ile Ala Gly Val
145                 150                 155                 160

Val Cys Ala Ile Phe Ala Ile Gly Ile Pro His Leu Ser Ala Leu Gly
                165                 170                 175

Ile Trp Leu Gly Val Ser Thr Ile Leu Ser Ile Ile Tyr Ile Ile Val
            180                 185                 190

Ala Ile Val Leu Ser Ala Lys Asp Gly Val Asn Lys Pro Glu Arg Asp
        195                 200                 205
```

```
Tyr Asn Ile Gln Gly Ser Ser Ile Asn Lys Leu Phe Thr Ile Thr Gly
    210                 215                 220

Ala Ala Ala Asn Leu Val Phe Ala Phe Asn Thr Gly Met Leu Pro Glu
225                 230                 235                 240

Ile Gln Ala Thr Val Lys Gln Pro Val Val Lys Asn Met Met Lys Ala
                245                 250                 255

Leu Tyr Phe Gln Phe Thr Val Gly Val Leu Pro Met Tyr Ala Val Thr
            260                 265                 270

Phe Ile Gly Tyr Trp Ala Tyr Gly Ser Ser Thr Ser Thr Tyr Leu Leu
        275                 280                 285

Asn Ser Val Ser Gly Pro Val Trp Val Lys Ala Leu Ala Asn Ile Ser
    290                 295                 300

Ala Phe Leu Gln Ser Val Ile Ser Leu His Ile Phe Ala Ser Pro Thr
305                 310                 315                 320

Tyr Glu Tyr Met Asp Thr Lys Tyr Gly Val Lys Gly Ser Pro Leu Ala
                325                 330                 335

Met Lys Asn Leu Leu Phe Arg Thr Val Ala Arg Gly Ser Tyr Ile Ala
            340                 345                 350

Val Ser Thr Leu Leu Ser Ala Leu Leu Pro Phe Leu Gly Asp Phe Met
        355                 360                 365

Ser Leu Thr Gly Ala Ile Ser Thr Phe Pro Leu Thr Phe Ile Leu Ala
    370                 375                 380

Asn His Met Tyr Leu Val Ala Met Asn Asp Glu Leu Ser Leu Val Gln
385                 390                 395                 400

Lys Leu Trp His Trp Leu Asn Val Cys Phe Phe Gly Leu Met Ser Leu
                405                 410                 415

Ala Ala Ala Ile Ala Ala Val Arg Leu Ile Ser Val Asp Ser Lys Asn
            420                 425                 430

Phe His Val Phe Ala Asp Val
        435


<210> SEQ ID NO 72
<211> LENGTH: 435
<212> TYPE: PRT
<213> ORGANISM: Glycine max
<220> FEATURE:
<221> NAME/KEY: misc_feature
<222> LOCATION: (1)..(435)
<223> OTHER INFORMATION: Ceres CLONE ID no. 526395
<220> FEATURE:
<221> NAME/KEY: misc_feature
<222> LOCATION: (197)..(197)
<223> OTHER INFORMATION: Xaa is any aa, unknown, or other
<220> FEATURE:
<221> NAME/KEY: misc_feature
<222> LOCATION: (236)..(236)
<223> OTHER INFORMATION: Xaa is any aa, unknown, or other
<220> FEATURE:
<221> NAME/KEY: misc_feature
<222> LOCATION: (243)..(243)
<223> OTHER INFORMATION: Xaa is any aa, unknown, or other
<220> FEATURE:
<221> NAME/KEY: misc_feature
<222> LOCATION: (259)..(259)
<223> OTHER INFORMATION: Xaa is any aa, unknown, or other
<220> FEATURE:
<221> NAME/KEY: misc_feature
<222> LOCATION: (270)..(270)
<223> OTHER INFORMATION: Xaa is any aa, unknown, or other
<220> FEATURE:
<221> NAME/KEY: misc_feature
<222> LOCATION: (288)..(288)
<223> OTHER INFORMATION: Xaa is any aa, unknown, or other
<220> FEATURE:
```

```
<221> NAME/KEY: misc_feature
<222> LOCATION: (292)..(292)
<223> OTHER INFORMATION: Xaa is any aa, unknown, or other
<220> FEATURE:
<221> NAME/KEY: misc_feature
<222> LOCATION: (299)..(299)
<223> OTHER INFORMATION: Xaa is any aa, unknown, or other
<220> FEATURE:
<221> NAME/KEY: misc_feature
<222> LOCATION: (300)..(300)
<223> OTHER INFORMATION: Xaa is any aa, unknown, or other
<220> FEATURE:
<221> NAME/KEY: misc_feature
<222> LOCATION: (320)..(320)
<223> OTHER INFORMATION: Xaa is any aa, unknown, or other
<220> FEATURE:
<221> NAME/KEY: misc_feature
<222> LOCATION: (336)..(336)
<223> OTHER INFORMATION: Xaa is any aa, unknown, or other
<220> FEATURE:
<221> NAME/KEY: misc_feature
<222> LOCATION: (341)..(341)
<223> OTHER INFORMATION: Xaa is any aa, unknown, or other
<220> FEATURE:
<221> NAME/KEY: misc_feature
<222> LOCATION: (344)..(344)
<223> OTHER INFORMATION: Xaa is any aa, unknown, or other

<400> SEQUENCE: 72

Met Thr Leu Ile Ser Asn Ser Asp Val Glu Ser His Ala Asp Val Gln
1               5                   10                  15

Ile Pro Asp Thr Ala His Gln Ile Ser Thr Asp Ser Trp Phe Gln Val
            20                  25                  30

Gly Phe Val Leu Thr Thr Gly Ile Asn Ser Ala Tyr Val Leu Gly Tyr
        35                  40                  45

Ser Gly Thr Ile Met Val Pro Leu Gly Trp Ala Gly Gly Val Val Gly
    50                  55                  60

Leu Ile Leu Ala Thr Ala Ile Ser Leu Tyr Ala Asn Ala Leu Ile Ala
65                  70                  75                  80

Arg Leu His Glu Tyr Gly Gly Thr Arg His Ile Arg Tyr Arg Asp Leu
                85                  90                  95

Ala Gly Phe Ile Tyr Gly Arg Lys Ala Tyr Ser Leu Thr Trp Ala Leu
            100                 105                 110

Gln Tyr Val Asn Leu Phe Met Ile Asn Ala Gly Tyr Ile Ile Leu Ala
        115                 120                 125

Gly Ser Ala Leu Lys Ala Thr Tyr Val Leu Phe Arg Glu Asp Asp Gly
    130                 135                 140

Met Lys Leu Pro Tyr Phe Ile Gly Ile Ala Gly Phe Val Cys Ala Met
145                 150                 155                 160

Phe Ala Ile Cys Ile Pro His Leu Ser Ala Leu Gly Ile Trp Leu Gly
                165                 170                 175

Phe Ser Thr Val Phe Ser Leu Val Tyr Ile Val Ile Ala Phe Val Leu
            180                 185                 190

Ser Ile Lys Asp Xaa Ile Lys Ser Pro Pro Arg Asp Tyr Ser Ile Pro
        195                 200                 205

Gly Thr Ser Thr Ser Lys Ile Ser Thr Thr Ile Gly Ala Ser Ala Asn
    210                 215                 220

Leu Val Phe Ala Tyr Asn Thr Gly Met Leu Pro Xaa Ile Gln Ala Thr
225                 230                 235                 240

Ile Arg Xaa Pro Val Val Lys Asn Met Met Lys Ala Leu Tyr Phe Gln
                245                 250                 255

Phe Thr Xaa Gly Val Leu Pro Leu Tyr Leu Val Thr Phe Xaa Gly Tyr
```

```
            260                 265                 270

Trp Ala Tyr Gly Ser Ser Thr Ala Thr Tyr Leu Met Ser Asp Val Xaa
        275                 280                 285

Gly Pro Val Xaa Ala Lys Ala Met Ala Asn Xaa Xaa Ala Phe Leu Gln
    290                 295                 300

Ser Val Ile Ala Leu His Ile Phe Ala Ser Pro Met Tyr Glu Tyr Xaa
305                 310                 315                 320

Asp Thr Lys Tyr Gly Ile Lys Gly Ser Ala Leu Ala Phe Lys Asn Xaa
                325                 330                 335

Ser Phe Arg Val Xaa Val Arg Xaa Gly Tyr Leu Thr Leu Asn Thr Phe
            340                 345                 350

Val Ser Ala Leu Leu Pro Phe Leu Gly Asp Phe Met Ser Leu Thr Gly
        355                 360                 365

Ala Ile Ser Thr Phe Pro Leu Thr Phe Ile Leu Ala Asn His Met Tyr
    370                 375                 380

Leu Val Ala Asn Ala Asn Lys Leu Thr Ser Ile Gln Lys Leu Trp His
385                 390                 395                 400

Trp Ile Asn Ile Cys Phe Phe Ala Phe Met Ser Val Ala Ala Thr Ile
                405                 410                 415

Ala Ala Leu Arg Leu Ile Asp Leu Asp Ser Lys Thr Tyr His Val Phe
            420                 425                 430

Ala Asp Ile
        435


<210> SEQ ID NO 73
<211> LENGTH: 447
<212> TYPE: PRT
<213> ORGANISM: Avicennia marina
<220> FEATURE:
<221> NAME/KEY: misc_feature
<222> LOCATION: (1)..(447)
<223> OTHER INFORMATION: Public GI no. 21069018

<400> SEQUENCE: 73

Met Glu Ser Gln Gly Arg Glu Asp Val Val Gly Cys Ser Gly Ala Gly
1               5                   10                  15

Gly Arg Val His Ser Asp Gly His Ile Asp Ile Glu Ile Pro Glu Thr
            20                  25                  30

Ala His Gln Ile Ser Asn Asp Ser Trp Phe Gln Ala Gly Phe Val Leu
        35                  40                  45

Thr Thr Gly Ile Asn Ser Ala Tyr Val Leu Gly Tyr Pro Gly Ala Val
    50                  55                  60

Met Val Pro Leu Gly Trp Ile Gly Gly Val Ile Gly Leu Ile Leu Ala
65                  70                  75                  80

Thr Val Val Ser Leu His Ala Asn Ala Leu Val Ala Lys Leu His Asp
                85                  90                  95

Phe Gly Gly Lys Arg Arg Ile Arg Tyr Arg Asp Leu Ala Gly Ser Ile
            100                 105                 110

Tyr Gly Gly Lys Ala Tyr Ser Ile Thr Trp Gly Met Gln Tyr Val Asn
        115                 120                 125

Leu Val Met Ile Asn Val Gly Tyr Ile Ile Leu Ala Gly Asn Ser Leu
    130                 135                 140

Lys Ala Val Tyr Leu Leu Phe Arg Asp Asp His Val Met Lys Leu Pro
145                 150                 155                 160

His Phe Ile Ala Ile Ala Gly Leu Ala Cys Gly Leu Phe Ala Ile Ser
                165                 170                 175
```

```
Val Pro His Leu Ser Ala Leu Arg Asn Trp Leu Ala Phe Ser Thr Leu
            180                 185                 190

Phe Ser Met Ile Tyr Ile Val Gly Gly Ile Ala Leu Ala Ile Lys Asp
        195                 200                 205

Gly Phe Lys Ala Pro Pro Arg Asp Tyr Ser Ile Pro Gly Thr Lys Thr
    210                 215                 220

Ser Arg Ile Phe Thr Thr Ile Gly Ala Ser Ala Asn Leu Val Phe Ser
225                 230                 235                 240

Phe Asn Thr Gly Met Leu Pro Glu Ile Gln Ala Thr Val Arg Pro Pro
                245                 250                 255

Val Val Glu Asn Met Met Lys Gly Leu Tyr Phe Gln Phe Thr Val Gly
            260                 265                 270

Val Val Pro Met Tyr Ala Ile Ile Phe Ala Gly Tyr Trp Ala Tyr Gly
        275                 280                 285

Ser Thr Thr Ser Ser Tyr Leu Leu Asn Asn Val His Gly Pro Ile Trp
    290                 295                 300

Leu Lys Thr Thr Thr Asn Ile Ser Ala Phe Leu Gln Ser Val Ile Ala
305                 310                 315                 320

Leu His Ile Phe Ala Ser Pro Met Tyr Glu Phe Leu Asp Thr Lys Tyr
                325                 330                 335

Gly Ile Lys Gly Ser Ala Leu Ala Val Arg Asn Leu Ser Phe Arg Ile
            340                 345                 350

Leu Val Arg Gly Gly Tyr Val Ala Met Thr Ser Leu Val Ser Ala Leu
        355                 360                 365

Leu Pro Phe Leu Gly Asp Phe Met Ser Leu Thr Gly Ala Leu Ser Thr
    370                 375                 380

Phe Pro Leu Thr Phe Ile Leu Ala Asn His Met Tyr Leu Val Ala Asn
385                 390                 395                 400

Arg Asn Lys Met Ser Leu Leu Gln Lys Asn Trp His Trp Leu Asn Val
                405                 410                 415

Val Leu Phe Ser Cys Met Ala Val Ala Ala Ala Val Ala Ala Leu Arg
            420                 425                 430

Leu Ile Ala Val Asp Ser Arg Thr Tyr His Val Phe Ala Asp Ile
        435                 440                 445
```

<210> SEQ ID NO 74
<211> LENGTH: 453
<212> TYPE: PRT
<213> ORGANISM: Atriplex hortensis
<220> FEATURE:
<221> NAME/KEY: misc_feature
<222> LOCATION: (1)..(453)
<223> OTHER INFORMATION: Public GI no. 8571474

<400> SEQUENCE: 74

```
Met Ser Ser Tyr Asp Pro Glu Asn Ala Ala Thr Asn Gly Val Pro Pro
1               5                   10                  15

Val Lys Asn Asp Asn Ser Asn His Gln Gln Gln His Gln Gln Thr Val
            20                  25                  30

Val Val Pro Glu Thr Ala His Gln Ile Ser Thr Asp Ser Trp Leu Gln
        35                  40                  45

Val Gly Phe Val Leu Thr Thr Gly Ile Asn Ser Ala Tyr Val Leu Gly
    50                  55                  60

Tyr Ser Gly Ala Ile Met Val Pro Leu Gly Trp Ile Pro Ala Val Leu
65                  70                  75                  80
```

-continued

```
Gly Leu Ile Ala Ala Thr Leu Ile Ser Leu Tyr Ala Asn Ser Leu Val
                85                  90                  95

Ala Lys Leu His Glu Tyr Gly Gly Lys Arg His Ile Arg Tyr Arg Asp
            100                 105                 110

Leu Ala Gly Phe Ile Tyr Gly Pro Lys Ala Tyr Ser Leu Thr Trp Ala
        115                 120                 125

Leu Gln Tyr Ile Asn Leu Phe Met Ile Asn Thr Gly Phe Ile Ile Leu
    130                 135                 140

Ala Gly Ser Ser Ile Lys Ala Ala Tyr His Leu Phe Thr Asp Asp Pro
145                 150                 155                 160

Ala Leu Lys Leu Pro Tyr Cys Ile Ile Ile Ser Gly Phe Val Cys Ala
                165                 170                 175

Leu Phe Ala Ile Gly Ile Pro His Leu Ser Ala Leu Arg Ile Trp Leu
            180                 185                 190

Gly Val Ser Thr Phe Phe Gly Leu Ile Tyr Ile Ile Ile Ala Ile Ala
        195                 200                 205

Leu Ser Leu Lys Asp Gly Ile Asn Ser Pro Pro Arg Asp Tyr Ser Val
    210                 215                 220

Pro Thr Glu Arg Gly Lys Val Phe Thr Thr Ile Gly Ala Ala Ala Asn
225                 230                 235                 240

Leu Val Phe Ala Phe Asn Thr Gly Met Leu Pro Glu Ile Gln Ala Thr
                245                 250                 255

Val Arg Lys Pro Val Val Gly Asn Met Met Lys Gly Leu Tyr Phe Gln
            260                 265                 270

Phe Thr Ala Gly Val Val Pro Met Tyr Ala Ile Val Phe Ile Gly Tyr
        275                 280                 285

Trp Ala Tyr Gly Asn Lys Thr Asp Ser Tyr Leu Leu Asn Asn Val His
    290                 295                 300

Gly Pro Val Trp Leu Lys Ala Leu Ala Asn Ile Ser Thr Phe Leu Gln
305                 310                 315                 320

Thr Val Ile Ala Leu His Ile Phe Ala Ser Pro Met Tyr Glu Tyr Leu
                325                 330                 335

Asp Thr Arg Phe Gly Ile Thr Gly Ser Ala Leu Asn Pro Lys Asn Leu
            340                 345                 350

Gly Ser Arg Val Leu Ile Arg Gly Gly Tyr Leu Ala Val Asn Thr Phe
        355                 360                 365

Val Ala Ala Leu Leu Pro Phe Leu Gly Asp Phe Met Ser Leu Thr Gly
    370                 375                 380

Ala Ile Ser Thr Phe Pro Leu Thr Phe Ile Leu Ala Asn His Met Tyr
385                 390                 395                 400

Phe Lys Ala Lys Arg Asn Lys Leu Ser Met Ala Met Lys Ile Trp Leu
                405                 410                 415

Trp Ile Asn Ile Val Phe Phe Ser Cys Met Ala Val Ala Ser Phe Ile
            420                 425                 430

Ala Ala Leu Arg Leu Ile Ala Thr Asp Ser Lys Gln Tyr His Val Phe
        435                 440                 445

Ala Asp Leu Glu Gly
    450
```

<210> SEQ ID NO 75
<211> LENGTH: 434
<212> TYPE: PRT
<213> ORGANISM: Oryza sativa (japonica cultivar-group)
<220> FEATURE:
<221> NAME/KEY: misc_feature

```
<222> LOCATION: (1)..(434)
<223> OTHER INFORMATION: Public GI no. 50933631

<400> SEQUENCE: 75

Met Asn Ile Asp Met Ala Asn Ser Asp Asp Lys Ala Leu Ile Ser Glu
1               5                   10                  15

Asp Thr Ala His Gln Ile Ser Ala Asp Pro Trp Tyr Gln Val Gly Phe
            20                  25                  30

Val Leu Thr Thr Gly Val Asn Ser Ala Tyr Val Leu Gly Tyr Ser Gly
        35                  40                  45

Ser Val Met Val Pro Leu Gly Trp Ile Gly Gly Thr Cys Gly Leu Ile
    50                  55                  60

Leu Ala Ala Ala Ile Ser Leu Tyr Ala Asn Ala Leu Leu Ala Arg Leu
65                  70                  75                  80

His Glu Ile Gly Gly Lys Arg His Ile Arg Tyr Arg Asp Leu Ala Gly
                85                  90                  95

His Ile Tyr Gly Arg Lys Met Tyr Ser Leu Thr Trp Ala Leu Gln Tyr
            100                 105                 110

Val Asn Leu Phe Met Ile Asn Thr Gly Phe Ile Ile Leu Ala Gly Gln
        115                 120                 125

Ala Leu Lys Ala Thr Tyr Val Leu Phe Arg Asp Asp Gly Val Leu Lys
    130                 135                 140

Leu Pro Tyr Cys Ile Ala Leu Ser Gly Phe Val Cys Ala Leu Phe Ala
145                 150                 155                 160

Phe Gly Ile Pro Tyr Leu Ser Ala Leu Arg Ile Trp Leu Gly Phe Ser
                165                 170                 175

Thr Phe Phe Ser Leu Ile Tyr Ile Thr Ile Ala Phe Val Leu Ser Leu
            180                 185                 190

Arg Asp Gly Ile Thr Thr Pro Ala Lys Asp Tyr Thr Ile Pro Gly Ser
        195                 200                 205

His Ser Ala Arg Ile Phe Thr Thr Ile Gly Ala Val Ala Asn Leu Val
    210                 215                 220

Phe Ala Tyr Asn Thr Gly Met Leu Pro Glu Ile Gln Ala Thr Ile Arg
225                 230                 235                 240

Pro Pro Val Val Lys Asn Met Glu Lys Ala Leu Trp Phe Gln Phe Thr
                245                 250                 255

Val Gly Ser Leu Pro Leu Tyr Ala Val Thr Phe Met Gly Tyr Trp Ala
            260                 265                 270

Tyr Gly Ser Ser Thr Ser Ser Tyr Leu Leu Asn Ser Val Lys Gly Pro
        275                 280                 285

Val Trp Val Lys Ala Met Ala Asn Leu Ser Ala Phe Leu Gln Thr Val
    290                 295                 300

Ile Ala Leu His Ile Phe Ala Ser Pro Met Tyr Glu Phe Leu Asp Thr
305                 310                 315                 320

Lys Tyr Gly Ser Gly His Gly Gly Pro Phe Ala Ile His Asn Val Met
                325                 330                 335

Phe Arg Val Gly Val Arg Gly Gly Tyr Leu Thr Val Asn Thr Leu Val
            340                 345                 350

Ala Ala Met Leu Pro Phe Leu Gly Asp Phe Met Ser Leu Thr Gly Ala
        355                 360                 365

Leu Ser Thr Phe Pro Leu Thr Phe Val Leu Ala Asn His Met Tyr Leu
    370                 375                 380

Met Val Lys Arg His Lys Leu Ser Thr Leu Gln Ile Ser Trp His Trp
385                 390                 395                 400
```

```
Leu Asn Val Ala Gly Phe Ser Leu Leu Ser Ile Ala Ala Ala Val Ala
                405                 410                 415

Ala Leu Arg Leu Ile Met Val Asp Ser Arg Thr Tyr His Leu Phe Ala
            420                 425                 430

Asp Leu


<210> SEQ ID NO 76
<211> LENGTH: 473
<212> TYPE: PRT
<213> ORGANISM: Oryza sativa (japonica cultivar-group)
<220> FEATURE:
<221> NAME/KEY: misc_feature
<222> LOCATION: (1)..(473)
<223> OTHER INFORMATION: Public GI no. 53749423

<400> SEQUENCE: 76

Met Asp Gln His Gln Leu Asp Glu Glu Asn Gln Arg Ala Ala Leu Phe
1               5                   10                  15

His Ser Ser Ala Pro Ser Ser Ser Leu Gly Ala Asp Gly Glu Glu Glu
            20                  25                  30

Arg Glu Thr Val Pro Leu Leu Ser Cys Lys Met Ala Asp Asp Lys Ser
        35                  40                  45

Asp Thr Val Gln Val Ser Glu Asp Thr Ala His Gln Ile Ser Ile Asp
    50                  55                  60

Pro Trp Tyr Gln Val Gly Phe Ile Leu Thr Thr Gly Val Asn Ser Ala
65                  70                  75                  80

Tyr Val Leu Gly Tyr Ser Ala Ser Ile Met Val Pro Leu Gly Trp Ile
                85                  90                  95

Gly Gly Thr Cys Gly Leu Ile Leu Ala Ala Ala Ile Ser Met Tyr Ala
            100                 105                 110

Asn Ala Leu Leu Ala His Leu His Glu Val Gly Gly Lys Arg His Ile
        115                 120                 125

Arg Tyr Arg Asp Leu Ala Gly His Ile Tyr Gly Arg Lys Met Tyr Ser
    130                 135                 140

Leu Thr Trp Ala Leu Gln Tyr Val Asn Leu Phe Met Ile Asn Thr Gly
145                 150                 155                 160

Leu Ile Ile Leu Ala Gly Gln Ala Leu Lys Ala Ile Tyr Val Leu Phe
                165                 170                 175

Arg Asp Asp Gly Val Leu Lys Leu Pro Tyr Cys Ile Ala Leu Ser Gly
            180                 185                 190

Phe Val Cys Ala Leu Phe Ala Phe Gly Ile Pro Tyr Leu Ser Ala Leu
        195                 200                 205

Arg Ile Trp Leu Gly Leu Ser Thr Val Phe Ser Leu Ile Tyr Ile Met
    210                 215                 220

Ile Ala Phe Val Met Ser Leu Arg Asp Gly Ile Thr Thr Pro Ala Lys
225                 230                 235                 240

Asp Tyr Thr Ile Pro Gly Ser His Ser Asp Arg Ile Phe Thr Thr Ile
                245                 250                 255

Gly Ala Val Ala Asn Leu Val Phe Ala Tyr Asn Thr Gly Met Leu Pro
            260                 265                 270

Glu Ile Gln Ala Thr Ile Arg Pro Pro Val Val Lys Asn Met Glu Lys
        275                 280                 285

Ala Leu Trp Phe Gln Phe Thr Val Gly Ser Leu Pro Leu Tyr Ala Val
    290                 295                 300

Thr Phe Met Gly Tyr Trp Ala Tyr Gly Ser Ser Thr Ser Ser Tyr Leu
```

-continued

```
305                 310                 315                 320

Leu Asn Ser Val Lys Gly Pro Ile Trp Ile Lys Thr Val Ala Asn Leu
                325                 330                 335

Ser Ala Phe Leu Gln Thr Val Ile Ala Leu His Ile Phe Ala Ser Pro
            340                 345                 350

Met Tyr Glu Phe Leu Asp Thr Arg Phe Gly Ser Gly His Gly Gly Pro
        355                 360                 365

Phe Ala Ile His Asn Ile Met Phe Arg Val Gly Val Arg Gly Gly Tyr
    370                 375                 380

Leu Thr Val Asn Thr Leu Val Ala Ala Met Leu Pro Phe Leu Gly Asp
385                 390                 395                 400

Phe Met Ser Leu Thr Gly Ala Leu Ser Thr Phe Pro Leu Thr Phe Val
                405                 410                 415

Leu Ala Asn His Met Tyr Leu Thr Val Lys Gln Asn Lys Met Ser Ile
            420                 425                 430

Phe Arg Lys Cys Trp His Trp Leu Asn Val Val Gly Phe Ser Cys Leu
        435                 440                 445

Ser Val Ala Ala Ala Val Ala Ala Val Arg Leu Ile Thr Val Asp Tyr
    450                 455                 460

Ser Thr Tyr His Leu Phe Ala Asp Met
465                 470


<210> SEQ ID NO 77
<211> LENGTH: 442
<212> TYPE: PRT
<213> ORGANISM: Lycopersicon esculentum
<220> FEATURE:
<221> NAME/KEY: misc_feature
<222> LOCATION: (1)..(442)
<223> OTHER INFORMATION: Public GI no. 4584852

<400> SEQUENCE: 77

Met Ala Thr Thr Ser Phe His His Pro Leu Leu Pro Asn Val His Asn
1               5                   10                  15

Asp Asp Glu Leu Ala Ile His Ile Pro Ser Ser Ala His Gln Val Ser
            20                  25                  30

Asn Asp Ser Trp Phe Gln Val Gly Val Val Leu Ser Thr Gly Ile Asn
        35                  40                  45

Ser Ala Phe Ala Leu Gly Tyr Ala Gly Leu Ile Met Val Pro Leu Gly
    50                  55                  60

Trp Val Gly Gly Val Val Gly Leu Ile Leu Ser Ser Ala Ile Ser Leu
65                  70                  75                  80

Tyr Ala Ser Thr Leu Ile Ala Lys Leu His Glu Tyr Gly Gly Arg Arg
                85                  90                  95

His Ile Arg Tyr Arg Asp Leu Ala Gly Phe Met Tyr Gly Gln Thr Ala
            100                 105                 110

Tyr Ser Leu Val Trp Ala Ser Gln Tyr Ala Asn Leu Phe Leu Ile Asn
        115                 120                 125

Thr Gly Tyr Val Ile Leu Gly Gly Gln Ala Leu Lys Ala Phe Tyr Val
    130                 135                 140

Leu Phe Arg Asp Asp His Gln Met Lys Leu Pro His Phe Ile Ala Val
145                 150                 155                 160

Ala Gly Leu Ala Cys Val Leu Phe Ala Ile Ala Ile Pro His Leu Ser
                165                 170                 175

Ala Leu Arg Ile Trp Leu Gly Phe Ser Thr Phe Phe Ser Leu Val Tyr
            180                 185                 190
```

```
Ile Cys Ile Val Ile Thr Leu Ser Leu Lys Asp Gly Leu Glu Ala Pro
        195                 200                 205

Pro Arg Asp Tyr Ser Ile Pro Gly Thr Lys Asn Ser Lys Thr Trp Ala
    210                 215                 220

Thr Ile Gly Ala Ala Ala Asn Leu Val Phe Ala Tyr Asn Thr Gly Met
225                 230                 235                 240

Leu Pro Glu Ile Gln Ala Thr Val Arg Glu Pro Val Val Asp Asn Met
                245                 250                 255

Ile Lys Ala Leu Asn Phe Gln Phe Thr Leu Gly Val Ile Pro Met His
            260                 265                 270

Ala Val Thr Tyr Ile Gly Tyr Trp Ala Tyr Gly Ser Ser Ala Ser Ser
        275                 280                 285

Tyr Leu Leu Asn Asn Val Ser Gly Pro Ile Trp Leu Lys Gly Met Ala
    290                 295                 300

Asn Ile Ala Ala Phe Leu Gln Ser Ile Ile Ala Leu His Ile Phe Ala
305                 310                 315                 320

Ser Pro Thr Tyr Glu Phe Leu Asp Thr Lys Tyr Gly Val Thr Gly Ser
                325                 330                 335

Ala Leu Ala Cys Lys Asn Leu Ala Phe Arg Ile Ile Val Arg Gly Gly
            340                 345                 350

Tyr Ile Ala Ile Thr Ala Phe Leu Ser Ala Leu Leu Pro Phe Leu Gly
        355                 360                 365

Asp Phe Met Asn Leu Ala Gly Ala Ile Ser Thr Phe Pro Leu Thr Phe
    370                 375                 380

Ile Leu Pro Asn His Met Tyr Ile Val Ala Lys Arg Lys Lys Leu Ser
385                 390                 395                 400

Phe Leu Lys Lys Ser Trp His Trp Leu Asn Ile Ile Phe Phe Ser Cys
                405                 410                 415

Ile Ala Val Ala Ala Phe Val Ala Ala Leu Arg Phe Ile Thr Val Asp
            420                 425                 430

Ser Thr Thr Tyr His Val Phe Ala Asp Leu
        435                 440


<210> SEQ ID NO 78
<211> LENGTH: 450
<212> TYPE: PRT
<213> ORGANISM: Hordeum vulgare subsp. vulgare
<220> FEATURE:
<221> NAME/KEY: misc_feature
<222> LOCATION: (1)..(450)
<223> OTHER INFORMATION: Public GI no. 16215723

<400> SEQUENCE: 78

Met Ala Met Pro Pro Ala Glu Lys Val Ile Val Val Asp Ala Asn Pro
1               5                   10                  15

Ser Lys Asn Gly His Gly Asp Glu Ile Asp Asp Leu Pro Val Ala Asp
            20                  25                  30

Ala Thr Ser His Gln Ile Gly Val Asp Pro Trp Tyr Gln Val Ala Phe
        35                  40                  45

Val Leu Thr Thr Gly Val Asn Ser Ala Tyr Val Leu Gly Tyr Ser Gly
    50                  55                  60

Ser Leu Met Val Pro Leu Gly Trp Val Gly Gly Thr Val Gly Leu Leu
65                  70                  75                  80

Leu Ala Ala Ala Val Ser Met Tyr Ala Asn Ala Leu Leu Gly Arg Leu
                85                  90                  95
```

-continued

```
His Leu Leu Gly Gly Lys Arg His Ile Arg Tyr Arg Asp Leu Ala Gly
            100                 105                 110

His Ile Tyr Gly Pro Lys Met Tyr Arg Leu Thr Trp Ala Met Gln Tyr
        115                 120                 125

Val Asn Leu Phe Met Ile Asn Thr Gly Phe Ile Ile Ile Ala Gly Gln
    130                 135                 140

Ala Leu Lys Ala Leu Tyr Leu Leu Ile Ser Asn Asp Gly Ala Met Lys
145                 150                 155                 160

Leu Pro Tyr Cys Ile Ala Val Ser Gly Phe Val Cys Ala Leu Phe Ala
                165                 170                 175

Phe Gly Ile Pro Tyr Leu Ser Ala Leu Arg Ile Trp Leu Gly Phe Ser
            180                 185                 190

Thr Val Phe Ser Leu Thr Tyr Ile Val Ala Ala Cys Thr Leu Ser Leu
        195                 200                 205

Lys Asp Gly Met Arg Ser Pro Pro Arg Asp Tyr Ser Ile Gln Gly Asp
    210                 215                 220

Pro Ser Ser Arg Val Phe Thr Thr Ile Gly Ala Ala Ala Ser Leu Val
225                 230                 235                 240

Phe Ala Tyr Asn Thr Gly Met Leu Pro Glu Ile Gln Ala Thr Val Arg
                245                 250                 255

Ala Pro Val Val Lys Asn Met Glu Lys Ala Leu Trp Phe Gln Phe Thr
            260                 265                 270

Ala Gly Cys Val Pro Leu Tyr Ala Ile Ile Val Ile Gly Tyr Trp Ala
        275                 280                 285

Tyr Gly Asn Gln Thr Thr Thr Tyr Leu Leu Asn Asn Val His Gly Pro
    290                 295                 300

Val Trp Ile Lys Ala Val Ala Asn Leu Ser Ala Phe Leu Gln Thr Val
305                 310                 315                 320

Ile Ala Leu His Ile Phe Ala Ser Pro Met Tyr Glu Tyr Leu Asp Thr
                325                 330                 335

Arg Phe Gly Ser Lys Val Gly Gly Pro Phe Ala Met His Asn Val Ile
            340                 345                 350

Phe Arg Val Gly Val Arg Gly Gly Tyr Leu Ala Val Asn Thr Leu Met
        355                 360                 365

Ala Ala Met Leu Pro Phe Leu Gly Asp Phe Met Ser Leu Thr Gly Ala
    370                 375                 380

Leu Ser Thr Phe Pro Leu Thr Phe Val Leu Ala Asn His Met Tyr Leu
385                 390                 395                 400

Val Ser Asn Arg Gln Arg Leu Ser Ser Leu Gln Lys Ser Trp His Trp
                405                 410                 415

Leu Asn Ile Val Phe Phe Thr Ile Leu Ser Ile Thr Ala Ala Ile Ala
            420                 425                 430

Ala Leu Arg Leu Ile Ala Arg Asp Ser Lys Glu Tyr His Ile Phe Ala
        435                 440                 445

Asp Val
    450
```

```
<210> SEQ ID NO 79
<211> LENGTH: 441
<212> TYPE: PRT
<213> ORGANISM: Lycopersicon esculentum
<220> FEATURE:
<221> NAME/KEY: misc_feature
<222> LOCATION: (1)..(441)
<223> OTHER INFORMATION: Public GI no. 4584848
```

<400> SEQUENCE: 79

```
Met Gly Asn Asn Arg Tyr Asn Ser Pro Ser Arg Glu Asp Lys Asn Asp
1               5                   10                  15

Glu Glu Ala Ser Val Ile Ile Pro Glu Thr Ala His Gln Val Ser Asn
            20                  25                  30

Asp Ser Trp Phe Gln Val Gly Val Val Leu Ser Met Gly Val Asn Ser
        35                  40                  45

Ala Tyr Ala Leu Gly Tyr Ser Gly Thr Ile Met Val Pro Leu Gly Trp
    50                  55                  60

Ile Gly Gly Val Val Gly Leu Val Met Ser Thr Ile Val Ser Leu Tyr
65                  70                  75                  80

Ala Ser Thr Ile Met Ala Lys Leu His Glu Val Gly Gly Lys Arg His
                85                  90                  95

Ile Arg Tyr Arg Asp Leu Ala Gly Phe Leu Tyr Gly Arg Thr Ala Tyr
            100                 105                 110

Leu Leu Ile Trp Ala Leu Gln Tyr Ala Asn Leu Phe Leu Ile Asn Ile
        115                 120                 125

Gly Tyr Val Ile Met Ser Gly Ser Ala Leu Lys Ala Phe Tyr Met Leu
    130                 135                 140

Phe Arg Asp Asp His Met Leu Lys Leu Pro His Phe Ile Ala Ile Ala
145                 150                 155                 160

Gly Val Ala Cys Ile Leu Phe Ala Ile Ala Thr Pro His Leu Ser Ala
                165                 170                 175

Leu Arg Val Trp Leu Gly Phe Ser Thr Leu Phe Met Ile Leu Tyr Leu
            180                 185                 190

Ala Ile Ala Phe Val Leu Ser Val Gln Asp Gly Val Lys Ala Pro Pro
        195                 200                 205

Arg Asp Tyr His Ile Pro Gly Ser Gly Glu Asn Lys Ile Trp Ala Ile
    210                 215                 220

Ile Gly Ala Ile Gly Asn Leu Phe Phe Ala Phe Asn Thr Gly Met Ile
225                 230                 235                 240

Pro Glu Ile Gln Ala Thr Ile Arg Gln Pro Val Val Gly Asn Met Val
                245                 250                 255

Lys Ala Leu Asn Phe Gln Phe Thr Val Gly Val Val Pro Met His Ala
            260                 265                 270

Val Thr Tyr Ile Gly Tyr Trp Ala Tyr Gly Ser Val Val Ser Ser Tyr
        275                 280                 285

Leu Leu Asn Asn Val His Gly Pro Ala Trp Val Leu Gly Val Ala His
    290                 295                 300

Leu Ser Ala Phe Phe Gln Ala Ile Ile Thr Leu His Ile Phe Ala Ser
305                 310                 315                 320

Pro Thr Tyr Glu Tyr Leu Asp Thr Lys Tyr Gly Val Lys Gly Ser Ala
                325                 330                 335

Leu Ala Pro Arg Asn Ile Leu Phe Arg Leu Val Val Arg Gly Gly Tyr
            340                 345                 350

Leu Val Met Thr Thr Phe Leu Ser Ala Leu Leu Pro Phe Leu Gly Asn
        355                 360                 365

Phe Met Ser Leu Thr Gly Ala Ile Ser Thr Ile Pro Leu Thr Phe Ile
    370                 375                 380

Leu Pro Asn His Met Tyr Ile Ile Ala Lys Lys Asp Lys Leu Asn Ser
385                 390                 395                 400

Leu Gln Lys Ser Trp His Trp Leu Asn Ile Val Val Phe Gly Cys Val
                405                 410                 415
```

```
Ser Val Ala Ala Phe Val Ala Ala Leu Lys Leu Thr Val Val Gln Thr
            420                 425                 430

Gln Thr Tyr His Val Phe Ala Asp Leu
        435                 440


<210> SEQ ID NO 80
<211> LENGTH: 439
<212> TYPE: PRT
<213> ORGANISM: Lycopersicon esculentum
<220> FEATURE:
<221> NAME/KEY: misc_feature
<222> LOCATION: (1)..(439)
<223> OTHER INFORMATION: Public GI no. 4584850

<400> SEQUENCE: 80

Met Gly Glu Glu Lys Glu Val Ile Ser His Val Ile Thr Thr Pro Pro
1               5                   10                  15

Phe Glu Val Glu Val Pro Lys Thr Leu His Gln Ile Gly Gln Asp Ser
            20                  25                  30

Trp Phe Gln Val Gly Leu Val Leu Thr Thr Thr Val Asn Cys Ala Tyr
        35                  40                  45

Ala Leu Gly Tyr Ala Gly Thr Ile Met Val Pro Leu Gly Trp Ile Gly
    50                  55                  60

Gly Val Thr Gly Met Val Leu Ser Thr Ile Ile Ser Leu Tyr Ala Ser
65                  70                  75                  80

Thr Leu Met Ala Lys Ile His Gln Tyr Gly Glu Lys Arg His Ile Arg
                85                  90                  95

Tyr Arg Asp Leu Ala Gly Phe Met Tyr Gly Tyr Arg Ala Tyr Ala Ile
            100                 105                 110

Val Trp Gly Leu Gln Tyr Ala Asn Leu Phe Leu Ile Asn Ile Gly Phe
        115                 120                 125

Ile Ile Leu Gly Gly Gln Ala Leu Lys Ala Phe Tyr Leu Leu Phe Arg
    130                 135                 140

Glu Asp His Glu Met Lys Leu Pro Tyr Phe Ile Ile Ile Ala Gly Leu
145                 150                 155                 160

Ala Cys Val Phe Phe Ala Val Ser Val Pro His Leu Ser Ala Leu Gly
                165                 170                 175

Val Trp Met Ala Val Ser Thr Phe Leu Ser Ile Val Tyr Phe Ser Ile
            180                 185                 190

Ala Phe Ala Leu Cys Leu Lys Asp Gly Ile Asn Ala Pro Pro Arg Asp
        195                 200                 205

Tyr Ser Ile Pro Gly Ser Ser Ser Ser Arg Thr Phe Thr Thr Ile Gly
    210                 215                 220

Ala Ala Ala Ser Leu Val Phe Val Tyr Asn Thr Gly Met Ile Pro Glu
225                 230                 235                 240

Ile Gln Ala Thr Val Arg Ala Pro Val Val Asp Asn Met Leu Lys Ala
                245                 250                 255

Leu Tyr Phe Gln Phe Thr Ile Gly Ala Val Pro Val His Ala Val Thr
            260                 265                 270

Tyr Met Gly Tyr Trp Ala Tyr Gly Ser Lys Ser Ser Ser Tyr Leu Leu
        275                 280                 285

Tyr Asn Val Ser Gly Pro Val Trp Leu Arg Gly Leu Ala Asn Ile Ala
    290                 295                 300

Ala Phe Phe Gln Ser Ile Ile Thr Leu His Ile Phe Ala Ser Pro Thr
305                 310                 315                 320
```

-continued

```
Tyr Glu Tyr Leu Asp Thr Lys Tyr Arg Ile Ser Gly Ser Val Leu Ala
            325                 330                 335

Phe Arg Asn Leu Ser Phe Arg Thr Val Val Arg Gly Gly Tyr Leu Ala
            340                 345                 350

Ile Thr Ile Phe Leu Ser Ala Leu Leu Pro Phe Leu Gly Asp Phe Met
        355                 360                 365

Ser Phe Thr Gly Ala Ile Ser Thr Ile Pro Leu Thr Phe Ile Leu Pro
    370                 375                 380

Asn His Met Tyr Ile Val Ala Met Arg Lys Gln Ile Ser Ser Leu Gln
385                 390                 395                 400

Lys Ser Trp His Trp Phe Asn Ile Val Phe Phe Ser Cys Leu Ala Val
            405                 410                 415

Ala Ala Leu Val Ala Ala Val Arg Leu Ile Ala Met Asp Ser Lys Thr
            420                 425                 430

Tyr His Ala Phe Ala Asp Leu
        435


<210> SEQ ID NO 81
<211> LENGTH: 446
<212> TYPE: PRT
<213> ORGANISM: Avicennia marina
<220> FEATURE:
<221> NAME/KEY: misc_feature
<222> LOCATION: (1)..(446)
<223> OTHER INFORMATION: Public GI no. 21069016

<400> SEQUENCE: 81

Met Asp Val Arg Gly Gly Glu Asp Val Thr Gly Gly Ser Gly Ala Gly
1               5                   10                  15

Arg Lys Val His Ser Glu Asp Met Ala Val Glu Val Pro Glu Thr Ala
            20                  25                  30

His Gln Ile Ser Asn Asp Ser Trp Leu Gln Ala Gly Phe Val Leu Thr
        35                  40                  45

Thr Gly Val Asn Ser Ala Tyr Val Leu Gly Tyr Ser Gly Ala Val Met
    50                  55                  60

Val Pro Leu Gly Trp Ile Gly Gly Val Val Gly Leu Ile Leu Ala Thr
65                  70                  75                  80

Leu Val Ser Leu His Ala Asn Ala Leu Val Ala Gln Leu His Glu Tyr
                85                  90                  95

Gly Gly Lys Arg His Ile Arg Tyr Arg Asp Leu Ala Gly Arg Ile Tyr
            100                 105                 110

Gly Arg Arg Ala Tyr Ser Val Thr Trp Gly Met Gln Tyr Val Asn Leu
        115                 120                 125

Phe Met Ile Asn Val Gly Phe Val Ile Leu Ala Gly Asn Ser Leu Lys
    130                 135                 140

Ala Val Tyr Thr Leu Phe Arg His Asp His Val Met Lys Leu Pro His
145                 150                 155                 160

Phe Ile Ala Ile Ala Ala Ile Ala Cys Gly Leu Phe Ala Ile Ser Ile
                165                 170                 175

Pro His Leu Ser Ala Met Arg Ile Trp Leu Ala Phe Ser Met Phe Phe
            180                 185                 190

Ser Leu Val Tyr Ile Ile Val Gly Phe Ala Leu Ser Leu Lys Asp Gly
        195                 200                 205

Ile Glu Ala Pro Pro Arg Asp Tyr Thr Leu Pro Glu Lys Gly Ala Asp
    210                 215                 220

Lys Val Phe Thr Ile Ile Gly Ala Ala Ala Glu Leu Val Phe Ser Phe
```

-continued

```
225                 230                 235                 240

Asn Thr Gly Met Leu Pro Glu Ile Gln Ala Thr Val Arg Pro Pro Val
                245                 250                 255

Ile Gly Asn Met Met Lys Ala Leu Tyr Phe Gln Phe Thr Val Gly Val
            260                 265                 270

Val Pro Met Tyr Ser Ile Ile Phe Val Gly Tyr Trp Ala Tyr Gly Ser
        275                 280                 285

Lys Thr Thr Ser Tyr Leu Leu Asn Asn Val His Gly Pro Ile Trp Leu
    290                 295                 300

Met Thr Val Ala Asn Ile Ala Ala Phe Leu Gln Ser Val Ile Ser Leu
305                 310                 315                 320

His Ile Phe Ala Ser Pro Met Tyr Glu Ile Trp Ile Pro Asp Leu Glu
                325                 330                 335

Ser Lys Glu Val Leu Trp Pro Ile Arg Asn Leu Ser Phe Arg Val Val
            340                 345                 350

Val Arg Gly Gly Tyr Val Ala Thr Thr Ala Phe Val Ser Ala Leu Leu
        355                 360                 365

Pro Phe Leu Gly Asp Phe Met Ser Leu Thr Gly Ala Ile Ser Thr Phe
    370                 375                 380

Pro Leu Thr Phe Ile Leu Ala Asn His Met Tyr Leu Val Ala Lys Gly
385                 390                 395                 400

Asn Lys Leu Ser Pro Leu His Lys Thr Gly Leu Trp Leu Asn Ile Gly
                405                 410                 415

Phe Phe Gly Cys Leu Ala Val Ala Ala Ala Val Ala Ala Leu Arg Glu
            420                 425                 430

Ile Val Val Asp Ser Lys Thr Tyr His Leu Phe Ala Asp Ile
        435                 440                 445
```

<210> SEQ ID NO 82
<211> LENGTH: 831
<212> TYPE: DNA
<213> ORGANISM: Arabidopsis thaliana
<220> FEATURE:
<221> NAME/KEY: misc_feature
<222> LOCATION: (1)..(831)
<223> OTHER INFORMATION: Ceres CDNA ID no. 5669462
<220> FEATURE:
<221> NAME/KEY: CDS
<222> LOCATION: (1)..(828)
<223> OTHER INFORMATION: Referenced by SEQ ID NO: 83

<400> SEQUENCE: 82

```
atggcggctt ctacattgta caaatcctgt cttcttcaac ccaagtctgg ctccaccact     60

cgccgcctaa acccttctct cgttaaccct cttacgaatc ccacaagagt ttccgttttg    120

gggaagagtc gtagagatgt ctttgcgaaa gcttcgattg aaatggcgga atcgaattcg    180

ataccttccg ttgttgtcaa ttcctctaag cagcatggtc caatcatcgt gattgataat    240

tacgacagct tcacatacaa tctctgccag tatatgggag agctaggatg ccattttgaa    300

gtttaccgca atgatgaact tacagtagaa gagctgaaaa aaaaaaatcc aagaggggtg    360

ttgatttctc cagggcctgg tacccctcaa gactctggga tttccttgca aactgttttg    420

gaactcggac cacttgttcc tttatttgga gtatgtatgg gtttgcagtg tataggagaa    480

gcatttggag gaaagattgt gcggtcacca tttggtgtta tgcatgggaa aagctcaatg    540

gttcactatg atgagaaagg agaagaaggc ttgttctctg gattatcaaa ccctttcatt    600

gtaggtagat atcacagtct cgtgatcgaa aaagatacat ttcctagtga tgaactcgag    660
```

```
gttacagcat ggacagaaga tggtctggta atggctgccc gtcacagaaa gtacaagcat    720

atacagggag tccaatttca tccggagagt attataacaa ctgagggcaa gacaattgtc    780

cgcaatttca tcaaaatagt agagaaaaag gagtccgaga agctgacata g             831


<210> SEQ ID NO 83
<211> LENGTH: 276
<212> TYPE: PRT
<213> ORGANISM: Arabidopsis thaliana
<220> FEATURE:
<221> NAME/KEY: misc_feature
<222> LOCATION: (76)..(266)
<223> OTHER INFORMATION: Pfam Name: GATase; Pfam Description: Glutamine
      amidotransferase class-I

<400> SEQUENCE: 83

Met Ala Ala Ser Thr Leu Tyr Lys Ser Cys Leu Leu Gln Pro Lys Ser
1               5                   10                  15

Gly Ser Thr Thr Arg Arg Leu Asn Pro Ser Leu Val Asn Pro Leu Thr
            20                  25                  30

Asn Pro Thr Arg Val Ser Val Leu Gly Lys Ser Arg Arg Asp Val Phe
        35                  40                  45

Ala Lys Ala Ser Ile Glu Met Ala Glu Ser Asn Ser Ile Pro Ser Val
    50                  55                  60

Val Val Asn Ser Ser Lys Gln His Gly Pro Ile Ile Val Ile Asp Asn
65                  70                  75                  80

Tyr Asp Ser Phe Thr Tyr Asn Leu Cys Gln Tyr Met Gly Glu Leu Gly
                85                  90                  95

Cys His Phe Glu Val Tyr Arg Asn Asp Glu Leu Thr Val Glu Glu Leu
            100                 105                 110

Lys Lys Lys Asn Pro Arg Gly Val Leu Ile Ser Pro Gly Pro Gly Thr
        115                 120                 125

Pro Gln Asp Ser Gly Ile Ser Leu Gln Thr Val Leu Glu Leu Gly Pro
    130                 135                 140

Leu Val Pro Leu Phe Gly Val Cys Met Gly Leu Gln Cys Ile Gly Glu
145                 150                 155                 160

Ala Phe Gly Gly Lys Ile Val Arg Ser Pro Phe Gly Val Met His Gly
                165                 170                 175

Lys Ser Ser Met Val His Tyr Asp Glu Lys Gly Glu Glu Gly Leu Phe
            180                 185                 190

Ser Gly Leu Ser Asn Pro Phe Ile Val Gly Arg Tyr His Ser Leu Val
        195                 200                 205

Ile Glu Lys Asp Thr Phe Pro Ser Asp Glu Leu Glu Val Thr Ala Trp
    210                 215                 220

Thr Glu Asp Gly Leu Val Met Ala Ala Arg His Arg Lys Tyr Lys His
225                 230                 235                 240

Ile Gln Gly Val Gln Phe His Pro Glu Ser Ile Ile Thr Thr Glu Gly
                245                 250                 255

Lys Thr Ile Val Arg Asn Phe Ile Lys Ile Val Glu Lys Lys Glu Ser
            260                 265                 270

Glu Lys Leu Thr
        275


<210> SEQ ID NO 84
<211> LENGTH: 273
<212> TYPE: PRT
<213> ORGANISM: Arabidopsis thaliana
<220> FEATURE:
```

<221> NAME/KEY: misc_feature
<222> LOCATION: (1)..(273)
<223> OTHER INFORMATION: Public GI no. 21594026

<400> SEQUENCE: 84

```
Met Ala Ala Thr Thr Leu Tyr Asn Ser Cys Leu Leu Gln Pro Lys Tyr
1               5                   10                  15

Gly Phe Thr Thr Arg Arg Leu Asn Gln Ser Leu Val Asn Pro Leu Thr
            20                  25                  30

Asn Pro Thr Arg Val Ser Val Leu Trp Lys Ser Arg Arg Asp Val Ile
        35                  40                  45

Ala Lys Ala Ser Ile Glu Met Ala Glu Ser Asn Ser Ile Ser Ser Val
    50                  55                  60

Val Val Asn Ser Ser Gly Pro Ile Ile Val Ile Asp Asn Tyr Asp Ser
65                  70                  75                  80

Phe Thr Tyr Asn Leu Cys Gln Tyr Met Gly Glu Leu Gly Cys His Phe
                85                  90                  95

Glu Val Tyr Arg Asn Asp Glu Leu Thr Val Glu Glu Leu Lys Arg Lys
            100                 105                 110

Lys Pro Arg Gly Leu Leu Ile Ser Pro Gly Pro Gly Thr Pro Gln Asp
        115                 120                 125

Ser Gly Ile Ser Leu Gln Thr Val Leu Glu Leu Gly Pro Leu Val Pro
    130                 135                 140

Leu Phe Gly Val Cys Met Gly Leu Gln Cys Ile Gly Glu Ala Phe Gly
145                 150                 155                 160

Gly Lys Ile Val Arg Ser Pro Phe Gly Val Met His Gly Lys Ser Ser
                165                 170                 175

Met Val His Tyr Asp Glu Lys Gly Glu Glu Gly Leu Phe Ser Gly Leu
            180                 185                 190

Ser Asn Pro Phe Leu Val Gly Arg Tyr His Ser Leu Val Ile Glu Lys
        195                 200                 205

Asp Ser Phe Pro Ser Asp Glu Leu Glu Val Thr Ala Trp Thr Glu Asp
    210                 215                 220

Gly Leu Val Met Ala Ala Arg His Arg Lys Tyr Lys His Ile Gln Gly
225                 230                 235                 240

Val Gln Phe His Pro Glu Ser Ile Ile Thr Thr Glu Gly Lys Thr Ile
                245                 250                 255

Val Arg Asn Phe Ile Lys Leu Val Glu Lys Lys Glu Ser Glu Lys Leu
            260                 265                 270

Ala
```

<210> SEQ ID NO 85
<211> LENGTH: 273
<212> TYPE: PRT
<213> ORGANISM: Arabidopsis thaliana
<220> FEATURE:
<221> NAME/KEY: misc_feature
<222> LOCATION: (1)..(273)
<223> OTHER INFORMATION: Ceres CLONE ID no. 6495

<400> SEQUENCE: 85

```
Met Ala Ala Thr Thr Leu Tyr Asn Ser Cys Leu Leu Gln Pro Lys Tyr
1               5                   10                  15

Gly Phe Thr Thr Arg Arg Leu Asn Gln Ser Leu Val Asn Pro Leu Thr
            20                  25                  30

Asn Pro Thr Arg Val Ser Val Leu Trp Lys Ser Arg Arg Asp Val Ile
        35                  40                  45
```

```
Ala Lys Ala Ser Ile Glu Met Ala Glu Ser Asn Ser Ile Ser Ser Val
    50                  55                  60

Val Val Asn Ser Ser Gly Pro Ile Ile Val Ile Asp Asn Tyr Asp Ser
65                  70                  75                  80

Phe Thr Tyr Asn Leu Cys Gln Tyr Met Gly Glu Leu Gly Cys His Phe
                85                  90                  95

Glu Val Tyr Arg Asn Asp Glu Leu Thr Val Glu Glu Leu Lys Arg Lys
            100                 105                 110

Lys Pro Arg Gly Leu Leu Ile Ser Pro Gly Pro Gly Thr Pro Gln Asp
        115                 120                 125

Ser Gly Ile Ser Leu Gln Thr Val Leu Glu Leu Gly Pro Leu Val Pro
    130                 135                 140

Leu Phe Gly Val Cys Met Gly Leu Gln Cys Ile Gly Glu Ala Phe Gly
145                 150                 155                 160

Gly Lys Ile Val Arg Ser Pro Phe Gly Val Met His Gly Lys Ser Ser
                165                 170                 175

Met Val His Tyr Asp Glu Lys Gly Glu Glu Gly Leu Phe Ser Gly Leu
            180                 185                 190

Ser Asn Pro Phe Leu Val Gly Arg Tyr His Ser Leu Val Ile Glu Lys
        195                 200                 205

Asp Ser Phe Pro Ser Asp Glu Leu Glu Val Thr Ala Trp Thr Glu Asp
    210                 215                 220

Gly Leu Val Met Ala Ala Arg His Arg Lys Tyr Lys His Ile Gln Gly
225                 230                 235                 240

Val Gln Phe His Pro Glu Ser Ile Ile Thr Thr Glu Gly Lys Thr Ile
                245                 250                 255

Val Arg Asn Phe Ile Lys Leu Val Glu Lys Lys Glu Ser Glu Lys Leu
            260                 265                 270

Ala


<210> SEQ ID NO 86
<211> LENGTH: 273
<212> TYPE: PRT
<213> ORGANISM: Arabidopsis thaliana
<220> FEATURE:
<221> NAME/KEY: misc_feature
<222> LOCATION: (1)..(273)
<223> OTHER INFORMATION: Public GI no. 9758358

<400> SEQUENCE: 86

Met Ala Ala Thr Thr Leu Tyr Asn Ser Cys Leu Leu Gln Pro Lys Tyr
1               5                   10                  15

Gly Phe Thr Thr Arg Arg Leu Asn Gln Ser Leu Val Asn Ser Leu Thr
            20                  25                  30

Asn Pro Thr Arg Val Ser Val Leu Trp Lys Ser Arg Arg Asp Val Ile
        35                  40                  45

Ala Lys Ala Ser Ile Glu Met Ala Glu Ser Asn Ser Ile Ser Ser Val
    50                  55                  60

Val Val Asn Ser Ser Gly Pro Ile Ile Val Ile Asp Asn Tyr Asp Ser
65                  70                  75                  80

Phe Thr Tyr Asn Leu Cys Gln Tyr Met Gly Glu Leu Gly Cys His Phe
                85                  90                  95

Glu Val Tyr Arg Asn Asp Glu Leu Thr Val Glu Glu Leu Lys Arg Lys
            100                 105                 110

Lys Pro Arg Gly Leu Leu Ile Ser Pro Gly Pro Gly Thr Pro Gln Asp
```

```
        115                 120                 125

Ser Gly Ile Ser Leu Gln Thr Val Leu Glu Leu Gly Pro Leu Val Pro
    130                 135                 140

Leu Phe Gly Val Cys Met Gly Leu Gln Cys Ile Gly Glu Ala Phe Gly
145                 150                 155                 160

Gly Lys Ile Val Arg Ser Pro Phe Gly Val Met His Gly Lys Ser Ser
                165                 170                 175

Met Val His Tyr Asp Glu Lys Gly Glu Glu Gly Leu Phe Ser Gly Leu
            180                 185                 190

Ser Asn Pro Phe Leu Val Gly Arg Tyr His Ser Leu Val Ile Glu Lys
        195                 200                 205

Asp Ser Phe Pro Ser Asp Glu Leu Glu Val Thr Ala Trp Thr Glu Asp
    210                 215                 220

Gly Leu Val Met Ala Ala Arg His Arg Lys Tyr Lys His Ile Gln Gly
225                 230                 235                 240

Val Gln Phe His Pro Glu Ser Ile Ile Thr Thr Glu Gly Lys Thr Ile
                245                 250                 255

Val Arg Asn Phe Ile Lys Leu Val Glu Lys Lys Glu Ser Glu Lys Leu
            260                 265                 270

Ala


<210> SEQ ID NO 87
<211> LENGTH: 279
<212> TYPE: PRT
<213> ORGANISM: Brassica napus
<220> FEATURE:
<221> NAME/KEY: misc_feature
<222> LOCATION: (1)..(279)
<223> OTHER INFORMATION: Ceres CLONE ID no. 967151
<220> FEATURE:
<221> NAME/KEY: misc_feature
<222> LOCATION: (143)..(143)
<223> OTHER INFORMATION: Xaa is any aa, unknown, or other
<220> FEATURE:
<221> NAME/KEY: misc_feature
<222> LOCATION: (168)..(168)
<223> OTHER INFORMATION: Xaa is any aa, unknown, or other
<220> FEATURE:
<221> NAME/KEY: misc_feature
<222> LOCATION: (188)..(188)
<223> OTHER INFORMATION: Xaa is any aa, unknown, or other
<220> FEATURE:
<221> NAME/KEY: misc_feature
<222> LOCATION: (199)..(199)
<223> OTHER INFORMATION: Xaa is any aa, unknown, or other
<220> FEATURE:
<221> NAME/KEY: misc_feature
<222> LOCATION: (208)..(208)
<223> OTHER INFORMATION: Xaa is any aa, unknown, or other
<220> FEATURE:
<221> NAME/KEY: misc_feature
<222> LOCATION: (226)..(226)
<223> OTHER INFORMATION: Xaa is any aa, unknown, or other
<220> FEATURE:
<221> NAME/KEY: misc_feature
<222> LOCATION: (230)..(230)
<223> OTHER INFORMATION: Xaa is any aa, unknown, or other
<220> FEATURE:
<221> NAME/KEY: misc_feature
<222> LOCATION: (237)..(237)
<223> OTHER INFORMATION: Xaa is any aa, unknown, or other
<220> FEATURE:
<221> NAME/KEY: misc_feature
<222> LOCATION: (241)..(241)
<223> OTHER INFORMATION: Xaa is any aa, unknown, or other
<220> FEATURE:
<221> NAME/KEY: misc_feature
<222> LOCATION: (253)..(253)
```

```
<223> OTHER INFORMATION: Xaa is any aa, unknown, or other
<220> FEATURE:
<221> NAME/KEY: misc_feature
<222> LOCATION: (257)..(257)
<223> OTHER INFORMATION: Xaa is any aa, unknown, or other
<220> FEATURE:
<221> NAME/KEY: misc_feature
<222> LOCATION: (260)..(260)
<223> OTHER INFORMATION: Xaa is any aa, unknown, or other
<220> FEATURE:
<221> NAME/KEY: misc_feature
<222> LOCATION: (264)..(264)
<223> OTHER INFORMATION: Xaa is any aa, unknown, or other
<220> FEATURE:
<221> NAME/KEY: misc_feature
<222> LOCATION: (271)..(271)
<223> OTHER INFORMATION: Xaa is any aa, unknown, or other
<220> FEATURE:
<221> NAME/KEY: misc_feature
<222> LOCATION: (277)..(277)
<223> OTHER INFORMATION: Xaa is any aa, unknown, or other

<400> SEQUENCE: 87

Met Ala Ala Thr Thr Leu Asn Asn Ser Ser Ser Leu Leu Gln Pro Lys
1               5                   10                  15

Ser Gly Ser Thr Thr Arg Leu Asn Pro Ser Ser Leu Leu Lys Pro Cys
            20                  25                  30

Pro Asn Pro Thr Arg Val Ser Phe Ser Gly Lys Ser Arg Gly His Val
        35                  40                  45

Val Thr Lys Ala Ser Ile Glu Met Ala His Ser Asn Ser Thr Pro Ala
    50                  55                  60

Ala Val Val Val Asn Ser Ser Ser Lys Gln Lys Gly Pro Ile Ile Val
65                  70                  75                  80

Ile Asp Asn Tyr Asp Ser Phe Thr Tyr Asn Leu Cys Gln Tyr Met Gly
                85                  90                  95

Glu Leu Gly Cys His Phe Glu Val Tyr Arg Asn Asp Glu Leu Thr Val
            100                 105                 110

Glu Glu Leu Lys Ser Lys Asn Pro Arg Gly Val Leu Ile Ser Pro Gly
        115                 120                 125

Pro Gly Thr Pro Gln Asp Ser Gly Ile Ser Leu Gln Thr Val Xaa Glu
    130                 135                 140

Leu Gly Pro Arg Val Pro Leu Phe Gly Val Cys Met Gly Leu Gln Cys
145                 150                 155                 160

Ile Gly Glu Ala Phe Gly Gly Xaa Ile Val Arg Ser Pro Tyr Gly Val
                165                 170                 175

Met His Gly Lys Ser Ser Met Val Pro Tyr Tyr Xaa Lys Gly Glu Glu
            180                 185                 190

Gly Leu Phe Ser Gly Leu Xaa Asn Pro Phe Leu Val Gly Arg Tyr Xaa
        195                 200                 205

Ser Leu Val Ile Glu Lys Asp Thr Phe Pro Ser Asp Glu Leu Glu Val
    210                 215                 220

Thr Xaa Trp Thr Glu Xaa Gly Leu Val Met Ala Ala Xaa His Arg Lys
225                 230                 235                 240

Xaa Lys His Ile Gln Gly Val Gln Phe His Pro Glu Xaa Ile Ile Thr
                245                 250                 255

Xaa Glu Gly Xaa Thr Ile Val Xaa Asn Phe Ile Lys Leu Val Xaa Lys
            260                 265                 270

Lys Glu Ala Glu Xaa Leu Thr
        275
```

```
<210> SEQ ID NO 88
<211> LENGTH: 282
<212> TYPE: PRT
<213> ORGANISM: Zea mays
<220> FEATURE:
<221> NAME/KEY: misc_feature
<222> LOCATION: (1)..(282)
<223> OTHER INFORMATION: Ceres CLONE ID no. 214246

<400> SEQUENCE: 88

Met Ala Cys Ser His Ile Val Ala Ala Ala Gly Val Ser Ser Pro Ala
1               5                   10                  15

Ala Ala Ala Ala Arg Ser Pro Ala His Ser Pro Ala Ser Ala Phe Ala
            20                  25                  30

Arg Leu Arg Ser Thr Pro Arg Phe Ala Ser Ala Gly Leu Ser Val Lys
        35                  40                  45

Gly Asn Gly Ala Ala Phe Pro Leu Val Ala Ala Ala Gly Pro Ala Ala
    50                  55                  60

Ala Ala Pro Val Ala Asp Leu Asp Gly Arg Pro Ala Thr Glu Lys Gln
65                  70                  75                  80

Pro Ile Ile Val Ile Asp Asn Tyr Asp Ser Phe Thr Tyr Asn Leu Cys
                85                  90                  95

Gln Tyr Met Gly Glu Leu Gly Leu Asn Phe Glu Val Tyr Arg Asn Asp
            100                 105                 110

Glu Leu Thr Ile Glu Asp Val Arg Arg Lys Asn Pro Arg Gly Ile Leu
        115                 120                 125

Ile Ser Pro Gly Pro Gly Glu Pro Gln Asp Ser Gly Ile Ser Leu Gln
    130                 135                 140

Thr Val Leu Glu Leu Gly Pro Thr Ile Pro Ile Phe Gly Val Cys Met
145                 150                 155                 160

Gly Leu Gln Cys Ile Gly Glu Ala Phe Gly Gly Lys Ile Ile Arg Ala
                165                 170                 175

Pro Ser Gly Val Met His Gly Lys Ser Ser Pro Val Tyr Tyr Asp Glu
            180                 185                 190

Glu Leu Gly Lys Ala Leu Phe Asn Gly Leu Pro Asn Pro Phe Thr Ala
        195                 200                 205

Ala Arg Tyr His Ser Leu Val Ile Glu Arg Glu Thr Phe Pro His Asp
    210                 215                 220

Ala Leu Glu Ala Thr Ala Trp Thr Glu Asp Gly Leu Ile Met Ala Ala
225                 230                 235                 240

Arg His Lys Lys Tyr Lys His Ile Gln Gly Val Gln Phe His Pro Glu
                245                 250                 255

Ser Ile Ile Thr Pro Glu Gly Lys Lys Ile Ile Leu Asn Phe Val Arg
            260                 265                 270

Phe Ile Glu Glu Leu Glu Lys Gln Arg Ser
        275                 280


<210> SEQ ID NO 89
<211> LENGTH: 282
<212> TYPE: PRT
<213> ORGANISM: Zea mays
<220> FEATURE:
<221> NAME/KEY: misc_feature
<222> LOCATION: (1)..(282)
<223> OTHER INFORMATION: Ceres CLONE ID no. 257290

<400> SEQUENCE: 89

Met Ala Cys Ser His Ile Val Ala Ala Ala Gly Val Ser Ser Pro Ala
1               5                   10                  15
```

```
Ala Ala Ala Ala Arg Ser Pro Ala His Ser Pro Ala Ser Ala Phe Ala
            20                  25                  30

Arg Leu Arg Ser Thr Pro Arg Phe Ala Ser Ala Gly Leu Ser Val Lys
        35                  40                  45

Gly Asn Gly Ala Ala Phe Pro Leu Val Ala Ala Ala Gly Pro Ala Ala
    50                  55                  60

Ala Ala Pro Val Ala Asp Leu Asp Gly Arg Pro Ala Thr Glu Lys Gln
65                  70                  75                  80

Pro Ile Ile Val Ile Asp Asn Tyr Asp Ser Phe Thr Tyr Asn Leu Cys
                85                  90                  95

Gln Tyr Met Gly Glu Leu Gly Leu Asn Phe Glu Val Tyr Arg Asn Asp
            100                 105                 110

Glu Leu Thr Ile Glu Asp Val Arg Arg Lys Asn Pro Arg Gly Ile Leu
        115                 120                 125

Ile Ser Pro Gly Pro Gly Glu Pro Gln Asp Ser Gly Ile Ser Leu Gln
    130                 135                 140

Thr Val Leu Glu Leu Gly Pro Thr Ile Pro Ile Phe Gly Val Cys Met
145                 150                 155                 160

Gly Leu Gln Cys Ile Gly Glu Ala Phe Gly Gly Lys Ile Ile Arg Ala
                165                 170                 175

Pro Ser Gly Val Met His Gly Lys Ser Ser Pro Val Tyr Tyr Asp Glu
            180                 185                 190

Glu Leu Gly Lys Ala Leu Phe Asn Gly Leu Pro Asn Pro Phe Thr Ala
        195                 200                 205

Ala Arg Tyr His Ser Leu Val Ile Glu Gln Glu Thr Phe Pro His Asp
    210                 215                 220

Ala Leu Glu Ala Thr Ala Trp Thr Glu Asp Gly Leu Ile Met Ala Ala
225                 230                 235                 240

Arg His Lys Lys Tyr Lys His Ile Gln Gly Val Gln Phe His Pro Glu
                245                 250                 255

Ser Ile Ile Thr Pro Glu Gly Lys Lys Ile Ile Leu Asn Phe Val Arg
            260                 265                 270

Phe Ile Glu Glu Leu Glu Lys Gln Arg Ser
        275                 280
```

```
<210> SEQ ID NO 90
<211> LENGTH: 282
<212> TYPE: PRT
<213> ORGANISM: Zea mays
<220> FEATURE:
<221> NAME/KEY: misc_feature
<222> LOCATION: (1)..(282)
<223> OTHER INFORMATION: Ceres CLONE ID no. 341958

<400> SEQUENCE: 90

Met Ala Cys Ser His Leu Ala Ala Ala Gly Gly Ser Ser Pro Ala Ala
1               5                   10                  15

Ala Ala Val Val Arg Ser Pro Thr His Ser Pro Ala Ala Ala Phe Ala
            20                  25                  30

Arg Leu Arg Ser Thr Pro Arg Phe Ala Ser Ala Gly Leu Ser Val Lys
        35                  40                  45

Gly Asn Gly Ala Ala Phe Pro Leu Val Ala Ala Ala Gly Pro Ala Ala
    50                  55                  60

Ala Ala Pro Val Ala Asp Leu Asp Gly Arg Pro Ala Thr Glu Lys Gln
65                  70                  75                  80
```

```
Pro Ile Ile Val Ile Asp Asn Tyr Asp Ser Phe Thr Tyr Asn Leu Cys
                85                  90                  95

Gln Tyr Met Gly Glu Leu Gly Leu Asn Phe Glu Val Tyr Arg Asn Asp
            100                 105                 110

Glu Leu Thr Ile Glu Asp Val Arg Arg Lys Asn Pro Arg Gly Ile Leu
        115                 120                 125

Ile Ser Pro Gly Pro Gly Glu Pro Gln Asp Ser Gly Ile Ser Leu Gln
    130                 135                 140

Thr Val Leu Glu Leu Gly Pro Thr Ile Pro Ile Phe Gly Val Cys Met
145                 150                 155                 160

Gly Leu Gln Cys Ile Gly Glu Ala Phe Gly Gly Lys Ile Ile Arg Ala
                165                 170                 175

Pro Ser Gly Val Met His Gly Lys Ser Ser Pro Val Tyr Tyr Asp Glu
            180                 185                 190

Glu Leu Gly Lys Ala Leu Phe Asn Gly Leu Pro Asn Pro Phe Thr Ala
        195                 200                 205

Ala Arg Tyr His Ser Leu Val Ile Glu Gln Glu Thr Phe Pro His Asp
    210                 215                 220

Ala Leu Glu Ala Thr Ala Trp Thr Glu Asp Gly Leu Ile Met Ala Ala
225                 230                 235                 240

Arg His Lys Lys Tyr Lys His Ile Gln Gly Val Gln Phe His Pro Glu
                245                 250                 255

Ser Ile Ile Thr Pro Glu Gly Lys Lys Ile Ile Leu Asn Phe Val Arg
            260                 265                 270

Phe Ile Glu Glu Leu Glu Lys Gln Arg Ser
        275                 280


<210> SEQ ID NO 91
<211> LENGTH: 284
<212> TYPE: PRT
<213> ORGANISM: Triticum aestivum
<220> FEATURE:
<221> NAME/KEY: misc_feature
<222> LOCATION: (1)..(284)
<223> OTHER INFORMATION: Ceres CLONE ID no. 686561

<400> SEQUENCE: 91

Met Ala Cys Thr His Leu Ala Ala Ala Ser Ser Pro Ala Thr Thr Ala
1               5                   10                  15

Ala Ala Leu Arg Ala Arg Ala Thr Ala Pro Ala Ala Gly Phe Ala Arg
            20                  25                  30

Leu Pro Ala Thr Leu His Pro Glu Asn Gly Gly Leu Ala Leu Arg Gly
        35                  40                  45

Arg Arg Ala Val Thr Pro Val Val Leu Ala Ala Gly Pro Ala Ala Ala
    50                  55                  60

Ala Pro Val Ala Asp Arg Asp Gly Thr Pro Ala Ala Val Lys Gln Pro
65                  70                  75                  80

Ile Ile Val Ile Asp Asn Tyr Asp Ser Phe Thr Tyr Asn Leu Cys Gln
                85                  90                  95

Tyr Met Gly Glu Leu Gly Leu Asn Phe Glu Val Tyr Arg Asn Asp Glu
            100                 105                 110

Leu Thr Ile Glu Glu Val Lys Arg Met Lys Pro Arg Gly Ile Leu Ile
        115                 120                 125

Ser Pro Gly Pro Gly Glu Pro Gln Asp Ser Gly Ile Ser Leu Gln Thr
    130                 135                 140

Val Leu Glu Leu Gly Pro Thr Ile Pro Ile Phe Gly Val Cys Met Gly
```

```
145                 150                 155                 160

Leu Gln Cys Ile Gly Glu Ala Phe Gly Gly Lys Ile Ile Arg Val Pro
                165                 170                 175

Ser Gly Val Met His Gly Lys Ser Ser Pro Val Tyr Tyr Asp Glu Val
            180                 185                 190

Leu Gly Lys Ser Ile Phe Glu Gly Leu Ser Asn Pro Phe Thr Ala Ala
        195                 200                 205

Arg Tyr His Ser Leu Val Ile Glu Glu Glu Thr Phe Pro His Asp Glu
    210                 215                 220

Leu Glu Val Thr Ala Trp Thr Glu Asp Gly Leu Val Met Ala Ala Arg
225                 230                 235                 240

His Lys Lys Tyr Thr His Ile Gln Gly Val Gln Phe His Pro Glu Ser
                245                 250                 255

Ile Ile Thr Pro Glu Gly Lys Lys Ile Ile Leu Asn Phe Ala Arg Tyr
            260                 265                 270

Val Glu Glu Phe Glu Lys Gln Thr Ser Glu Gly Lys
        275                 280


<210> SEQ ID NO 92
<211> LENGTH: 273
<212> TYPE: PRT
<213> ORGANISM: Oryza sativa (japonica cultivar-group)
<220> FEATURE:
<221> NAME/KEY: misc_feature
<222> LOCATION: (1)..(273)
<223> OTHER INFORMATION: Public GI no. 50918343

<400> SEQUENCE: 92

Met Ala Thr Ala Ala Arg Leu Leu Pro Lys Ile Gln Ser Pro Ala Ser
1               5                   10                  15

Pro Ala Val Ala Glu Ala Arg Arg Arg Arg Pro Ser Ser Leu Arg Leu
            20                  25                  30

Gly Val Thr Ser Gly Pro Ala Arg Thr Leu Lys Gln Lys Leu Val Ala
        35                  40                  45

Lys Ser Ala Val Ser Val Val Glu Gly Glu Asn Ala Phe Asp Gly Val
    50                  55                  60

Lys Gln Asp Thr Arg Pro Ile Ile Val Ile Asp Asn Tyr Asp Ser Phe
65                  70                  75                  80

Thr Tyr Asn Leu Cys Gln Tyr Met Gly Glu Val Gly Ala Asn Phe Glu
                85                  90                  95

Val Tyr Arg Asn Asp Asp Ile Thr Val Glu Glu Ile Lys Lys Ile Ser
            100                 105                 110

Pro Arg Gly Ile Leu Ile Ser Pro Gly Pro Gly Thr Pro Gln Asp Ser
        115                 120                 125

Gly Ile Ser Leu Gln Thr Val Gln Asp Leu Gly Pro Ser Thr Pro Leu
    130                 135                 140

Phe Gly Val Cys Met Gly Leu Gln Cys Ile Gly Glu Ala Phe Gly Gly
145                 150                 155                 160

Lys Val Val Arg Ser Pro Tyr Gly Val Val His Gly Lys Gly Ser Leu
                165                 170                 175

Val His Tyr Glu Glu Lys Leu Asp Gly Thr Leu Phe Ser Gly Leu Pro
            180                 185                 190

Asn Pro Phe Gln Ala Gly Arg Tyr His Ser Leu Val Ile Glu Lys Asp
        195                 200                 205

Ser Phe Pro His Asp Ala Leu Glu Ile Thr Ala Trp Thr Asp Asp Gly
    210                 215                 220
```

```
Leu Ile Met Ala Ala Arg His Arg Lys Tyr Lys His Ile Gln Gly Val
225                 230                 235                 240

Gln Phe His Pro Glu Ser Ile Ile Thr Thr Glu Gly Arg Leu Met Val
                245                 250                 255

Lys Asn Phe Ile Lys Ile Ile Glu Gly Tyr Glu Ala Leu Asn Cys Leu
            260                 265                 270

Pro


<210> SEQ ID NO 93
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Promoter of ME Line ME08125

<400> SEQUENCE: 93

tcttggtcat ggcttcttgg ttattgcata gaagccagaa gaaccaagtg agcgctgagc     60

ctgttgtgtc tctaccagct aacatgaagg acaagattgt gtctctaagg aatctgtcat    120

cacttggatt caacaacttg tacttagtcg tgtcaacatt tatagaagac atcaacaaat    180

ctttagaaga agaagaatca atcccttggc tgatctcatc tctcttagaa gctatgcact    240

tagagcaaac acgatcgaaa atcgcgtgag ctcttttcag cttcaactca gctccaaccc    300

caatcaatct ttgcatcttc cacaccacct ccggcttgaa atgtctgtag aaaatagctt    360

cctctgcatc gtctaaggct cttgcaaact cgatttccgg catttccacc gagagacaac    420

ctggatcata cccggttgct aaaacaaagg tagtgtcaaa cgtgaatctt tggaaaacat    480

cttgtaagtc cacgacgagt ttctctttag caacatgatc aagaagtggc acaagccctt    540

tctctagctt actcaagctt gtagctaatg aaaacctttg aaaatcggga tgattcatca    600

tgctttgaga agatttcctt agatccttcc acaaatctga atccgcgttg aaaatcccat    660

ctcccaaaac gtcaaataac ttcttgaatt cggttccttt cgggtaattc gcaaagtttg    720

agctcatgat gtgatggata ttagcaggat caacggtgaa caacatgtcg atgcccccta    780

aaaaagggcc tatgaaaaga tagtttaagt tgccgtcctc aagaacctcg gttataaagt    840

cgtaaactcg agggagcacg gtaagtaaac ccggaagcat gcccaggagc ggccagtttg    900

tgagaaatga acggtgtggt ttcttgctga tcaggaaaat tcgaaagata aggaaacaaa    960

agaaagcaat ggagatttca agtaagctga ccaaagccat                          1000


<210> SEQ ID NO 94
<211> LENGTH: 1954
<212> TYPE: DNA
<213> ORGANISM: Arabidopsis thaliana
<220> FEATURE:
<221> NAME/KEY: misc_feature
<222> LOCATION: (1)..(1954)
<223> OTHER INFORMATION: Ceres Promoter p326

<400> SEQUENCE: 94

gtgggtaaaa gtatccttct ttgtgcattt ggtattttta agcatgtaat aagaaaaacc     60

aaaatagacg gctggtattt aataaaagga gactaatgta tgtatagtat atgatttgtg    120

tggaatataa taaagttgta aaatatagat gtgaagcgag tatctatctt ttgactttca    180

aaggtgatcg atcgtgttct ttgtgatagt tttggtcgtc ggtctacaag tcaacaacca    240

ccttgaagtt ttcgcgtctc ggtttcctct tcgcatctgg tatccaatag catacatata    300
```

```
ccagtgcgga aaatggcgaa gactagtggg cttgaaccat aaggtttggc cccaatacgg    360

attccaaaca acaagcctag cgcagtcttt tgggatgcat aagactaaac tgtcgcagtg    420

atagacgtaa gatatatcga cttgattgga atcgtctaag ctaataagtt taccttgacc    480

gtttatagtt gcgtcaacgt ccttatggag attgatgccc atcaaataaa cctgaaaatc    540

catcaccatg accaccataa actcccttgc tgccgctgct ttggcttgag caaggtgttt    600

ccttgtaaag ctccgatctt tggataaagt gttccacttt ttgcaagtag ctctgacccc    660

tctcagagat gtcaccggaa tcttagacag aacctcctct gccaaatcac ttggaagatc    720

ggacaatgtc atcattttg caggtaattt ctccttcgtt gctgctttgg cttgagcacg    780

gtgcttcttt gtaaagctcc gatctttgga taagagcgga tcggaatcct ctaggaggtg    840

ccagtccctt gacctattaa tttatagaag gttttagtgt attttgttcc aatttcttct    900

ctaacttaac aaataacaac tgcctcatag tcatgggctt caaattttat cgcttggtgt    960

atttcgttat ttgcaaggcc ttggcccatt ttgagcccaa taactaaatc tagccttttc   1020

agaccggaca tgaacttcgc atattggcgt aactgtgcag ttttaccttt ttcggatcag   1080

acaagatcag atttagacca cccaacaata gtcagtcata tttgacaacc taagctagcc   1140

gacactacta aaaagcaaac aaaagaagaa ttctatgttg tcattttacc ggtggcaagt   1200

ggacccttct ataaaagagt aaagagacag cctgtgtgtg tataatctct aattatgttc   1260

accgacacaa tcacacaaac ccttctctaa tcacacaact tcttcatgat ttacgacatt   1320

aattatcatt aactctttaa attcacttta catgctcaaa aatatctaat ttgcagcatt   1380

aatttgagta ccgataacta ttattataat cgtcgtgatt cgcaatcttc ttcattagat   1440

gctgtcaagt tgtactcgca cgcggtggtc cagtgaagca aatccaacgg tttaaaacct   1500

tcttacattt ctagatctaa tctgaaccgt cagatatcta gatctcattg tctgaacaca   1560

gttagatgaa actgggaatg aatctggacg aaattacgat cttacaccaa ccccctcgac   1620

gagctcgtat atataaagct tatacgctcc tccttcacct tcgtactact actaccacca   1680

catttcttta gctcaacctt cattactaat ctccttttaa ggtatgttca cttttcttcg   1740

attcatactt tctcaagatt cctgcatttc tgtagaattt gaaccaagtg tcgatttttg   1800

tttgagagaa gtgttgattt atagatctgg ttattgaatc tagattccaa tttttaattg   1860

attcgagttt gttatgtgtg tttatactac ttctcattga tcttgtttga tttctctgct   1920

ctgtattagg tttctttcgt gaatcagatc ggaa                               1954
```

```
<210> SEQ ID NO 95
<211> LENGTH: 881
<212> TYPE: DNA
<213> ORGANISM: Arabidopsis thaliana
<220> FEATURE:
<221> NAME/KEY: misc_feature
<222> LOCATION: (1)..(881)
<223> OTHER INFORMATION: Ceres Promoter YP0144

<400> SEQUENCE: 95

ggaaagaagc ggtttatgcg ctgcgcataa cactattatg tctcgggaga acaaagatgg     60

aagcaagagc ggtttgattg gaccgggact ctttagtggc cttgtttttg gctctacttc    120

tgatcattct cagtctggag ctagcgctgt ctctgattgt actgattctg ttgaacgaat    180

acagtttgag aataggcaga agaacaagaa gatgatgata ccgatgcagg ttctagtacc    240

ttcatcaatg aaatctccaa gtaattcaca tgaaggagaa acaaacatct atgacttcat    300
```

-continued

```
ggttccggag gagagagttc acggcggtgg gctagtaatg tctttacttg gtggctccat    360

tgatcgaaac tgaaagccat ttatggtaaa agtgtcacat tctcagcaaa aacctgtgta    420

aagctgtaaa atgtgtggga atctccgaat ctgtttgtag ccggttacgt tatgctggat    480

caaaaactca agatttgttg gatattgtta tgctggatcg gtggtgaaac cacttcccgg    540

ttgctaaata aataaacgtt tttgttttat aatctttttc actaaacggc agtatgggcc    600

tttagtgggc ttcctttaag cgaccaatac aatcgtcgca ccggaatcta ctaccattta    660

taggtttatt catgtaaaac ctcggaaaat ttgagagcca caacggtcaa gagacaaaaa    720

caacttgaag ataaagggat aaggaaggct tcctacatga tggacaacat ttctttccac    780

acaaattctc ataataaaaa tcttataata caaatactta cgtcataatc attcaatcta    840

gtccccatgt tttaaggtcc tgtttcttgt ctgatacaaa t                        881
```

<210> SEQ ID NO 96
<211> LENGTH: 1002
<212> TYPE: DNA
<213> ORGANISM: Arabidopsis thaliana
<220> FEATURE:
<221> NAME/KEY: misc_feature
<222> LOCATION: (1)..(1002)
<223> OTHER INFORMATION: Ceres Promoter YP0190

<400> SEQUENCE: 96

```
taaatagtga cattggtaag aagaaaaaaa acactattaa atagtgaaaa aatggtttat     60

aactctctta attaacatta cttattattg ctagcaccta aaatctccca caaaatattt    120

gttgtaaaac acaaatttac aaaatgattt tgtttttaaa ttagtaacac atgttcatat    180

atacgttaat aagaacatac cctatatgat tttatataaa aaaatttctt tgagacgtct    240

tattcttttt tctttaataa tatgcaattg tgagagtttg gatttgaatg gtagcattag    300

aagcaaactt gaaccaaaca tatttcatga agtcaaactt gaaccaatgt gatcactaat    360

cacagtgttc gcagtgtaag gcatcagaaa atagaagaag ggacatagct atgaatcata    420

taatcttgac acatgtttta taggttttag gtgtgtatgc taacaaaaaa tgagacagct    480

ttcttctaat agacttaata tttgggctaa atgtaccaca gttgtgaatt tcttacaaaa    540

atgggccgag ctacaaaaaa ctacaggccc actctcaact cttatcaaac gacagcgttt    600

tacttttttta aaagcacaca ctttttgttt ggtgtcggtg acggtgagtt tcgtccgctc    660

ttcctttaaa ttgaagcaac ggttttgatc cgatcaaatc caacggtgct gattacacaa    720

agcccgagac gaaaacgttg actattaagt taggttttaa tctcagccgt taatctacaa    780

atcaacggtt ccctgtaaaa cgaatcttcc ttccttcttc acttccgcgt cttctctctc    840

aatcacctca aaaaaatcga tttcatcaaa atattcaccc gcccgaattt gactctccga    900

tcatcgtctc cgaatctaga tcgacgagat caaaacccta gaaatctaaa tcggaatgag    960

aaattgattt tgatacgaat tagggatctg tgtgttgagg ac                      1002
```

<210> SEQ ID NO 97
<211> LENGTH: 1514
<212> TYPE: DNA
<213> ORGANISM: Arabidopsis thaliana
<220> FEATURE:
<221> NAME/KEY: misc_feature
<222> LOCATION: (1)..(1514)
<223> OTHER INFORMATION: Ceres Promoter p13879

<400> SEQUENCE: 97

```
tttcgatcct cttctttttt aggtttcttg atttgatgat cgccgccagt agagccgtcg     60
```

```
tcggaagttt cagagattaa aaccatcacc gtgtgagttg gtagcgaatt aacggaaagt     120

ctaagtcaag atttttaaa aagaaattta tgtgtgaaaa gaagccgttg tgtatattta     180

tataatttag aaaatgtttc atcattttaa ttaaaaaatt aataatttgt agaagaaaga     240

agcatttttt atacataaat catttacctt ctttactgtg tttttcttca cttacttcat     300

ttttactttt ttacaaaaaa gtgaaaagta aattacgtaa ttggtaacat aaattcactt     360

taaatttgca tatgttttgt tttcttcgga aactatatcg aaaagcaaac ggaaagaact     420

tcacaaaaaa ccctagctaa ctaaagacgc atgtgttctt cttattcttc atatatcctc     480

tgtttcttgt gttctgtttt gagtcttaca ttttcaatat ctgactctga ttactatatc     540

taaaagggaa catgaagaac ttgagaccat gttaaactgt acaatgcctt caaacatggc     600

taactaaaga tacattagat ggctttacag tgtgtaatgc ttattatctt taggtttttt     660

aaatcccttg tattaagtta tttaccaaat tatgttcttg tactgcttat tggcttggtt     720

gttgtgtgct ttgtaaacaa cacctttggc tttatttcat cctttgtaaa cctactggtc     780

tttgttcagc tcctcttgga agtgagtttg tatgcctgga acgggtttta atggagtgtt     840

tatcgacaaa aaaaaaatgt agcttttgaa atcacagaga gtagttttat attcaaatta     900

catgcatgca actaagtagc aacaaagttg atatggccga gttggtctaa ggcgccagat     960

taaggttctg gtccgaaagg gcgtgggttc aaatcccact gtcaacattc tctttttctc    1020

aaattaatat ttttctgcct caatggttca ggcccaatta tactagacta ctatcgcgac    1080

taaaataggg actagccgaa ttgatccggc ccagtatcag ttgtgtatca ccacgttatt    1140

tcaaatttca aactaaggga taaagatgtc atttgacata tgagatattt ttttgctcca    1200

ctgagatatt tttctttgtc ccaagataaa atatcttttc tcgcatcgtc gtctttccat    1260

ttgcgcatta aaccaaaaag tgtcacgtga tatgtcccca accactacga attttaacta    1320

cagatttaac catggttaaa ccagaattca cgtaaaccga ctctaaacct agaaaatatc    1380

taaaccttgg ttaatatctc agccccctta taaataacga gacttcgtct acatcgttct    1440

acacatctca ctgctcacta ctctcactgt aatcccttag atcttctttt caaatttcac    1500

cattgcactg gatg                                                      1514
```

```
<210> SEQ ID NO 98
<211> LENGTH: 1026
<212> TYPE: DNA
<213> ORGANISM: Arabidopsis thaliana
<220> FEATURE:
<221> NAME/KEY: misc_feature
<222> LOCATION: (1)..(1026)
<223> OTHER INFORMATION: Ceres Promoter YP0050

<400> SEQUENCE: 98
```

```
aatctgatct ctagtccagt cgattggtac ttgagggaaa catcatattt ttaaaccttg      60

tctcagtaag ctaacacaca ccccttgtga ttacttatcc atgtttatcc acaagaatgc     120

agttggattg agatattttc ttctttgttg aaatcaggcc tcaaggtgtt catgtggtct     180

gcaaaaaaat tcccaaaaat aaagatagtg acatctgaaa tcgataatgg attagacgaa     240

gagtttcgtg ttattccttg gtatgggcgg gtttggggac agatattttg gcacagacga     300

ggactaggcc actgtggtcc tgcagcatta ggtgtccctt ccatgtcctg cattacattt     360

tattgatgga ttcatcaccc tatctactac aacggctaca caaactatga agagttttgt     420

ttactaataa atgcccaagt gaggggtcga tcgaacccgg gacacgtttt tcagtttacc     480
```

-continued

```
atatagaatt atccttggaa cccttgatac tccatagaac atcaccacct ctgttgtcat    540

ctcaggaatc caggttcaaa cctagtctct ctctccctag tgggaggtat atggccactg    600

ggccaatgat gacaaaatgc aaaaaaaata aaatacattt gggttcatta tctaaaatat    660

ctcttgtgtt tgtaagtttt ggttgcacac tcgtgtggtt gaagtgtgtg tgagaggtac    720

tatacaatac actctgcttt tgttttgtac ctatctcttt ctcttctcca catatccaag    780

actttgggga taaagctgag atcattggtt gccatttggt tgtgtagaag caatcaccca    840

tttgctttat ccgaggttga taaatttcct cgggttctcc ttctgacacg tatgacaaat    900

tctaatagta tattcctcgt agatattacc tatatattct caatagttgc aggtacttaa    960

ggctttgtct tggcatcctc gtcctcttca gcaaaactcg tctctcttgc actccaaaaa   1020

gcaacc                                                              1026
```

<210> SEQ ID NO 99
<211> LENGTH: 2016
<212> TYPE: DNA
<213> ORGANISM: Arabidopsis thaliana
<220> FEATURE:
<221> NAME/KEY: misc_feature
<222> LOCATION: (1)..(2016)
<223> OTHER INFORMATION: Ceres Promoter p32449

<400> SEQUENCE: 99

```
gatcggcctt cttcaggtct tctctgtagc tctgttactt ctatcacagt tatcgggtat     60

ttgagaaaaa agagttagct aaaatgaatt tctccatata atcatggttt actacaggtt    120

tacttgattc gcgttagctt tatctgcatc caaagttttt tccatgatgt tatgtcatat    180

gtgataccgt tactatgttt ataactttat acagtctggt tcactggagt ttctgtgatt    240

atgttgagta catactcatt catcctttgg taactctcaa gtttaggttg tttgaattgc    300

ctctgttgtg atacttattg tctattgcat caatcttcta atgcaccacc ctagactatt    360

tgaacaaaga gctgtttcat tcttaaacct ctgtgtctcc ttgctaaatg gtcatgcttt    420

aatgtcttca cctgtctttc tcttctatag atatgtagtc ttgctagata gttagttcta    480

cagctctctt ttgtagtctt gttagagagt tagttgagat attacctctt aaaagtatcc    540

ttgaacgctt tccggttatg accaatttgt tgtagctcct tgtaagtaga acttactggg    600

accagcgaga cagtttatgt gaatgttcat gcttaagtgt cgaacgtatc tatctctact    660

atagctctgt agtcttgtta gacagttagt tttatatctc cattttttttg tagtcttgct    720

agttgagata ttacctcttc tcttcaaagt atccttgaac gctcaccggt tatgaaatct    780

ctacactata gctctgtagt cttgctagat agttagttct ttagctctct ttttgtagcc    840

tagttcttta gctctccttt tgtagccttg ctacagagta agatgggata ttacctcctt    900

gaacgctctc cggttatgac caatttgttg tagctccttg taagtagaac ttaggataga    960

gtgagtcaac tttaagaaag aacctagtat gtggcataac cagattgcag gctctgtctc   1020

ggctacagta acgtaactct atagctcttt gttttgttca gaaagaacca gtgattggat   1080

gattcgtcct tagaaactgg acctaacaac agtcattggc tttgaaatca agccacaaca   1140

atgcctatat gaaccgtcca tttcatttat ccgtttcaaa ccagcccatt acatttcgtc   1200

ccattgataa ccaaaagcgg ttcaatcaga ttatgtttta attttaccaa attctttatg   1260

aagtttaaat tatactcaca ttaaaaggat tattggataa tgtaaaaatt ctgaacaatt   1320

actgattttg gaaaattaac aaatattctt tgaaatagaa gaaaaagcct ttttcctttt   1380

gacaacaaca tataaaatca tactcccatt aaaaagattt taatgtaaaa ttctgaatat   1440
```

```
aagatatttt ttacaacaac aaccaaaaat atttattttt ttcctttttt acagcaacaa   1500

gaaggaaaaa cttttttttt tgtcaagaaa aggggagatt atgtaaacag ataaaacagg   1560

gaaaataact aaccgaactc tcttaattaa catcttcaaa taaggaaaat tatgatccgc   1620

atatttagga agatcaatgc attaaaacaa cttgcacgtg gaaagagaga ctatacgctc   1680

cacacaagtt gcactaatgg tacctctcac aaaccaatca aaatactgaa taatgccaac   1740

gtgtacaaat tagggtttta cctcacaacc atcgaacatt ctcgaaacat tttaaacagc   1800

ctggcgccat agatctaaac tctcatcgac caatttttga ccgtccgatg gaaactctag   1860

cctcaaccca aaactctata taaagaaatc ttttccttcg ttattgctta ccaaatacaa   1920

accctagccg ccttattcgt cttcttcgtt ctctagtttt ttcctcagtc tctgttctta   1980

gatcccttgt agtttccaaa tcttccgata aggcct                             2016
```

<210> SEQ ID NO 100
<211> LENGTH: 1823
<212> TYPE: DNA
<213> ORGANISM: Arabidopsis thaliana
<220> FEATURE:
<221> NAME/KEY: misc_feature
<222> LOCATION: (1)..(1823)
<223> OTHER INFORMATION: Ceres Promoter 21876

<400> SEQUENCE: 100

```
gtctcttaaa aaggatgaac aaacacgaaa ctggtggatt atacaaatgt cgccttatac     60

atatatcggt tattggccaa aagagctatt ttaccttatg gataatggtg ctactatggt    120

tggagttgga ggtgtagttc aggcttcacc ttctggttta agccctccaa tgggtaatgg    180

taaatttccg gcaaaaggtc ctttgagatc agccatgttt tccaatgttg aggtcttata    240

ttccaagtat gagaaaggta aaataaatgc gtttcctata gtggagttgc tagatagtag    300

tagatgttat gggctacgaa ttggtaagag agttcgattt tggactagtc cactcggata    360

ctttttcaat tatggtggtc ctggaggaat ctcttgtgga gtttgatatt tgcgagtata    420

atctttgaac ttgtgtagat tgtacccaaa accgaaaaca tatcctatat aaatttcatt    480

atgagagtaa aattgtttgt tttatgtatc atttctcaac tgtgattgag ttgactattg    540

aaaacatatc ttagataagt ttcgttatga gagttaatga tgattgatga catacacact    600

cctttatgat ggtgattcaa cgttttggag aaaatttatt tataatctct cataaattct    660

ccgttattag ttgaataaaa tcttaaatgt ctcctttaac catagcaaac caacttaaaa    720

atttagattt taaagttaag atggatattg tgattcaacg attaattatc gtaatgcata    780

ttgattatgt aaaataaaat ctaactaccg gaatttattc aataactcca ttgtgtgact    840

gcatttaaat atatgtttta tgtcccatta attaggctgt aatttcgatt tatcaattta    900

tatactagta ttaatttaat tccatagatt tatcaaagcc aactcatgac ggctagggtt    960

ttccgtcacc ttttcgatca tcaagagagt ttttttataa aaaaatttat acaattatac   1020

aatttcttaa ccaaacaaca cataattata agctatttaa catttcaaat tgaaaaaaaa   1080

aatgtatgag aattttgtgg atccattttt gtaattcttt gttgggtaaa ttcacaacca   1140

aaaaaataga aaggcccaaa acgcgtaagg gcaaattagt aaaagtagaa ccacaaagag   1200

aaagcgaaaa ccctagacac ctcgtagcta taagtaccct cgagtcgacc aggattaggg   1260

tgcgctctca tatttctcac attttcgtag ccgcaagact cctttcagat tcttacttgc   1320

aggttagata ttttctctct ttagtgtctc cgatcttcat cttcttatga ttattgtagc   1380
```

-continued

```
tgtttagggt ttagattctt agttttagct ctatattgac tgtgattatc gcttattctt   1440

tgctgttgtt atactgcttt tgattctcta gctttagatc cgtttactcg tcgatcaata   1500

ttgttcctat tgagtctgat gtataatcct ctgattaatt gatagcgttt agttttgata   1560

tcgtcttcgc atgtttttta tcatgtcgat ctgtatctgc tctggttata gttgattctg   1620

atgtatttgg ttggtgatgt tccttagatt tgatatacct gttgtctcgt ggtttgatat   1680

gatagctcaa ctggtgatat gtggttttgt ttcagtggat ctgtgtttga ttatattgtt   1740

gacgttttgg ttgttgtatg gttgatggtt gatgtatttt tgttgattct gatgtttcga   1800

tttttgtttt tgttttgaca gct                                           1823
```